United States Patent
Ginn et al.

(10) Patent No.: US 8,362,249 B2
(45) Date of Patent: *Jan. 29, 2013

(54) CXCR3 RECEPTOR ANTAGONISTS

(75) Inventors: John David Ginn, New Milford, CT (US); Daniel Richard Marshall, Norwalk, CT (US); Anthony S. Prokopowicz, Stormville, NY (US); Sabine Schlyer, New Milford, CT (US); Robert Sibley, North Haven, CT (US); Michael Robert Turner, Danbury, CT (US); Di Wu, Danbury, CT (US); Frank Wu, Ridgefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 210 days.

This patent is subject to a terminal disclaimer.

(21) Appl. No.: 12/764,136

(22) Filed: Apr. 21, 2010

(65) Prior Publication Data
US 2010/0273781 A1 Oct. 28, 2010

Related U.S. Application Data
(60) Provisional application No. 61/317,351, filed on Mar. 25, 2010, provisional application No. 61/172,869, filed on Apr. 27, 2009.

(51) Int. Cl.
| | |
|---|---|
| C07D 231/12 | (2006.01) |
| C07D 401/12 | (2006.01) |
| C07D 401/14 | (2006.01) |
| C07D 413/12 | (2006.01) |
| C07D 471/04 | (2006.01) |
| C07D 513/04 | (2006.01) |
| A61K 31/496 | (2006.01) |

(52) U.S. Cl. ........ 544/357; 544/362; 544/364; 544/371; 544/373; 514/252.11; 514/253.09; 514/253.1; 514/253.04; 514/254.05; 514/254.09

(58) Field of Classification Search .................. None
See application file for complete search history.

(56) References Cited

U.S. PATENT DOCUMENTS
| | | | |
|---|---|---|---|
| 2004/0192728 A1* | 9/2004 | Codd et al. ................. | 514/313 |
| 2009/0099201 A1* | 4/2009 | Bolin et al. ............... | 514/254.02 |
| 2009/0286766 A1* | 11/2009 | Sugasawa et al. ....... | 514/210.18 |
| 2010/0280028 A1* | 11/2010 | Kowalski et al. ......... | 514/234.5 |

FOREIGN PATENT DOCUMENTS
| | | | |
|---|---|---|---|
| WO | 2007/123268 | * | 1/2007 |
| WO | 2008/148849 | * | 12/2008 |

OTHER PUBLICATIONS
CA Registry No. 1025924-29-1, entered into the Registry File on Jun. 6, 2008, supplied by ChemZoo, Inc.*

* cited by examiner

*Primary Examiner* — Emily Bernhardt
(74) *Attorney, Agent, or Firm* — Michael P. Morris; Edward S. Lazer

(57) ABSTRACT

The present invention relates to compounds of formula (I):

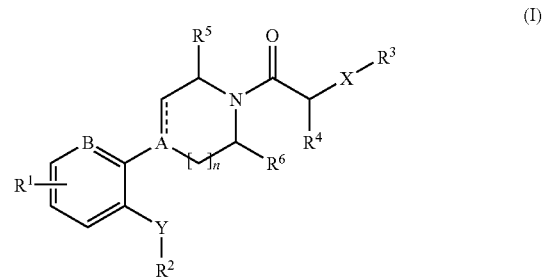

and pharmaceutically acceptable salts thereof, wherein $R^1$ to $R^6$, A, B, X, Y and n are as defined herein. The invention also relates to pharmaceutical compositions comprising these compounds, methods of using these compounds in the treatment of various diseases and disorders, processes for preparing these compounds and intermediates useful in these processes.

2 Claims, No Drawings

CXCR3 RECEPTOR ANTAGONISTS

FIELD OF THE INVENTION

This invention relates to heterocyclic compounds that are useful as antagonists of CXCR3 and are thus useful for treating a variety of diseases and disorders that are mediated or sustained through the interaction of CXCR3 and its ligands including multiple sclerosis, psoriasis, rheumatoid arthritis, inflammatory bowel disease and atherosclerosis. This invention also relates to pharmaceutical compositions comprising these compounds, methods of using these compounds in the treatment of various diseases and disorders, processes for preparing these compounds and intermediates useful in these processes.

BACKGROUND OF THE INVENTION

Chemokine receptors, a subclass of the G-protein coupled receptors (GPCRs) are expressed on the surface of T-cells and other leukocytes. The interaction of chemokine receptors with their ligands plays an important role in the migration of leukocytes to sites of inflammation (A. D. Luster, New Engl. J. Med., 1998, 338, 436). The chemokine receptor CXCR3 is preferentially expressed on T helper (Th1) cells but is also found on natural killer cells and subsets of dendritic cells. Three major chemokine ligands for CXCR3 have been identified: Mig (Monokine Induced by γ-IFN/CXCL9), IP-10 (γ-interferon inducible protein) and I-TAC (IFN-Inducible T Cell α Chemoattractant/CXCR11) (K. E. Cole et al., J. Exp. Med., 1998, 187, 2009; Y. Weng et al., J. Biol. Chem., 1998, 273, 18288).

Histological evaluations of numerous inflammatory lesions, including those from patients with multiple sclerosis (T. L. Sorenson et al., J. Clin. Invest., 1999, 103, 807), rheumatoid arthritis (S. Qin et al., J. Clin. Invest., 1998, 101, 746), psoriasis (J. Flier et al., J. Pathol., 2001, 194, 398) and inflammatory bowel disease (Y. H. Yuan et al., Inflamm. Bowel Dis., 2001, 7, 281) have shown elevated expression of CXCR3 ligands accompanied by an increased frequency of T cells bearing CXCR3. This is in marked contrast to what is found in most normal tissues, where expression of CXCR3 and its ligands is extremely low. This correlative evidence suggests a role of CXCR3 in Th1-mediated chronic inflammation.

Studies with CXCR3 and IP-10 deficient mice also suggest a role for CXCR3 and IP-10 in Th1 mediated disease. For example, in one study CXCR3−/− mice showed significant resistance to allograft rejection (W. W. Hancock et al., J. Exp. Med., 2000, 192, 1515). In another study, IP-10 deficient mice showed protection against the development of colitis (U. P. Singh et al., J. Immunol., 2003, 171, 1401). Further evidence of a role for CXCR3 and IP-10 as mediators of disease is provided by studies utilizing blocking antibodies. For example in a rat model of adjuvant induced arthritis (I. Salomon et al., J. Immunol., 2002, 169, 2685) a DNA vaccine approach to overexpress self IP-10 was used to induce the production of self-IP-10 antibodies. These Abs are specific for IP-10 and do not cross react with other proinflammatory cytokines or chemokines including Mig and I-TAC. Pretreatment with this vaccine protected rats from the development of severe arthritis and reduced the time to remission of symptoms. In addition, affinity purified anti-IP-10 from vaccinated rats could therapeutically transfer protection to newly diseased rats. In another study, this vaccine approach was successful in suppressing disease in a mouse model of multiple sclerosis (G. Wildbaum et al., J. Immunol., 2002, 168, 5885).

In a study of pulmonary inflammation, (N. Li et al., Acta Pharmacol. Sinica, 2008, 29, 14) CXCR3 knockout mice showed alleviated inflammation compared to wild type mice in cigarette smoke induced pulmonary injury as well as lower influx of inflammatory T cells. Similarly, in a model of nephrotoxic nephritis, CXCR3 knockout mice showed reduced influx of T cells, less severe nephritis and improved renal function compared to wild type mice (U. Panzer et al., J. Am. Soc. Nephroi., 2007, 18, 2071). Thus CXCR3 may play a role in inflammatory pulmonary diseases such as COPD and inflammatory kidney disease.

Studies such as those cited above suggest that inhibitors of CXCR3 may be useful in treating inflammatory and autoimmune diseases in which CXCR3-mediated cellular recruitment plays a role, including multiple sclerosis, psoriasis, rheumatoid arthritis, inflammatory bowel disease, COPD and kidney disease.

Recent work has also implicated CXCR3 in the pathogenesis of atherosclerosis. In one study (F. Mach et al., J. Clin. Invest., 1999, 104, 1041) CXCR3 was found expressed in all T lymphocytes within human atherosclerotic lesions. The ligands IP10, Mig and I-TAC were all found within lesion-associated cells including endothelial and smooth muscle cells (Mig and I-TAC) and macrophages (IP10), suggesting these ligands play a role in recruitment of activated T lymphocytes within vascular wall lesions in atherogenesis. Left untreated and allowed to progress, atherosclerosis can result in narrowing of the lumen of the artery and plaque rupture which can lead to coronary heart disease, myocardial infarction and stroke (J. Sanz and Z. A. Fayad, Nature, 2008, 451, 953).

Further evidence has come from genetic deletion studies in mice. CXCR3 deletion on an ApoE$^{-/-}$ background resulted in a significant reduction in atherosclerotic lesion formation following ten weeks on a high cholesterol diet (N. R. Veillard et al., Circulation, 2005, 112, 870). Moreover, deletion of the CXCR3 ligand, IP-10 on an ApoE$^{-/-}$ background similarly reduced atherosclerotic lesion load (E. Heller et al., Circulation, 2006, 113, 2301). More recently, NBI-74330 a CXCR3 antagonist was dosed prophylactically in a LDL receptor knockout model. Similar to the CXCR3 deletion studies in the ApoE−/− results, NBI-74330 significantly attenuated atherosclerotic lesion formation (E. J. A. van Wanrooij et al., Arterioscler. Thromb. Vasc. Biol., 2008, 28, 251).

As a result of studies such as those cited above implicating the interaction of CXCR3 and its ligands in the etiology of various inflammatory and autoimmune diseases as well as atherosclerosis, considerable effort has been directed towards discovering antagonists of this interaction. A number of inhibitors have been reported in the scientific literature, including small molecule antagonists, antibodies and modified ligands (see for example J. C. Medina et al., Ann. Rep. Med. Chem., 2005, 40, 215). However, to date, no CXCR3 antagonist has been approved as a marketed drug.

BRIEF SUMMARY OF THE INVENTION

The present invention provides novel compounds which block the interaction of CXCR3 and its ligands and are thus useful for treating diseases and disorders that are mediated or sustained through the activity of CXCR3 including multiple sclerosis, psoriasis, rheumatoid arthritis, inflammatory bowel disease, COPD, kidney disease and atherosclerosis, myocardial infarction and stroke. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In its broadest embodiment, the present invention relates compounds of formula (I):

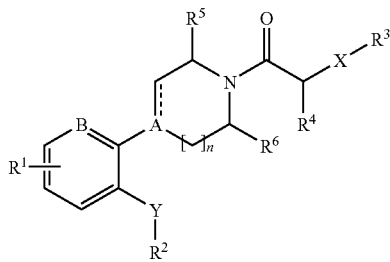

wherein:
A is C or N;
B is C or N;
X is —NHC(O)—, —N(CH$_3$)C(O)—, —NH—, or absent;
Y is —C(O)NH— or —NHC(O)—;
R$^1$ is H, —CN, halogen, —CF$_3$, —OCF$_3$, C$_{1-3}$alkyl, C$_{1-3}$alkoxy, —S(O)$_m$CH$_3$, amino, mono- or dimethylamino, —NHC(O)C$_{1-3}$alkyl, —NO$_2$ —C(O)NH$_2$, —C(O)NHC$_{1-3}$alkyl or —C(O)C$_{1-3}$alkyl;
R$^2$ is aryl, heteroaryl or C$_{3-10}$cycloalkyl each optionally substituted with one to three R$^7$;
R$^3$ is heteroaryl, heterocyclyl, aryl or C$_{3-10}$cycloalkyl each optionally substituted with one to three R$^8$;
R$^4$ is H or C$_{1-6}$alkyl;
R$^5$ and R$^6$ are each independently selected from H, C$_{1-2}$alkyl and phenyl; or R$^5$ and R$^6$ may join to form and ethyl bridge.
R$^7$ is —OH, oxo, hydroxyC$_{1-6}$alkyl, halogen, —(CH$_2$)$_m$—CN, nitro, C$_{1-6}$ alkyl, C$_{2-6}$ alkenyl, C$_{2-6}$ alkynyl, C$_{3-10}$ cycloalkyl, C$_{1-6}$ alkoxy, phenoxy, heteroaryloxy, C$_{1-6}$ alkoxycarbonyl, carboxyl, —C(O)C$_{1-6}$alkyl, —(CH$_2$)$_m$—NR$_9$R$_{10}$, —S(O)$_m$C$_{1-6}$alkyl, —NHS(O)$_2$C$_{1-6}$alkyl,NR$^9$C(O)C$_{1-6}$alkyl, —S(O)$_2$NR$_9$R$_{10}$, —C(O)NR$_9$R$_{10}$ heterocyclyl, heteroaryl, phenyl or benzyl, wherein each alkyl, alkenyl, alkynyl or alkoxy is optionally partially or fully halogenated and each heterocycle, heteroaryl, phenyl or benzyl of said R$^7$ is optionally substituted with one to three C$_{1-6}$ alkyl, C$_{1-6}$alkoxy(CH$_2$)$_m$, halogen, —CN, —CF$_3$, C$_{1-6}$ acyl, —NR$^9$R$^{10}$, —C(O)NR$^9$R$^{10}$, —OH, hydroxy C$_{1-6}$alkyl or —S(O)$_m$C$_{1-6}$alkyl;
R$^8$ is C$_{1-6}$ alkyl, C$_{2-6}$ alkenyl, C$_{2-6}$ alkynyl, carboxyl, C$_{3-10}$ cycloalkyl, C$_{1-6}$alkoxy, halogen, oxo, or phenyl, wherein each alkyl, alkenyl, alkynyl, cycloalkyl or alkoxy is optionally partially or fully halogenated;
R$^9$ and R$^{10}$ are independently selected from hydrogen, C$_{1-6}$ alkyl, C$_{1-6}$ acyl, C$_{3-10}$ cycloalkyl, hydroxyC$_{1-6}$ alkyl, C$_{1-6}$ alkyl C$_{1-6}$ alkoxy, C$_{1-6}$ alkylsulfonyl and C$_{1-6}$ alkoxycarbonyl;
m is 0-2;
n is 1 or 2;
----- is a single bond if A is N, or a single or double bond if A is C;
or the pharmaceutically acceptable salts thereof.

In another embodiment there is provided a compound of formula (I) as described above and wherein R$^3$ is aryl or heteroaryl, or the pharmaceutically acceptable salts thereof.

In another embodiment there is provided a compound of formula (I) as described in the broadest embodiment above wherein R$^2$ is aryl, and R$^3$ is aryl or heteroaryl, or the pharmaceutically acceptable salts thereof.

In another embodiment there is provided a compound of formula (I) as described in the broadest embodiment above wherein R$^2$ is heteroaryl, and R$^3$ is aryl or heteroaryl, or the pharmaceutically acceptable salts thereof.

In another embodiment there is provided a compound of formula (I) as described in the broadest embodiment above and wherein:
A is N;
or the pharmaceutically acceptable salts thereof.

In another embodiment there is provided a compound of formula (I) as described above and wherein:
X is —NHC(O)—, —N(CH$_3$)C(O)—, or absent;
R$^4$ is H;
R$^5$ and R$^6$ are H;
or the pharmaceutically acceptable salts thereof.

In another embodiment there is provided a compound of formula (I) as described above and wherein:
R$^1$ is H, —CN, —F, —Cl, —CF$_3$, —CH$_3$, —OCH$_3$, —C(O)NHCH$_3$ or —S(O)$_2$CH$_3$;
R$^2$ is benzoimidazolyl, benzooxazolyl, benzothiazolyl, benzo[b]thiophenyl, cyclohexyl, dibenzofuranyl, dibenzothiophenyl, 6,7-dihydro-4H-pyrano[4,3-d]thiazolyl , furanyl, imidazolyl, 1H-imidazo[4,3-c]pyridinyl, indolyl, isoindolyl, isoquinolinyl, isothiazolyl, isoxazolyl, oxazolyl, phenyl, pyranyl, pyrazinyl, pyrazolo[3,4-b]pyridinyl, pyrazolyl pyridazinyl, pyridinyl, pyrimidinyl, pyrrolyl, quinolinyl, 4,5,6,7-tetrahydrobenzothiazolyl, 1,2,3,4-tetrahydropyrido[2,3-d]pyrimidinyl, 4,5,6,7-tetrahydrothiazolo[4,5-c]pyridin-2-yl, thiadiazolyl, thiazolyl, thienyl or triazinyl each optionally substituted by one to three R$^7$;
R$^3$ is benzofuranyl, benzoimidazolyl, benzo[d]isothiazolyl, benzo[d]isoxazolyl, benzo[b]thiophenyl, benzotriazolyl, 1,4-diazepanyl, 2,3-dihydrobenzoimidazolyl, 3,3-dihydro-1H-indolyl, 1,3-dihydroisoindolyl, 3,4-dihydro-1H-isoquinolinyl, 1,3-dihydrobenzo[d]isothiazolyl, furanyl, furazany, imidazolidin-2-onyl, imidazolyl, imidazo[1,2-a]pyridinyl, imidazo[4,5-b]pyridinyl, imidazo[1,2-a]pyrimidinyl, imidazo[2,1-b]thiazolyl, indolyl, 1H-indazolyl, isoindolyl, isoquinolinyl, isothiazolyl, oxazolyl, phenyl, phthalazinyl, piperidinyl, pyrazolyl, pyridinyl, pyrrolo[2,3-b]pyridinyl, pyrrolo[2,3-c]pyridinyl, pyrrolo[3,2-b]pyridinyl, pyrrolo[3,2-c]pyridinyl, pyrrolo[2,3-d]pyrimidinyl, pyrrolyl, quinazolinyl, quinolinyl, thiadiazolyl or thiazolyl each optionally substituted with one to three R$^8$;
R$^7$ is —OH, oxo, halogen, —CN, nitro, C$_{1-6}$ alkyl, C$_{3-6}$ cycloalkyl, C$_{1-6}$ alkoxy, phenoxy, —C(O)C$_{1-6}$alkyl, —NR$_9$R$_{10}$, —S(O)$_2$C$_{1-6}$alkyl, —NHS(O)$_2$C$_{1-6}$alkyl, —NHC(O)C$_{1-6}$alkyl, —S(O)$_2$NR$_9$R$_{10}$, —C(O)NR$_9$R$_{10}$ morpholinyl, piperazinyl, pyridyl or phenyl, wherein each alkyl or alkoxy is optionally partially or fully halogenated and each morpholinyl, piperazinyl, pyridyl or phenyl of said R$^7$ is optionally substituted with one to three C$_{1-6}$ alkyl, C$_{1-6}$alkoxy, halogen, —CN, —CF$_3$, C$_{1-6}$ acyl, —NR$^9$R$^{10}$, —C(O)NR$^9$R$^{10}$, —OH, hydroxyC$_{1-6}$alkyl or —S(O)$_2$C$_{1-6}$alkyl;
R$^8$ is C$_{1-3}$ alkyl, C$_{3-6}$ cycloalkyl, C$_{1-3}$ alkoxy, carboxyl, halogen, oxo, or phenyl, wherein each alkyl, cycloalkyl or alkoxy is optionally partially or fully halogenated;
R$^9$ and R$^{10}$ are independently selected from hydrogen, C$_{1-6}$ alkyl, C$_{1-6}$ acyl, C$_{3-6}$ cycloalkyl, hydroxyC$_{1-3}$ alkyl and —S(O)$_2$CH$_3$;
or the pharmaceutically acceptable salts thereof.

In another embodiment there is provided a compound of formula (I) as described above and wherein:
$R^1$ is H, —CN, —F, —Cl, —CF$_3$, —CH$_3$ or —OCH$_3$;
$R^2$ is benzoimidazolyl, benzooxazolyl, benzothiazolyl, 6,7-dihydro-4H-pyrano[4,3-d]thiazolyl, 1H-imidazo[4,3-c]pyridinyl, indolyl, isoquinolinyl, isothiazolyl, oxazolyl, phenyl, pyrazinyl, pyrazolo[3,4-b]pyridinyl, pyrazolyl, pyridazinyl, pyridinyl, pyrimidinyl, quinolinyl, 1,2,3,4-tetrahydropyrido[2,3-d]pyrimidinyl, 4,5,6,7-tetrahydrothiazolo[4,5-c]pyridin-2-yl, thiadiazolyl, or thiazolyl, each optionally substituted by one to three $R^7$;
$R^3$ is benzofuranyl, benzo[d]isothiazolyl, benzo[d]isoxazolyl, 2,3-dihydrobenzoimidazolyl, 1,3-dihydroisoindolyl, 3,4-dihydro-1H-isoquinolinyl, imidazo[1,2-a]pyridinyl-, imidazo[1,2-a]pyrimidinyl, imidazo[2,1-b]thiazolyl, indolyl, 1H-indazolyl, phenyl, phthalazinyl, piperidinyl, pyrazolyl, pyrrolo[2,3-b]pyridinyl, pyrrolyl, quinazolinyl, quinolinyl or thiazolyl each optionally substituted with one to three $R^8$;
$R^7$ is —OH, oxo, —Cl, —F, —Br, —CN, $C_{1-6}$ alkyl, $C_{3-6}$ cycloalkyl, —OCH$_3$, phenoxy, —C(O)CH$_3$, —NR$_9$R$_{10}$, —S(O)$_2$CH$_3$, —NHS(O)$_2$CH$_3$, —NHC(O)CH$_3$, —S(O)$_2$NR$_9$R$_{10}$, —C(O)NR$_9$R$_{10}$ morpholinyl, piperazinyl, pyridyl or phenyl, wherein each alkyl or —OCH$_3$ is optionally partially or fully halogenated and each morpholinyl, piperazinyl, pyridyl or phenyl of said $R^7$ is optionally substituted with one to three —CH$_3$, —OCH$_3$, —Cl, —F, —Br, —CN, —CF$_3$, —C(O)CH$_3$, —NR$^9$R$^{10}$, —C(O)NR$^9$R$^{10}$, —OH or —S(O)$_2$CH$_3$;
$R^8$ is $C_{1-3}$ alkyl, —OCH$_3$, —Cl, —F, —Br, oxo, or phenyl, wherein each alkyl or —OCH$_3$ is optionally partially or fully halogenated;
$R^9$ and $R^{10}$ are independently selected from hydrogen, —CH$_3$, and —C(O)CH$_3$;
or the pharmaceutically acceptable salts thereof.

In another embodiment there is provided a compound of formula (I) as described in either of the two embodiments immediately above and wherein:
X is absent;
or the pharmaceutically acceptable salts thereof.

In another embodiment there is provided a compound of formula (I) as described in the embodiment two or three above this embodiment and wherein:
X is —NHC(O)—;
or the pharmaceutically acceptable salts thereof.

In another embodiment there is provided a compound of formula (I) as described in the embodiment two above this embodiment and wherein:
Y is —NHC(O)—;
or the pharmaceutically acceptable salts thereof.

In another embodiment there is provided a compound of formula (I) as described in the embodiment three above this embodiment and wherein:
Y is —C(O)NH—;
or the pharmaceutically acceptable salts thereof.

In another embodiment there is provided a compound of formula (I) as described in the embodiment three above this embodiment and wherein:
Y is —NHC(O)—;
or the pharmaceutically acceptable salts thereof.

In another embodiment there is provided a compound of formula (I) as described in the embodiment four above this embodiment and wherein:
Y is —C(O)NH—;
or the pharmaceutically acceptable salts thereof.

The following are representative compounds of the invention which can be made by the methods described in the general synthetic schemes, the synthetic examples, and known methods in the art.

TABLE 1

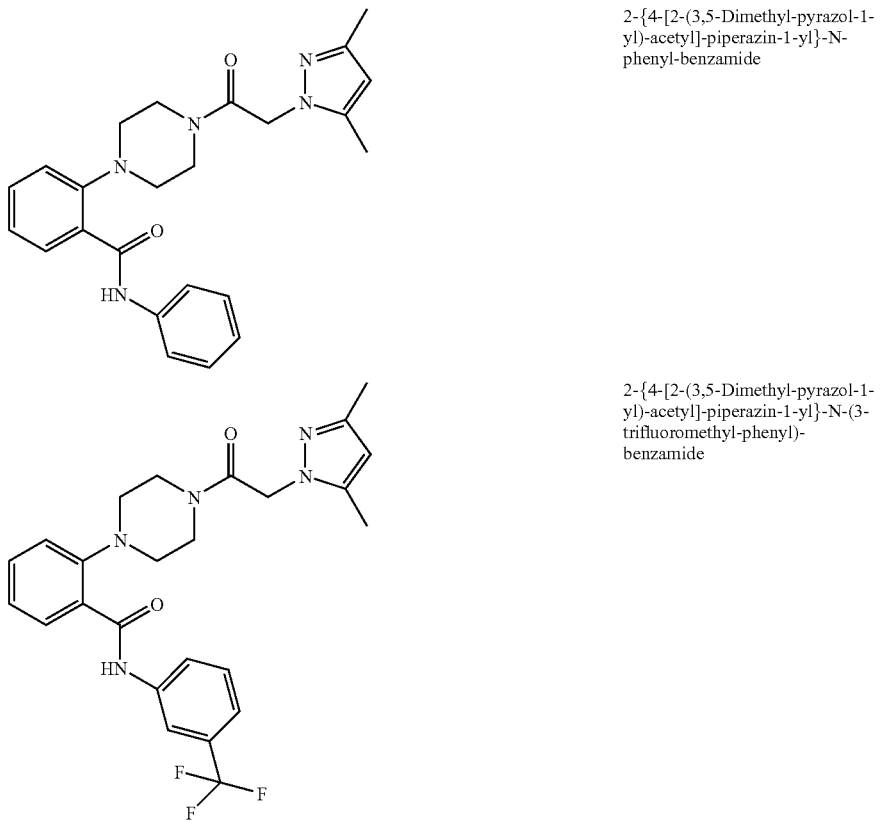

2-{4-[2-(3,5-Dimethyl-pyrazol-1-yl)-acetyl]-piperazin-1-yl}-N-phenyl-benzamide

2-{4-[2-(3,5-Dimethyl-pyrazol-1-yl)-acetyl]-piperazin-1-yl}-N-(3-trifluoromethyl-phenyl)-benzamide TABLE 1-continued
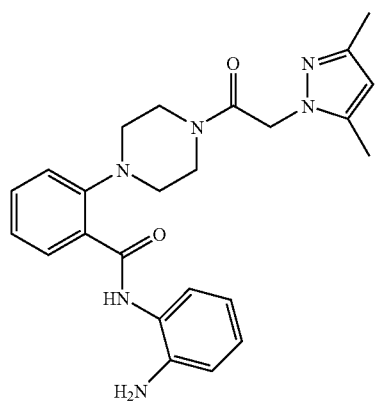 [SMILES: Cc1cc(C)n(CC(=O)N2CCN(c3ccccc3C(=O)Nc3ccccc3N)CC2)n1]
N-(2-Amino-phenyl)-2-{4-[2-(3,5-dimethyl-pyrazol-1-yl)-acetyl]-piperazin-1-yl}-benzamide
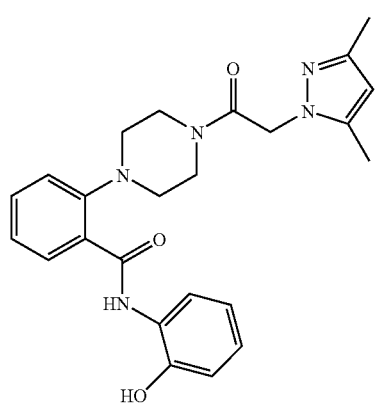 [SMILES: Cc1cc(C)n(CC(=O)N2CCN(c3ccccc3C(=O)Nc3ccccc3O)CC2)n1]
2-{4-[2-(3,5-Dimethyl-pyrazol-1-yl)-acetyl]-piperazin-1-yl}-N-(2-hydroxy-phenyl)-benzamide
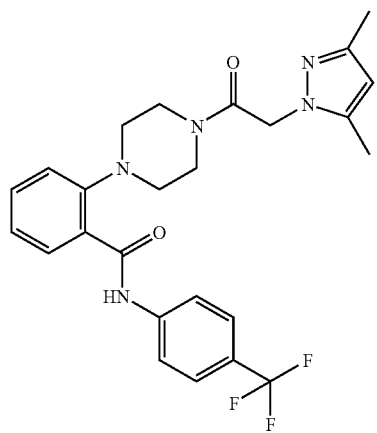 [SMILES: Cc1cc(C)n(CC(=O)N2CCN(c3ccccc3C(=O)Nc3ccc(C(F)(F)F)cc3)CC2)n1]
2-{4-[2-(3,5-Dimethyl-pyrazol-1-yl)-acetyl]-piperazin-1-yl}-N-(4-trifluoromethyl-phenyl)-benzamide TABLE 1-continued
| | |
|---|---|
| 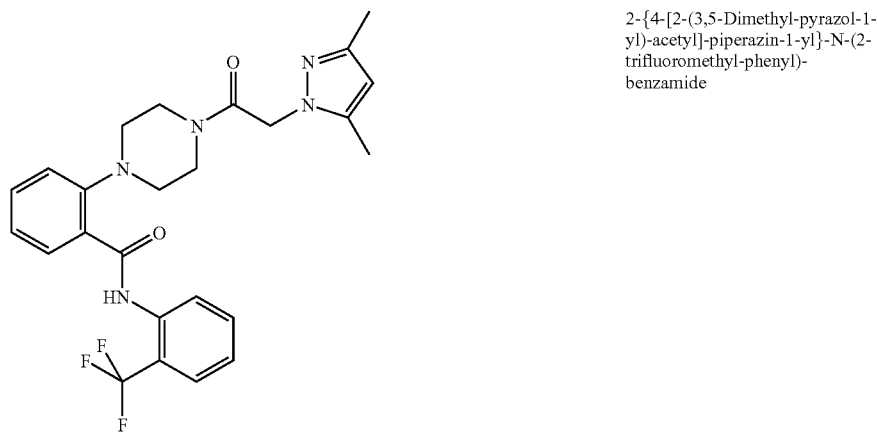 | 2-{4-[2-(3,5-Dimethyl-pyrazol-1-yl)-acetyl]-piperazin-1-yl}-N-(2-trifluoromethyl-phenyl)-benzamide |
| 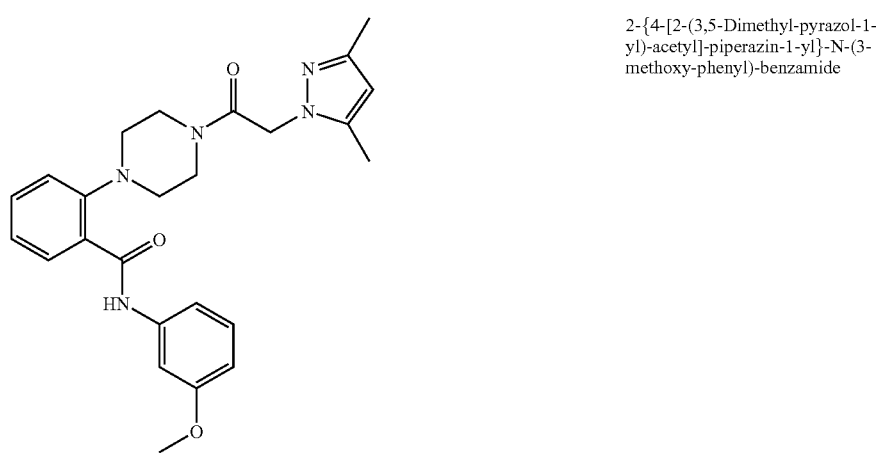 | 2-{4-[2-(3,5-Dimethyl-pyrazol-1-yl)-acetyl]-piperazin-1-yl}-N-(3-methoxy-phenyl)-benzamide |
| 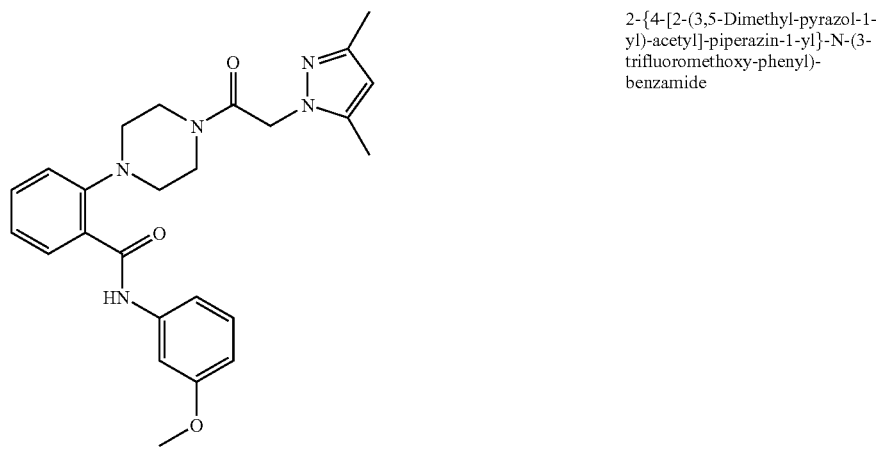 | 2-{4-[2-(3,5-Dimethyl-pyrazol-1-yl)-acetyl]-piperazin-1-yl}-N-(3-trifluoromethoxy-phenyl)-benzamide |

TABLE 1-continued
| | |
|---|---|
| 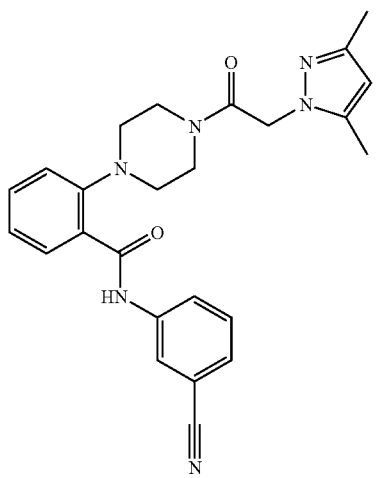 [SMILES: Cc1cc(C)n(CC(=O)N2CCN(c3ccccc3C(=O)Nc3cccc(C#N)c3)CC2)n1] | N-(3-Cyano-phenyl)-2-{4-[2-(3,5-dimethyl-pyrazol-1-yl)-acetyl]-piperazin-1-yl}-benzamide |
| 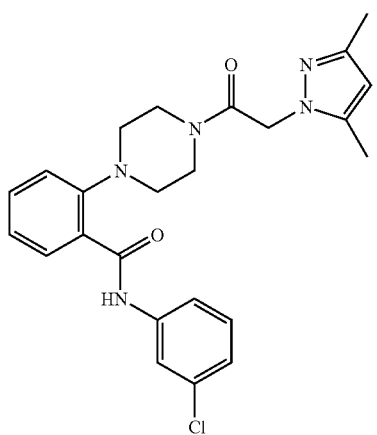 [SMILES: Cc1cc(C)n(CC(=O)N2CCN(c3ccccc3C(=O)Nc3cccc(Cl)c3)CC2)n1] | N-(3-Chloro-phenyl)-2-{4-[2-(3,5-dimethyl-pyrazol-1-yl)-acetyl]-piperazin-1-yl}-benzamide |
| 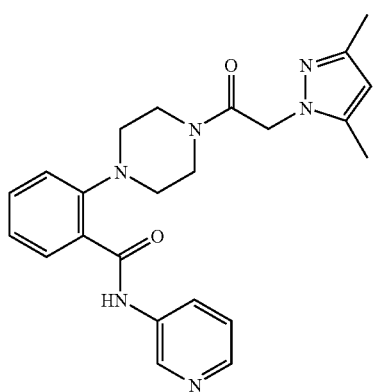 [SMILES: Cc1cc(C)n(CC(=O)N2CCN(c3ccccc3C(=O)Nc3cccnc3)CC2)n1] | 2-{4-[2-(3,5-Dimethyl-pyrazol-1-yl)-acetyl]-piperazin-1-yl}-N-pyridin-3-yl-benzamide |

TABLE 1-continued
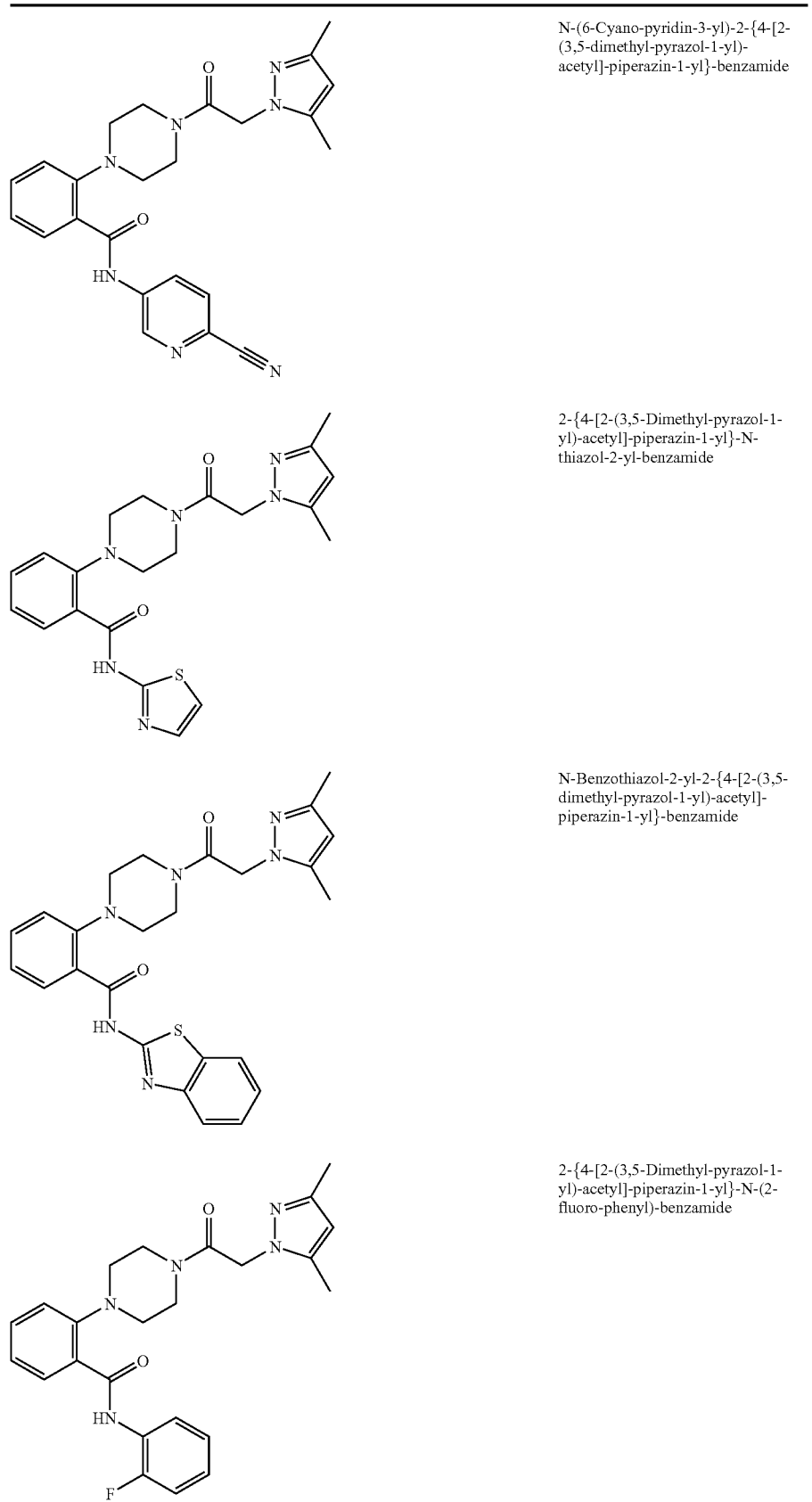
| | |
|---|---|
| | N-(6-Cyano-pyridin-3-yl)-2-{4-[2-(3,5-dimethyl-pyrazol-1-yl)-acetyl]-piperazin-1-yl}-benzamide |
| | 2-{4-[2-(3,5-Dimethyl-pyrazol-1-yl)-acetyl]-piperazin-1-yl}-N-thiazol-2-yl-benzamide |
| | N-Benzothiazol-2-yl-2-{4-[2-(3,5-dimethyl-pyrazol-1-yl)-acetyl]-piperazin-1-yl}-benzamide |
| | 2-{4-[2-(3,5-Dimethyl-pyrazol-1-yl)-acetyl]-piperazin-1-yl}-N-(2-fluoro-phenyl)-benzamide |

TABLE 1-continued
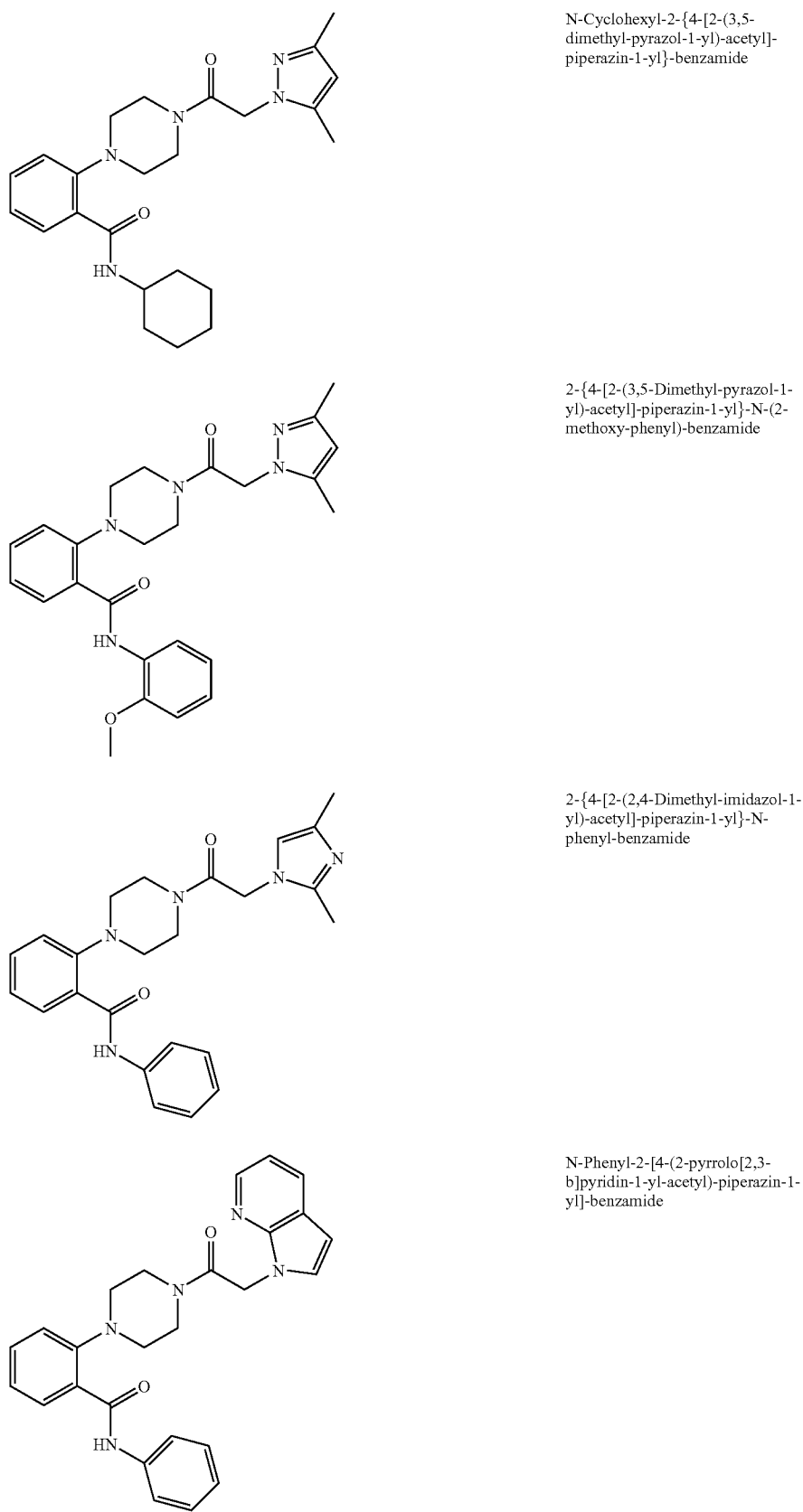
N-Cyclohexyl-2-{4-[2-(3,5-dimethyl-pyrazol-1-yl)-acetyl]-piperazin-1-yl}-benzamide
2-{4-[2-(3,5-Dimethyl-pyrazol-1-yl)-acetyl]-piperazin-1-yl}-N-(2-methoxy-phenyl)-benzamide
2-{4-[2-(2,4-Dimethyl-imidazol-1-yl)-acetyl]-piperazin-1-yl}-N-phenyl-benzamide
N-Phenyl-2-[4-(2-pyrrolo[2,3-b]pyridin-1-yl-acetyl)-piperazin-1-yl]-benzamide TABLE 1-continued
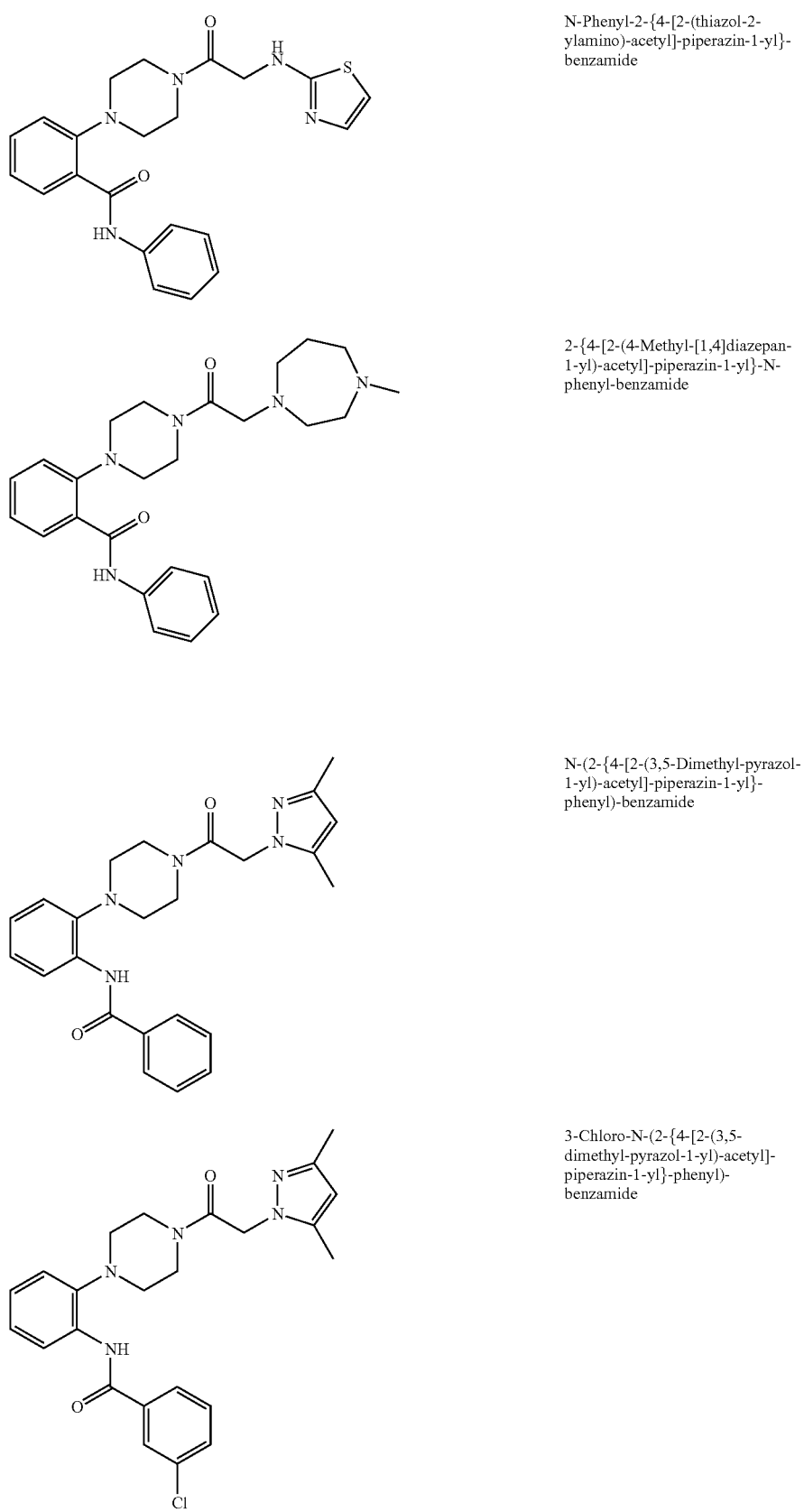
N-Phenyl-2-{4-[2-(thiazol-2-ylamino)-acetyl]-piperazin-1-yl}-benzamide
2-{4-[2-(4-Methyl-[1,4]diazepan-1-yl)-acetyl]-piperazin-1-yl}-N-phenyl-benzamide
N-(2-{4-[2-(3,5-Dimethyl-pyrazol-1-yl)-acetyl]-piperazin-1-yl}-phenyl)-benzamide
3-Chloro-N-(2-{4-[2-(3,5-dimethyl-pyrazol-1-yl)-acetyl]-piperazin-1-yl}-phenyl)-benzamide TABLE 1-continued
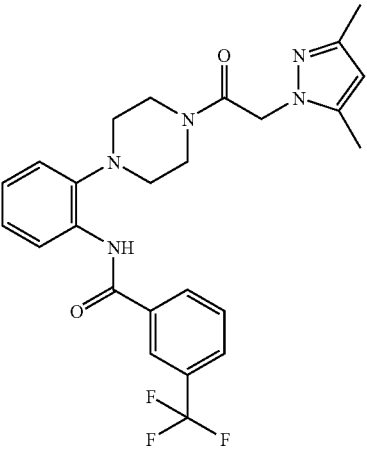 [SMILES: Cc1cc(C)n(CC(=O)N2CCN(c3ccccc3NC(=O)c3cccc(C(F)(F)F)c3)CC2)n1]
N-(2-{4-[2-(3,5-Dimethyl-pyrazol-1-yl)-acetyl]-piperazin-1-yl}-phenyl)-3-trifluoromethyl-benzamide
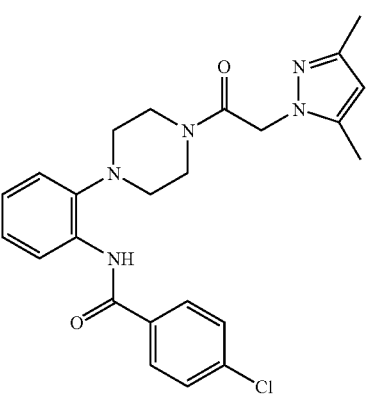 [SMILES: Cc1cc(C)n(CC(=O)N2CCN(c3ccccc3NC(=O)c3ccc(Cl)cc3)CC2)n1]
4-Chloro-N-(2-{4-[2-(3,5-dimethyl-pyrazol-1-yl)-acetyl]-piperazin-1-yl}-phenyl)-benzamide
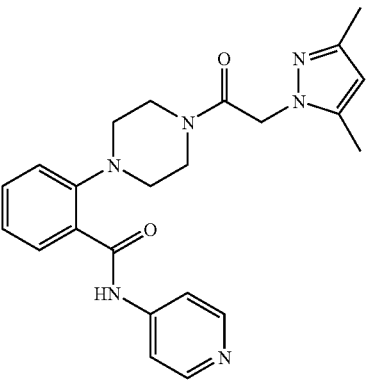 [SMILES: Cc1cc(C)n(CC(=O)N2CCN(c3ccccc3C(=O)Nc3ccncc3)CC2)n1]
2-{4-[2-(3,5-Dimethyl-pyrazol-1-yl)-acetyl]-piperazin-1-yl}-N-pyridin-4-yl-benzamide
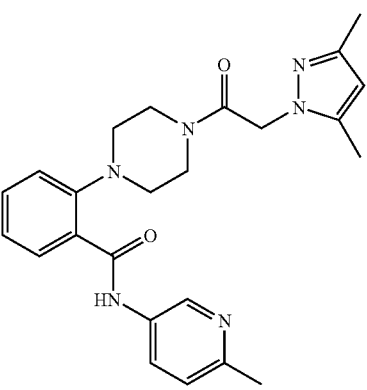 [SMILES: Cc1ccc(NC(=O)c2ccccc2N2CCN(C(=O)Cn3nc(C)cc3C)CC2)cn1]
2-{4-[2-(3,5-Dimethyl-pyrazol-1-yl)-acetyl]-piperazin-1-yl}-N-(6-methyl-pyridin-3-yl)-benzamide TABLE 1-continued
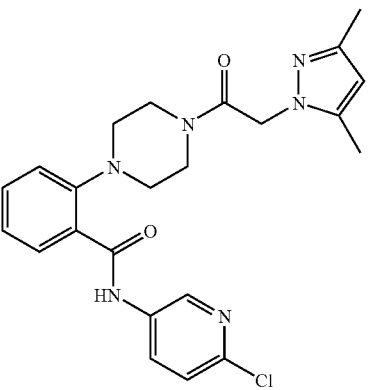 [SMILES: Cc1cc(C)n(CC(=O)N2CCN(c3ccccc3C(=O)Nc3ccc(Cl)nc3)CC2)n1]
N-(6-Chloro-pyridin-3-yl)-2-{4-[2-(3,5-dimethyl-pyrazol-1-yl-acetyl]-piperazin-1-yl}-benzamide
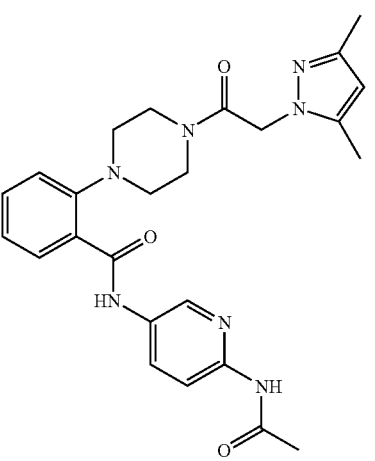 [SMILES: CC(=O)Nc1ccc(NC(=O)c2ccccc2N2CCN(C(=O)Cn3nc(C)cc3C)CC2)cn1]
N-(6-Acetylamino-pyridin-3-yl)-2-{4-[2-(3,5-dimethyl-pyrazol-1-yl)-acetyl]-piperazin-1-yl}-benzamide
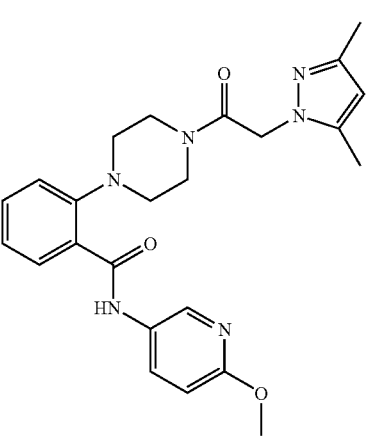 [SMILES: COc1ccc(NC(=O)c2ccccc2N2CCN(C(=O)Cn3nc(C)cc3C)CC2)cn1]
2-{4-[2-(3,5-Dimethyl-pyrazol-1-yl)-acetyl]-piperazin-1-yl}-N-(6-methoxy-pyridin-3-yl)-benzamide
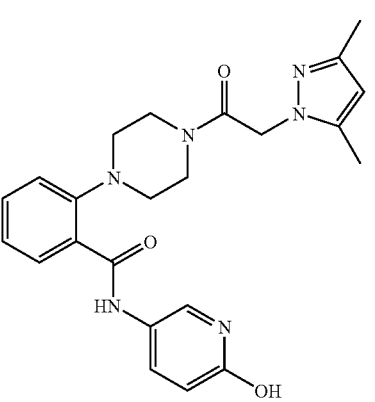 [SMILES: Cc1cc(C)n(CC(=O)N2CCN(c3ccccc3C(=O)Nc3ccc(O)nc3)CC2)n1]
2-{4-[2-(3,5-Dimethyl-pyrazol-1-yl)-acetyl]-piperazin-1-yl}-N-(6-hydroxy-pyridin-3-yl)-benzamide TABLE 1-continued
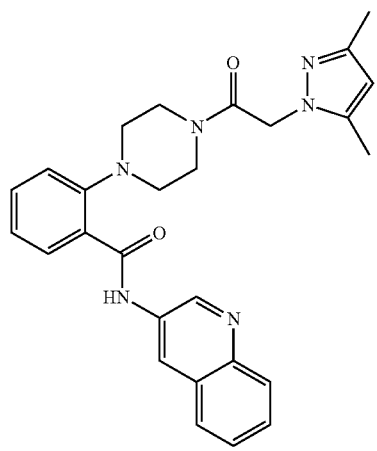 [SMILES: Cc1cc(C)n(CC(=O)N2CCN(c3ccccc3C(=O)Nc3cnc4ccccc4c3)CC2)n1]
2-{4-[2-(3,5-Dimethyl-pyrazol-1-yl)-acetyl]-piperazin-1-yl}-N-quinolin-3-yl-benzamide
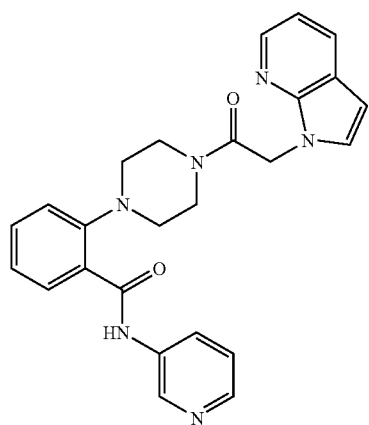 [SMILES: O=C(Nc1cccnc1)c1ccccc1N1CCN(C(=O)Cn2ccc3cccnc32)CC1]
N-Pyridin-3-yl-2-[4-(2-pyrrolo[2,3-b]pyridin-1-yl-acetyl)-piperazin-1-yl]-benzamide
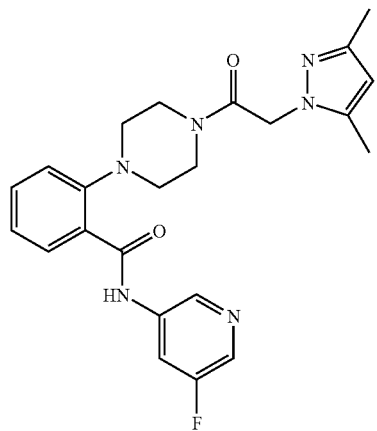 [SMILES: Cc1cc(C)n(CC(=O)N2CCN(c3ccccc3C(=O)Nc3cncc(F)c3)CC2)n1]
2-{4-[2-(3,5-Dimethyl-pyrazol-1-yl)-acetyl]-piperazin-1-yl}-N-(5-fluoro-pyridin-3-yl)-benzamide TABLE 1-continued
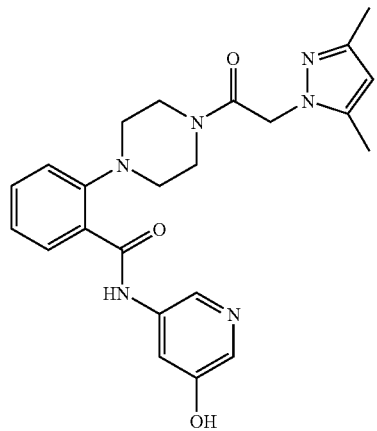 [SMILES: Cc1cc(C)n(CC(=O)N2CCN(c3ccccc3C(=O)Nc3cncc(O)c3)CC2)n1]
2-{4-[2-(3,5-Dimethyl-pyrazol-1-yl)-acetyl]-piperazin-1-yl}-N-(5-hydroxy-pyridin-3-yl)-benzamide
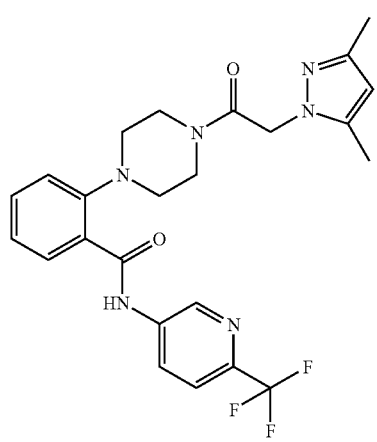 [SMILES: Cc1cc(C)n(CC(=O)N2CCN(c3ccccc3C(=O)Nc3ccc(C(F)(F)F)nc3)CC2)n1]
2-{4-[2-(3,5-Dimethyl-pyrazol-1-yl)-acetyl]-piperazin-1-yl}-N-(6-trifluoromethyl-pyridin-3-yl)-benzamide
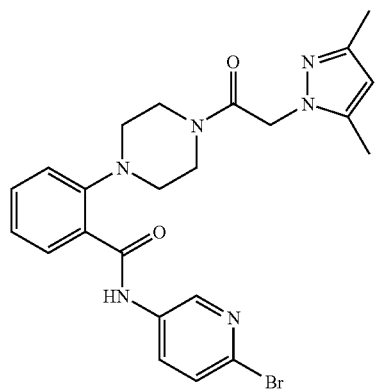
N-(6-Bromo-pyridin-3-yl)-2-{4-[2-(3,5-dimethyl-pyrazol-1-yl)-acetyl]-piperazin-1-yl}-benzamide TABLE 1-continued
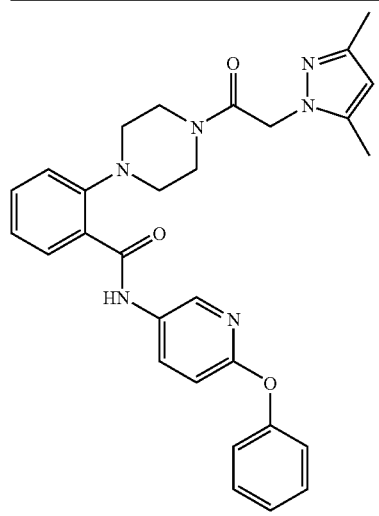
2-{4-[2-(3,5-Dimethyl-pyrazol-1-yl)-acetyl]-piperazin-1-yl}-N-(6-phenoxy-pyridin-3-yl)-benzamide
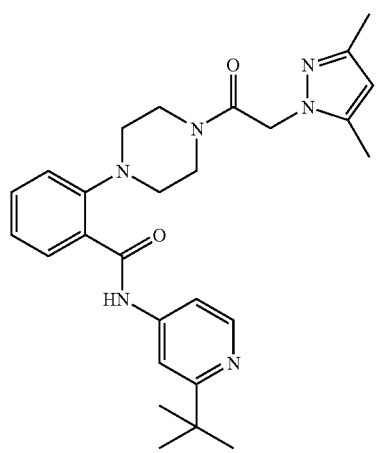 [SMILES: Cc1cc(C)n(CC(=O)N2CCN(c3ccccc3C(=O)Nc3ccnc(C(C)(C)C)c3)CC2)n1]
N-(2-tert-Butyl-pyridin-4-yl)-2-{4-[2-(3,5-dimethyl-pyrazol-1-yl)-acetyl]-piperazin-1-yl}-benzamide
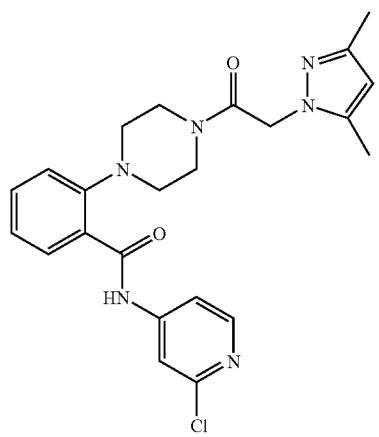 [SMILES: Cc1cc(C)n(CC(=O)N2CCN(c3ccccc3C(=O)Nc3ccnc(Cl)c3)CC2)n1]
N-(2-Chloro-pyridin-4-yl)-2-{4-[2-(3,5-dimethyl-pyrazol-1-yl)-acetyl]-piperazin-1-yl}-benzamide TABLE 1-continued
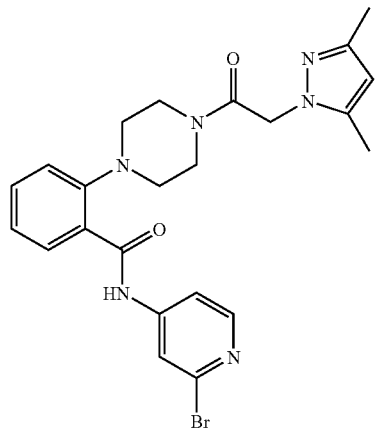 [SMILES: Cc1cc(C)n(CC(=O)N2CCN(c3ccccc3C(=O)Nc3ccnc(Br)c3)CC2)n1]
N-(2-Bromo-pyridin-4-yl)-2-{4-[2-(3,5-dimethyl-pyrazol-1-yl)-acetyl]-piperazin-1-yl}-benzamide
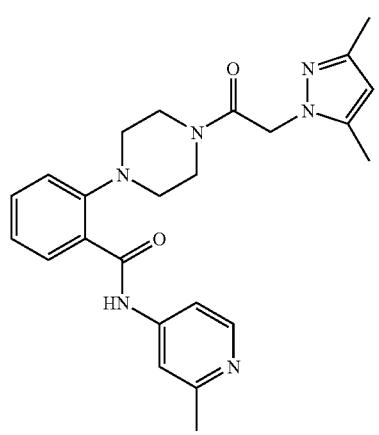 [SMILES: Cc1cc(NC(=O)c2ccccc2N2CCN(C(=O)Cn3nc(C)cc3C)CC2)ccn1]
2-{4-[2-(3,5-Dimethyl-pyrazol-1-yl)-acetyl]-piperazin-1-yl}-N-(2-methyl-pyridin-4-yl)-benzamide
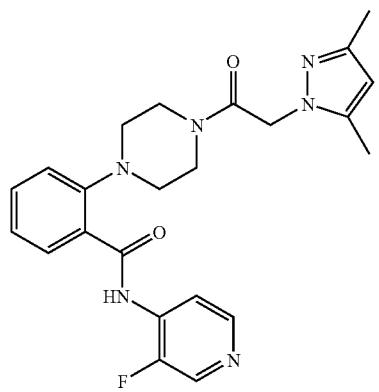 [SMILES: Cc1cc(C)n(CC(=O)N2CCN(c3ccccc3C(=O)Nc3ccncc3F)CC2)n1]
2-{4-[2-(3,5-Dimethyl-pyrazol-1-yl)-acetyl]-piperazin-1-yl}-N-(3-fluoro-pyridin-4-yl)-benzamide

TABLE 1-continued
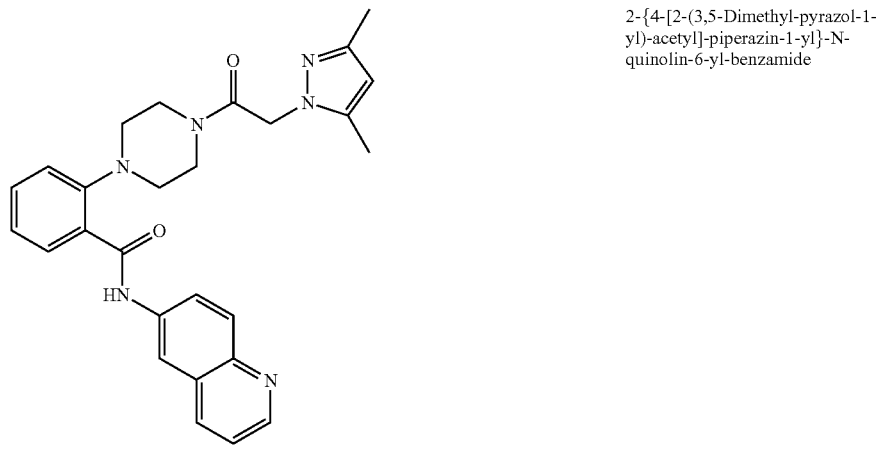
2-{4-[2-(3,5-Dimethyl-pyrazol-1-yl)-acetyl]-piperazin-1-yl}-N-quinolin-6-yl-benzamide
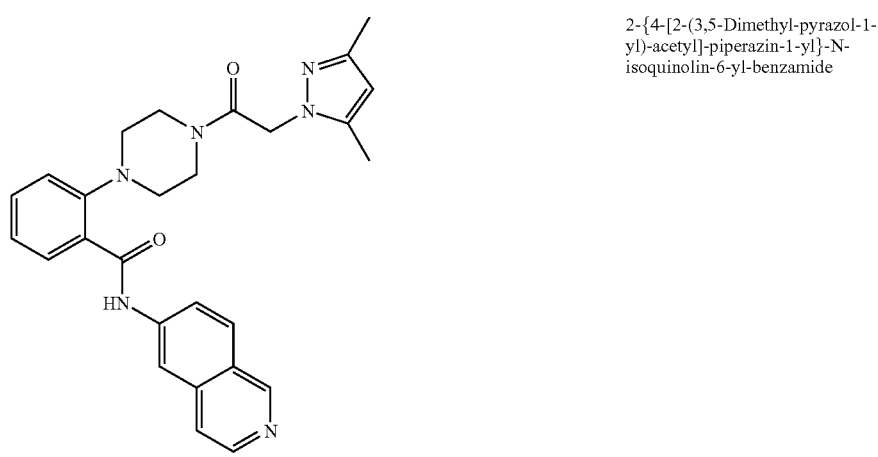
2-{4-[2-(3,5-Dimethyl-pyrazol-1-yl)-acetyl]-piperazin-1-yl}-N-isoquinolin-6-yl-benzamide
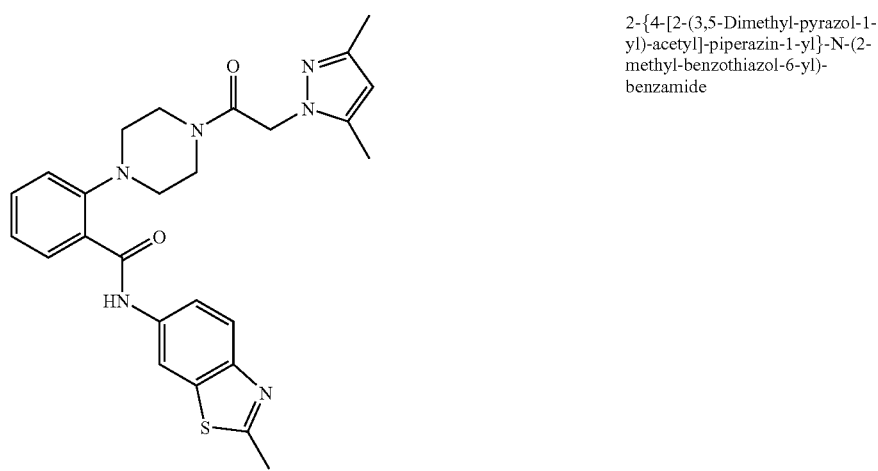
2-{4-[2-(3,5-Dimethyl-pyrazol-1-yl)-acetyl]-piperazin-1-yl}-N-(2-methyl-benzothiazol-6-yl)-benzamide TABLE 1-continued
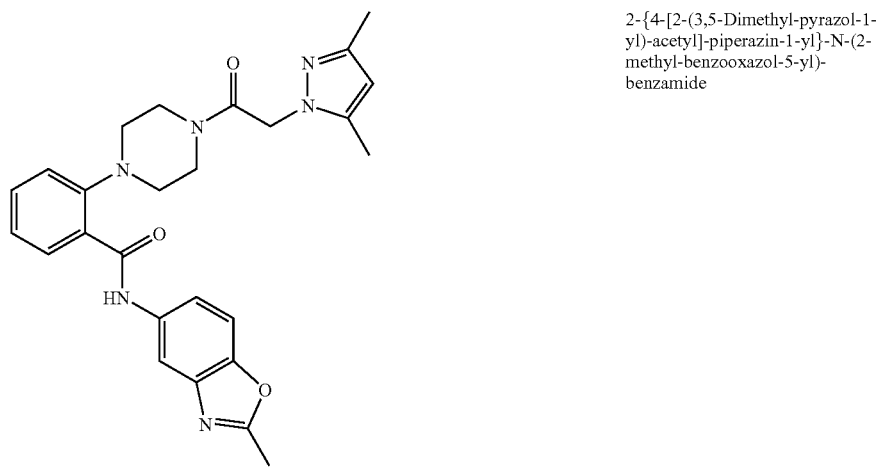
2-{4-[2-(3,5-Dimethyl-pyrazol-1-yl)-acetyl]-piperazin-1-yl}-N-(2-methyl-benzooxazol-5-yl)-benzamide
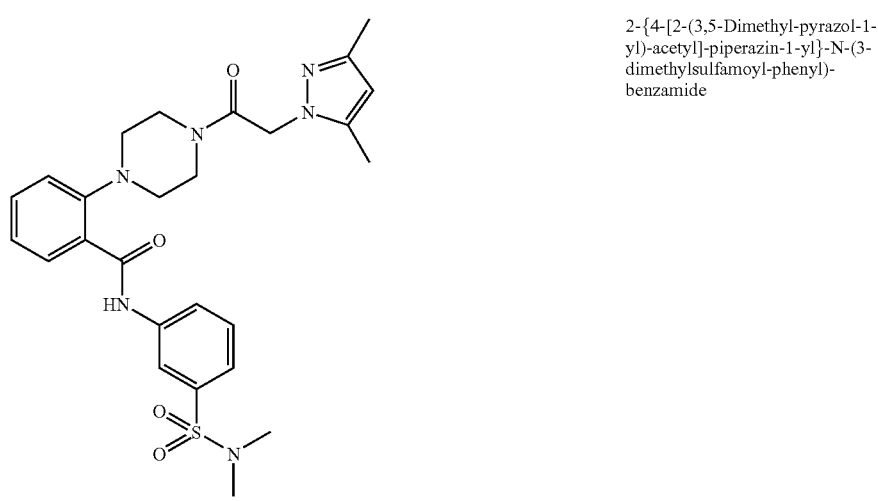
2-{4-[2-(3,5-Dimethyl-pyrazol-1-yl)-acetyl]-piperazin-1-yl}-N-(3-dimethylsulfamoyl-phenyl)-benzamide
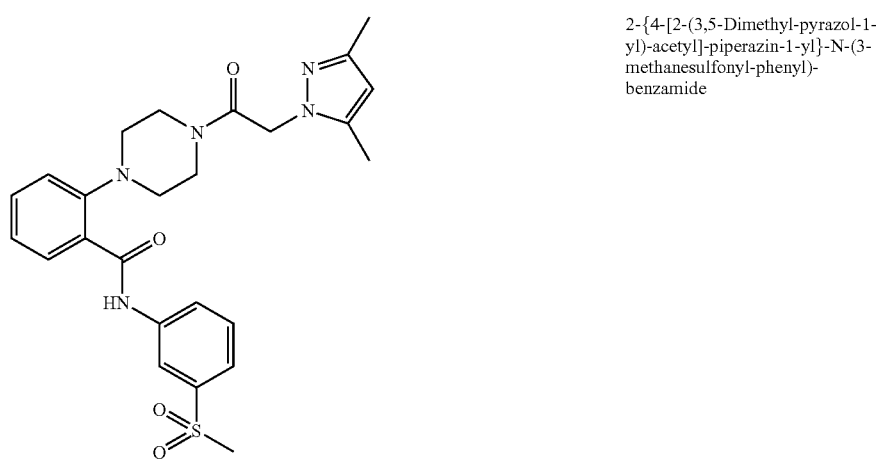
2-{4-[2-(3,5-Dimethyl-pyrazol-1-yl)-acetyl]-piperazin-1-yl}-N-(3-methanesulfonyl-phenyl)-benzamide TABLE 1-continued
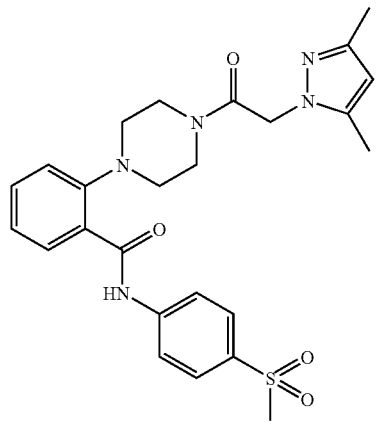 [SMILES: Cc1cc(C)n(CC(=O)N2CCN(c3ccccc3C(=O)Nc3ccc(S(C)(=O)=O)cc3)CC2)n1]
2-{4-[2-(3,5-Dimethyl-pyrazol-1-yl)-acetyl]-piperazin-1-yl}-N-(4-methanesulfonyl-phenyl)-benzamide
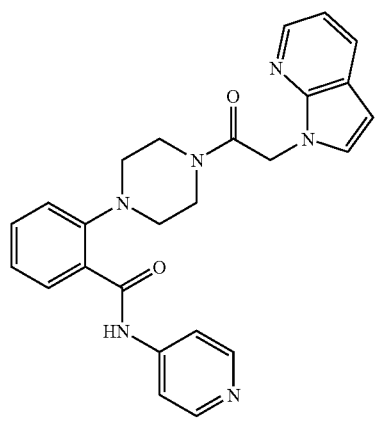 [SMILES: O=C(Nc1ccncc1)c1ccccc1N1CCN(C(=O)Cn2ccc3cccnc32)CC1]
N-Pyridin-4-yl-2-[4-(2-pyrrolo[2,3-b]pyridin-1-yl-acetyl)-piperazin-1-yl]-benzamide
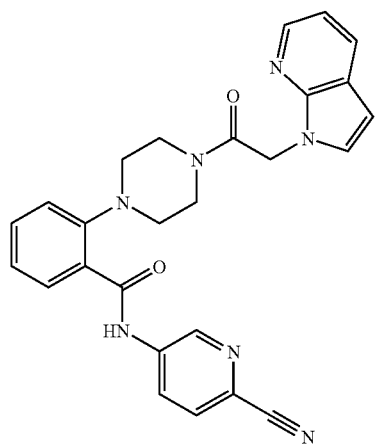 [SMILES: N#Cc1ccc(NC(=O)c2ccccc2N2CCN(C(=O)Cn3ccc4cccnc43)CC2)cn1]
N-(6-Cyano-pyridin-3-yl)-2-[4-(2-pyrrolo[2,3-b]pyridin-1-yl-acetyl)-piperazin-1-yl]-benzamide TABLE 1-continued
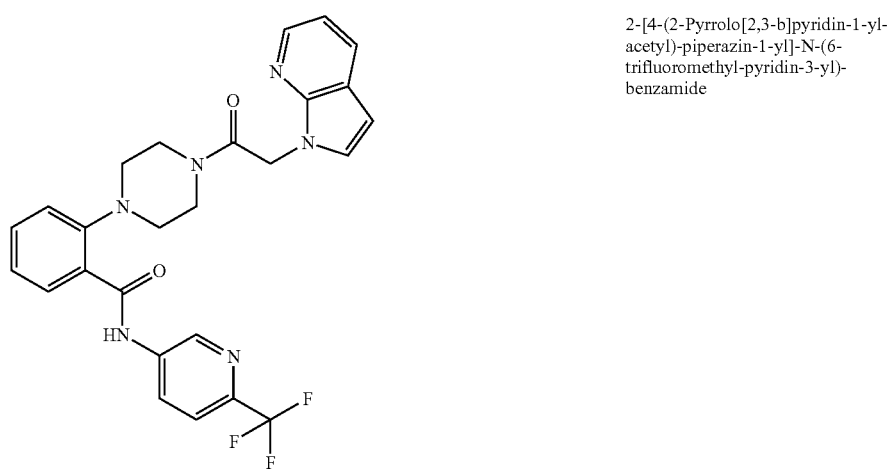
2-[4-(2-Pyrrolo[2,3-b]pyridin-1-yl-acetyl)-piperazin-1-yl]-N-(6-trifluoromethyl-pyridin-3-yl)-benzamide
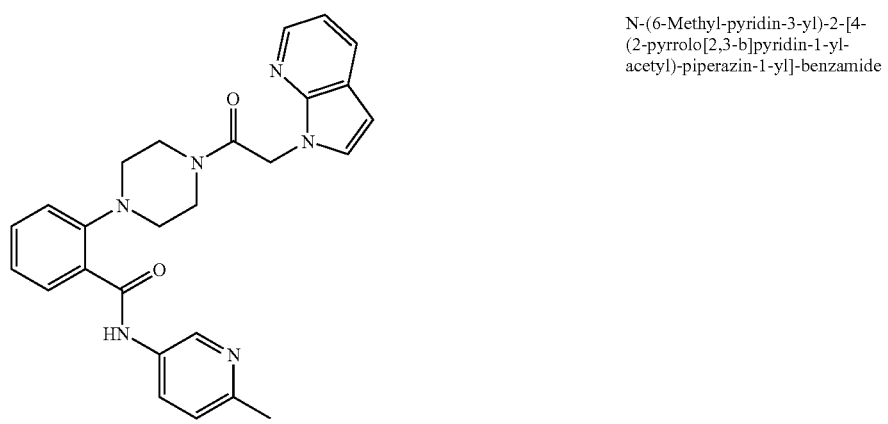
N-(6-Methyl-pyridin-3-yl)-2-[4-(2-pyrrolo[2,3-b]pyridin-1-yl-acetyl)-piperazin-1-yl]-benzamide
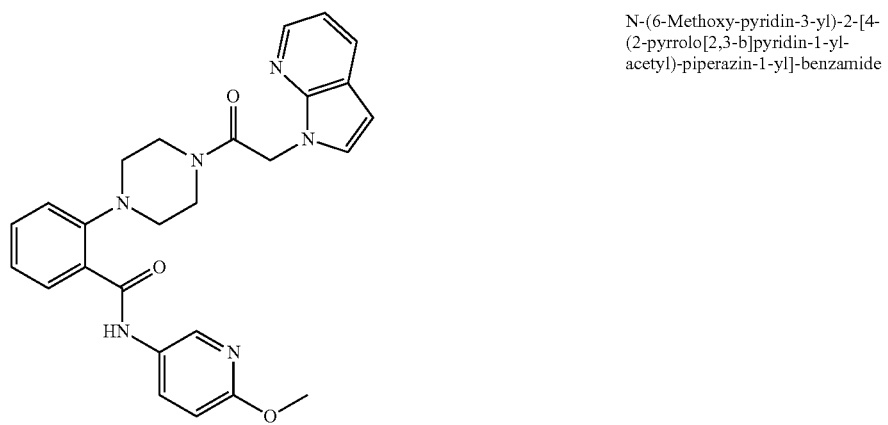
N-(6-Methoxy-pyridin-3-yl)-2-[4-(2-pyrrolo[2,3-b]pyridin-1-yl-acetyl)-piperazin-1-yl]-benzamide

| | |
|---|---|
| 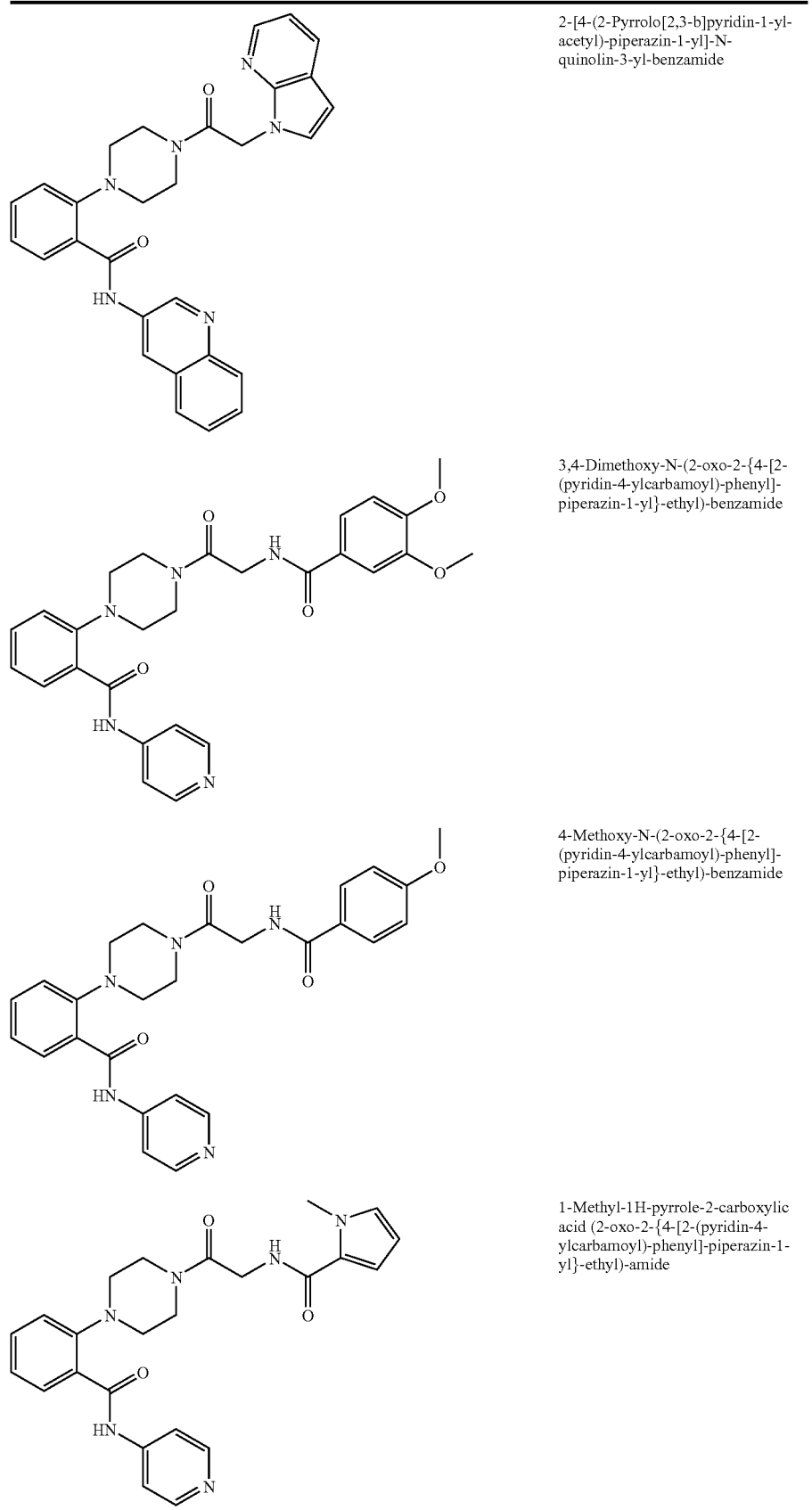 | 2-[4-(2-Pyrrolo[2,3-b]pyridin-1-yl-acetyl)-piperazin-1-yl]-N-quinolin-3-yl-benzamide |
| | 3,4-Dimethoxy-N-(2-oxo-2-{4-[2-(pyridin-4-ylcarbamoyl)-phenyl]-piperazin-1-yl}-ethyl)-benzamide |
| | 4-Methoxy-N-(2-oxo-2-{4-[2-(pyridin-4-ylcarbamoyl)-phenyl]-piperazin-1-yl}-ethyl)-benzamide |
| | 1-Methyl-1H-pyrrole-2-carboxylic acid (2-oxo-2-{4-[2-(pyridin-4-ylcarbamoyl)-phenyl]-piperazin-1-yl}-ethyl)-amide |

TABLE 1-continued
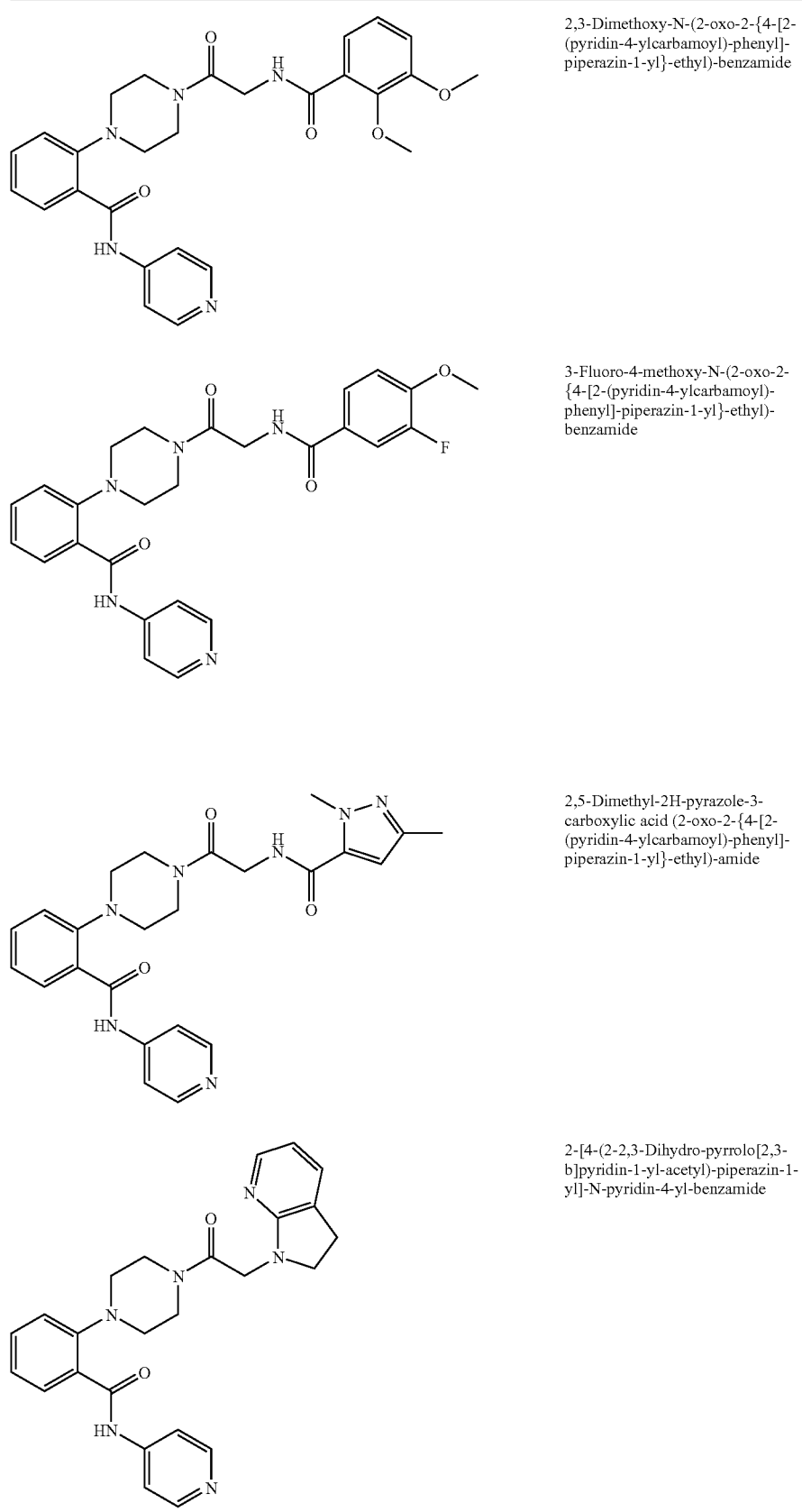
2,3-Dimethoxy-N-(2-oxo-2-{4-[2-(pyridin-4-ylcarbamoyl)-phenyl]-piperazin-1-yl}-ethyl)-benzamide
3-Fluoro-4-methoxy-N-(2-oxo-2-{4-[2-(pyridin-4-ylcarbamoyl)-phenyl]-piperazin-1-yl}-ethyl)-benzamide
2,5-Dimethyl-2H-pyrazole-3-carboxylic acid (2-oxo-2-{4-[2-(pyridin-4-ylcarbamoyl)-phenyl]-piperazin-1-yl}-ethyl)-amide
2-[4-(2-2,3-Dihydro-pyrrolo[2,3-b]pyridin-1-yl-acetyl)-piperazin-1-yl]-N-pyridin-4-yl-benzamide TABLE 1-continued
| | |
|---|---|
| 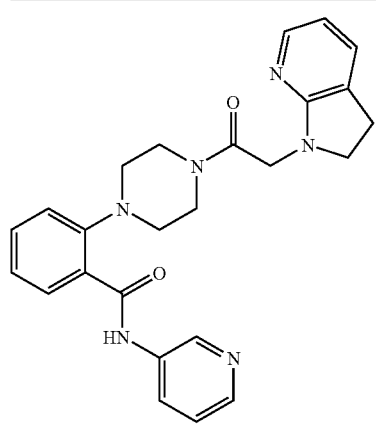 [SMILES: O=C(Nc1cccnc1)c1ccccc1N1CCN(C(=O)CN2CCc3cccnc32)CC1] | 2-[4-(2-2,3-Dihydro-pyrrolo[2,3-b]pyridin-1-yl-acetyl)-piperazin-1-yl]-N-pyridin-3-yl-benzamide |
| 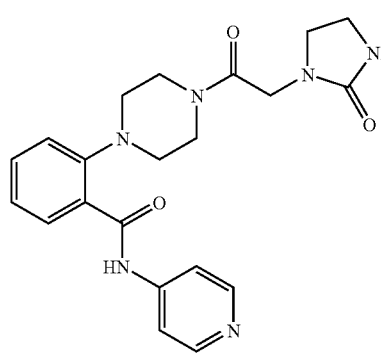 | 2-{4-[2-(2-Oxo-imidazolidin-1-yl)-acetyl]-piperazin-1-yl}-N-pyridin-4-yl-benzamide |
| 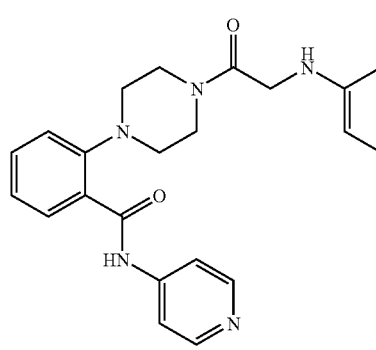 | 2-[4-(2-Phenylamino-acetyl)-piperazin-1-yl]-N-pyridin-4-yl-benzamide |
| 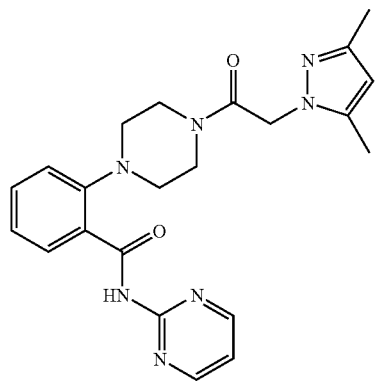 | 2-{4-[2-(3,5-Dimethyl-pyrazol-1-yl)-acetyl]-piperazin-1-yl}-N-pyrimidin-2-yl-benzamide |

| | |
|---|---|
| 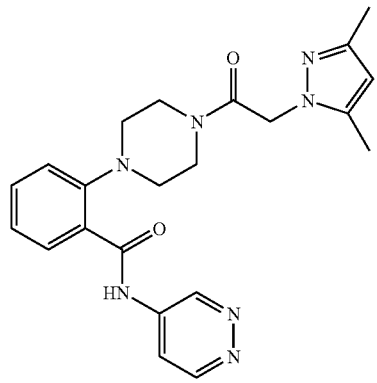 | 2-{4-[2-(3,5-Dimethyl-pyrazol-1-yl)-acetyl]-piperazin-1-yl}-N-pyridazin-4-yl-benzamide |
| 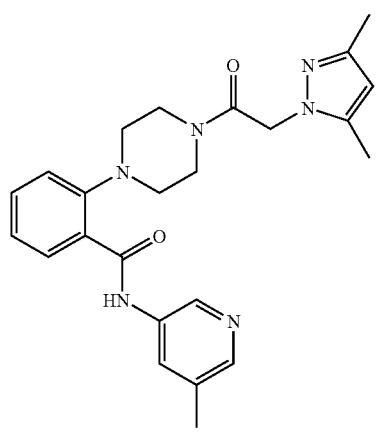 [SMILES: Cc1cncc(NC(=O)c2ccccc2N2CCN(C(=O)Cn3nc(C)cc3C)CC2)c1] | 2-{4-[2-(3,5-Dimethyl-pyrazol-1-yl)-acetyl]-piperazin-1-yl}-N-(5-methyl-pyridin-3-yl)-benzamide |
| 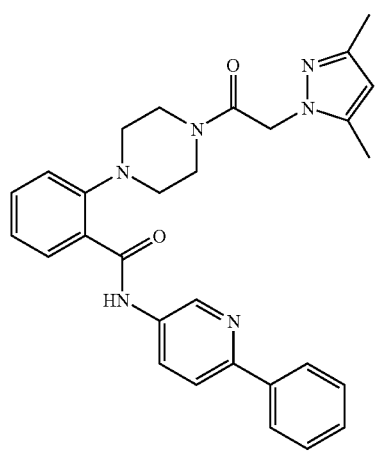 | 2-{4-[2-(3,5-Dimethyl-pyrazol-1-yl)-acetyl]-piperazin-1-yl}-N-(6-phenyl-pyridin-3-yl)-benzamide |

TABLE 1-continued
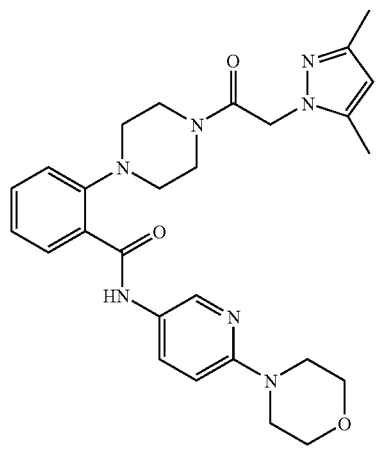 [SMILES: Cc1cc(C)n(CC(=O)N2CCN(c3ccccc3C(=O)Nc3ccc(N4CCOCC4)nc3)CC2)n1]
2-{4-[2-(3,5-Dimethyl-pyrazol-1-yl)-acetyl]-piperazin-1-yl}-N-(6-morpholin-4-yl-pyridin-3-yl)-benzamide
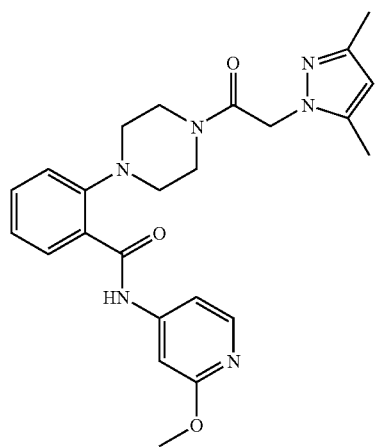 [SMILES: COc1cc(NC(=O)c2ccccc2N2CCN(C(=O)Cn3nc(C)cc3C)CC2)ccn1]
2-{4-[2-(3,5-Dimethyl-pyrazol-1-yl)-acetyl]-piperazin-1-yl}-N-(2-methoxy-pyridin-4-yl)-benzamide
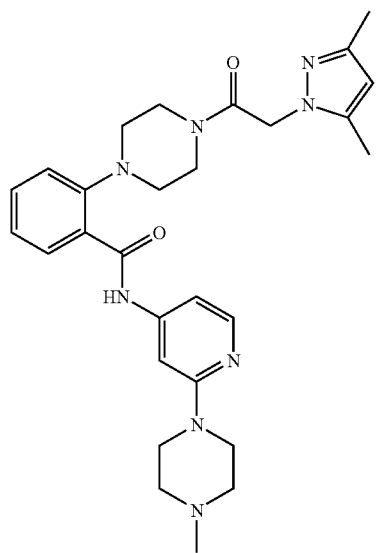 [SMILES: Cc1cc(C)n(CC(=O)N2CCN(c3ccccc3C(=O)Nc3ccnc(N4CCN(C)CC4)c3)CC2)n1]
2-{4-[2-(3,5-Dimethyl-pyrazol-1-yl)-acetyl]-piperazin-1-yl}-N-[2-(4-methyl-piperazin-1-yl)-pyridin-4-yl]-benzamide TABLE 1-continued
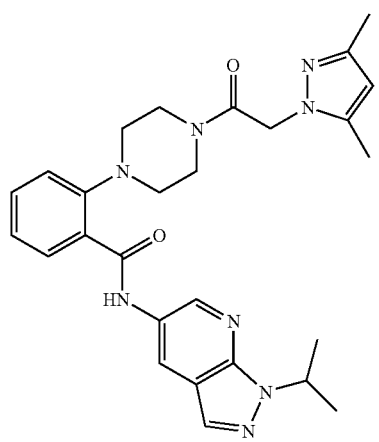 [SMILES: Cc1cc(C)n(CC(=O)N2CCN(c3ccccc3C(=O)Nc3cnc4c(cnn4C(C)C)c3)CC2)n1]
2-{4-[2-(3,5-Dimethyl-pyrazol-1-yl)-acetyl]-piperazin-1-yl}-N-(1-isopropyl-1H-pyrazolo[3,4-b]pyridin-5-yl)-benzamide
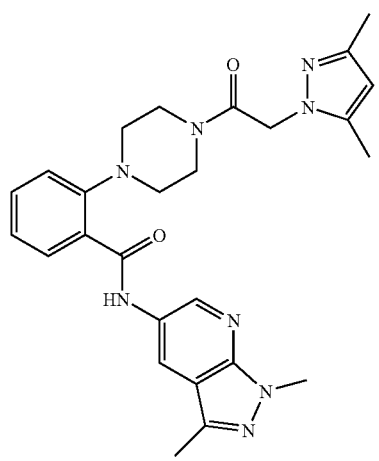 [SMILES: Cc1cc(C)n(CC(=O)N2CCN(c3ccccc3C(=O)Nc3cnc4c(c3)c(C)nn4C)CC2)n1]
N-(1,3-Dimethyl-1H-pyrazolo[3,4-b]pyridin-5-yl)-2-{4-[2-(3,5-dimethyl-pyrazol-1-yl)-acetyl]-piperazin-1-yl}-benzamide
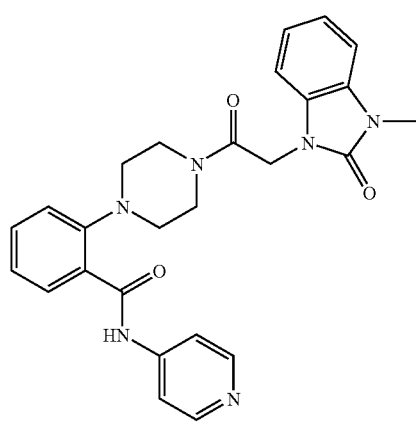 [SMILES: Cn1c(=O)n(CC(=O)N2CCN(c3ccccc3C(=O)Nc3ccncc3)CC2)c2ccccc21]
2-{4-[2-(3-Methyl-2-oxo-2,3-dihydro-benzoimidazol-1-yl)-acetyl]-piperazin-1-yl}-N-pyridin-4-yl-benzamide TABLE 1-continued
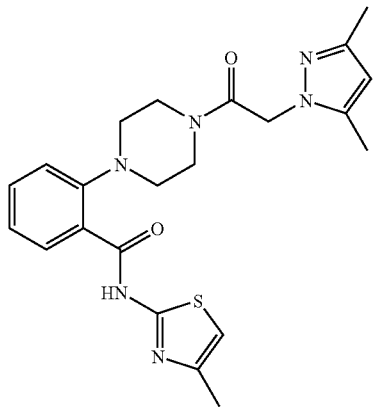 [SMILES: Cc1csc(NC(=O)c2ccccc2N2CCN(C(=O)Cn3nc(C)cc3C)CC2)n1]
2-{4-[2-(3,5-Dimethyl-pyrazol-1-yl)-acetyl]-piperazin-1-yl}-N-(4-methyl-thiazol-2-yl)-benzamide
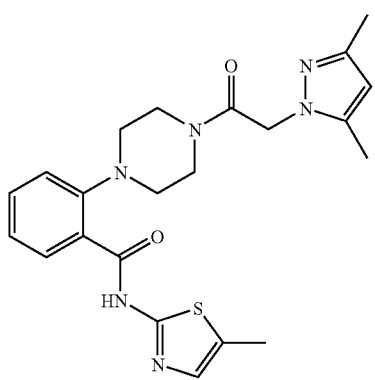 [SMILES: Cc1cc(C)n(CC(=O)N2CCN(c3ccccc3C(=O)Nc3ncc(C)s3)CC2)n1]
2-{4-[2-(3,5-Dimethyl-pyrazol-1-yl)-acetyl]-piperazin-1-yl}-N-(5-methyl-thiazol-2-yl)-benzamide
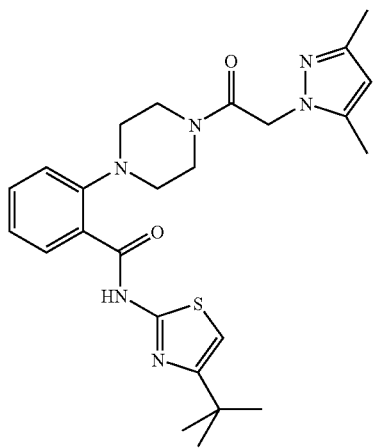 [SMILES: Cc1cc(C)n(CC(=O)N2CCN(c3ccccc3C(=O)Nc3nc(C(C)(C)C)cs3)CC2)n1]
N-(4-tert-Butyl-thiazol-2-yl)-2-{4-[2-(3,5-dimethyl-pyrazol-1-yl)-acetyl]-piperazin-1-yl}-benzamide TABLE 1-continued
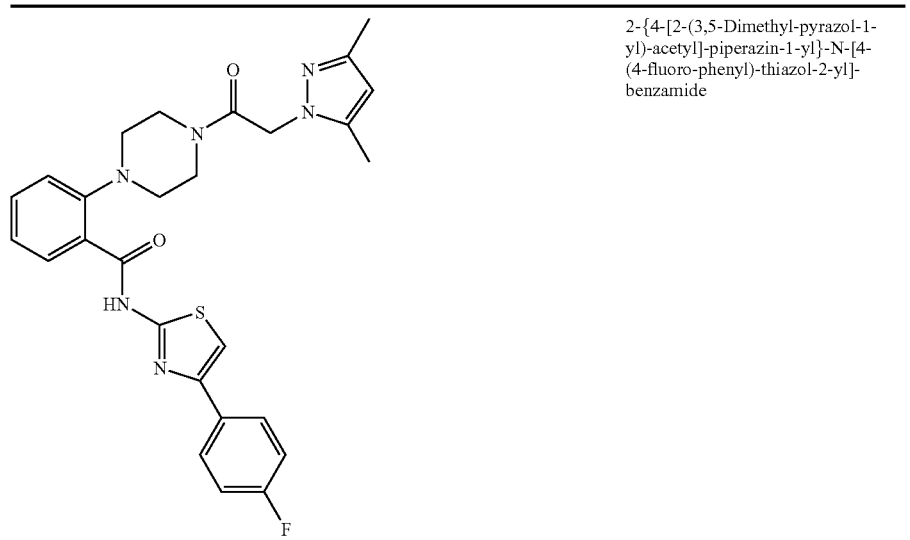
2-{4-[2-(3,5-Dimethyl-pyrazol-1-yl)-acetyl]-piperazin-1-yl}-N-[4-(4-fluoro-phenyl)-thiazol-2-yl]-benzamide
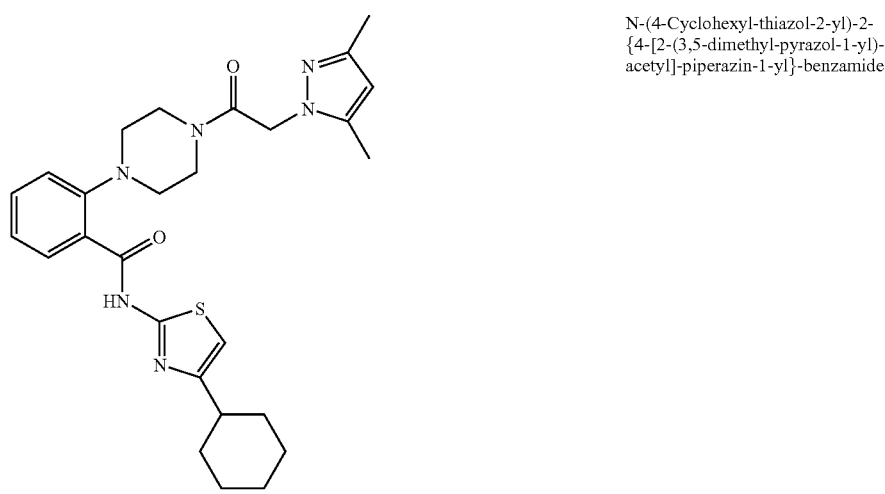
N-(4-Cyclohexyl-thiazol-2-yl)-2-{4-[2-(3,5-dimethyl-pyrazol-1-yl)-acetyl]-piperazin-1-yl}-benzamide
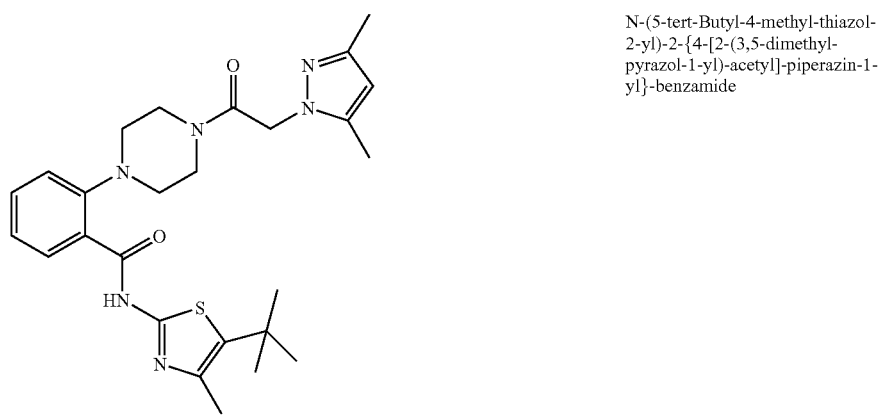
N-(5-tert-Butyl-4-methyl-thiazol-2-yl)-2-{4-[2-(3,5-dimethyl-pyrazol-1-yl)-acetyl]-piperazin-1-yl}-benzamide TABLE 1-continued
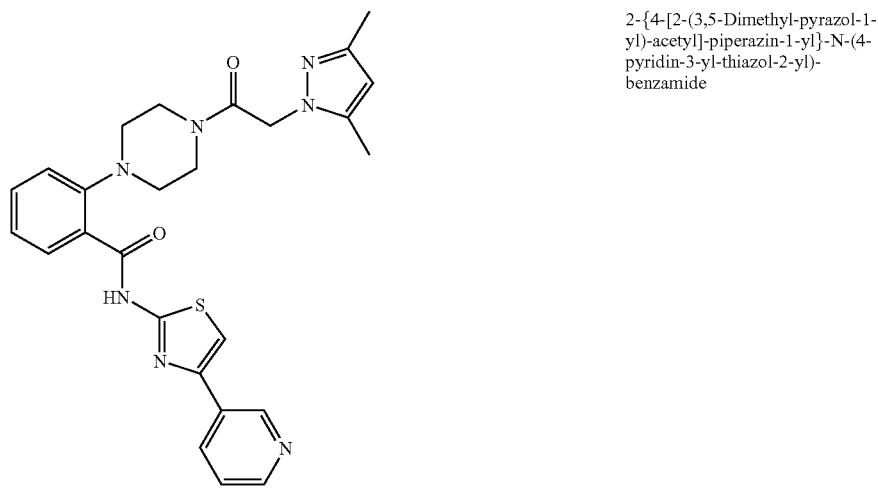
2-{4-[2-(3,5-Dimethyl-pyrazol-1-yl)-acetyl]-piperazin-1-yl}-N-(4-pyridin-3-yl-thiazol-2-yl)-benzamide
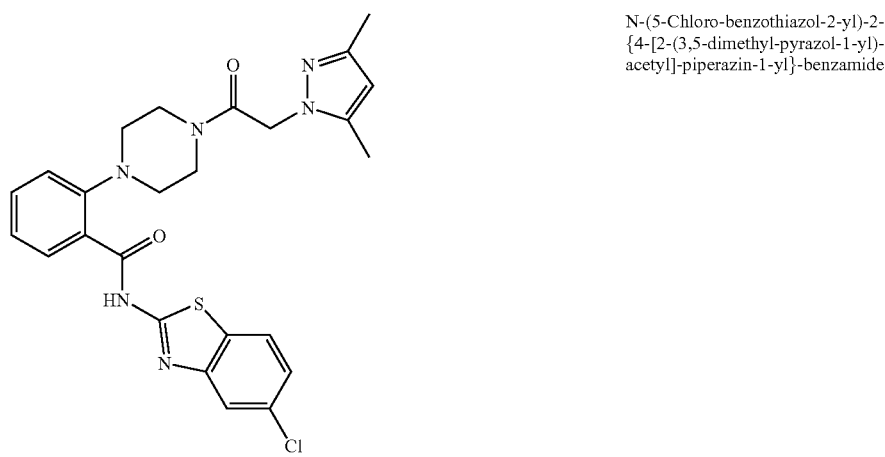
N-(5-Chloro-benzothiazol-2-yl)-2-{4-[2-(3,5-dimethyl-pyrazol-1-yl)-acetyl]-piperazin-1-yl}-benzamide
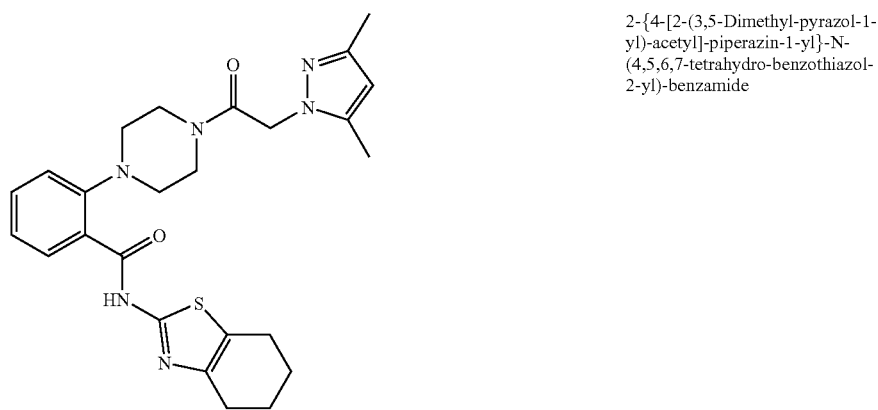
2-{4-[2-(3,5-Dimethyl-pyrazol-1-yl)-acetyl]-piperazin-1-yl}-N-(4,5,6,7-tetrahydro-benzothiazol-2-yl)-benzamide TABLE 1-continued

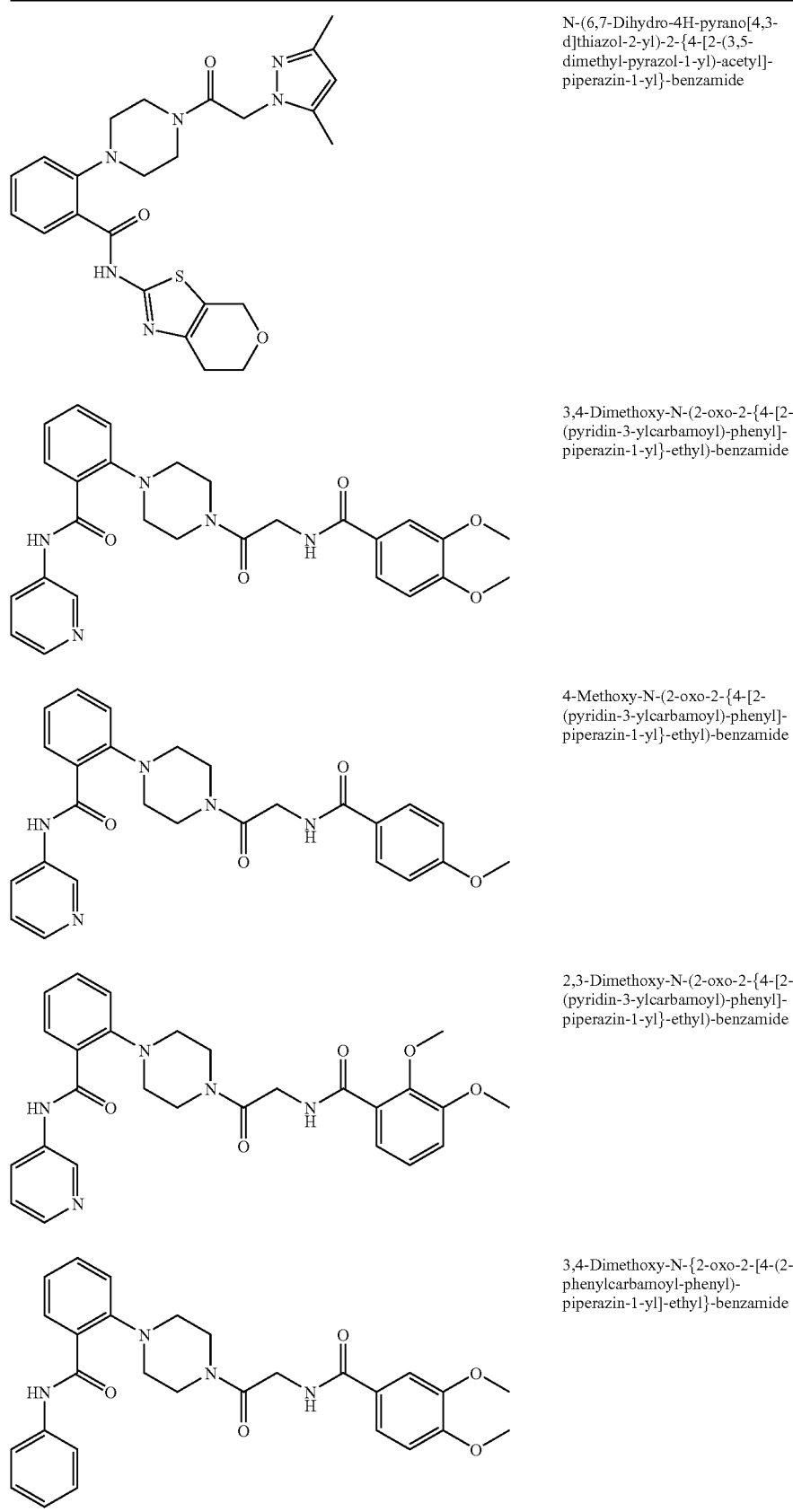

N-(6,7-Dihydro-4H-pyrano[4,3-d]thiazol-2-yl)-2-{4-[2-(3,5-dimethyl-pyrazol-1-yl)-acetyl]-piperazin-1-yl}-benzamide 3,4-Dimethoxy-N-(2-oxo-2-{4-[2-(pyridin-3-ylcarbamoyl)-phenyl]-piperazin-1-yl}-ethyl)-benzamide 4-Methoxy-N-(2-oxo-2-{4-[2-(pyridin-3-ylcarbamoyl)-phenyl]-piperazin-1-yl}-ethyl)-benzamide 2,3-Dimethoxy-N-(2-oxo-2-{4-[2-(pyridin-3-ylcarbamoyl)-phenyl]-piperazin-1-yl}-ethyl)-benzamide 3,4-Dimethoxy-N-{2-oxo-2-[4-(2-phenylcarbamoyl-phenyl)-piperazin-1-yl]-ethyl}-benzamide TABLE 1-continued

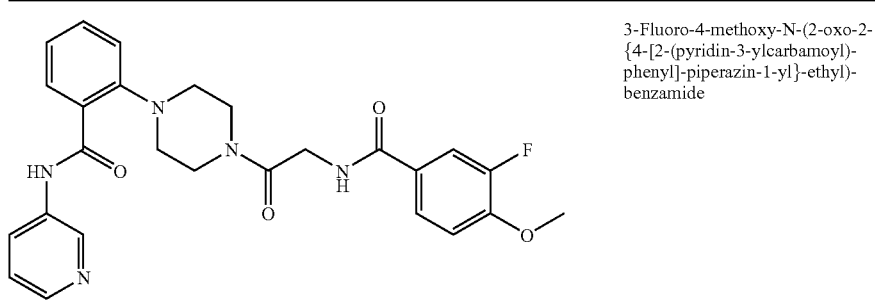

3-Fluoro-4-methoxy-N-(2-oxo-2-{4-[2-(pyridin-3-ylcarbamoyl)-phenyl]-piperazin-1-yl}-ethyl)-benzamide

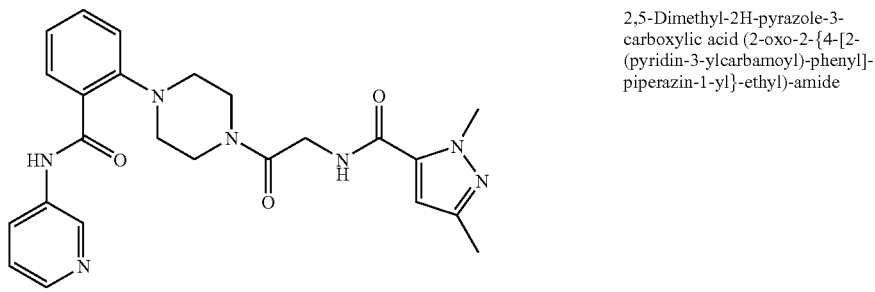

2,5-Dimethyl-2H-pyrazole-3-carboxylic acid (2-oxo-2-{4-[2-(pyridin-3-ylcarbamoyl)-phenyl]-piperazin-1-yl}-ethyl)-amide

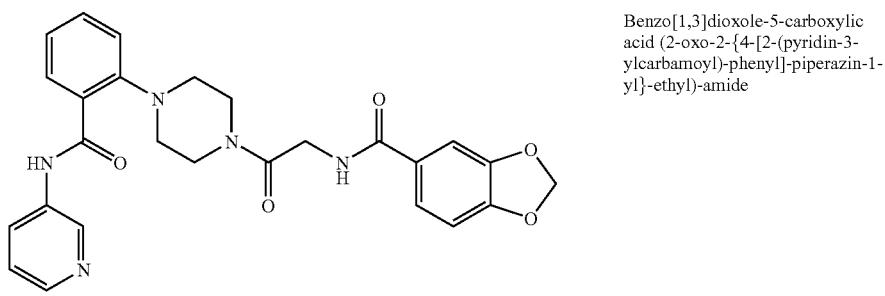

Benzo[1,3]dioxole-5-carboxylic acid (2-oxo-2-{4-[2-(pyridin-3-ylcarbamoyl)-phenyl]-piperazin-1-yl}-ethyl)-amide

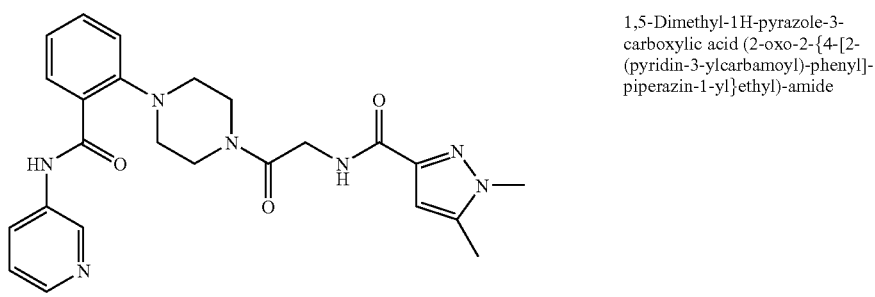

1,5-Dimethyl-1H-pyrazole-3-carboxylic acid (2-oxo-2-{4-[2-(pyridin-3-ylcarbamoyl)-phenyl]-piperazin-1-yl}ethyl)-amide

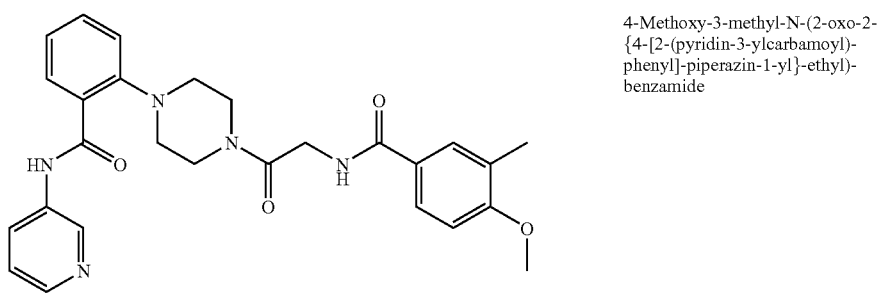

4-Methoxy-3-methyl-N-(2-oxo-2-{4-[2-(pyridin-3-ylcarbamoyl)-phenyl]-piperazin-1-yl}-ethyl)-benzamide TABLE 1-continued

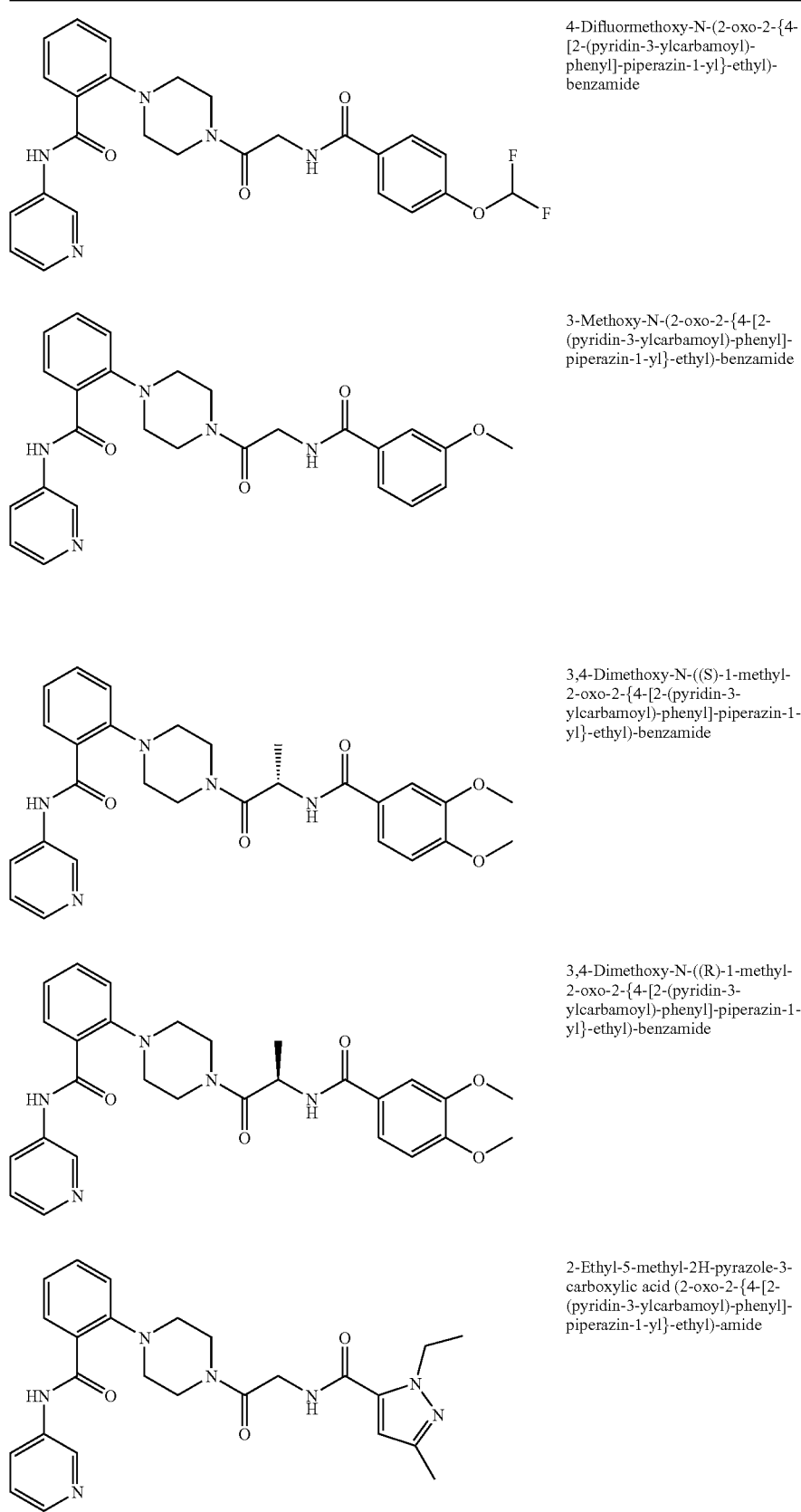

4-Difluormethoxy-N-(2-oxo-2-{4-[2-(pyridin-3-ylcarbamoyl)-phenyl]-piperazin-1-yl}-ethyl)-benzamide 3-Methoxy-N-(2-oxo-2-{4-[2-(pyridin-3-ylcarbamoyl)-phenyl]-piperazin-1-yl}-ethyl)-benzamide 3,4-Dimethoxy-N-((S)-1-methyl-2-oxo-2-{4-[2-(pyridin-3-ylcarbamoyl)-phenyl]-piperazin-1-yl}-ethyl)-benzamide 3,4-Dimethoxy-N-((R)-1-methyl-2-oxo-2-{4-[2-(pyridin-3-ylcarbamoyl)-phenyl]-piperazin-1-yl}-ethyl)-benzamide 2-Ethyl-5-methyl-2H-pyrazole-3-carboxylic acid (2-oxo-2-{4-[2-(pyridin-3-ylcarbamoyl)-phenyl]-piperazin-1-yl}-ethyl)-amide TABLE 1-continued

| Structure | Name |
|---|---|
| 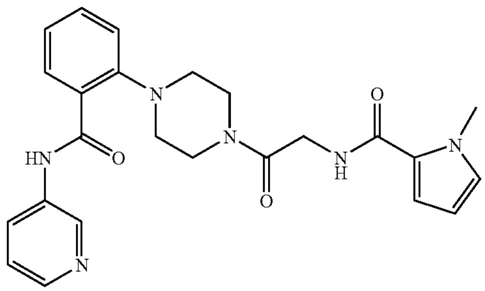 [SMILES: Cn1cccc1C(=O)NCC(=O)N1CCN(c2ccccc2C(=O)Nc2cccnc2)CC1] | 1-Methyl-1H-pyrrole-2-carboxylic acid (2-oxo-2-{4-[2-(pyridin-3-ylcarbamoyl)-phenyl]-piperazin-1-yl}-ethyl)-amide |
| 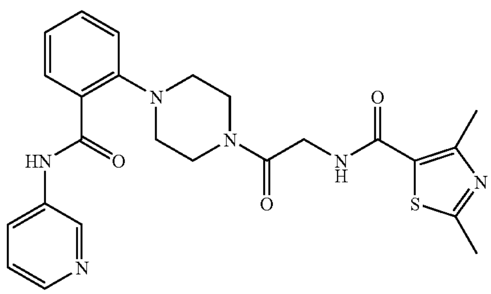 [SMILES: Cc1nc(C)c(C(=O)NCC(=O)N2CCN(c3ccccc3C(=O)Nc3cccnc3)CC2)s1] | 2,4-Dimethyl-thiazole-5-carboxylic acid (2-oxo-2-{4-[2-(pyridin-3-ylcarbamoyl)-phenyl]-piperazin-1-yl}-ethyl)-amide |
| 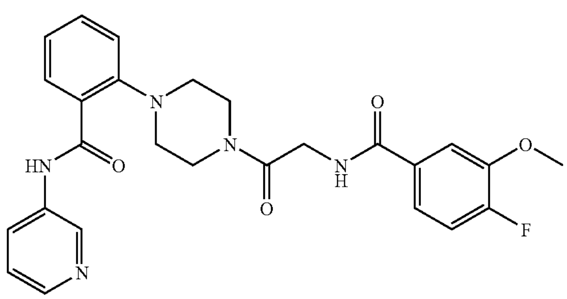 [SMILES: COc1cc(C(=O)NCC(=O)N2CCN(c3ccccc3C(=O)Nc3cccnc3)CC2)ccc1F] | 4-Fluoro-3-methoxy-N-(2-oxo-2-{4-[2-(pyridin-3-ylcarbamoyl)-phenyl]-piperazin-1-yl}-ethyl)-benzamide |
| 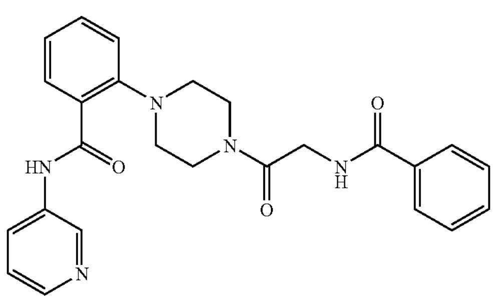 [SMILES: O=C(NCC(=O)N1CCN(c2ccccc2C(=O)Nc2cccnc2)CC1)c1ccccc1] | 2-[4-(2-Benzoylamino-acetyl)-piperazin-1-yl]-N-pyridin-3-yl-benzamide |
| 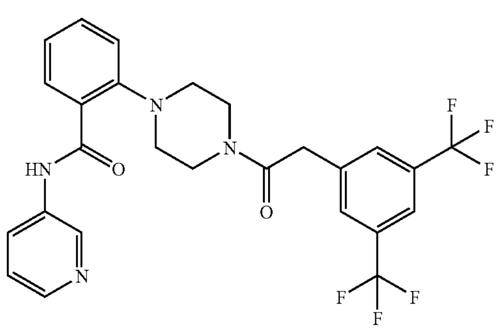 [SMILES: O=C(Nc1cccnc1)c1ccccc1N1CCN(C(=O)Cc2cc(C(F)(F)F)cc(C(F)(F)F)c2)CC1] | 2-{4-[2-(3,5-Bis-trifluoromethyl-phenyl)-acetyl]-piperazin-1-yl}-N-pyridin-3-yl-benzamide |

TABLE 1-continued

| | |
|---|---|
| 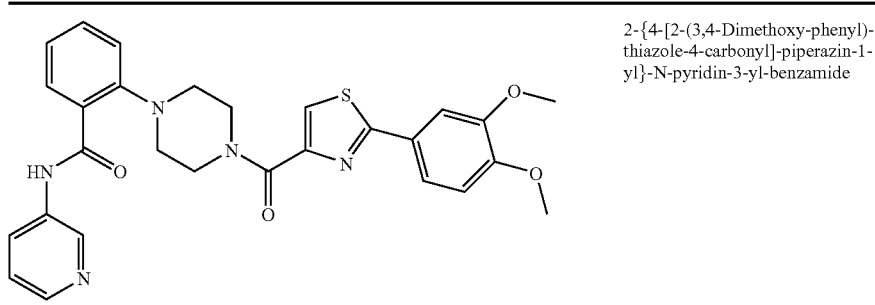 | 2-{4-[2-(3,4-Dimethoxy-phenyl)-thiazole-4-carbonyl]-piperazin-1-yl}-N-pyridin-3-yl-benzamide |
| 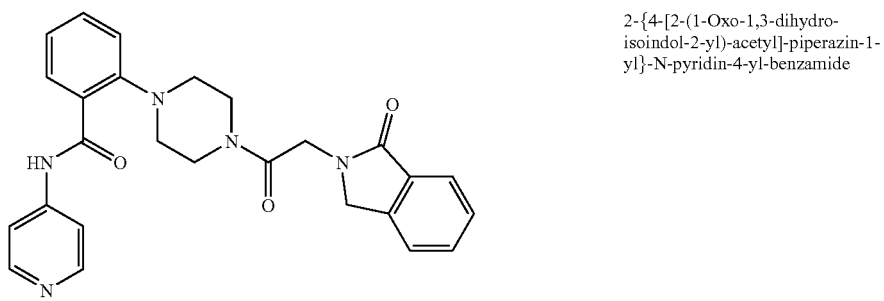 | 2-{4-[2-(1-Oxo-1,3-dihydro-isoindol-2-yl)-acetyl]-piperazin-1-yl}-N-pyridin-4-yl-benzamide |
| 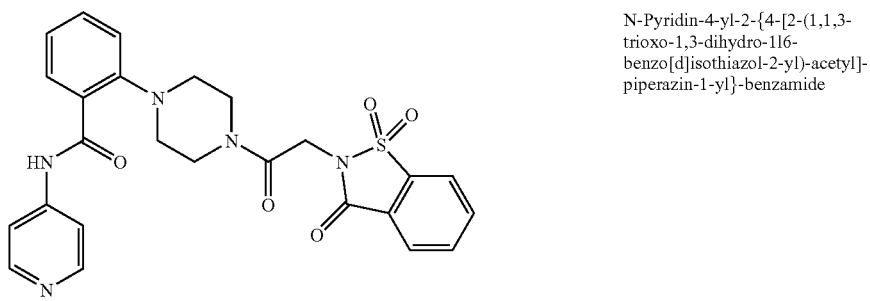 | N-Pyridin-4-yl-2-{4-[2-(1,1,3-trioxo-1,3-dihydro-1l6-benzo[d]isothiazol-2-yl)-acetyl]-piperazin-1-yl}-benzamide |
| 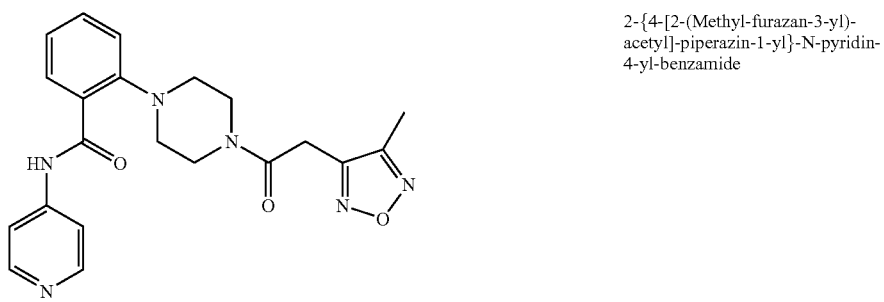 | 2-{4-[2-(Methyl-furazan-3-yl)-acetyl]-piperazin-1-yl}-N-pyridin-4-yl-benzamide |
| 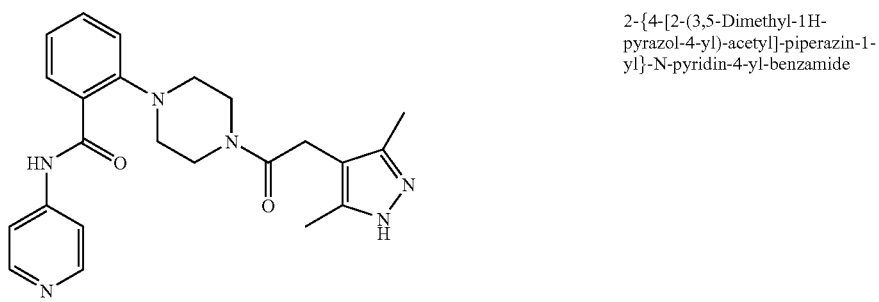 | 2-{4-[2-(3,5-Dimethyl-1H-pyrazol-4-yl)-acetyl]-piperazin-1-yl}-N-pyridin-4-yl-benzamide |

TABLE 1-continued
| | |
|---|---|
| 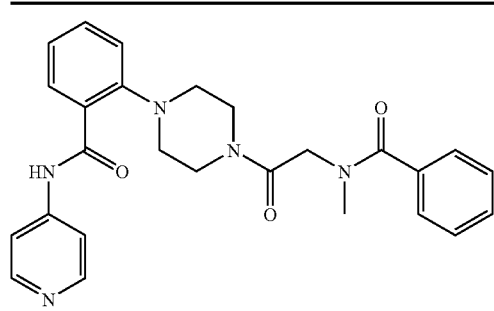 | 2-{4-[2-(Benzoyl-methyl-amino)-acetyl]-piperazin-1-yl}-N-pyridin-4-yl-benzamide |
| 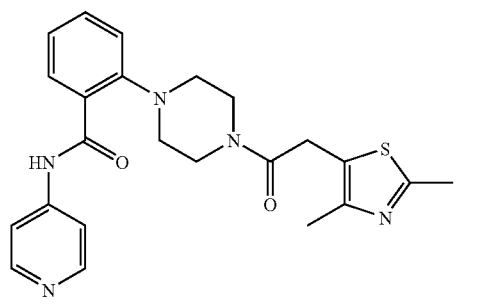 [SMILES: Cc1nc(C)c(CC(=O)N2CCN(c3ccccc3C(=O)Nc3ccncc3)CC2)s1] | 2-{4-[2-(2,4-Dimethyl-thiazol-5-yl)-acetyl]-piperazin-1-yl}-N-pyridin-4-yl-benzamide |
| 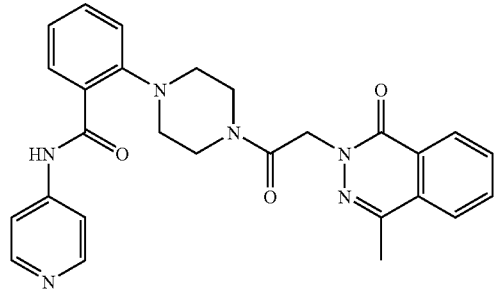 [SMILES: Cc1nn(CC(=O)N2CCN(c3ccccc3C(=O)Nc3ccncc3)CC2)c(=O)c2ccccc12] | 2-{4-[2-(4-Methyl-1-oxo-1H-phthalazin-2-yl)-acetyl]-piperazin-1-yl}-N-pyridin-4-yl-benzamide |
| 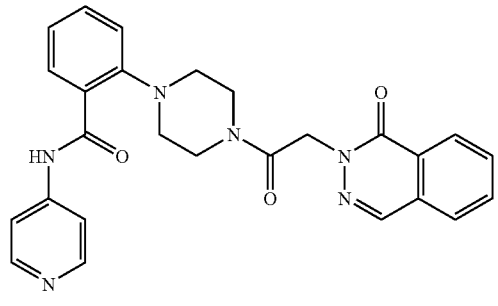 | 2-{4-[2-(1-Oxo-1H-phthalazin-2-yl)-acetyl]-piperazin-1-yl}-N-pyridin-4-yl-benzamide |
| 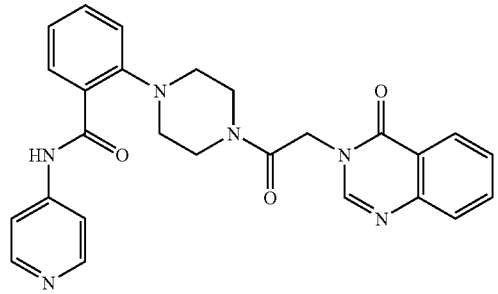 | 2-{4-[2-(Oxo-4H-quinazolin-3-yl)-acetyl]-piperazin-1-yl}-N-pyridin-4-yl-benzamide |

TABLE 1-continued

| Structure | Name |
|---|---|
| 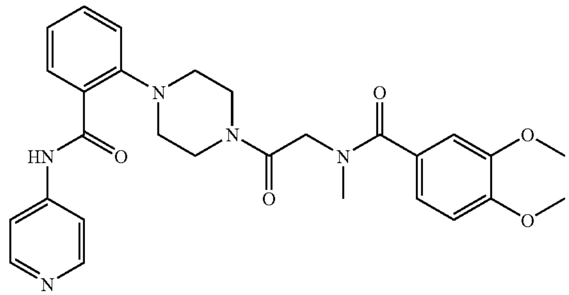 [SMILES: COc1ccc(C(=O)N(C)CC(=O)N2CCN(c3ccccc3C(=O)Nc3ccncc3)CC2)cc1OC] | 3,4-Dimethoxy-N-methyl-N-(2-oxo-2-{4-[2-(pyridin-4-ylcarbamoyl)-phenyl]-piperazin-1-yl}-ethyl)-benzamide |
| 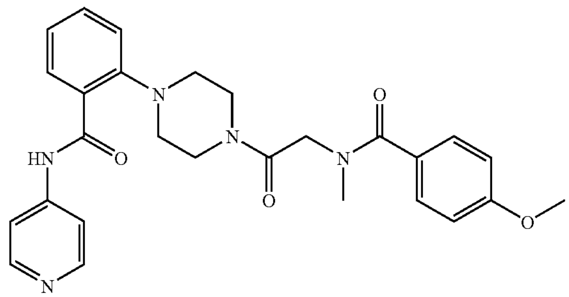 [SMILES: COc1ccc(C(=O)N(C)CC(=O)N2CCN(c3ccccc3C(=O)Nc3ccncc3)CC2)cc1] | 4-Methoxy-N-methyl-N-(2-oxo-2-{4-[2-(pyridin-4-ylcarbamoyl)-phenyl]-piperazin-1-yl}-ethyl)-benzamide |
| 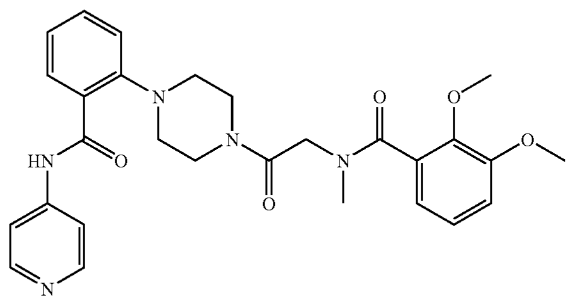 [SMILES: COc1cccc(C(=O)N(C)CC(=O)N2CCN(c3ccccc3C(=O)Nc3ccncc3)CC2)c1OC] | 2,3-Dimethoxy-N-methyl-N-(2-oxo-2-{4-[2-(pyridin-4-ylcarbamoyl)-phenyl]-piperazin-1-yl}-ethyl)-benzamide |
| 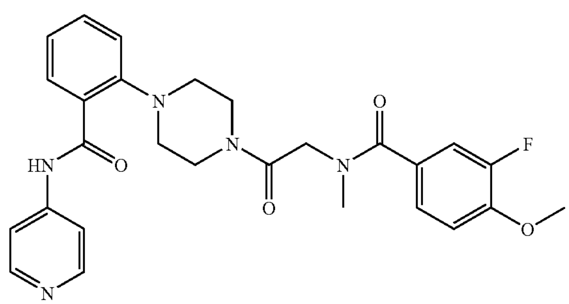 [SMILES: COc1ccc(C(=O)N(C)CC(=O)N2CCN(c3ccccc3C(=O)Nc3ccncc3)CC2)cc1F] | 3-Fluoro-4-methoxy-N-methyl-N-(2-oxo-2-{4-[2-(pyridin-4-ylcarbamoyl)-phenyl]-piperazin-1-yl}-ethyl)-benzamide |
| 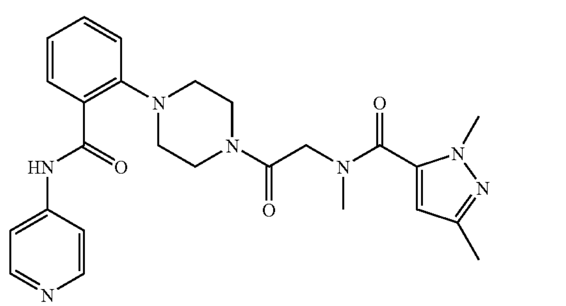 [SMILES: Cc1cc(C(=O)N(C)CC(=O)N2CCN(c3ccccc3C(=O)Nc3ccncc3)CC2)n(C)n1] | 2,5-Dimethyl-2H-pyrazole-3-carboxylic acid methyl-(2-oxo-2-{4-[2-(pyridin-4-ylcarbamoyl)-phenyl]-piperazin-1-yl}-ethyl)-amide |

TABLE 1-continued

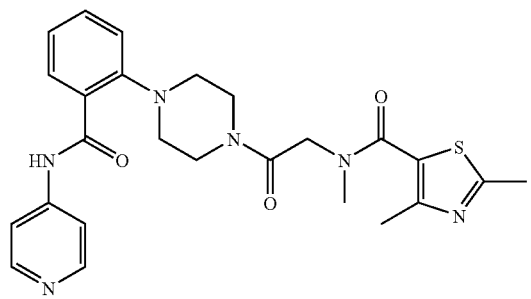 [SMILES: Cc1nc(C)c(C(=O)N(C)CC(=O)N2CCN(c3ccccc3C(=O)Nc3ccncc3)CC2)s1]

2,4-Dimethyl-thiazole-5-carboxylic acid methyl-(2-oxo-2-{4-[2-(pyridin-4-ylcarbamoyl)-phenyl]-piperazin-1-yl}-ethyl)-amide

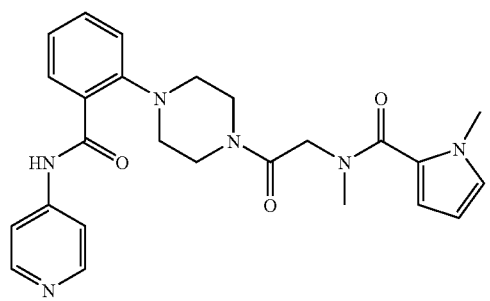 [SMILES: CN(CC(=O)N1CCN(c2ccccc2C(=O)Nc2ccncc2)CC1)C(=O)c1cccn1C]

1-Methyl-1H-pyrrole-2-carboxylic acid methyl-(2-oxo-2-{4-[2-(pyridin-4-ylcarbamoyl)-phenyl]-piperazin-1-yl}-ethyl)-amide

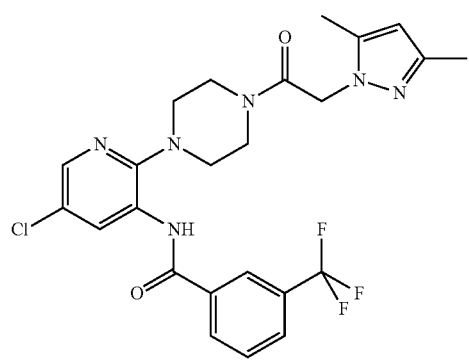 [SMILES: Cc1cc(C)n(CC(=O)N2CCN(c3ncc(Cl)cc3NC(=O)c3cccc(C(F)(F)F)c3)CC2)n1]

N-(5-Chloro-2-{4-[2-(3,5-dimethyl-pyrazol-1-yl)-acetyl]-piperazin-1-yl}-pyridin-3-yl)-3-trifluoromethyl-benzamide

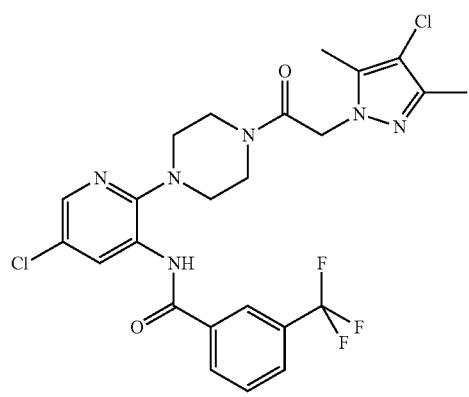 [SMILES: Cc1nn(CC(=O)N2CCN(c3ncc(Cl)cc3NC(=O)c3cccc(C(F)(F)F)c3)CC2)c(C)c1Cl]

N-(5-Chloro-2-{4-[2-(4-chloro-3,5-dimethyl-2H-pyrrol-2-yl)-acetyl]-piperazin-1-yl}-pyridin-3-yl)-3-trifluoromethyl-benzamide TABLE 1-continued
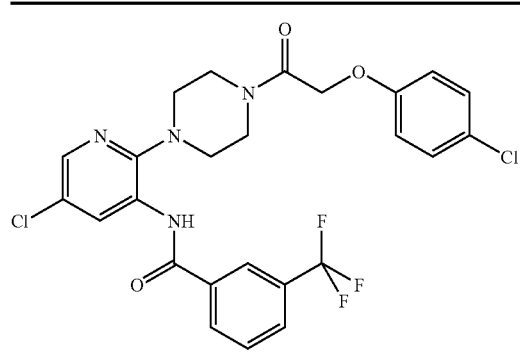
N-(5-Chloro-2-{4-[2-(4-chloro-phenoxy)-acetyl]-piperazin-1-yl}-pyridin-3-yl)-3-trifluoromethyl-benzamide
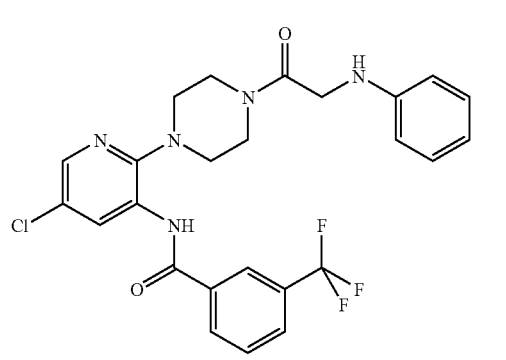 [SMILES: O=C(Nc1cc(Cl)cnc1N1CCN(C(=O)CNc2ccccc2)CC1)c1cccc(C(F)(F)F)c1]
N-{5-Chloro-2-[4-(2-phenylamino-acetyl)-piperazin-1-yl]-pyridin-3-yl}-3-trifluoromethyl-benzamide
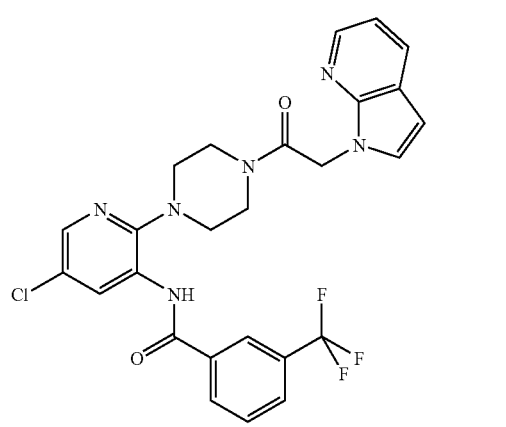 [SMILES: O=C(Nc1cc(Cl)cnc1N1CCN(C(=O)Cn2ccc3cccnc32)CC1)c1cccc(C(F)(F)F)c1]
N-{5-Chloro-2-[4-(2-pyrrolo[2,3-b]pyridin-1-yl-acetyl)-piperazin-1-yl]-pyridin-3-yl}-3-trifluoromethyl-benzamide
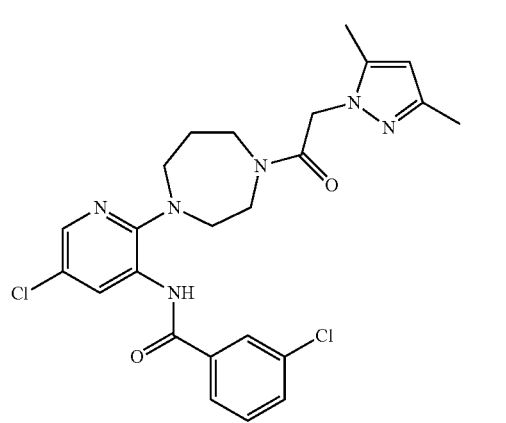 [SMILES: Cc1cc(C)n(CC(=O)N2CCCN(c3ncc(Cl)cc3NC(=O)c3cccc(Cl)c3)CC2)n1]
3-Chloro-N-(5-chloro-2-{4-[2-(3,5-dimethyl-pyrazol-1-yl)-acetyl]-[1,4]diazepan-1-yl}-pyridin-3-yl)-benzamide TABLE 1-continued
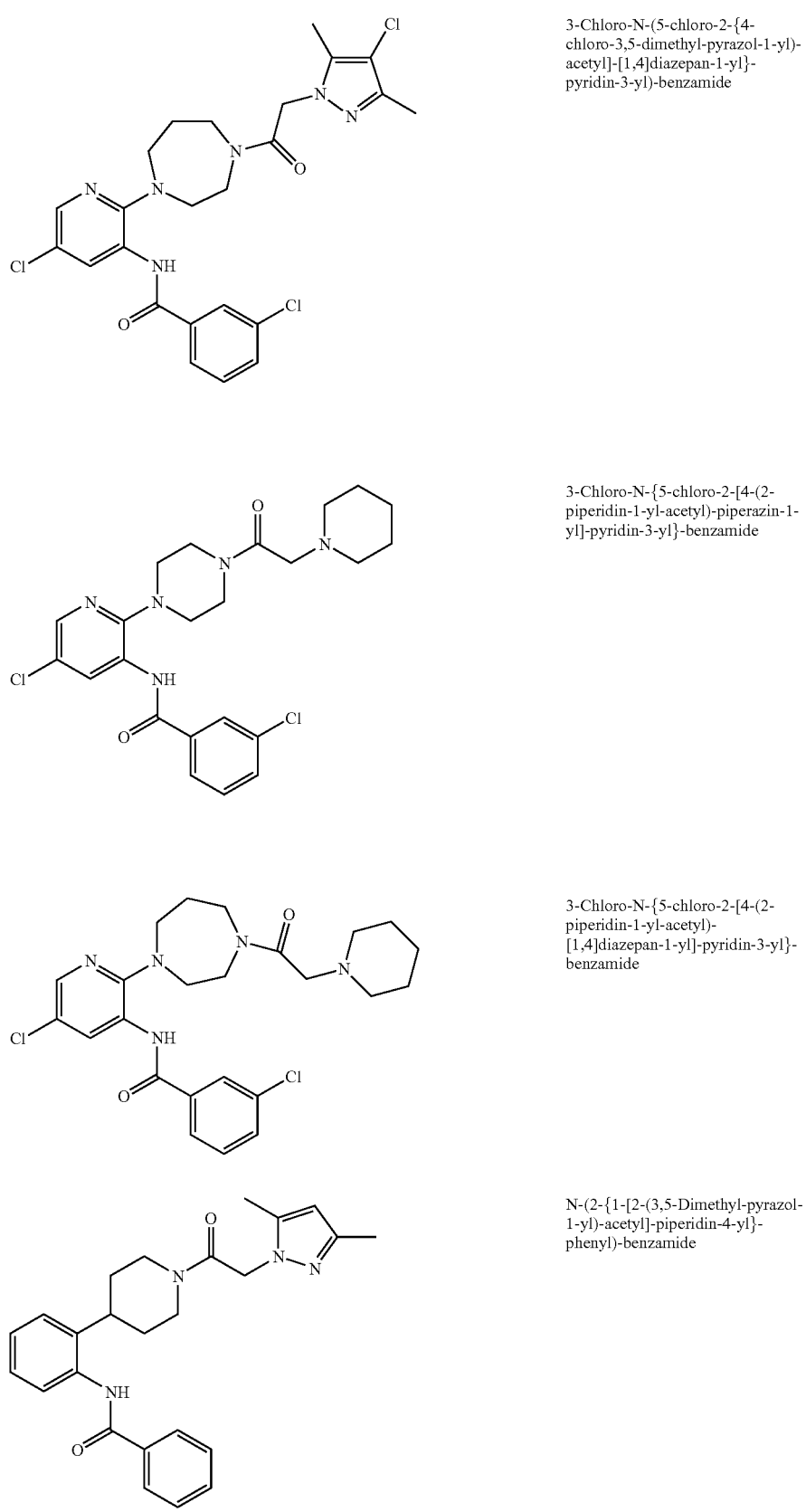
3-Chloro-N-(5-chloro-2-{4-chloro-3,5-dimethyl-pyrazol-1-yl)-acetyl]-[1,4]diazepan-1-yl}-pyridin-3-yl)-benzamide
3-Chloro-N-{5-chloro-2-[4-(2-piperidin-1-yl-acetyl)-piperazin-1-yl]-pyridin-3-yl}-benzamide
3-Chloro-N-{5-chloro-2-[4-(2-piperidin-1-yl-acetyl)-[1,4]diazepan-1-yl]-pyridin-3-yl}-benzamide
N-(2-{1-[2-(3,5-Dimethyl-pyrazol-1-yl)-acetyl]-piperidin-4-yl}-phenyl)-benzamide TABLE 1-continued
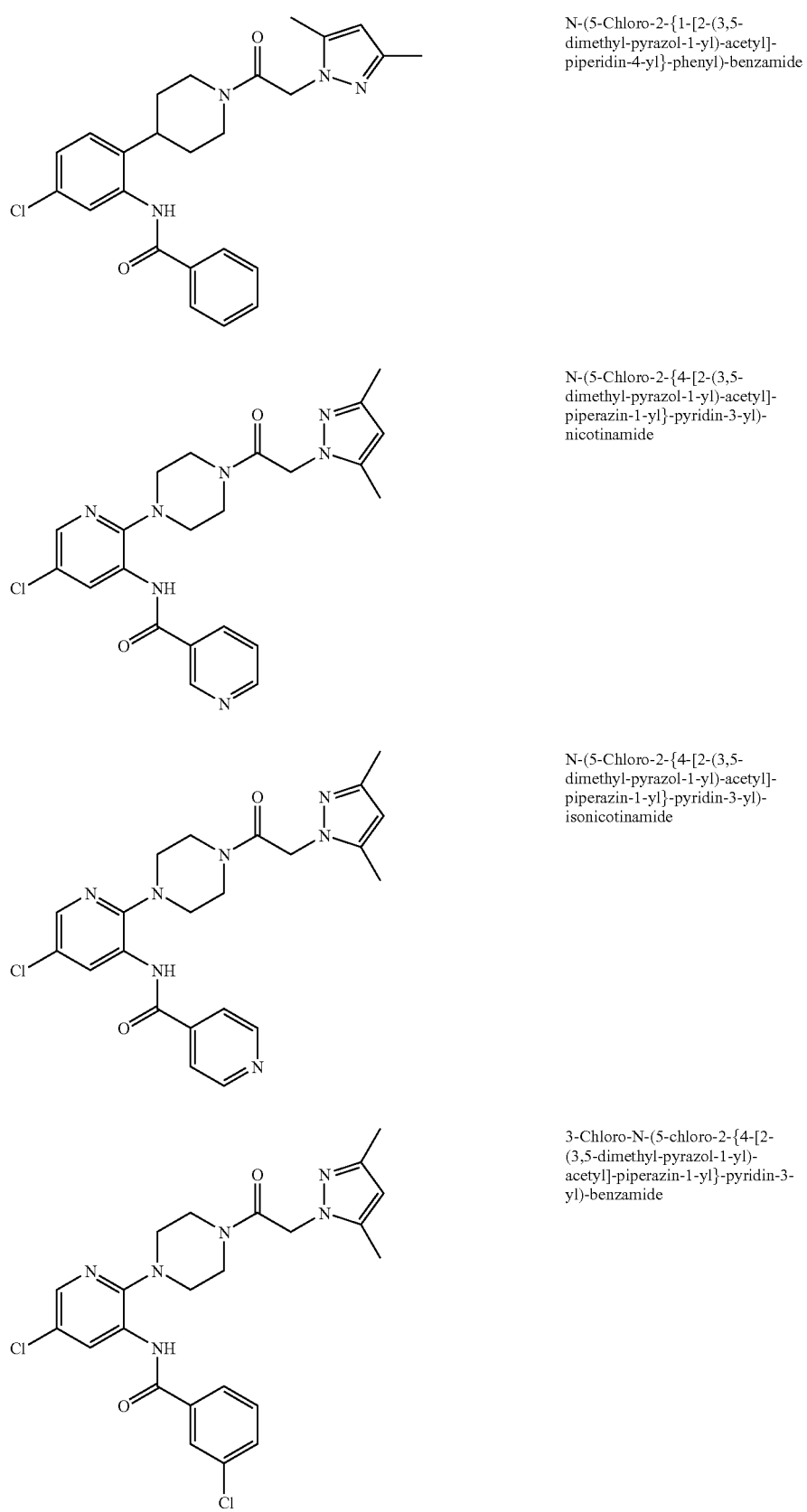
N-(5-Chloro-2-{1-[2-(3,5-dimethyl-pyrazol-1-yl)-acetyl]-piperidin-4-yl}-phenyl)-benzamide
N-(5-Chloro-2-{4-[2-(3,5-dimethyl-pyrazol-1-yl)-acetyl]-piperazin-1-yl}-pyridin-3-yl)-nicotinamide
N-(5-Chloro-2-{4-[2-(3,5-dimethyl-pyrazol-1-yl)-acetyl]-piperazin-1-yl}-pyridin-3-yl)-isonicotinamide
3-Chloro-N-(5-chloro-2-{4-[2-(3,5-dimethyl-pyrazol-1-yl)-acetyl]-piperazin-1-yl}-pyridin-3-yl)-benzamide TABLE 1-continued
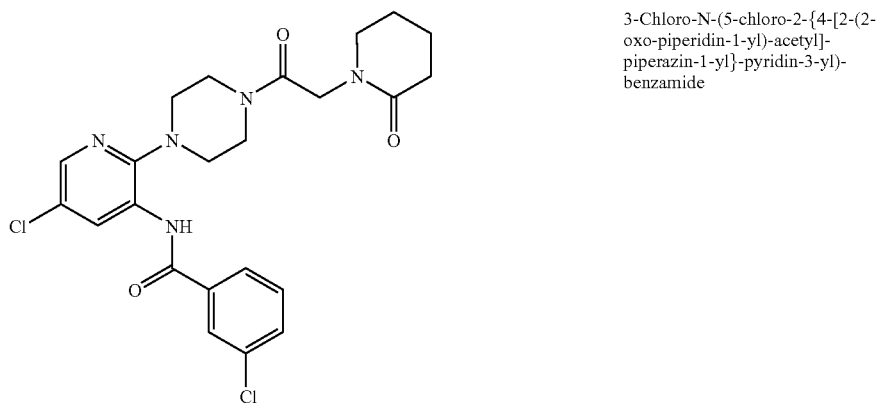
3-Chloro-N-(5-chloro-2-{4-[2-(2-oxo-piperidin-1-yl)-acetyl]-piperazin-1-yl}-pyridin-3-yl)-benzamide
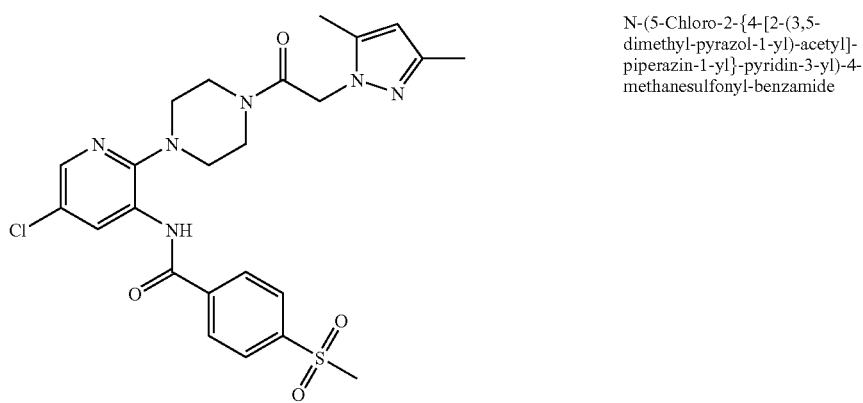
N-(5-Chloro-2-{4-[2-(3,5-dimethyl-pyrazol-1-yl)-acetyl]-piperazin-1-yl}-pyridin-3-yl)-4-methanesulfonyl-benzamide
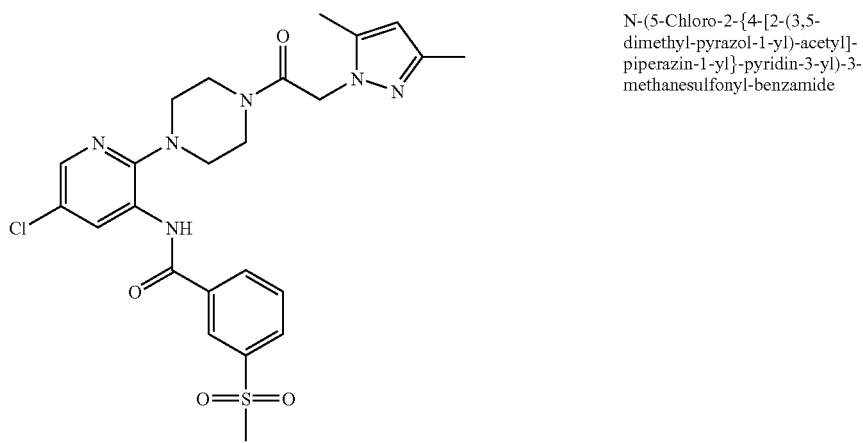
N-(5-Chloro-2-{4-[2-(3,5-dimethyl-pyrazol-1-yl)-acetyl]-piperazin-1-yl}-pyridin-3-yl)-3-methanesulfonyl-benzamide TABLE 1-continued
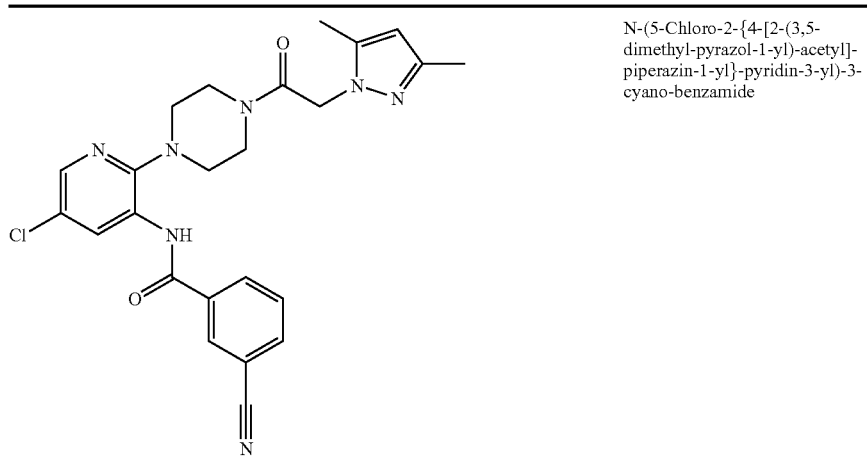
N-(5-Chloro-2-{4-[2-(3,5-dimethyl-pyrazol-1-yl)-acetyl]-piperazin-1-yl}-pyridin-3-yl)-3-cyano-benzamide
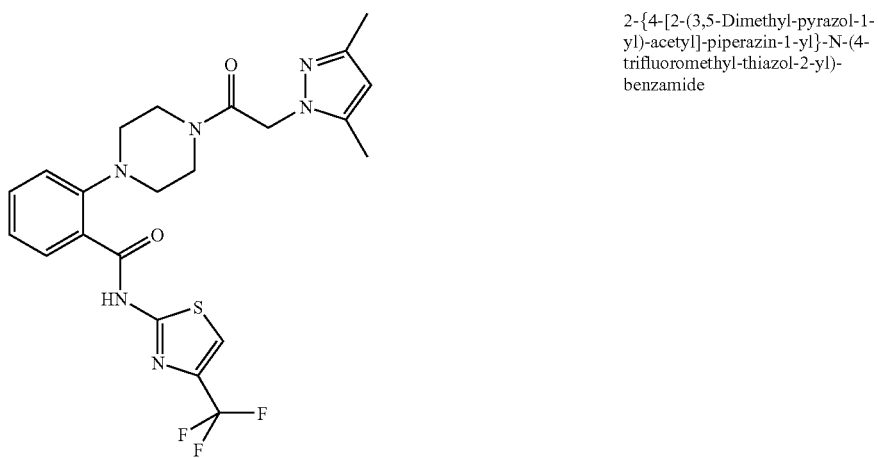
2-{4-[2-(3,5-Dimethyl-pyrazol-1-yl)-acetyl]-piperazin-1-yl}-N-(4-trifluoromethyl-thiazol-2-yl)-benzamide
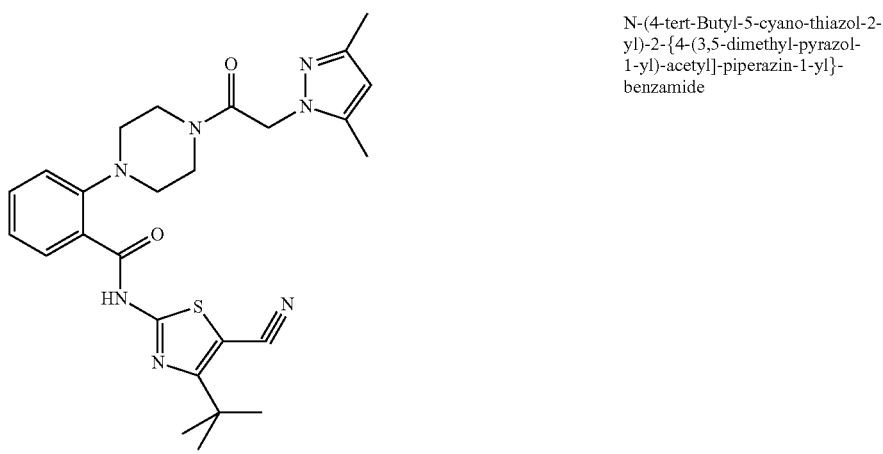
N-(4-tert-Butyl-5-cyano-thiazol-2-yl)-2-{4-(3,5-dimethyl-pyrazol-1-yl)-acetyl]-piperazin-1-yl}-benzamide TABLE 1-continued
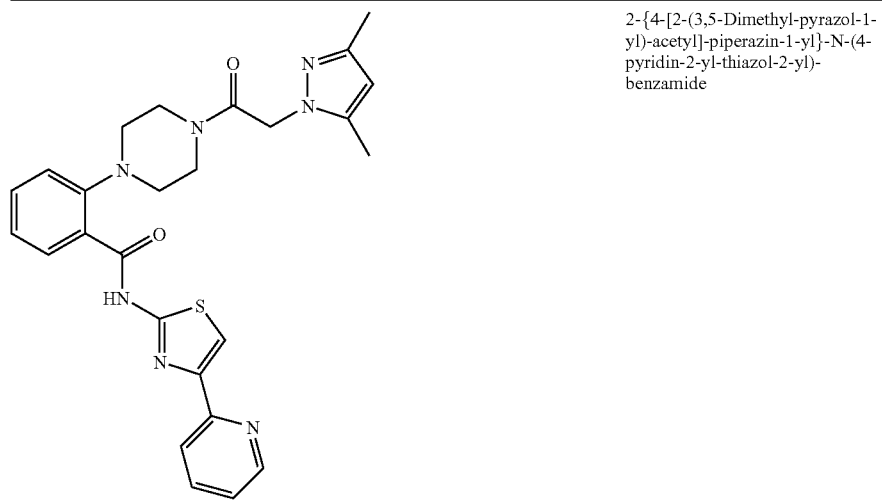
2-{4-[2-(3,5-Dimethyl-pyrazol-1-yl)-acetyl]-piperazin-1-yl}-N-(4-pyridin-2-yl-thiazol-2-yl)-benzamide
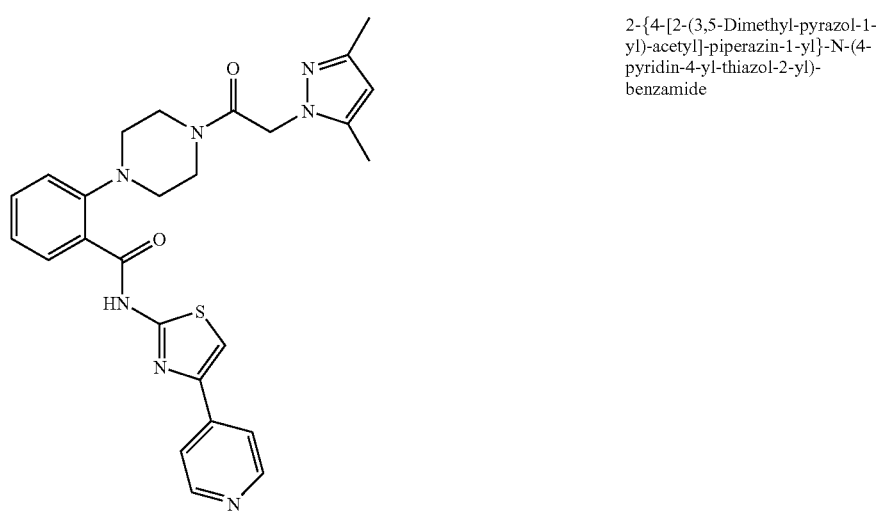
2-{4-[2-(3,5-Dimethyl-pyrazol-1-yl)-acetyl]-piperazin-1-yl}-N-(4-pyridin-4-yl-thiazol-2-yl)-benzamide
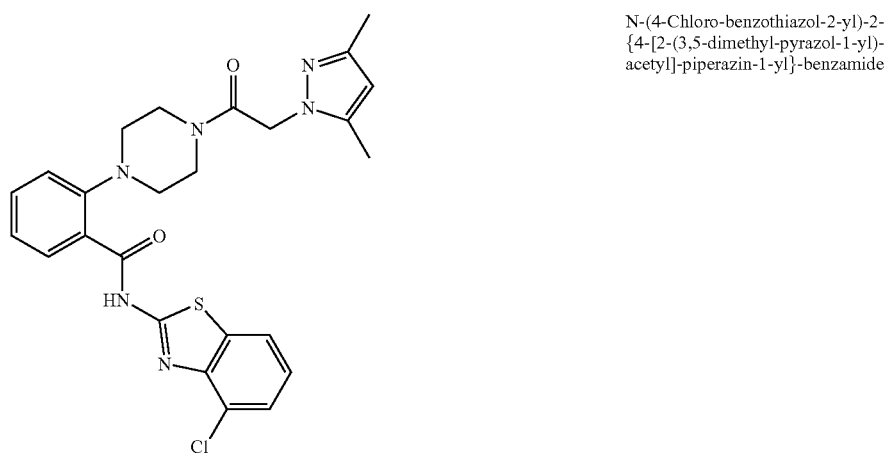
N-(4-Chloro-benzothiazol-2-yl)-2-{4-[2-(3,5-dimethyl-pyrazol-1-yl)-acetyl]-piperazin-1-yl}-benzamide TABLE 1-continued
| | |
|---|---|
| 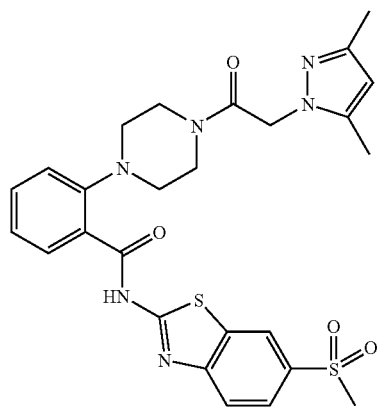 [SMILES: Cc1cc(C)n(CC(=O)N2CCN(c3ccccc3C(=O)Nc3nc4ccc(S(C)(=O)=O)cc4s3)CC2)n1] | 2-{4-[2-(3,5-Dimethyl-pyrazol-1-yl)-acetyl]-piperazin-1-yl}-N-(6-methanesulfonyl-benzothiazol-2-yl)-benzamide |
| 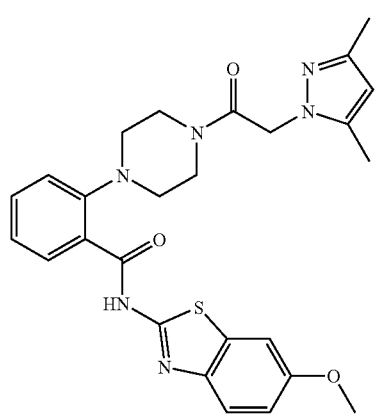 [SMILES: COc1ccc2nc(NC(=O)c3ccccc3N3CCN(C(=O)Cn4nc(C)cc4C)CC3)sc2c1] | 2-{4-[2-(3,5-Dimethyl-pyrazol-1-yl)-acetyl]-piperazin-1-yl}-N-(6-methoxy-benzothiazol-2-yl)-benzamide |
| 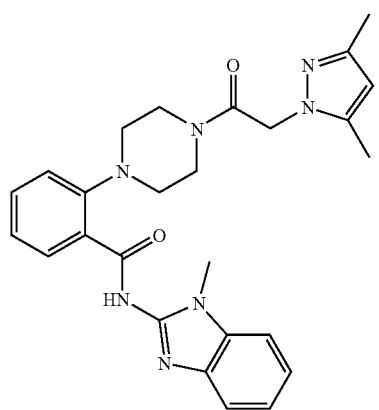 [SMILES: Cc1cc(C)n(CC(=O)N2CCN(c3ccccc3C(=O)Nc3nc4ccccc4n3C)CC2)n1] | 2-{4-[2-(3,5-Dimethyl-pyrazol-1-yl)-acetyl]-piperazin-1-yl}-N-(1-methyl-1H-benzoimidazol-2-yl)-benzamide |
| 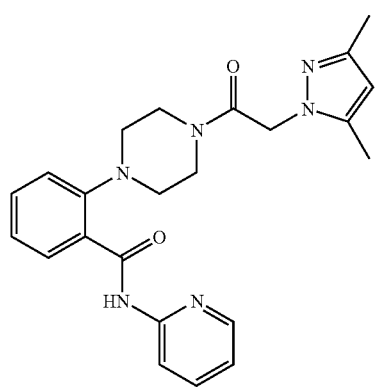 [SMILES: Cc1cc(C)n(CC(=O)N2CCN(c3ccccc3C(=O)Nc3ccccn3)CC2)n1] | 2-{4-[2-(3,5-Dimethyl-pyrazol-1-yl)-acetyl]-piperazin-1-yl}-N-pyridin-2-yl-benzamide |

TABLE 1-continued
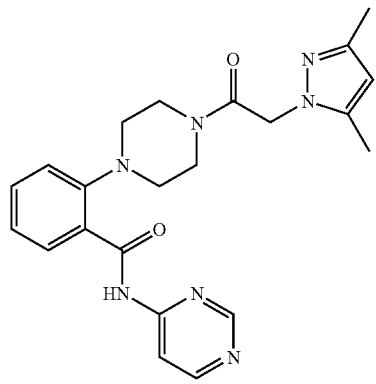 [SMILES: Cc1cc(C)n(CC(=O)N2CCN(c3ccccc3C(=O)Nc3ccncn3)CC2)n1]
2-{4-[2-(3,5-Dimethyl-pyrazol-1-yl)-acetyl]-piperazin-1-yl}-N-pyrimidin-4-yl-benzamide
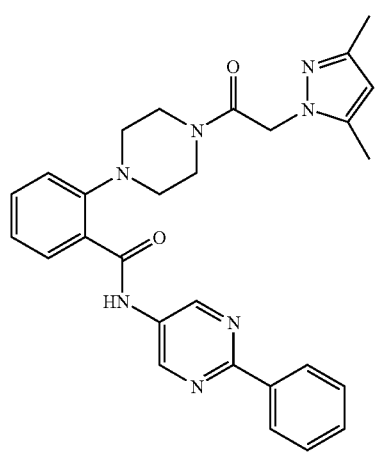 [SMILES: Cc1cc(C)n(CC(=O)N2CCN(c3ccccc3C(=O)Nc3cnc(-c4ccccc4)nc3)CC2)n1]
2-{4-[2-(3,5-Dimethyl-pyrazol-1-yl)-acetyl]-piperazin-1-yl}-N-(2-phenyl-pyrimidin-5-yl)-benzamide
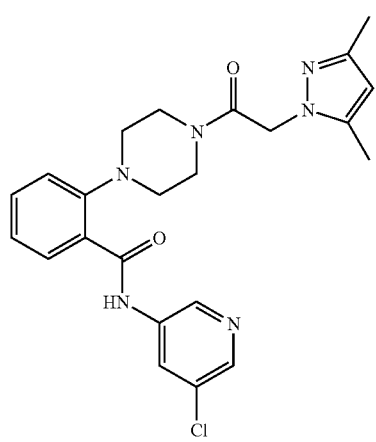 [SMILES: Cc1cc(C)n(CC(=O)N2CCN(c3ccccc3C(=O)Nc3cncc(Cl)c3)CC2)n1]
N-(5-Chloro-pyridin-3-yl)-2-{4-[2-(3,5-dimethyl-pyrazol-1-yl)-acetyl]-piperazin-1-yl}-benzamide TABLE 1-continued
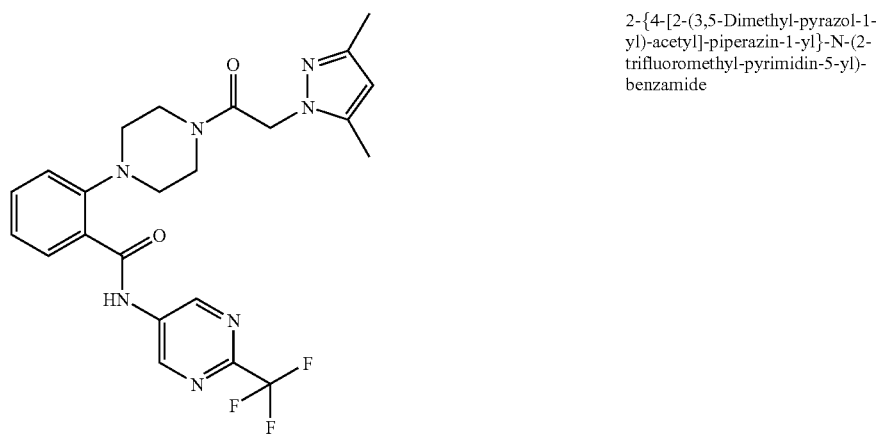
2-{4-[2-(3,5-Dimethyl-pyrazol-1-yl)-acetyl]-piperazin-1-yl}-N-(2-trifluoromethyl-pyrimidin-5-yl)-benzamide
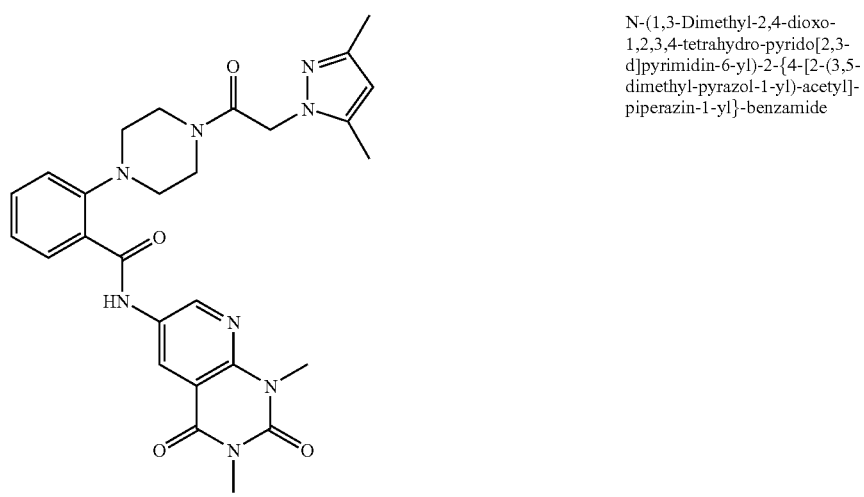
N-(1,3-Dimethyl-2,4-dioxo-1,2,3,4-tetrahydro-pyrido[2,3-d]pyrimidin-6-yl)-2-{4-[2-(3,5-dimethyl-pyrazol-1-yl)-acetyl]-piperazin-1-yl}-benzamide
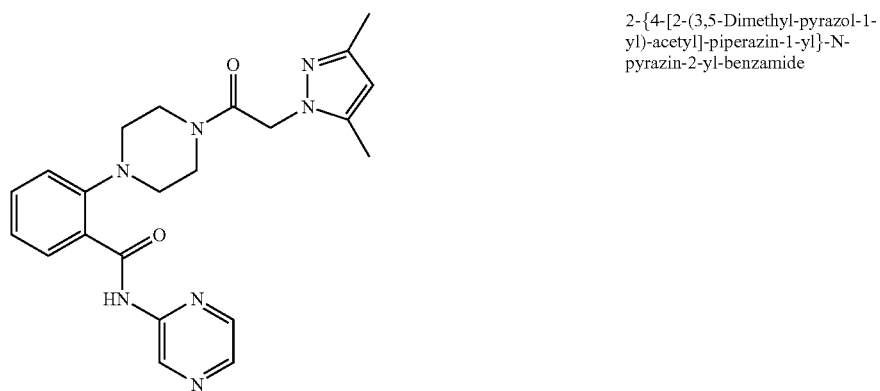
2-{4-[2-(3,5-Dimethyl-pyrazol-1-yl)-acetyl]-piperazin-1-yl}-N-pyrazin-2-yl-benzamide TABLE 1-continued
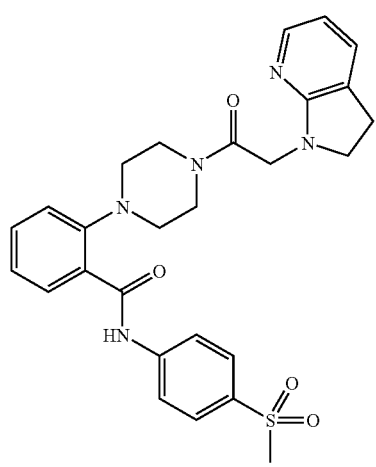 [SMILES: CS(=O)(=O)c1ccc(NC(=O)c2ccccc2N2CCN(C(=O)CN3CCc4cccnc43)CC2)cc1]
2-[4-(2-2,3-Dihydro-pyrrolo[2,3-b]pyridin-1-yl-acetyl)-piperazin-1-yl]-N-(4-methanesulfonyl-phenyl)-benzamide
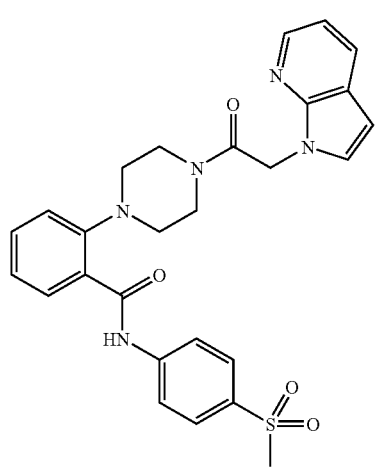 [SMILES: CS(=O)(=O)c1ccc(NC(=O)c2ccccc2N2CCN(C(=O)Cn3ccc4cccnc43)CC2)cc1]
N-(4-Methanesulfonyl-phenyl)-2-[4-(2-pyrrolo[2,3-b]pyridin-1-yl-acetyl)-piperazin-1-yl]-benzamide
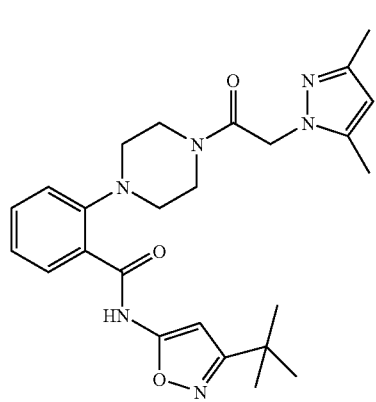 [SMILES: Cc1cc(C)n(CC(=O)N2CCN(c3ccccc3C(=O)Nc3cc(C(C)(C)C)no3)CC2)n1]
N-(3-tert-Butyl-isoxazol-5-yl)-2-{4-[2-(3,5-dimethyl-pyrazol-1-yl)-acetyl]-piperazin-1-yl}-benzamide TABLE 1-continued

| Structure | Name |
|---|---|
| 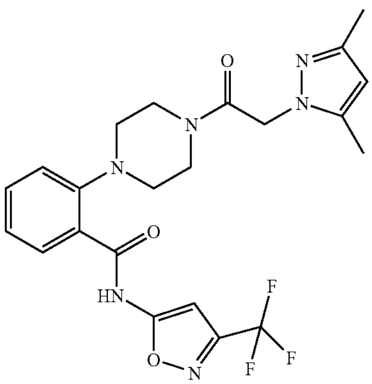 [SMILES: Cc1cc(C)n(CC(=O)N2CCN(c3ccccc3C(=O)Nc3cc(C(F)(F)F)no3)CC2)n1] | 2-{4-[2-(3,5-Dimethyl-pyrazol-1-yl)-acetyl]-piperazin-1-yl}-N-(3-trifluoromethyl-isoxazol-5-yl)-benzamide |
| 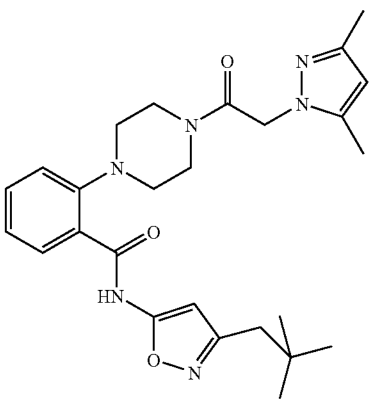 [SMILES: Cc1cc(C)n(CC(=O)N2CCN(c3ccccc3C(=O)Nc3cc(CC(C)(C)C)no3)CC2)n1] | N-[3-(2,2-Dimethyl-propyl)-isoxazol-5-yl]-2-{4-[2-(3,5-dimethyl-pyrazol-1-yl)-acetyl]-piperazin-1-yl}-benzamide |
| 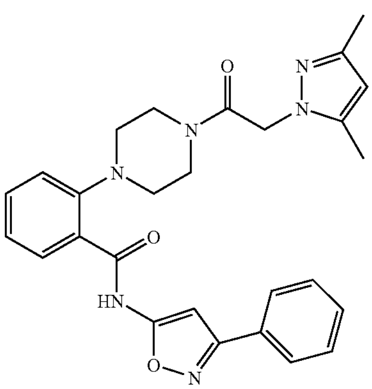 [SMILES: Cc1cc(C)n(CC(=O)N2CCN(c3ccccc3C(=O)Nc3cc(-c4ccccc4)no3)CC2)n1] | 2-{4-[2-(3,5-Dimethyl-pyrazol-1-yl)-acetyl]-piperazin-1-yl}-N-(3-phenyl-isoxazol-5-yl)-benzamide |
| 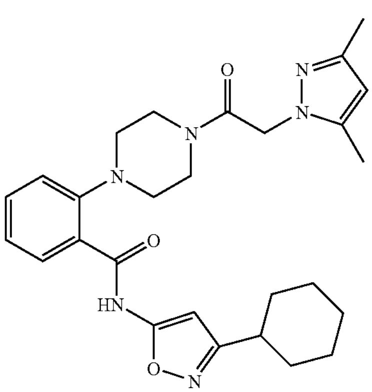 [SMILES: Cc1cc(C)n(CC(=O)N2CCN(c3ccccc3C(=O)Nc3cc(C4CCCCC4)no3)CC2)n1] | N-(3-Cyclohexyl-isoxazol-5-yl)-2-{4-[2-(3,5-dimethyl-pyrazol-1-yl)-acetyl]-piperazin-1-yl}-benzamide |

TABLE 1-continued
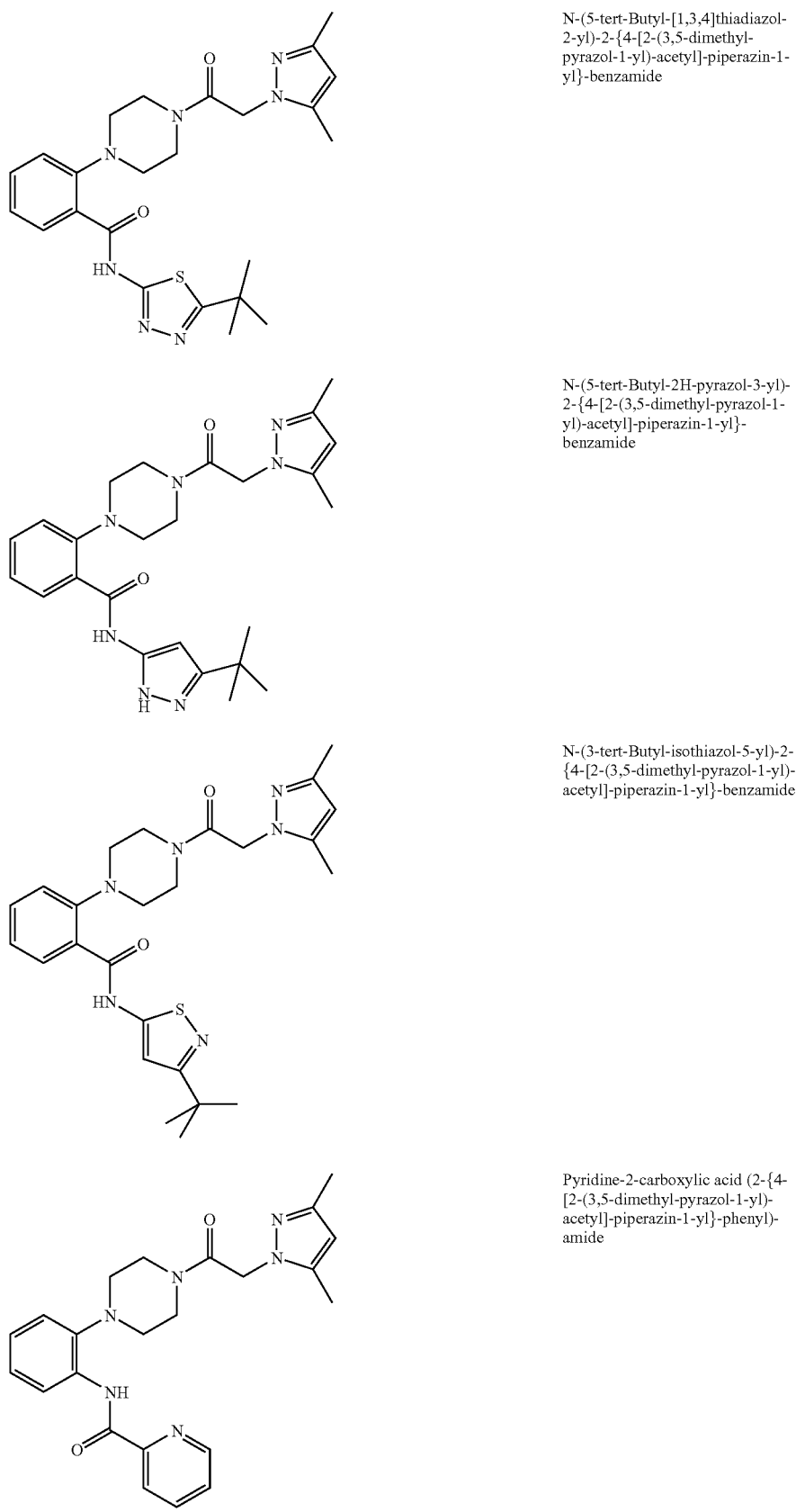
N-(5-tert-Butyl-[1,3,4]thiadiazol-2-yl)-2-{4-[2-(3,5-dimethyl-pyrazol-1-yl)-acetyl]-piperazin-1-yl}-benzamide
N-(5-tert-Butyl-2H-pyrazol-3-yl)-2-{4-[2-(3,5-dimethyl-pyrazol-1-yl)-acetyl]-piperazin-1-yl}-benzamide
N-(3-tert-Butyl-isothiazol-5-yl)-2-{4-[2-(3,5-dimethyl-pyrazol-1-yl)-acetyl]-piperazin-1-yl}-benzamide
Pyridine-2-carboxylic acid (2-{4-[2-(3,5-dimethyl-pyrazol-1-yl)-acetyl]-piperazin-1-yl}-phenyl)-amide TABLE 1-continued
| | |
|---|---|
| 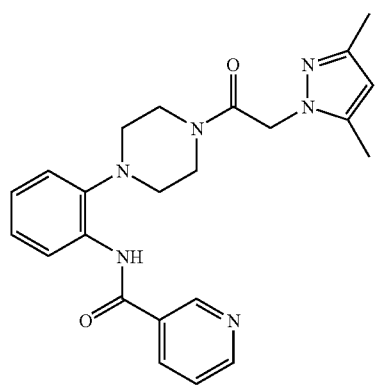 [SMILES: Cc1cc(C)n(CC(=O)N2CCN(c3ccccc3NC(=O)c3cccnc3)CC2)n1] | N-(2-{4-[2-(3,5-Dimethyl-pyrazol-1-yl)-acetyl]-piperazin-1-yl}-phenyl)-nicotinamide |
| 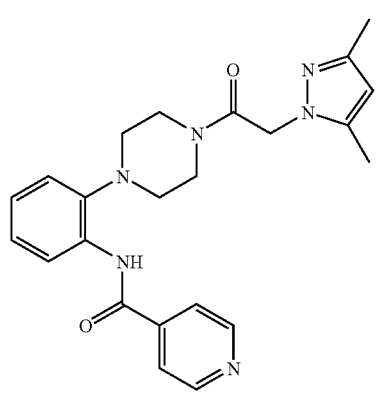 [SMILES: Cc1cc(C)n(CC(=O)N2CCN(c3ccccc3NC(=O)c3ccncc3)CC2)n1] | N-(2-{4-[2-(3,5-Dimethyl-pyrazol-1-yl)-acetyl]-piperazin-1-yl}-phenyl)-isonicotinamide |
| 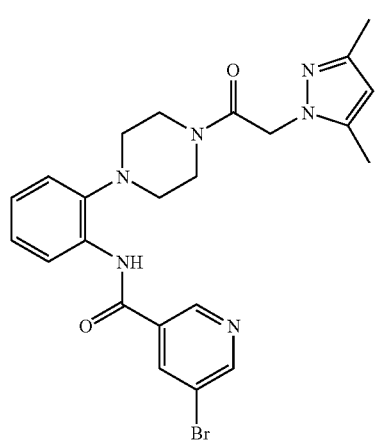 [SMILES: Cc1cc(C)n(CC(=O)N2CCN(c3ccccc3NC(=O)c3cncc(Br)c3)CC2)n1] | 5-Bromo-N-(2-{4-[2-(3,5-dimethyl-pyrazol-1-yl)-acetyl]-piperazin-1-yl}-phenyl)-nicotinamide |
| 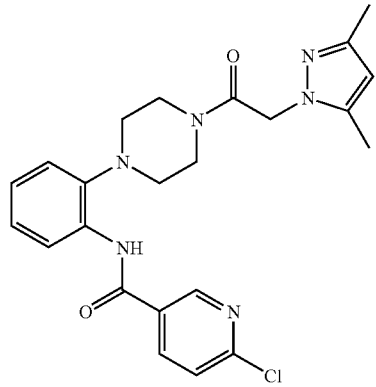 [SMILES: Cc1cc(C)n(CC(=O)N2CCN(c3ccccc3NC(=O)c3ccc(Cl)nc3)CC2)n1] | 6-Chloro-N-(2-{4-[2-(3,5-dimethyl-pyrazol-1-yl)-acetyl]-piperazin-1-yl}-phenyl)-nicotinamide |

TABLE 1-continued
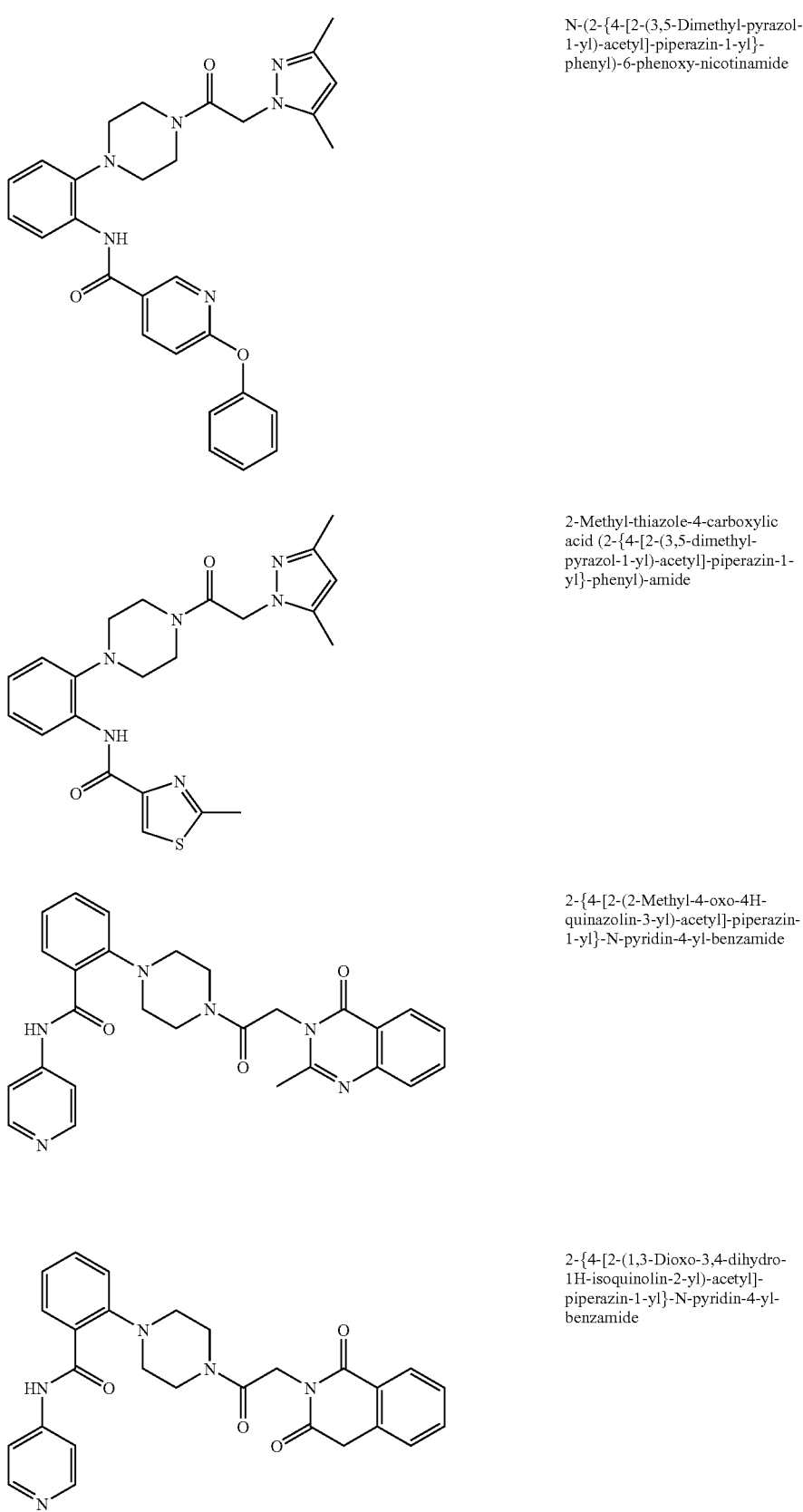
N-(2-{4-[2-(3,5-Dimethyl-pyrazol-1-yl)-acetyl]-piperazin-1-yl}-phenyl)-6-phenoxy-nicotinamide
2-Methyl-thiazole-4-carboxylic acid (2-{4-[2-(3,5-dimethyl-pyrazol-1-yl)-acetyl]-piperazin-1-yl}-phenyl)-amide
2-{4-[2-(2-Methyl-4-oxo-4H-quinazolin-3-yl)-acetyl]-piperazin-1-yl}-N-pyridin-4-yl-benzamide
2-{4-[2-(1,3-Dioxo-3,4-dihydro-1H-isoquinolin-2-yl)-acetyl]-piperazin-1-yl}-N-pyridin-4-yl-benzamide TABLE 1-continued
| | |
|---|---|
| 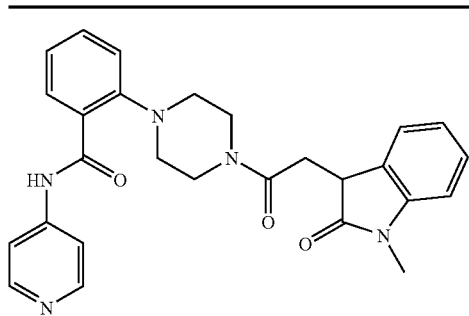 | 2-{4-[2-(1-Methyl-2-oxo-2,3-dihydro-1H-indol-3-yl)-acetyl]-piperazin-1-yl}-N-pyridin-4-yl-benzamide |
| 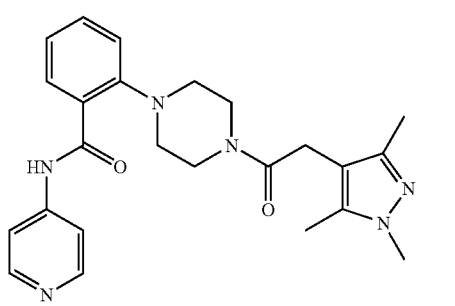 [SMILES: Cc1nn(C)c(C)c1CC(=O)N1CCN(c2ccccc2C(=O)Nc2ccncc2)CC1] | N-Pyridin-4-yl-2-{4-[2-(1,3,5-trimethyl-1H-pyrazol-4-yl)-acetyl]-piperazin-1-yl}-benzamide |
| 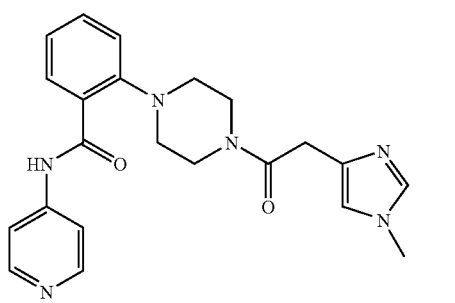 [SMILES: Cn1cnc(CC(=O)N2CCN(c3ccccc3C(=O)Nc3ccncc3)CC2)c1] | 2-{4-[2-(1-Methyl-1H-imidazol-4-yl)-acetyl]-piperazin-1-yl}-N-pyridin-4-yl-benzamide |
| 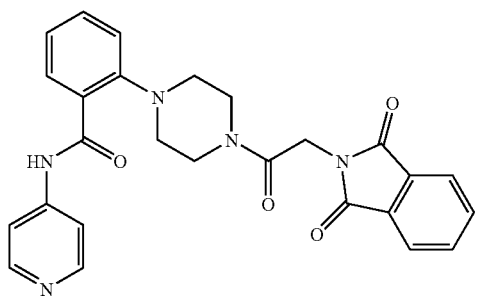 [SMILES: O=C(Nc1ccncc1)c1ccccc1N1CCN(C(=O)CN2C(=O)c3ccccc3C2=O)CC1] | 2-{4-[2-(1,3-Dioxo-1,3-dihydro-isoindol-2-yl)-acetyl]-piperazin-1-yl}-N-pyridin-4-yl-benzamide |
| 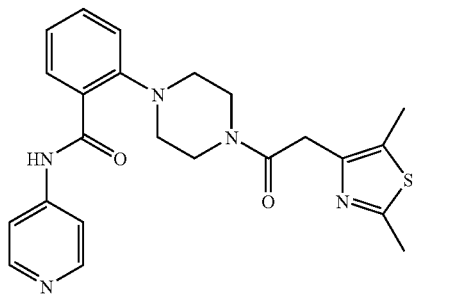 [SMILES: Cc1nc(CC(=O)N2CCN(c3ccccc3C(=O)Nc3ccncc3)CC2)c(C)s1] | 2-{4-[2-(2,5-Dimethyl-thiazol-4-yl)-acetyl]-piperazin-1-yl}-N-pyridin-4-yl-benzamide |

TABLE 1-continued
| | |
|---|---|
| 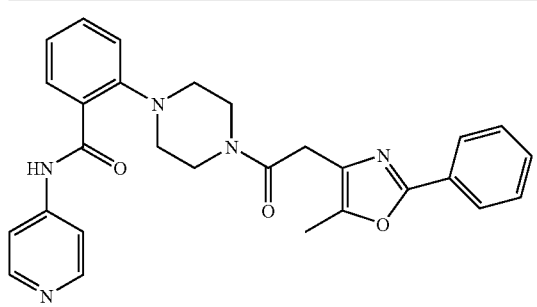 [SMILES: Cc1oc(-c2ccccc2)nc1CC(=O)N1CCN(c2ccccc2C(=O)Nc2ccncc2)CC1] | 2-{4-[2-(5-Methyl-2-phenyl-oxazol-4-yl)-acetyl]-piperazin-1-yl}-N-pyridin-4-yl-benzamide |
| 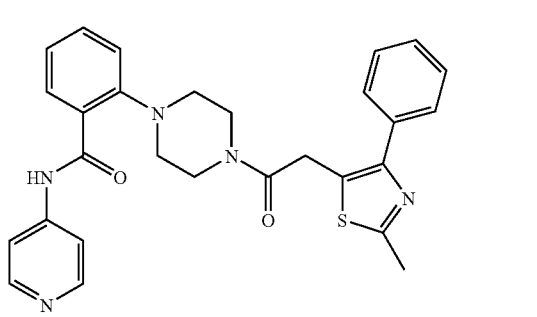 [SMILES: Cc1nc(-c2ccccc2)c(CC(=O)N2CCN(c3ccccc3C(=O)Nc3ccncc3)CC2)s1] | 2-{4-[2-(2-Methyl-4-phenyl-thiazol-5-yl)-acetyl]-piperazin-1-yl}-N-pyridin-4-yl-benzamide |
| 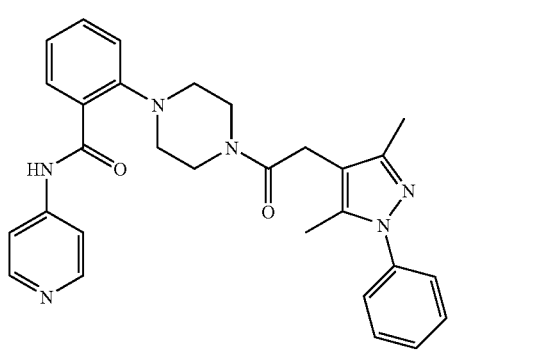 [SMILES: Cc1nn(-c2ccccc2)c(C)c1CC(=O)N1CCN(c2ccccc2C(=O)Nc2ccncc2)CC1] | 2-{4-[2-(3,5-Dimethyl-1-phenyl-1H-pyrazol-4-yl)-acetyl]-piperazin-1-yl}-N-pyridin-4-yl-benzamide |
| 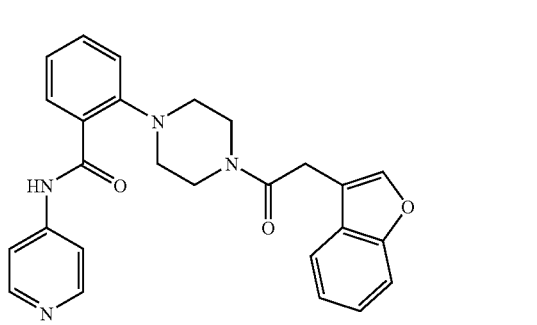 [SMILES: O=C(Nc1ccncc1)c1ccccc1N1CCN(C(=O)Cc2coc3ccccc23)CC1] | 2-[4-(2-Benzofuran-3-yl-acetyl)-piperazin-1-yl]-N-pyridin-4-yl-benzamide |
| 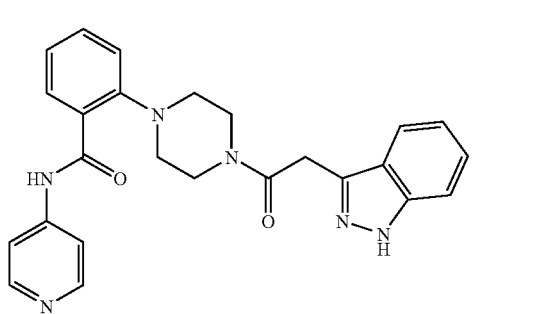 [SMILES: O=C(Nc1ccncc1)c1ccccc1N1CCN(C(=O)Cc2n[nH]c3ccccc23)CC1] | 2-[4-(2-1H-Indazol-3-yl-acetyl)-piperazin-1-yl]-N-pyridin-4-yl-benzamide |

TABLE 1-continued
| | |
|---|---|
| 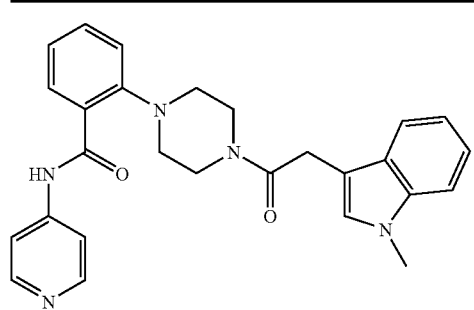 | 2-{4-[2-(1-Methyl-1H-indol-3-yl)-acetyl]-piperazin-1-yl}-N-pyridin-4-yl-benzamide |
| 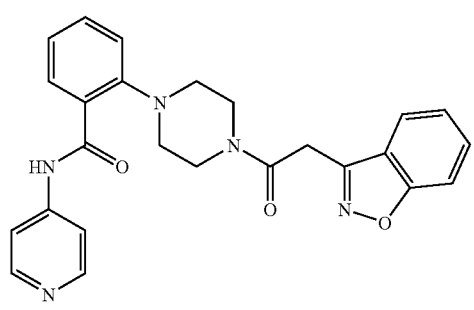 [SMILES: O=C(Nc1ccncc1)c1ccccc1N1CCN(C(=O)Cc2noc3ccccc23)CC1] | 2-[4-(2-Benzo[d]isoxazol-3-yl-acetyl)-piperazin-1-yl]-N-pyridin-4-yl-benzamide |
| 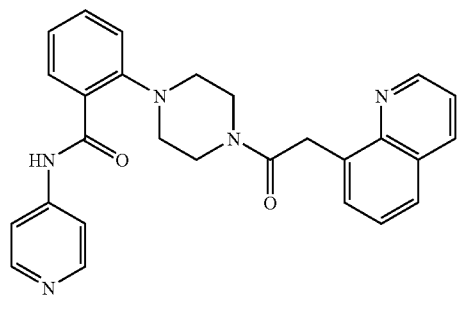 [SMILES: O=C(Nc1ccncc1)c1ccccc1N1CCN(C(=O)Cc2cccc3cccnc23)CC1] | N-Pyridin-4-yl-2-[4-(2-quinolin-8-yl-acetyl)-piperazin-1-yl]-benzamide |
| 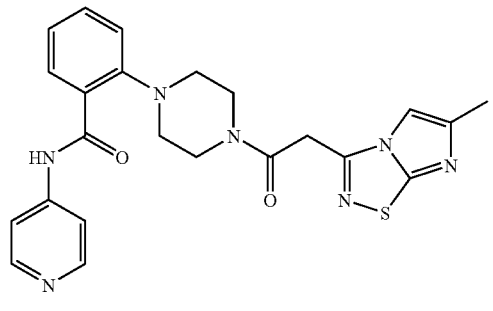 [SMILES: Cc1cn2c(CC(=O)N3CCN(c4ccccc4C(=O)Nc4ccncc4)CC3)nsc2n1] | 2-{4-[2-(6-Methyl-imidazol[2,1-b]thiazol-3-yl)-acetyl]-piperazin-1-yl}-N-pyridin-4-yl-benzamide |
| 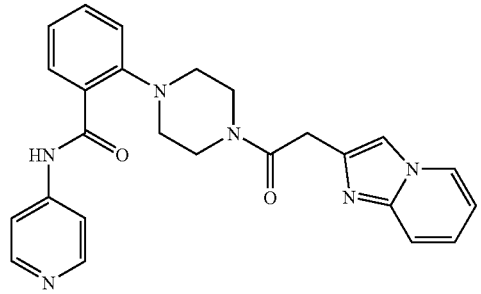 [SMILES: O=C(Nc1ccncc1)c1ccccc1N1CCN(C(=O)Cc2cn3ccccc3n2)CC1] | 2-[4-(2-Imidazo[1,2-a]pyridin-2-yl-acetyl)-piperazin-1-yl]-N-pyridin-4-yl-benzamide |

TABLE 1-continued
| | |
|---|---|
| 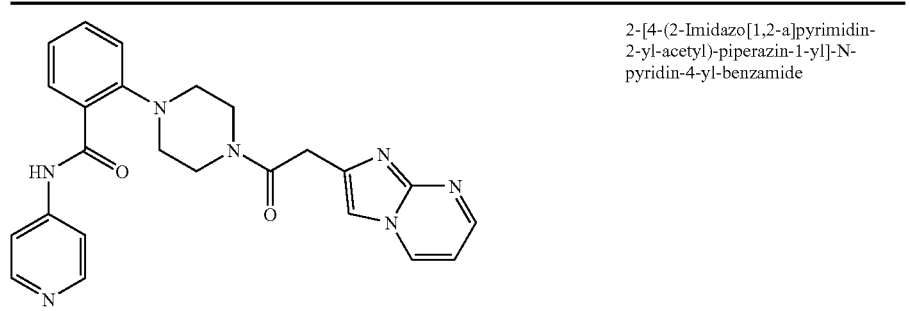 | 2-[4-(2-Imidazo[1,2-a]pyrimidin-2-yl-acetyl)-piperazin-1-yl]-N-pyridin-4-yl-benzamide |
| 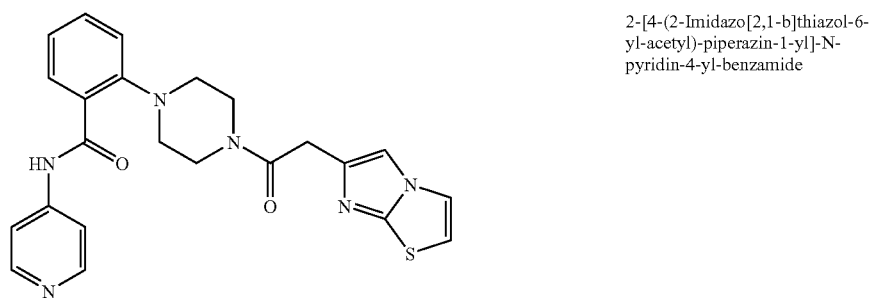 | 2-[4-(2-Imidazo[2,1-b]thiazol-6-yl-acetyl)-piperazin-1-yl]-N-pyridin-4-yl-benzamide |
| 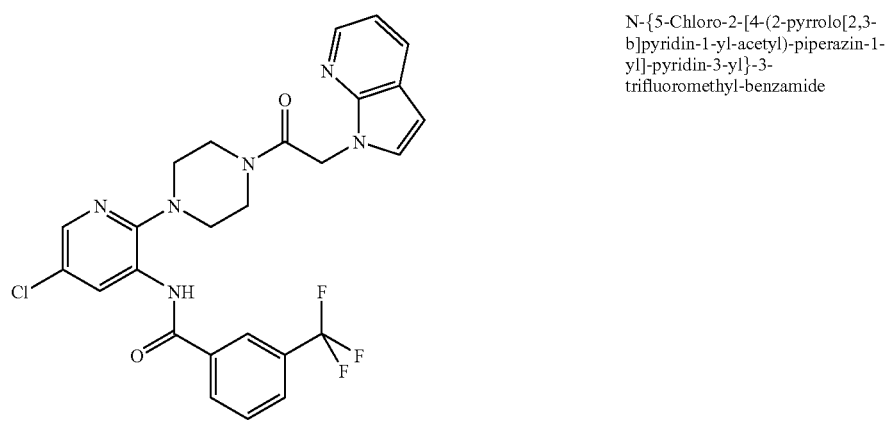 | N-{5-Chloro-2-[4-(2-pyrrolo[2,3-b]pyridin-1-yl-acetyl)-piperazin-1-yl]-pyridin-3-yl}-3-trifluoromethyl-benzamide |
| 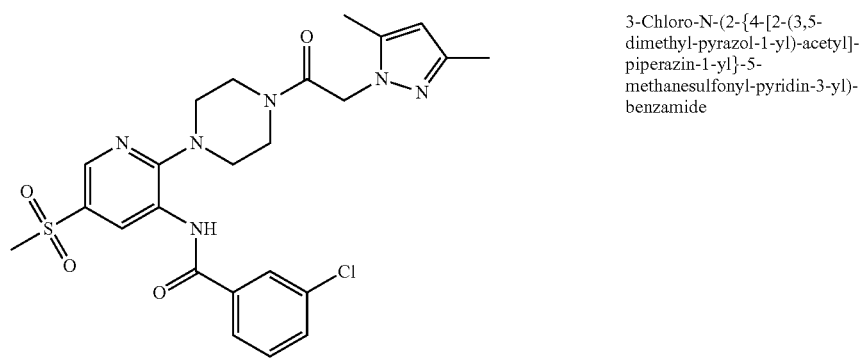 | 3-Chloro-N-(2-{4-[2-(3,5-dimethyl-pyrazol-1-yl)-acetyl]-piperazin-1-yl}-5-methanesulfonyl-pyridin-3-yl)-benzamide |

TABLE 1-continued

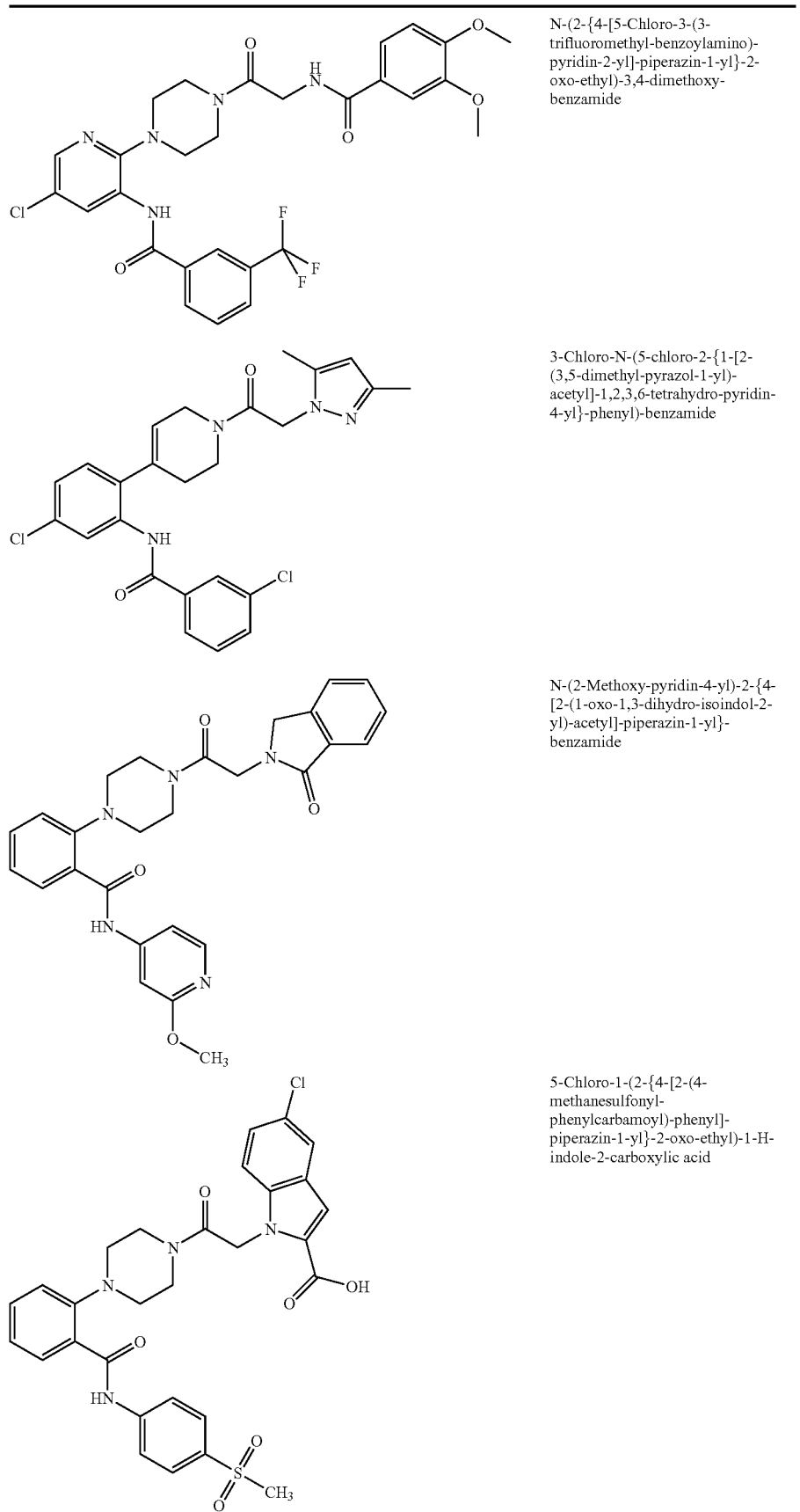

N-(2-{4-[5-Chloro-3-(3-trifluoromethyl-benzoylamino)-pyridin-2-yl]-piperazin-1-yl}-2-oxo-ethyl)-3,4-dimethoxy-benzamide 3-Chloro-N-(5-chloro-2-{1-[2-(3,5-dimethyl-pyrazol-1-yl)-acetyl]-1,2,3,6-tetrahydro-pyridin-4-yl}-phenyl)-benzamide N-(2-Methoxy-pyridin-4-yl)-2-{4-[2-(1-oxo-1,3-dihydro-isoindol-2-yl)-acetyl]-piperazin-1-yl}-benzamide 5-Chloro-1-(2-{4-[2-(4-methanesulfonyl-phenylcarbamoyl)-phenyl]-piperazin-1-yl}-2-oxo-ethyl)-1-H-indole-2-carboxylic acid TABLE 1-continued
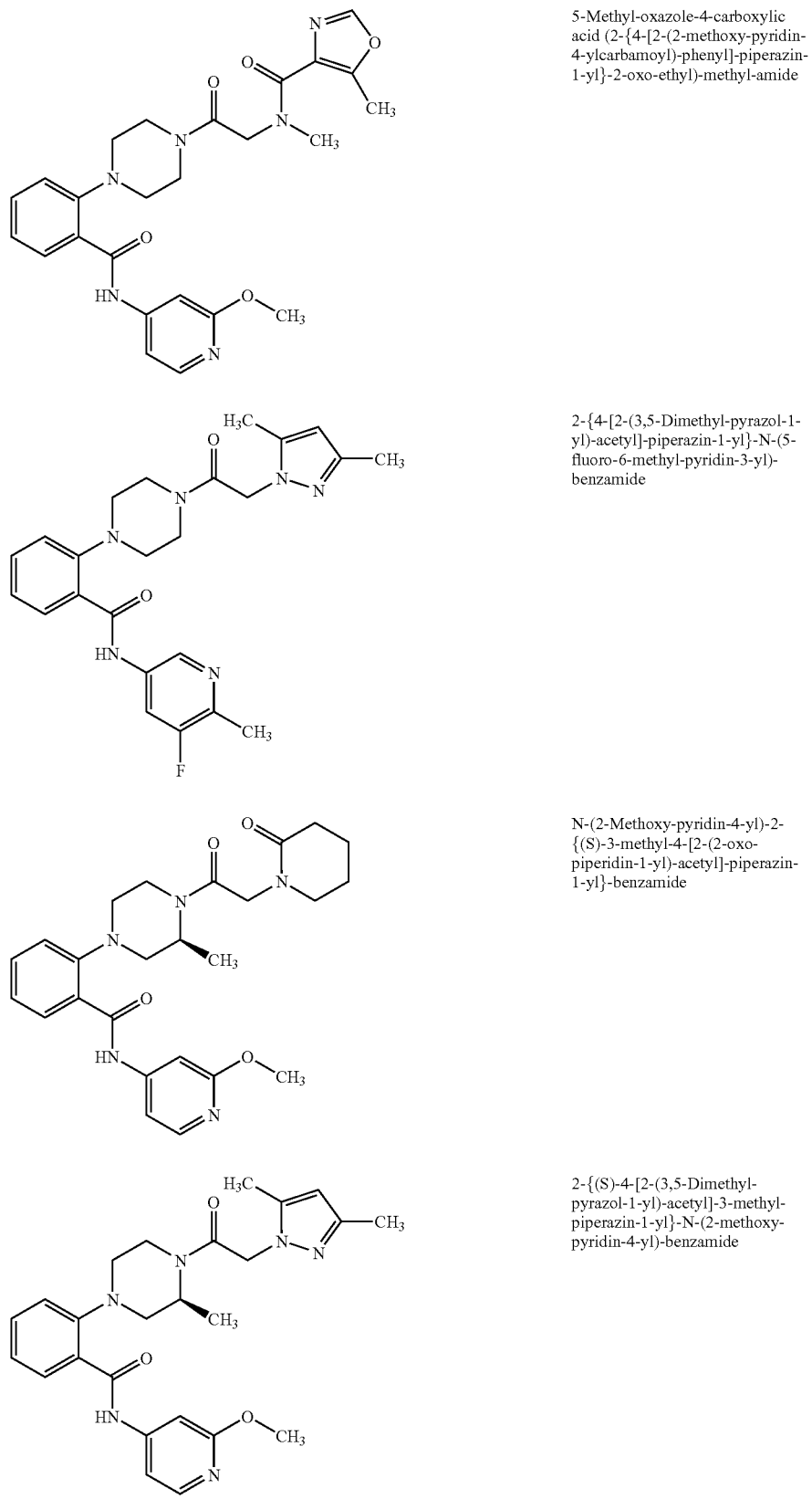
5-Methyl-oxazole-4-carboxylic acid (2-{4-[2-(2-methoxy-pyridin-4-ylcarbamoyl)-phenyl]-piperazin-1-yl}-2-oxo-ethyl)-methyl-amide
2-{4-[2-(3,5-Dimethyl-pyrazol-1-yl)-acetyl]-piperazin-1-yl}-N-(5-fluoro-6-methyl-pyridin-3-yl)-benzamide
N-(2-Methoxy-pyridin-4-yl)-2-{(S)-3-methyl-4-[2-(2-oxo-piperidin-1-yl)-acetyl]-piperazin-1-yl}-benzamide
2-{(S)-4-[2-(3,5-Dimethyl-pyrazol-1-yl)-acetyl]-3-methyl-piperazin-1-yl}-N-(2-methoxy-pyridin-4-yl)-benzamide TABLE 1-continued
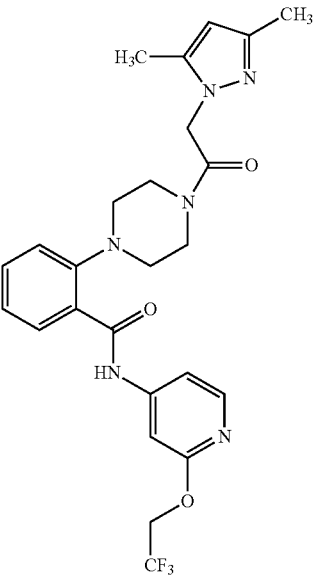 [SMILES: Cc1cc(C)n(CC(=O)N2CCN(c3ccccc3C(=O)Nc3ccnc(OCC(F)(F)F)c3)CC2)n1]
2-{4-[2-(3,5-Dimethyl-pyrazol-1-yl)-acetyl]-piperazin-1-yl}-N-[2-(2,2,2-trifluoro-ethoxy)-pyridin-4-yl]-benzamide
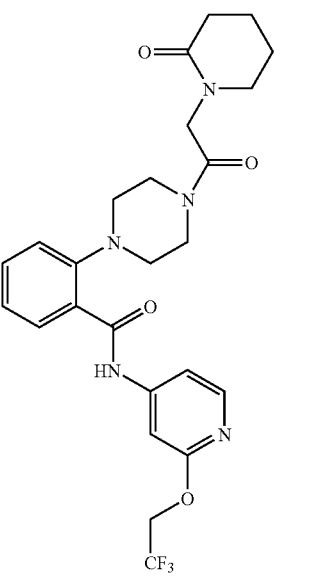 [SMILES: O=C(Nc1ccnc(OCC(F)(F)F)c1)c1ccccc1N1CCN(C(=O)CN2CCCCC2=O)CC1]
2-{4-[2-(2-Oxo-piperidin-1-yl)-acetyl]-piperazin-1-yl}-N-[2-(2,2,2-trifluoro-ethoxy)-pyridin-4-yl]-benzamide
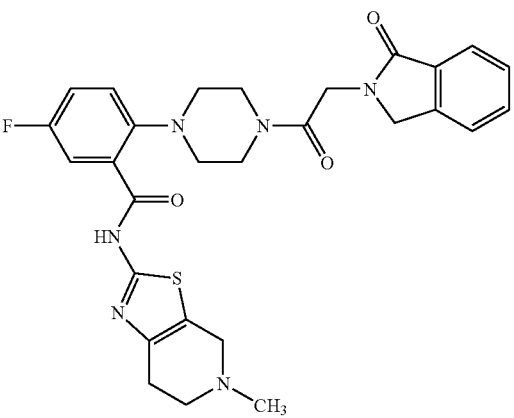 [SMILES: CN1CCc2nc(NC(=O)c3cc(F)ccc3N3CCN(C(=O)CN4Cc5ccccc5C4=O)CC3)sc2C1]
5-Fluoro-N-(5-methyl-4,5,6,7-tetrahydro-thiazolo[5,4-c]pyridin-2-yl)-2-{4-[2-(1-oxo-1,3-dihydro-isoindol-2-yl)-acetyl]-piperazin-1-yl}-benzamide TABLE 1-continued

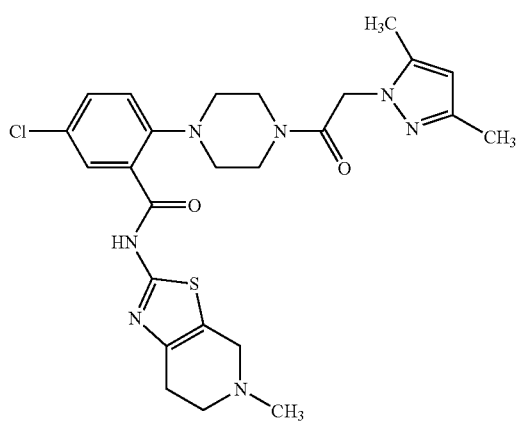 [SMILES: Cc1cc(C)n(CC(=O)N2CCN(c3ccc(Cl)cc3C(=O)Nc3nc4c(s3)CN(C)CC4)CC2)n1]

5-Chloro-2-{4-[2-(3,5-dimethyl-pyrazol-1-yl)-acetyl]-piperazin-1-yl}-N-(5-methyl-4,5,6,7-tetrahydro-thiazolo[5,4-c]pyridin-2-yl)-benzamide

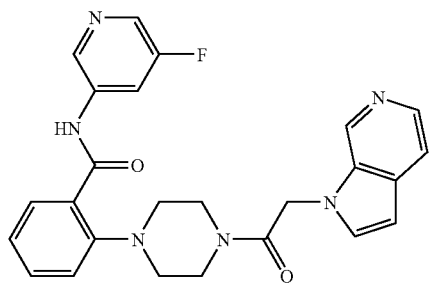 [SMILES: O=C(Nc1cncc(F)c1)c1ccccc1N1CCN(C(=O)Cn2ccc3ccncc32)CC1]

N-(5-Fluoro-pyridin-3-yl)-2-[4-(2-pyrrolo[2,3-c]pyridin-1-yl-acetyl)-piperazin-1-yl]-benzamide

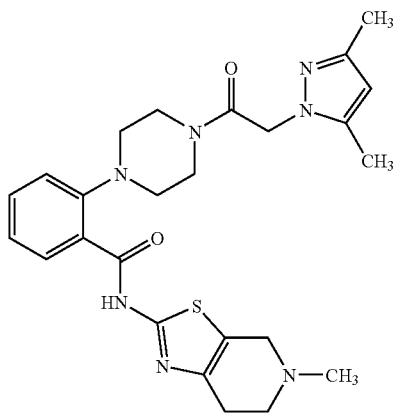 [SMILES: Cc1cc(C)n(CC(=O)N2CCN(c3ccccc3C(=O)Nc3nc4c(s3)CN(C)CC4)CC2)n1]

2-{4-[2-(3,5-Dimethyl-pyrazol-1-yl)-acetyl]-piperazin-1-yl}-N-(5-methyl-4,5,6,7-tetrahydro-thiazolo[5,4-c]pyridin-2-yl)-benzamide

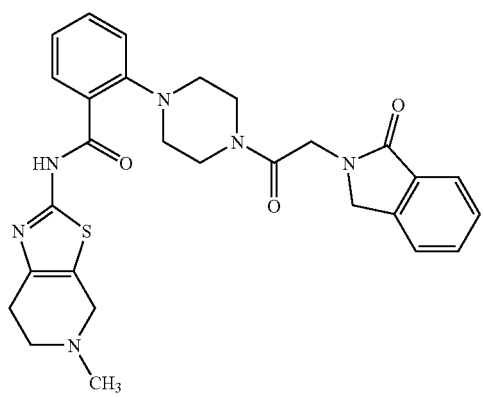 [SMILES: CN1CCc2nc(NC(=O)c3ccccc3N3CCN(C(=O)CN4Cc5ccccc5C4=O)CC3)sc2C1]

N-(5-Methyl-4,5,6,7-tetrahydro-thiazolo[5,4-c]pyridin-2-yl)-2-{4-[2-(1-oxo-1,3-dihydro-isoindol-2-yl)-acetyl]-piperazin-1-yl}-benzamide TABLE 1-continued
| | |
|---|---|
| 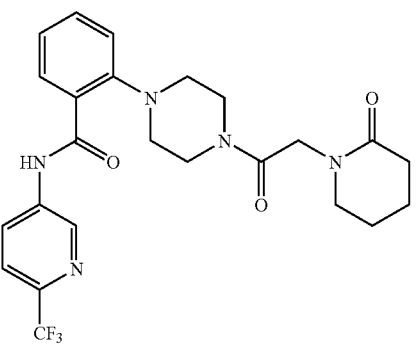 [SMILES: O=C(Nc1ccc(C(F)(F)F)nc1)c1ccccc1N1CCN(C(=O)CN2CCCCC2=O)CC1] | 2-{4-[2-(2-Oxo-piperidin-1-yl)-acetyl]-piperazin-1-yl}-N-(6-trifluoromethyl-pyridin-3-yl)-benzamide |
| 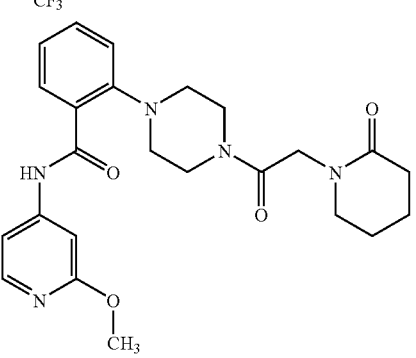 | N-(2-Methoxy-pyridin-4-yl)-2-{4-[2-(2-oxo-piperidin-1-yl)-acetyl]-piperazin-1-yl}-benzamide |
| 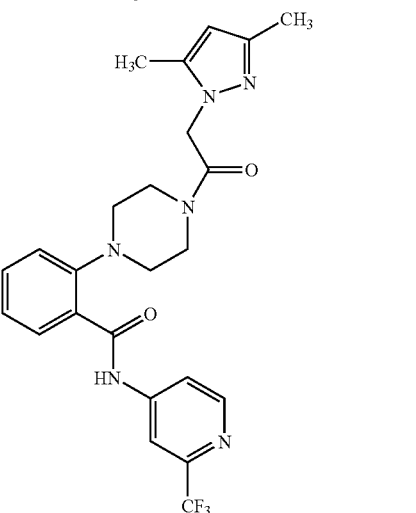 [SMILES: Cc1cc(C)n(CC(=O)N2CCN(c3ccccc3C(=O)Nc3ccnc(C(F)(F)F)c3)CC2)n1] | 2-{4-[2-(3,5-Dimethyl-pyrazol-1-yl)-acetyl]-piperazin-1-yl}-N-(2-trifluoromethyl-pyridin-4-yl)-benzamide |
| 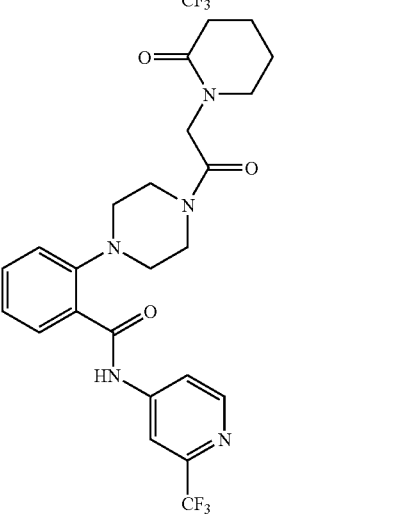 | 2-{4-[2-(2-Oxo-piperidin-1-yl)-acetyl]-piperazin-1-yl}-N-(2-trifluoromethyl-pyridin-4-yl)-benzamide |

TABLE 1-continued

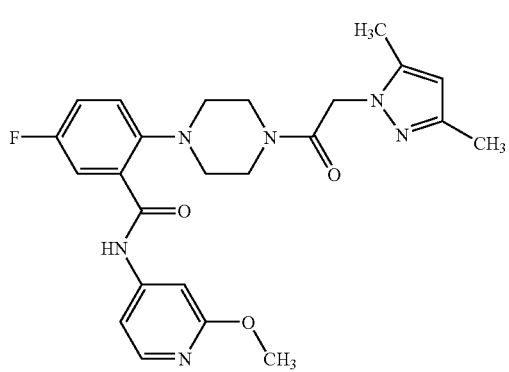 [SMILES: COc1cc(NC(=O)c2cc(F)ccc2N2CCN(C(=O)Cn3nc(C)cc3C)CC2)ccn1]

2-{4-[2-(3,5-Dimethyl-pyrazol-1-yl)-acetyl]-piperazin-1-yl}-5-fluoro-N-(2-methoxy-pyridin-4-yl)-benzamide

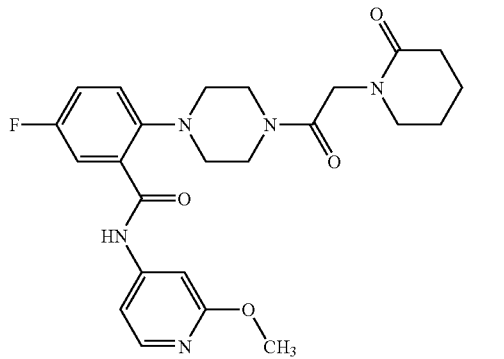 [SMILES: COc1cc(NC(=O)c2cc(F)ccc2N2CCN(C(=O)CN3CCCCC3=O)CC2)ccn1]

5-Fluoro-N-(2-methoxy-pyridin-4-yl)-2-{4-[2-(2-oxo-piperidin-1-yl)-acetyl]-piperazin-1-yl}-benzamide

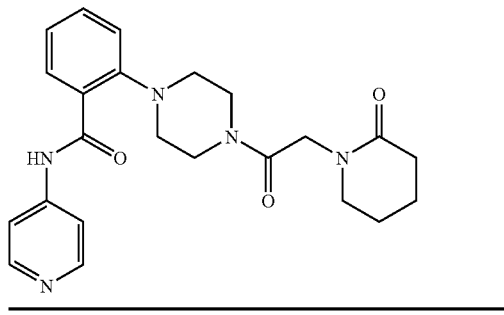

2-{4-[2-(2-Oxo-piperidin-1-yl)-acetyl]-piperazin-1-yl}-N-pyridin-4-yl-benzamide

In one embodiment, the invention relates to a compound selected from compounds described in Table 1, or the pharmaceutically acceptable salts thereof.

In another embodiment the invention relates to a compound selected from:

2-{4-[2-(3,5-Dimethyl-pyrazol-1-yl)-acetyl]-piperazin-1-yl}-N-phenyl-benzamide;
2-{4-[2-(3,5-Dimethyl-pyrazol-1-yl)-acetyl]-piperazin-1-yl}-N-(3-trifluoromethyl-phenyl)-benzamide;
2-{4-[2-(3,5-Dimethyl-pyrazol-1-yl)-acetyl]-piperazin-1-yl}-N-(4-trifluoromethyl-phenyl)-benzamide;
2-{4-[2-(3,5-Dimethyl-pyrazol-1-yl)-acetyl]-piperazin-1-yl}-N-(3-methoxy-phenyl)-benzamide;
2-{4-[2-(3,5-Dimethyl-pyrazol-1-yl)-acetyl]-piperazin-1-yl}-N-(3-trifluoromethoxy-phenyl)-benzamide;
N-(3-Cyano-phenyl)-2-{4-[2-(3,5-dimethyl-pyrazol-1-yl)-acetyl]-piperazin-1-yl}-benzamide;
N-(3-Chloro-phenyl)-2-{4-[2-(3,5-dimethyl-pyrazol-1-yl)-acetyl]-piperazin-1-yl}-benzamide;
2-{4-[2-(3,5-Dimethyl-pyrazol-1-yl)-acetyl]-piperazin-1-yl}-N-pyridin-3-yl-benzamide;
N-(6-Cyano-pyridin-3-yl)-2-{4-[2-(3,5-dimethyl-pyrazol-1-yl)-acetyl]-piperazin-1-yl}-benzamide;
2-{4-[2-(3,5-Dimethyl-pyrazol-1-yl)-acetyl]-piperazin-1-yl}-N-thiazol-2-yl-benzamide;
N-Benzothiazol-2-yl-2-{4-[2-(3,5-dimethyl-pyrazol-1-yl)-acetyl]-piperazin-1-yl}-benzamide;
2-{4-[2-(3,5-Dimethyl-pyrazol-1-yl)-acetyl]-piperazin-1-yl}-N-(2-fluoro-phenyl)-benzamide;
2-{4-[2-(2,4-Dimethyl-imidazol-1-yl)-acetyl]-piperazin-1-yl}-N-phenyl-benzamide;
N-Phenyl-2-[4-(2-pyrrolo[2,3-b]pyridin-1-yl-acetyl)-piperazin-1-yl]-benzamide;
N-(2-{4-[2-(3,5-Dimethyl-pyrazol-1-yl)-acetyl]-piperazin-1-yl}-phenyl)-benzamide;
3-Chloro-N-(2-{4-[2-(3,5-dimethyl-pyrazol-1-yl)-acetyl]-piperazin-1-yl}-phenyl)-benzamide;
N-(2-{4-[2-(3,5-Dimethyl-pyrazol-1-yl)-acetyl]-piperazin-1-yl}-phenyl)-3-trifluoromethyl-benzamide;
4-Chloro-N-(2-{4-[2-(3,5-dimethyl-pyrazol-1-yl)-acetyl]-piperazin-1-yl}-phenyl)-benzamide;
2-{4-[2-(3,5-Dimethyl-pyrazol-1-yl)-acetyl]-piperazin-1-yl}-N-pyridin-4-yl-benzamide;
2-{4-[2-(3,5-Dimethyl-pyrazol-1-yl)-acetyl]-piperazin-1-yl}-N-(6-methyl-pyridin-3-yl)-benzamide;

N-(6-Chloro-pyridin-3-yl)-2-{4-[2-(3,5-dimethyl-pyrazol-1-yl)-acetyl]-piperazin-1-yl}-benzamide;
N-(6-Acetylamino-pyridin-3-yl)-2-{4-[2-(3,5-dimethyl-pyrazol-1-yl)-acetyl]-piperazin-1-yl}-benzamide;
2-{4-[2-(3,5-Dimethyl-pyrazol-1-yl)-acetyl]-piperazin-1-yl}-N-(6-methoxy-pyridin-3-yl)-benzamide;
2-{4-[2-(3,5-Dimethyl-pyrazol-1-yl)-acetyl]-piperazin-1-yl}-N-quinolin-3-yl-benzamide;
N-Pyridin-3-yl-2-[4-(2-pyrrolo[2,3-b]pyridin-1-yl-acetyl)-piperazin-1-yl]-benzamide;
2-{4-[2-(3,5-Dimethyl-pyrazol-1-yl)-acetyl]-piperazin-1-yl}-N-(5-fluoro-pyridin-3-yl)-benzamide;
2-{4-[2-(3,5-Dimethyl-pyrazol-1-yl)-acetyl]-piperazin-1-yl}-N-(5-hydroxy-pyridin-3-yl)-benzamide;
2-{4-[2-(3,5-Dimethyl-pyrazol-1-yl)-acetyl]-piperazin-1-yl}-N-(6-trifluoromethyl-pyridin-3-yl)-benzamide;
N-(6-Bromo-pyridin-3-yl)-2-{4-[2-(3,5-dimethyl-pyrazol-1-yl)-acetyl]-piperazin-1-yl}-benzamide;
2-{4-[2-(3,5-Dimethyl-pyrazol-1-yl)-acetyl]-piperazin-1-yl}-N-(6-phenoxy-pyridin-3-yl)-benzamide;
N-(2-tert-Butyl-pyridin-4-yl)-2-{4-[2-(3,5-dimethyl-pyrazol-1-yl)-acetyl]-piperazin-1-yl}-benzamide;
N-(2-Chloro-pyridin-4-yl)-2-{4-[2-(3,5-dimethyl-pyrazol-1-yl)-acetyl]-piperazin-1-yl}-benzamide;
N-(2-Bromo-pyridin-4-yl)-2-{4-[2-(3,5-dimethyl-pyrazol-1-yl)-acetyl]-piperazin-1-yl}-benzamide;
2-{4-[2-(3,5-Dimethyl-pyrazol-1-yl)-acetyl]-piperazin-1-yl}-N-(2-methyl-pyridin-4-yl)-benzamide;
2-{4-[2-(3,5-Dimethyl-pyrazol-1-yl)-acetyl]-piperazin-1-yl}-N-(3-fluoro-pyridin-4-yl)-benzamide;
2-{4-[2-(3,5-Dimethyl-pyrazol-1-yl)-acetyl]-piperazin-1-yl}-N-quinolin-6-yl-benzamide;
2-{4-[2-(3,5-Dimethyl-pyrazol-1-yl)-acetyl]-piperazin-1-yl}-N-isoquinolin-6-yl-benzamide;
2-{4-[2-(3,5-Dimethyl-pyrazol-1-yl)-acetyl]-piperazin-1-yl}-N-(2-methyl-benzothiazol-6-yl)-benzamide;
2-{4-[2-(3,5-Dimethyl-pyrazol-1-yl)-acetyl]-piperazin-1-yl}-N-(2-methyl-benzooxazol-5-yl)-benzamide;
2-{4-[2-(3,5-Dimethyl-pyrazol-1-yl)-acetyl]-piperazin-1-yl}-N-(3-dimethylsulfamoyl-phenyl)-benzamide;
2-{4-[2-(3,5-Dimethyl-pyrazol-1-yl)-acetyl]-piperazin-1-yl}-N-(3-methanesulfonyl-phenyl)-benzamide;
2-{4-[2-(3,5-Dimethyl-pyrazol-1-yl)-acetyl]-piperazin-1-yl}-N-(4-methanesulfonyl-phenyl)-benzamide;
N-Pyridin-4-yl-2-[4-(2-pyrrolo[2,3-b]pyridin-1-yl-acetyl)-piperazin-1-yl]-benzamide;
N-(6-Cyano-pyridin-3-yl)-2-[4-(2-pyrrolo[2,3-b]pyridin-1-yl-acetyl)-piperazin-1-yl]-benzamide;
2-[4-(2-Pyrrolo[2,3-b]pyridin-1-yl-acetyl)-piperazin-1-yl]-N-(6-trifluoromethyl-pyridin-3-yl)-benzamide;
N-(6-Methyl-pyridin-3-yl)-2-[4-(2-pyrrolo[2,3-b]pyridin-1-yl-acetyl)-piperazin-1-yl]-benzamide;
N-(6-Methoxy-pyridin-3-yl)-2-[4-(2-pyrrolo[2,3-b]pyridin-1-yl-acetyl)-piperazin-1-yl]-benzamide;
2-[4-(2-Pyrrolo[2,3-b]pyridin-1-yl-acetyl)-piperazin-1-yl]-N-quinolin-3-yl-benzamide;
3,4-Dimethoxy-N-(2-oxo-2-{4-[2-(pyridin-4-ylcarbamoyl)-phenyl]-piperazin-1-yl}-ethyl)-benzamide;
4-Methoxy-N-(2-oxo-2-{4-[2-(pyridin-4-ylcarbamoyl)-phenyl]-piperazin-1-yl}-ethyl)-benzamide;
1-Methyl-1H-pyrrole-2-carboxylic acid (2-oxo-2-{4-[2-(pyridin-4-ylcarbamoyl)-phenyl]-piperazin-1-yl}-ethyl)-amide;
2,3-Dimethoxy-N-(2-oxo-2-{4-[2-(pyridin-4-ylcarbamoyl)-phenyl]-piperazin-1-yl}-ethyl)-benzamide;
3-Fluoro-4-methoxy-N-(2-oxo-2-{4-[2-(pyridin-4-ylcarbamoyl)-phenyl]-piperazin-1-yl}-ethyl)-benzamide;
2,5-Dimethyl-2H-pyrazole-3-carboxylic acid (2-oxo-2-{4-[2-(pyridin-4-ylcarbamoyl)-phenyl]-piperazin-1-yl}-ethyl)-amide;
2-[4-(2-2,3-Dihydro-pyrrolo[2,3-b]pyridin-1-yl-acetyl)-piperazin-1-yl]-N-pyridin-4-yl-benzamide;
2-[4-(2-2,3-Dihydro-pyrrolo[2,3-b]pyridin-1-yl-acetyl)-piperazin-1-yl]-N-pyridin-3-yl-benzamide;
2-[4-(2-Phenylamino-acetyl)-piperazin-1-yl]-N-pyridin-4-yl-benzamide;
2-{4-[2-(3,5-Dimethyl-pyrazol-1-yl)-acetyl]-piperazin-1-yl}-N-pyridazin-4-yl-benzamide;
2-{4-[2-(3,5-Dimethyl-pyrazol-1-yl)-acetyl]-piperazin-1-yl}-N-(5-methyl-pyridin-3-yl)-benzamide;
2-{4-[2-(3,5-Dimethyl-pyrazol-1-yl)-acetyl]-piperazin-1-yl}-N-(6-phenyl-pyridin-3-yl)-benzamide;
2-{4-[2-(3,5-Dimethyl-pyrazol-1-yl)-acetyl]-piperazin-1-yl}-N-(6-morpholin-4-yl-pyridin-3-yl)-benzamide;
2-{4-[2-(3,5-Dimethyl-pyrazol-1-yl)-acetyl]-piperazin-1-yl}-N-(2-methoxy-pyridin-4-yl)-benzamide;
2-{4-[2-(3,5-Dimethyl-pyrazol-1-yl)-acetyl]-piperazin-1-yl}-N-[2-(4-methyl-piperazin-1-yl)-pyridin-4-yl]-benzamide;
2-{4-[2-(3,5-Dimethyl-pyrazol-1-yl)-acetyl]-piperazin-1-yl}-N-(1-isopropyl-1H-pyrazolo[3,4-b]pyridin-5-yl)-benzamide;
N-(1,3-Dimethyl-1H-pyrazolo[3,4-b]pyridin-5-yl)-2-{4-[2-(3,5-dimethyl-pyrazol-1-yl)-acetyl]-piperazin-1-yl}-benzamide;
2-{4-[2-(3-Methyl-2-oxo-2,3-dihydro-benzoimidazol-1-yl)-acetyl]-piperazin-1-yl}-N-pyridin-4-yl-benzamide;
2-{4-[2-(3,5-Dimethyl-pyrazol-1-yl)-acetyl]-piperazin-1-yl}-N-(4-methyl-thiazol-2-yl)-benzamide;
2-{4-[2-(3,5-Dimethyl-pyrazol-1-yl)-acetyl]-piperazin-1-yl}-N-(5-methyl-thiazol-2-yl)-benzamide;
N-(4-tert-Butyl-thiazol-2-yl)-2-{4-[2-(3,5-dimethyl-pyrazol-1-yl)-acetyl]-piperazin-1-yl}-benzamide;
N-(5-tert-Butyl-4-methyl-thiazol-2-yl)-2-{4-[2-(3,5-dimethyl-pyrazol-1-yl)-acetyl]-piperazin-1-yl}-benzamide;
2-{4-[2-(3,5-Dimethyl-pyrazol-1-yl)-acetyl]-piperazin-1-yl}-N-(4-pyridin-3-yl-thiazol-2-yl)-benzamide;
N-(5-Chloro-benzothiazol-2-yl)-2-{4-[2-(3,5-dimethyl-pyrazol-1-yl)-acetyl]-piperazin-1-yl}-benzamide;
2-{4-[2-(3,5-Dimethyl-pyrazol-1-yl)-acetyl]-piperazin-1-yl}-N-(4,5,6,7-tetrahydro-benzothiazol-2-yl)-benzamide;
N-(6,7-Dihydro-4H-pyrano[4,3-d]thiazol-2-yl)-2-{4-[2-(3,5-dimethyl-pyrazol-1-yl)-acetyl]-piperazin-1-yl}-benzamide;
4-Methoxy-N-(2-oxo-2-{4-[2-(pyridin-3-ylcarbamoyl)-phenyl]-piperazin-1-yl}-ethyl)-benzamide;
2,3-Dimethoxy-N-(2-oxo-2-{4-[2-(pyridin-3-ylcarbamoyl)-phenyl]-piperazin-1-yl}-ethyl)-benzamide;
3,4-Dimethoxy-N-{2-oxo-2-[4-(2-phenylcarbamoyl-phenyl)-piperazin-1-yl]-ethyl}-benzamide;
3-Fluoro-4-methoxy-N-(2-oxo-2-{4-[2-(pyridin-3-ylcarbamoyl)-phenyl]-piperazin-1-yl}-ethyl)-benzamide;
Benzo[1,3]dioxole-5-carboxylic acid (2-oxo-2-{4-[2-(pyridin-3-ylcarbamoyl)-phenyl]-piperazin-1-yl}-ethyl)-amide;
1,5-Dimethyl-1H-pyrazole-3-carboxylic acid (2-oxo-2-{4-[2-(pyridin-3-ylcarbamoyl)-phenyl]-piperazin-1-yl}-ethyl)-amide;
4-Methoxy-3-methyl-N-(2-oxo-2-{4-[2-(pyridin-3-ylcarbamoyl)-phenyl]-piperazin-1-yl}-ethyl)-benzamide;
4-Difluormethoxy-N-(2-oxo-2-{4-[2-(pyridin-3-ylcarbamoyl)-phenyl]-piperazin-1-yl}-ethyl)-benzamide;

2-Ethyl-5-methyl-2H-pyrazole-3-carboxylic acid (2-oxo-2-{4-[2-(pyridin-3-ylcarbamoyl)-phenyl]-piperazin-1-yl}-ethyl)-amide;

1-Methyl-1H-pyrrole-2-carboxylic acid (2-oxo-2-{4-[2-(pyridin-3-ylcarbamoyl)-phenyl]-piperazin-1-yl}-ethyl)-amide;

2,4-Dimethyl-thiazole-5-carboxylic acid (2-oxo-2-{4-[2-(pyridin-3-ylcarbamoyl)-phenyl]-piperazin-1-yl}-ethyl)-amide;

2-[4-(2-Benzoylamino-acetyl)-piperazin-1-yl]-N-pyridin-3-yl-benzamide;

2-{4-[2-(1-Oxo-1,3-dihydro-isoindol-2-yl)-acetyl]-piperazin-1-yl}-N-pyridin-4-yl-benzamide;

N-Pyridin-4-yl-2-{4-[2-(1,1,3-trioxo-1,3-dihydro-1l6-benzo[d]isothiazol-2-yl)-acetyl]-piperazin-1-yl}-benzamide;

2-{4-[2-(Benzoyl-methyl-amino)-acetyl]-piperazin-1-yl}-N-pyridin-4-yl-benzamide;

2-{4-[2-(2,4-Dimethyl-thiazol-5-yl)-acetyl]-piperazin-1-yl}-N-pyridin-4-yl-benzamide;

2-{4-[2-(4-Methyl-1-oxo-1H-phthalazin-2-yl)-acetyl]-piperazin-1-yl}-N-pyridin-4-yl-benzamide;

2-{4-[2-(1-Oxo-1H-phthalazin-2-yl)-acetyl]-piperazin-1-yl}-N-pyridin-4-yl-benzamide;

2-{4-[2-(4-Oxo-4H-quinazolin-3-yl)-acetyl]-piperazin-1-yl}-N-pyridin-4-yl-benzamide;

4-Methoxy-N-methyl-N-(2-oxo-2-{4-[2-(pyridin-4-ylcarbamoyl)-phenyl]-piperazin-1-yl}-ethyl)-benzamide;

2,3-Dimethoxy-N-methyl-N-(2-oxo-2-{4-[2-(pyridin-4-ylcarbamoyl)-phenyl]-piperazin-1-yl}-ethyl)-benzamide;

3-Fluoro-4-methoxy-N-methyl-N-(2-oxo-2-{4-[2-(pyridin-4-ylcarbamoyl)-phenyl]-piperazin-1-yl}-ethyl)-benzamide;

1-Methyl-1H-pyrrole-2-carboxylic acid methyl-(2-oxo-2-{4-[2-(pyridin-4-ylcarbamoyl)-phenyl]-piperazin-1-yl}-ethyl)-amide;

N-(5-Chloro-2-{4-[2-(3,5-dimethyl-pyrazol-1-yl)-acetyl]-piperazin-1-yl}-pyridin-3-yl)-3-trifluoromethyl-benzamide;

N-(5-Chloro-2-{4-[2-(4-chloro-3,5-dimethyl-2H-pyrrol-2-yl)-acetyl]-piperazin-1-yl}-pyridin-3-yl)-3-trifluoromethyl-benzamide;

3-Chloro-N-(5-chloro-2-{4-[2-(3,5-dimethyl-pyrazol-1-yl)-acetyl]-[1,4]diazepan-1-yl}-pyridin-3-yl)-benzamide;

3-Chloro-N-(5-chloro-2-{4-[2-(4-chloro-3,5-dimethyl-pyrazol-1-yl)-acetyl]-[1,4]diazepan-1-yl}-pyridin-3-yl)-benzamide;

3-Chloro-N-{5-chloro-2-[4-(2-piperidin-1-yl-acetyl)-[1,4]diazepan-1-yl]-pyridin-3-yl}-benzamide;

N-(5-Chloro-2-{1-[2-(3,5-dimethyl-pyrazol-1-yl)-acetyl]-piperidin-4-yl}-phenyl)-benzamide;

N-(5-Chloro-2-{4-[2-(3,5-dimethyl-pyrazol-1-yl)-acetyl]-piperazin-1-yl}-pyridin-3-yl)-isonicotinamide;

3-Chloro-N-(5-chloro-2-{4-[2-(3,5-dimethyl-pyrazol-1-yl)-acetyl]-piperazin-1-yl}-pyridin-3-yl)-benzamide;

3-Chloro-N-(5-chloro-2-{4-[2-(2-oxo-piperidin-1-yl)-acetyl]-piperazin-1-yl}-pyridin-3-yl)-benzamide;

N-(5-Chloro-2-{4-[2-(3,5-dimethyl-pyrazol-1-yl)-acetyl]-piperazin-1-yl}-pyridin-3-yl)-4-methanesulfonyl-benzamide;

N-(5-Chloro-2-{4-[2-(3,5-dimethyl-pyrazol-1-yl)-acetyl]-piperazin-1-yl}-pyridin-3-yl)-3-methanesulfonyl-benzamide;

N-(5-Chloro-2-{4-[2-(3,5-dimethyl-pyrazol-1-yl)-acetyl]-piperazin-1-yl}-pyridin-3-yl)-3-cyano-benzamide;

2-{4-[2-(3,5-Dimethyl-pyrazol-1-yl)-acetyl]-piperazin-1-yl}-N-(4-trifluoromethyl-thiazol-2-yl)-benzamide;

N-(4-tert-Butyl-5-cyano-thiazol-2-yl)-2-{4-[2-(3,5-dimethyl-pyrazol-1-yl)-acetyl]-piperazin-1-yl}-benzamide;

2-{4-[2-(3,5-Dimethyl-pyrazol-1-yl)-acetyl]-piperazin-1-yl}-N-(4-pyridin-2-yl-thiazol-2-yl)-benzamide;

2-{4-[2-(3,5-Dimethyl-pyrazol-1-yl)-acetyl]-piperazin-1-yl}-N-(4-pyridin-4-yl-thiazol-2-yl)-benzamide;

N-(4-Chloro-benzothiazol-2-yl)-2-{4-[2-(3,5-dimethyl-pyrazol-1-yl)-acetyl]-piperazin-1-yl}-benzamide;

2-{4-[2-(3,5-Dimethyl-pyrazol-1-yl)-acetyl]-piperazin-1-yl}-N-(6-methanesulfonyl-benzothiazol-2-yl)-benzamide;

2-{4-[2-(3,5-Dimethyl-pyrazol-1-yl)-acetyl]-piperazin-1-yl}-N-(6-methoxy-benzothiazol-2-yl)-benzamide;

2-{4-[2-(3,5-Dimethyl-pyrazol-1-yl)-acetyl]-piperazin-1-yl}-N-(2-phenyl-pyrimidin-5-yl)-benzamide;

N-(5-Chloro-pyridin-3-yl)-2-{4-[2-(3,5-dimethyl-pyrazol-1-yl)-acetyl]-piperazin-1-yl}-benzamide;

2-{4-[2-(3,5-Dimethyl-pyrazol-1-yl)-acetyl]-piperazin-1-yl}-N-(2-trifluoromethyl-pyrimidin-5-yl)-benzamide;

N-(1,3-Dimethyl-2,4-dioxo-1,2,3,4-tetrahydro-pyrido[2,3-d]pyrimidin-6-yl)-2-{4-[2-(3,5-dimethyl-pyrazol-1-yl)-acetyl]-piperazin-1-yl}-benzamide;

2-{4-[2-(3,5-Dimethyl-pyrazol-1-yl)-acetyl]-piperazin-1-yl}-N-pyrazin-2-yl-benzamide;

2-[4-(2-2,3-Dihydro-pyrrolo[2,3-b]pyridin-1-yl-acetyl)-piperazin-1-yl]-N-(4-methanesulfonyl-phenyl)-benzamide;

N-(4-Methanesulfonyl-phenyl)-2-[4-(2-pyrrolo[2,3-b]pyridin-1-yl-acetyl)-piperazin-1-yl]-benzamide;

N-(3-tert-Butyl-is oxazol-5-yl)-2-{4-[2-(3,5-dimethyl-pyrazol-1-yl)-acetyl]-piperazin-1-yl}-benzamide;

2-{4-[2-(3,5-Dimethyl-pyrazol-1-yl)-acetyl]-piperazin-1-yl}-N-(3-trifluoromethyl-isoxazol-5-yl)-benzamide;

N-[3-(2,2-Dimethyl-propyl)-isoxazol-5-yl]-2-{4-[2-(3,5-dimethyl-pyrazol-1-yl)-acetyl]-piperazin-1-yl}-benzamide;

2-{4-[2-(3,5-Dimethyl-pyrazol-1-yl)-acetyl]-piperazin-1-yl}-N-(3-phenyl-isoxazol-5-yl)-benzamide;

N-(3-Cyclohexyl-isoxazol-5-yl)-2-{4-[2-(3,5-dimethyl-pyrazol-1-yl)-acetyl]-piperazin-1-yl}-benzamide;

N-(5-tert-Butyl-[1,3,4]thiadiazol-2-yl)-2-{4-[2-(3,5-dimethyl-pyrazol-1-yl)-acetyl]-piperazin-1-yl}-benzamide;

N-(5-tert-Butyl-2H-pyrazol-3-yl)-2-{4-[2-(3,5-dimethyl-pyrazol-1-yl)-acetyl]-piperazin-1-yl}-benzamide;

N-(3-tert-Butyl-is othiazol-5-yl)-2-{4-[2-(3,5-dimethyl-pyrazol-1-yl)-acetyl]-pipeazin-1-yl}-benzamide;

N-(2-{4-[2-(3,5-Dimethyl-pyrazol-1-yl)-acetyl]-piperazin-1-yl}-phenyl)-nicotinamide;

N-(2-{4-[2-(3,5-Dimethyl-pyrazol-1-yl)-acetyl]-piperazin-1-yl}-phenyl)-isonicotinamide;

5-Bromo-N-(2-{4-[2-(3,5-dimethyl-pyrazol-1-yl)-acetyl]-piperazin-1-yl}-phenyl)-nicotinamide;

6-Chloro-N-(2-{4-[2-(3,5-dimethyl-pyrazol-1-yl)-acetyl]-piperazin-1-yl}-phenyl)-nicotinamide;

N-(2-{4-[2-(3,5-Dimethyl-pyrazol-1-yl)-acetyl]-piperazin-1-yl}-phenyl)-6-phenoxy-nicotinamide;

2-{4-[2-(2-Methyl-4-oxo-4H-quinazolin-3-yl)-acetyl]-piperazin-1-yl}-N-pyridin-4-yl-benzamide;

N-Pyridin-4-yl-2-{4-[2-(1,3,5-trimethyl-1H-pyrazol-4-yl)-acetyl]-piperazin-1-yl}-benzamide;

2-{4-[2-(1,3-Dioxo-1,3-dihydro-isoindol-2-yl)-acetyl]-piperazin-1-yl}-N-pyridin-4-yl-benzamide;

2-{4-[2-(2,5-Dimethyl-thiazol-4-yl)-acetyl]-piperazin-1-yl}-N-pyridin-4-yl-benzamide;

2-{4-[2-(3,5-Dimethyl-1-phenyl-1H-pyrazol-4-yl)-acetyl]-piperazin-1-yl}-N-pyridin-4-yl-benzamide;

2-[4-(2-Benzofuran-3-yl-acetyl)-piperazin-1-yl]-N-pyridin-4-yl-benzamide;

2-[4-(2-1H-Indazol-3-yl-acetyl)-piperazin-1-yl]-N-pyridin-4-yl-benzamide;

2-[4-(2-Benzo[d]isoxazol-3-yl-acetyl)-piperazin-1-yl]-N-pyridin-4-yl-benzamide;

N-Pyridin-4-yl-2-[4-(2-quinolin-8-yl-acetyl)-piperazin-1-yl]-benzamide;

2-[4-(2-Imidazo[1,2-a]pyridin-2-yl-acetyl)-piperazin-1-yl]-N-pyridin-4-yl-benzamide;

N-{5-Chloro-2-[4-(2-pyrrolo[2,3-b]pyridin-1-yl-acetyl)-piperazin-1-yl]-pyridin-3-yl}-3-trifluoromethyl-benzamide;

3-Chloro-N-(2-{4-[2-(3,5-dimethyl-pyrazol-1-yl)-acetyl]-piperazin-1-yl}-5-methanesulfonyl-pyridin-3-yl)-benzamide;

N-(2-{4-[5-Chloro-3-(3-trifluoromethyl-benzoylamino)-pyridin-2-yl]-piperazin-1-yl}-2-oxo-ethyl)-3,4-dimethoxy-benzamide;

3-Chloro-N-(5-chloro-2-{1-[2-(3,5-dimethyl-pyrazol-1-yl)-acetyl]-1,2,3,6-tetrahydro-pyridin-4-yl}-phenyl)-benzamide;

N-(2-Methoxy-pyridin-4-yl)-2-{4-[2-(1-oxo-1,3-dihydro-isoindol-2-yl)-acetyl]-piperazin-1-yl}-benzamide;

5-Chloro-1-(2-{4-[2-(4-methanesulfonyl-phenylcarbamoyl)-phenyl]-piperazin-1-yl}-2-oxo-ethyl)-1-H-indole-2-carboxylic acid;

5-Methyl-oxazole-4-carboxylic acid (2-{4-[2-(2-methoxy-pyridin-4-ylcarbamoyl)-phenyl]-piperazin-1-yl}-2-oxo-ethyl)-methyl-amide;

2-{4-[2-(3,5-Dimethyl-pyrazol-1-yl)-acetyl]-piperazin-1-yl}-N-(5-fluoro-6-methyl-pyridin-3-yl)-benzamide;

N-(2-Methoxy-pyridin-4-yl)-2-{(S)-3-methyl-4-[2-(2-oxo-piperidin-1-yl)-acetyl]-piperazin-1-yl}-benzamide;

2-{(S)-4-[2-(3,5-Dimethyl-pyrazol-1-yl)-acetyl]-3-methyl-piperazin-1-yl}-N-(2-methoxy-pyridin-4-yl)-benzamide;

2-{4-[2-(3,5-Dimethyl-pyrazol-1-yl)-acetyl]-piperazin-1-yl}-N-[2-(2,2,2-trifluoro-ethoxy)-pyridin-4-yl]-benzamide;

2-{4-[2-(2-Oxo-piperidin-1-yl)-acetyl]-piperazin-1-yl}-N-[2-(2,2,2-trifluoro-ethoxy)-pyridin-4-yl]-benzamide;

5-Fluoro-N-(5-methyl-4,5,6,7-tetrahydro-thiazolo[5,4-c]pyridin-2-yl)-2-{4-[2-(1-oxo-1,3-dihydro-isoindol-2-yl)-acetyl]-piperazin-1-yl}-benzamide;

5-Chloro-2-{4-[2-(3,5-dimethyl-pyrazol-1-yl)-acetyl]-piperazin-1-yl}-N-(5-methyl-4,5,6,7-tetrahydro-thiazolo[5,4-c]pyridin-2-yl)-benzamide;

N-(5-Fluoro-pyridin-3-yl)-2-[4-(2-pyrrolo[2,3-c]pyridin-1-yl-acetyl)-piperazin-1-yl]-benzamide;

2-{4-[2-(3,5-Dimethyl-pyrazol-1-yl)-acetyl]-piperazin-1-yl}-N-(5-methyl-4,5,6,7-tetrahydro-thiazolo[5,4-c]pyridin-2-yl)-benzamide;

N-(5-Methyl-4,5,6,7-tetrahydro-thiazolo[5,4-c]pyridin-2-yl)-2-{4-[2-(1-oxo-1,3-dihydro-isoindol-2-yl)-acetyl]-piperazin-1-yl}-benzamide;

2-{4-[2-(2-Oxo-piperidin-1-yl)-acetyl]-piperazin-1-yl}-N-(6-trifluoromethyl-pyridin-3-yl)-benzamide;

N-(2-Methoxy-pyridin-4-yl)-2-{4-[2-(2-oxo-piperidin-1-yl)-acetyl]-piperazin-1-yl}-benzamide;

2-{4-[2-(3,5-Dimethyl-pyrazol-1-yl)-acetyl]-piperazin-1-yl}-N-(2-trifluoromethyl-pyridin-4-yl)-benzamide;

2-{4-[2-(2-Oxo-piperidin-1-yl)-acetyl]-piperazin-1-yl}-N-(2-trifluoromethyl-pyridin-4-yl)-benzamide;

2-{4-[2-(3,5-Dimethyl-pyrazol-1-yl)-acetyl]-piperazin-1-yl}-5-fluoro-N-(2-methoxy-pyridin-4-yl)-benzamide;

5-Fluoro-N-(2-methoxy-pyridin-4-yl)-2-{4-[2-(2-oxo-piperidin-1-yl)-acetyl]-piperazin-1-yl}-benzamide;

2-{4-[2-(2-Oxo-piperidin-1-yl)-acetyl]-piperazin-1-yl}-N-pyridin-4-yl-benzamide;

or the pharmaceutically acceptable salts thereof.

In another embodiment, the invention relates to a compound selected from:

2-{4-[2-(3,5-Dimethyl-pyrazol-1-yl)-acetyl]-piperazin-1-yl}-N-[2-(4-methyl-piperazin-1-yl)-pyridin-4-yl]-benzamide;

2-{4-[2-(3,5-Dimethyl-pyrazol-1-yl)-acetyl]-piperazin-1-yl}-N-(2-methoxy-pyridin-4-yl)-benzamide;

N-(2-Methoxy-pyridin-4-yl)-2-{4-[2-(1-oxo-1,3-dihydro-isoindol-2-yl)-acetyl]-piperazin-1-yl}-benzamide;

5-Chloro-1-(2-{4-[2-(4-methanesulfonyl-phenylcarbamoyl)-phenyl]-piperazin-1-yl}-2-oxo-ethyl)-1-H-indole-2-carboxylic acid;

5-Methyl-oxazole-4-carboxylic acid (2-{4-[2-(2-methoxy-pyridin-4-ylcarbamoyl)-phenyl]-piperazin-1-yl}-2-oxo-ethyl)-methyl-amide;

2-{4-[2-(3,5-Dimethyl-pyrazol-1-yl)-acetyl]-piperazin-1-yl}-N-(5-fluoro-6-methyl-pyridin-3-yl)-benzamide;

N-(2-Methoxy-pyridin-4-yl)-2-{(S)-3-methyl-4-[2-(2-oxo-piperidin-1-yl)-acetyl]-piperazin-1-yl}-benzamide;

2-{(S)-4-[2-(3,5-Dimethyl-pyrazol-1-yl)-acetyl]-3-methyl-piperazin-1-yl}-N-(2-methoxy-pyridin-4-yl)-benzamide;

2-{4-[2-(3,5-Dimethyl-pyrazol-1-yl)-acetyl]-piperazin-1-yl}-N-[2-(2,2,2-trifluoro-ethoxy)-pyridin-4-yl]-benzamide;

2-{4-[2-(2-Oxo-piperidin-1-yl)-acetyl]-piperazin-1-yl}-#N!-[2-(2,2,2-trifluoro-ethoxy)-pyridin-4-yl]-benzamide;

5-Fluoro-N-(5-methyl-4,5,6,7-tetrahydro-thiazolo[5,4-c]pyridin-2-yl)-2-{4-[2-(1-oxo-1,3-dihydro-isoindol-2-yl)-acetyl]-piperazin-1-yl}-benzamide;

5-Chloro-2-{4-[2-(3,5-dimethyl-pyrazol-1-yl)-acetyl]-piperazin-1-yl}-N-(5-methyl-4,5,6,7-tetrahydro-thiazolo[5,4-c]pyridin-2-yl)-benzamide;

N-(5-Fluoro-pyridin-3-yl)-2-[4-(2-pyrrolo[2,3-c]pyridin-1-yl-acetyl)-piperazin-1-yl]-benzamide;

2-{4-[2-(3,5-Dimethyl-pyrazol-1-yl)-acetyl]-piperazin-1-yl}-N-(5-methyl-4,5,6,7-tetrahydro-thiazolo[5,4-c]pyridin-2-yl)-benzamide;

N-(5-Methyl-4,5,6,7-tetrahydro-thiazolo[5,4-c]pyridin-2-yl)-2-{4-[2-(1-oxo-1,3-dihydro-isoindon-2-yl)-acetyl]-piperazin-1-yl}-benzamide;

2-{4-[2-(2-Oxo-piperidin-1-yl)-acetyl]-piperazin-1-yl}-N-(6-trifluoromethyl-pyridin-3-yl)-benzamide;

N-(2-Methoxy-pyridin-4-yl)-2-{4-[2-(2-oxo-piperidin-1-yl)-acetyl]-piperazin-1-yl}-benzamide;

2-{4-[2-(3,5-Dimethyl-pyrazol-1-yl)-acetyl]-piperazin-1-yl}-N-(2-trifluoromethyl-pyridin-4-yl)-benzamide;

2-{4-[2-(2-Oxo-piperidin-1-yl)-acetyl]-piperazin-1-yl}-N-(2-trifluoromethyl-pyridin-4-yl)-benzamide;

2-{4-[2-(3,5-Dimethyl-pyrazol-1-yl)-acetyl]-piperazin-1-yl}-5-fluoro-N-(2-methoxy-pyridin-4-yl)-benzamide;

5-Fluoro-N-(2-methoxy-pyridin-4-yl)-2-{4-[2-(2-oxo-piperidin-1-yl)-acetyl]-piperazin-1-yl}-benzamide;

2-{4-[2-(2-Oxo-piperidin-1-yl)-acetyl]-piperazin-1-yl}-N-pyridin-4-yl-benzamide;

or a pharmaceutically acceptable salt thereof.

For all compounds disclosed hereinabove in this application, in the event the nomenclature is in conflict with the structure, it shall be understood that the compound is defined by the structure.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorou, fluorine and chlorine, e.g., $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-6}$alkoxy" is a $C_{1-6}$ alkyl with a terminal oxygen, such as methoxy, ethoxy, propoxy, butoxy. All alkyl, alkenyl, and alkynyl groups shall be understood as being branched or unbranched where structurally possible and unless otherwise specified. Other more specific definitions are as follows:

The term "alkyl" refers to both branched and unbranched alkyl groups. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom. "Alkanoyl" refers to an alkyl group linked to a carbonyl group (C=O).

In all alkyl groups or carbon chains, one or more carbon atoms can be optionally replaced by heteroatoms such as 0, S or N. It shall be understood that if N is not substituted then it is NH. It shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo. As used herein, "nitrogen" and "sulfur" include any oxidized form of nitrogen and sulfur and the quaternized form of any basic nitrogen. For example, for a —S—$C_{1-6}$ alkyl radical, unless otherwise specified, shall be understood to include —S(O)—$C_{1-6}$ alkyl and —S(O)$_2$—$C_{1-6}$ alkyl.

The term "$C_{3-10}$ cycloalkyl" refers to a nonaromatic 3 to 10-membered (but preferably, 3 to 6-membered) monocyclic carbocyclic radical or a nonaromatic 6 to 10-membered fused bicyclic, bridged bicyclic, or spirocyclic carbocyclic radical. The $C_{3-10}$ cycloakyl may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[3.3.0] octane, bicyclo[4.3.0] nonane, and bicyclo[4.4.0]decanyl (decahydronaphthalenyl). Non-limiting examples of 6 to 10-membered bridged bicyclic carbocyclic radicals include bicyclo[2.2.2]heptanyl, bicyclo[2.2.2]octanyl, and bicyclo[3.2.1]octanyl. Non-limiting examples of 6 to 10-membered spirocyclic carbocyclic radicals include but are not limited to spiro[3,3]heptanyl, spiro[3,4]octanyl and spiro[4,4]heptanyl.

As used herein, the term "aryl" refers to an aromatic hydrocarbon rings containing from six to ten carbon ring atoms (e.g., a $C_{6-10}$ aryl). The term $C_{6-10}$ aryl includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl.

As used herein, the term "heterocyclyl" refers to a "5 to 11-membered heterocycle" and includes stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1] heptanyl, 3-azabicyclo[3.1.0]hexanyl, and 3-azabicyclo [3.2.11octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl.

As used herein, the term "heteroaryl" refers to a "5 to 11-membered heteroaryl" and includes aromatic 5 to 6-membered monocyclic heteroaryls and aromatic 7 to 11-membered heteroaryl bicyclic rings where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, pyranyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic rings include benzimidazolyl, 1,3-dihydrobenzoimidazol-2-one, quinolinyl, dihydro-2H-quinolinyl, isoquinolinyl, quinazolinyl, indazolyl, thieno [2,3-d]pyrimidinyl, indolyl, isoindolyl, indazolyl, benzotriazolyl, benzofuranyl, benzopyranyl, benzodioxolyl, benzoxazolyl, benzothiazolyl, pyrrolo[2,3-b]pyridinyl, and imidazo[4,5-b]pyridinyl.

It will be understood that when a heterocyclyl or heteroaryl contains a S ring atom, such S ring atom can be present in the ring in its divalent, tetravalent, or hexavalent form, i.e., —S—, —S(O)— or —S(O)$_2$—.

Each aryl or heteroaryl unless otherwise specified includes it's partially or fully hydrogenated derivatives. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art. It will be understood that one to three carbon ring moieties in the each of the $C_{3-10}$ carbocyclic rings, the 5 to 11-membered heterocyclic rings, the nonaromatic portion of the bicyclic aryl or heteroaryl rings, and the nonaromatic portion of the bicyclic heteroaryl rings can independently be replaced with a carbonyl, thiocarbonyl, or iminyl moiety, i.e., —C(=O)—, —C(=S)— and —C(=NR$^8$)—, respectively, where R$^8$ is as defined above. The term "heteroatom" as used herein shall be understood to mean atoms other than carbon such as O, N, and S.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —CH$_2$CHF$_2$, —CF$_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—(C$_1$-C$_4$ alkyl)$_4$$^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula (I) may be made using the general synthetic methods described below, which also constitute part of the invention.

General Synthetic Methods

The compounds of the invention may be prepared by the methods described below. In each of the schemes below, the groups R$^1$ to R$^5$, A, B, and X and Y are as defined above for general formula (I) unless noted otherwise. Optimum reaction conditions and reaction times may vary depending on the particular reactants used. Unless otherwise specified, solvents, temperatures, pressures and other reaction conditions may be readily selected by one of ordinary skill in the art. Amide bond formations may be carried out by standard coupling conditions well-known in the art (see, for example, M. Bodanszky, *The Practice of Peptide Synthesis* (Springer-Verlag: 1984), which is hereby incorporated by reference in its entirety), for example, by reacting a carboxylic acid and an amine in the presence of 1-(3-dimethylaminopropyl)-3-ethylcarbodiimide (EDC) and 1-hydroxybenzotriazole. Specific procedures are provided in the Synthetic Examples section. Typically, reaction progress may be monitored by thin layer chromatography (TLC) or HPLC-MS if desired. Intermediates and products may be purified by chromatography on silica gel, recrystallization, HPLC and/or reverse phase HPLC.

Starting materials and reagents are either commercially available or may be prepared by one skilled in the art using methods described in the chemical literature. Initial products of formula (I) may be modified further by methods known in the art to produce additional compounds of formula (I).

Compounds of formula (I) where A is N, ----- is a single bond and Y=—C(O)NH— may be prepared as shown in Scheme 1.

Scheme 1

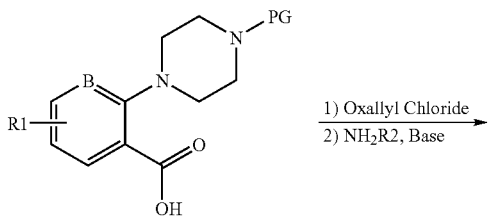

II

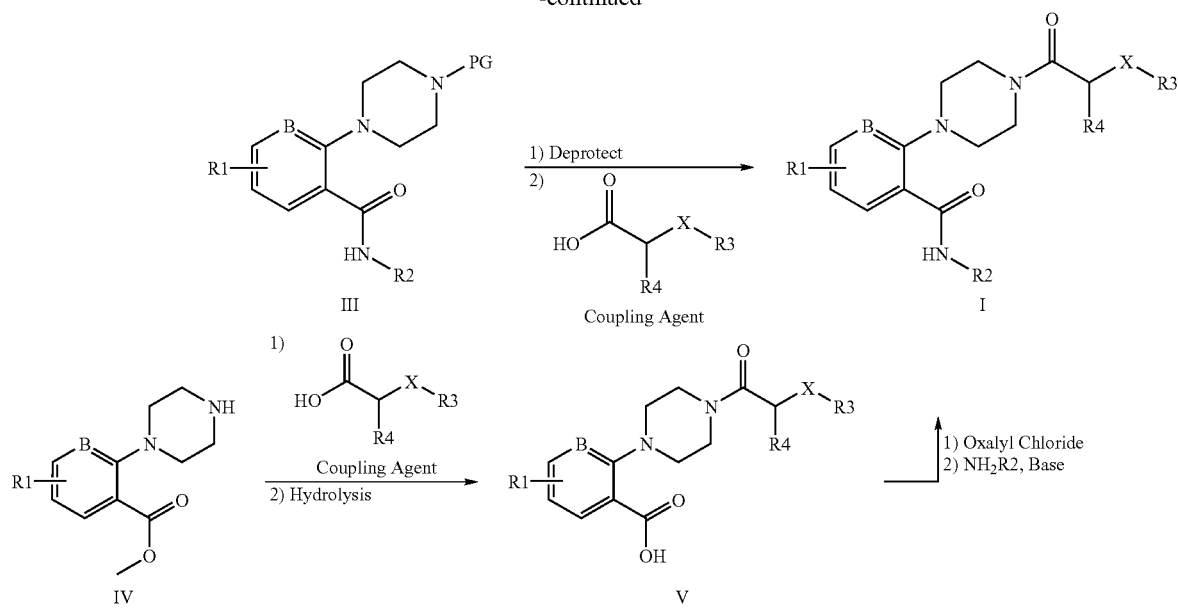

As illustrated in Scheme 1, a carboxylic acid of formula (II), where PG is a protecting group such as a t-Boc group is coupled with an amine bearing $R^2$ under standard coupling conditions such as converting the acid to the acid chloride by treatment with oxalyl chloride followed by reaction with $R^2NH_2$ in the presence of a base such as diisopropylethylamine to provide the desired amide of formula (III). The protecting group may then be removed by methods known in the art, for example by treatment with an acid such as trifluoroacetic acid if PG is a t-Boc group. This is followed by coupling the resulting amine with the desired carboxylic acid bearing X, $R^3$ and $R^4$ using standard coupling conditions, for example by reaction in the presence of carbonyl diimidazole in a suitable solvent such as DMF to provide the desired compound of formula (I). In an alternate procedure using the ester intermediate IV, the unprotected piperidine nitrogen may be coupled first to the carboxylic acid bearing X, $R^3$ and $R^4$, followed by hydrolysis of the ester and coupling of the resulting carboxylic acid to $R^2NH_2$ to provide the desired compound of formula (I).

Compounds of formula (I) where A is N, B is C, ----- is a single bond and Y=—NHC(O)— may be prepared as illustrated in Scheme 2.

Scheme 2

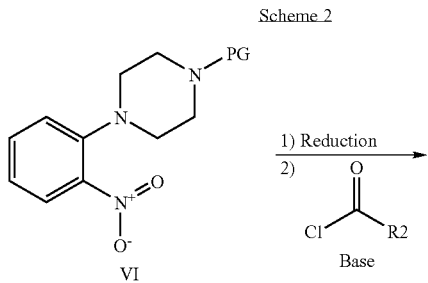

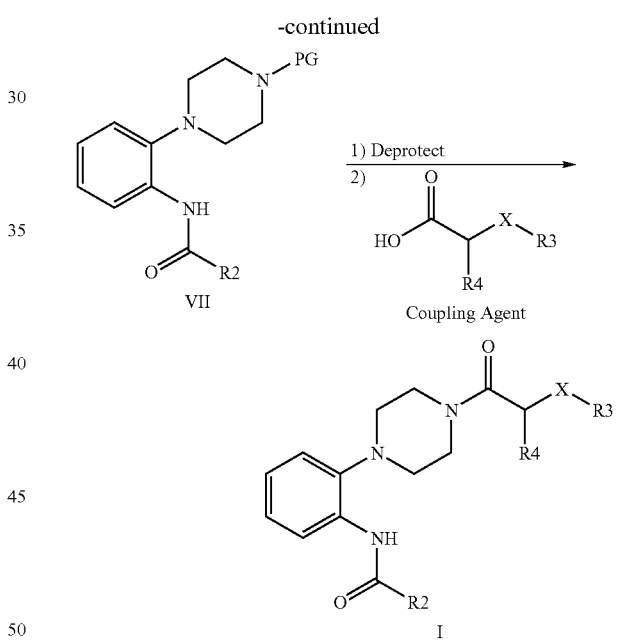

As illustrated in Scheme 2, the nitrobenzene intermediate VI is treated with a suitable reducing agent such as hydrogen or $NaBH_4$ in the presence of Pd on carbon to give the corresponding aniline intermediate which is then converted to the desired amide intermediate VII by treatment of $R^2C(O)Cl$ in the presence of a suitable base as illustrated above or $R^2C(O)$ $CO_2H$ using standard coupling conditions known in the art. The protecting group PG is then removed and the resulting amine coupled with the carboxylic acid bearing X, $R^3$ and $R^4$ as described in Scheme 1 to provide the desired compound of formula (I).

Compounds of formula (I) where A is N, B is N, ----- is a single bond, n=1 or 2 and Y=—NHC(O)— may be prepared as illustrated in Scheme 3.

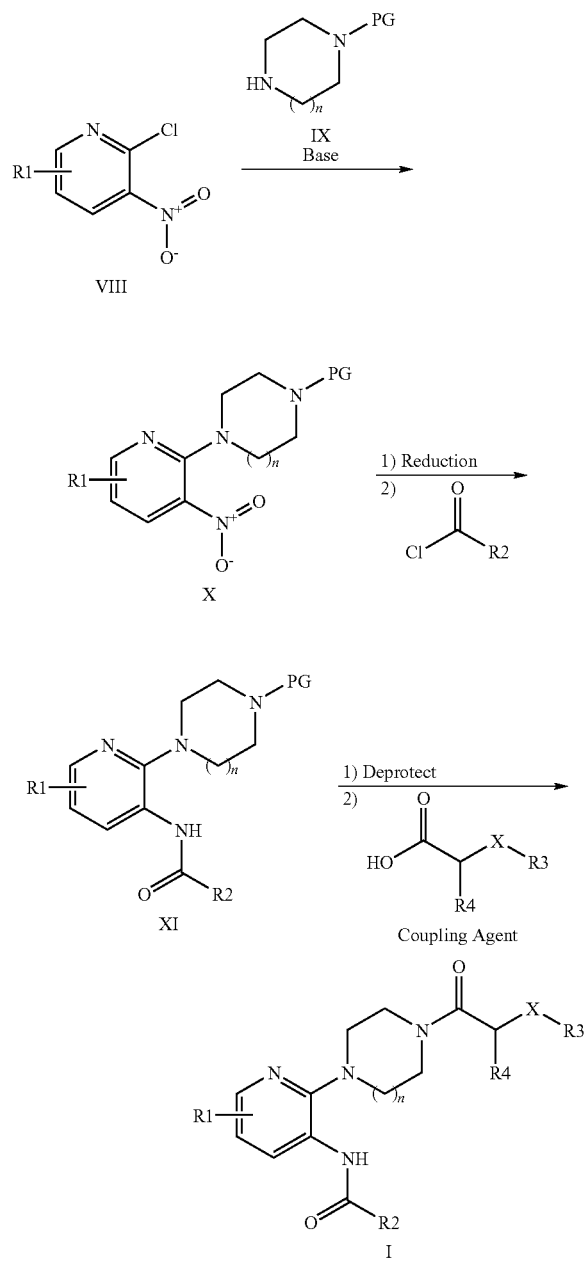

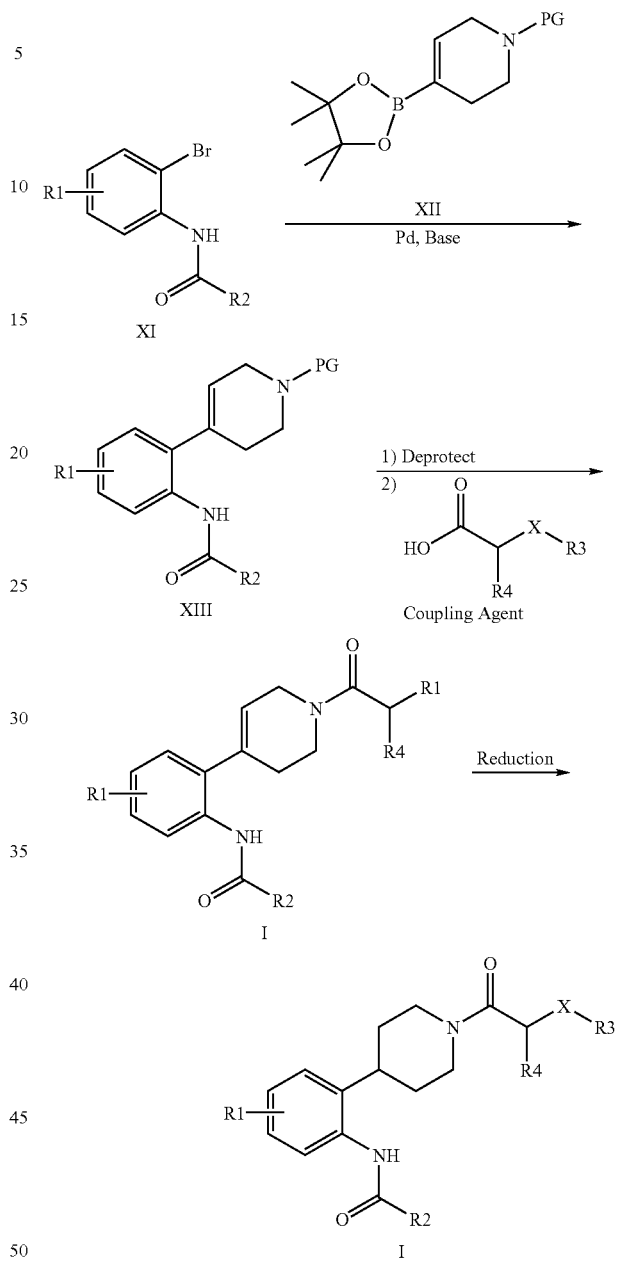

As illustrated in Scheme 3, the chloropyridine intermediate VIII is reacted with the protected heterocycle intermediate IX in the presence of a suitable base such as potassium carbonate, in a suitable solvent such as DMF to provide intermediate X. The nitro group of intermediate X is then treated with a suitable reducing agent such as hydrogen in the presence of Pd on carbon followed by acylation of the resulting amino pyridine intermediate with an acid chloride to provide intermediate XI. Deprotection and coupling as described for intermediate III in Scheme 1 provides the desired compound of formula (I).

Compounds of formula (I) where A is C, ═══ is a single or double bond, and Y═—NHC(O)— may be prepared as illustrated in Scheme 4.

As illustrated in Scheme 4, the bromo intermediate XI is treated with the boronic acid ester XII in the presence of a Pd catalyst such as Bis(triphenylphosphine)Palladium chloride and a suitable base such as sodium carbonate to give intermediate XII. This is deprotected and coupled to the desired carboxylic acid as described in the above schemes to provide the desired compound of formula (I) having ═══ being a double bond. The corresponding compound of formula (I) having ═══ being a single bond may be prepared by reduction of the olefin, for example by treatment with hydrogen in the presence of Pd on carbon.

All of the compounds in Table I were prepared by the methods illustrated above and in the Synthetic Examples section below.

SYNTHETIC EXAMPLES

Example 1

Synthesis of 2-{4-[2-(3,5-dimethyl-pyrazol-1-yl)-acetyl]-piperazin-1-yl}-N-phenyl-benzamide

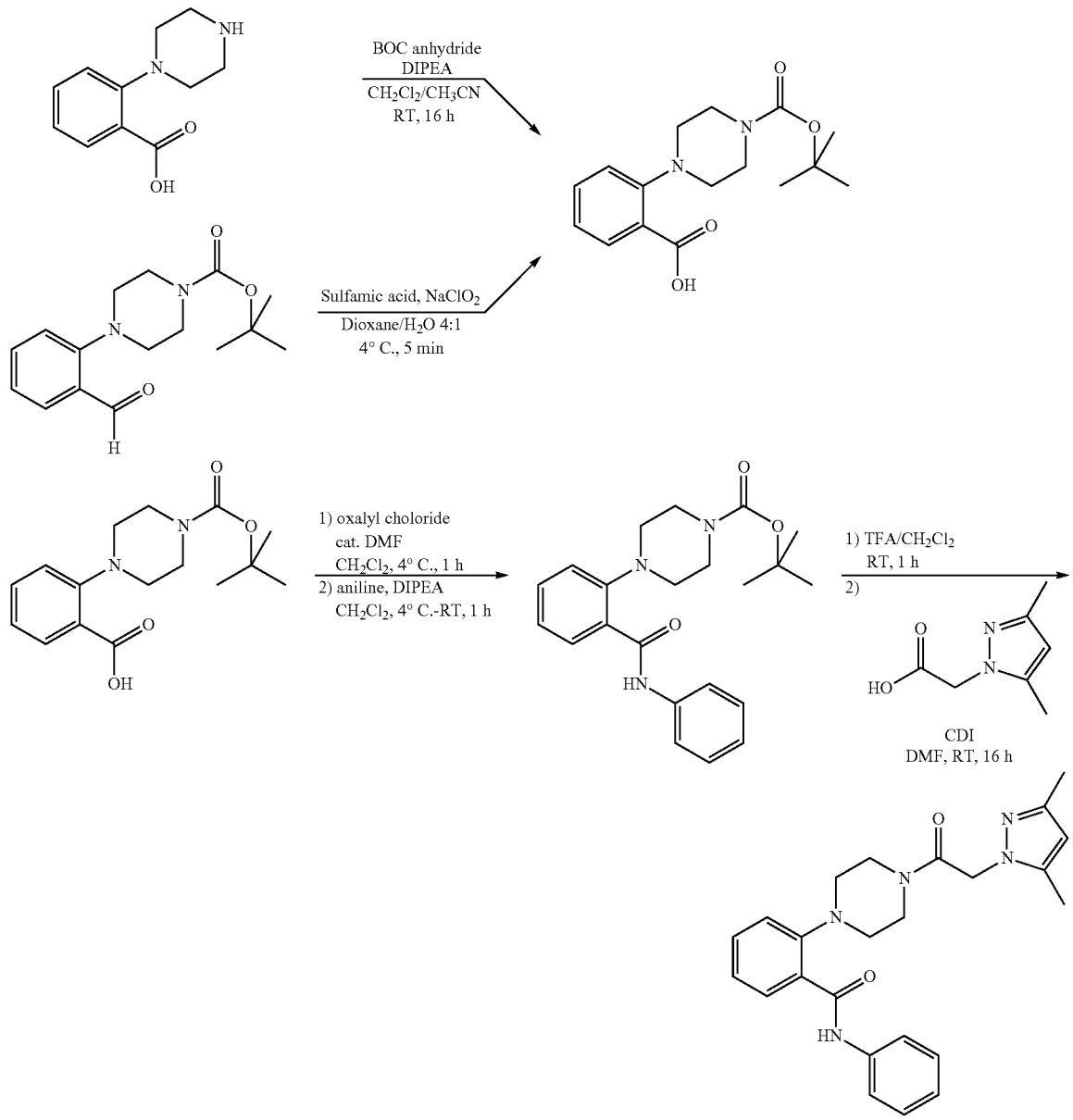

2-Piperazin-1-yl-benzoic acid (2.000 g, 9.79 mmol) is suspended in 100 mL of CH$_2$Cl$_2$. To this is added diisopropylethyl amine (2.22 mL, 12.00 mmol) and BOC anhydride (2.07 g, 9.50 mmol). After 1 hour, an additional 100 mL of anhydrous CH$_3$CN is added and the mixture is stirred overnight. The mixture is diluted with 250 mL of EtOAc, followed by 250 mL of sat. NH$_4$Cl. The organic phase is washed with 2×250 mL of H$_2$O and 1×250 mL of brine. The organic phase is dried with MgSO$_4$, filtered and concentrated to give 2.37 g of 4-(2-carboxy-phenyl)-piperazine-1-carboxylic acid tert-butyl ester, 80% yield.

An alternative method for preparing this intermediate is as follows. 4-(2-Formyl-phenyl)-piperazine-1-carboxylic acid tert-butyl ester (0.50 g, 1.72 mmol) is dissolved in 80 mL of dioxane and 20 mL of H$_2$O. The mixture is cooled to 4° C. To this is added sulfamic acid (1.36 g, 14.00 mmol) in one portion. The mixture is stirred for an additional 30 min. To this is added 3 mL of a solution of NaClO$_2$ (0.343 g, 3.80 mmol) in a dropwise manner. The reaction is quenched reaction with addition of 50 mL of H$_2$O and 50 mL of brine. The mixture is extracted with 3×100 mL of CH$_2$Cl$_2$. The organic phase is washed with 2×50 mL of brine, dried (MgSO$_4$), filtered and concentrated to give 500 mg of 4-(2-carboxy-phenyl)-piperazine-1-carboxylic acid tert-butyl ester, 95% yield.

4-(2-Carboxy-phenyl)-piperazine-1-carboxylic acid tert-butyl ester, (0.100 g, 0.326 mmol) is dissolved in 5 mL of dry CH$_2$Cl$_2$ under Ar. The mixture is cooled to 4° C. and a 2 M solution of oxalyl chloride (0.245 mL, 0.489 mmol) is added in a dropwise fashion resulting in gas evolution. The mixture is stirred for 30 min, 1 drop of DMF is then added and the mixture is stirred at room temperature for an additional 30 min. The mixture is then cooled to 4° C. and aniline (0.030 mL, 0.326 mmol) and diisopropylethyl amine (0.100 mL) are added. The reaction is warmed to room temperature and stirred for 1 h. The reaction mixture is diluted with 50 mL EtOAc and quenched with 20 mL of saturated $NH_4Cl$. The organic phase is washed with 2×20 mL of $H_2O$ and 1×20 mL of brine, dried ($MgSO_4$), filtered and concentrated. The crude product is purified using a $SiO_2$ prep plate, eluting with 50% EtOAc/hexanes to give 0.065 g of 4-(2-phenylcarbamoyl-phenyl)-piperazine-1-carboxylic acid tert-butyl ester.

4-(2-Phenylcarbamoyl-phenyl)-piperazine-1-carboxylic acid tert-butyl ester (0.065 g, 0.171 mmol) in a vial is dissolved into 1 mL of $CH_2Cl_2$ and 1 mL of TFA. The mixture is stirred for 1 h. The mixture is concentrated to dryness to give crude N-phenyl-2-piperazin-1-yl-benzamide trifluoroacetamide. To a vial containing the amine salt is added 1.0 mL of a premixed solution, containing (3,5-dimethyl-pyrazol-1-yl)-acetic acid (0.023 g, 0.150 mmol) and carbonyl diimidazole (0.028 g, 0.170 mmol) (premixed for 1 h). The mixture is stirred overnight. The mixture is partially purified mixture via preparative HPLC (20%-100% $CH_3CN/H_2O$) and then purified via the preparative HPLC system (30%-70% CH3CN/H2O) to give the title compound (0.043 g, 69% yield). MS MH+=418.2

The following compounds are prepared analogously:

2-{4-[2-(3,5-Dimethyl-pyrazol-1-yl)-acetyl]-piperazin-1-yl}-N-(3-trifluoromethyl-phenyl)-benzamide. MS MH+=486.2

2-{4-[2-(3,5-Dimethyl-pyrazol-1-yl)-acetyl]-piperazin-1-yl}-N-(4-trifluoromethyl-phenyl)-benzamide. MS MH+=486.5

2-{4-[2-(3,5-Dimethyl-pyrazol-1-yl)-acetyl]-piperazin-1-yl}-N-(2-trifluoromethyl-phenyl)-benzamide. MS MH+=486.5

2-{4-[2-(3,5-Dimethyl-pyrazol-1-yl)-acetyl]-piperazin-1-yl}-N-(3-methoxy-phenyl)-benzamide.MS MH+=448.5

2-{4-[2-(3,5-Dimethyl-pyrazol-1-yl)-acetyl]-piperazin-1-yl}-N-(3-trifluoromethoxy-phenyl)-benzamide. MS MH+=502.5

N-(3-Cyano-phenyl)-2-{4-[2-(3,5-dimethyl-pyrazol-1-yl)-acetyl]-piperazin-1-yl}-benzamide. MS MH+=443.5

N-(3-Chloro-phenyl)-2-{4-[2-(3,5-dimethyl-pyrazol-1-yl)-acetyl]-piperazin-1-yl}-benzamide. MS MH+=452.6

N-Benzyl-2-{4-[2-(3,5-dimethyl-pyrazol-1-yl)-acetyl]-piperazin-1-yl}-benzamide. MS MH+=432.5

2-{4-[2-(3,5-Dimethyl-pyrazol-1-yl)-acetyl]-piperazin-1-yl}-N-pyridin-3-yl-benzamide. MS MH+=419.5

N-(6-Cyano-pyridin-3-yl)-2-{4-[2-(3,5-dimethyl-pyrazol-1-yl)-acetyl]-piperazin-1-yl}-benzamide. MS MH+=444.5

2-{4-[2-(3,5-Dimethyl-pyrazol-1-yl)-acetyl]-piperazin-1-yl}-N-thiazol-2-yl-benzamide. MS MH+=425.4

N-Benzothiazol-2-yl-2-{4-[2-(3,5-dimethyl-pyrazol-1-yl)-acetyl]-piperazin-1-yl}-benzamide. MS MH+=475.5

2-{4-[2-(3,5-Dimethyl-pyrazol-1-yl)-acetyl]-piperazin-1-yl}-N-(2-fluoro-phenyl)-benzamide. MS MH+=436.2

N-Cyclohexyl-2-{4-[2-(3,5-dimethyl-pyrazol-1-yl)-acetyl]-piperazin-1-yl}-benzamide. MS MH+=424.4

2-{4-[2-(3,5-Dimethyl-pyrazol-1-yl)-acetyl]-piperazin-1-yl}-N-(2-methoxy-phenyl)-benzamide. MS MH+=448.2

2-[4-(2-2,3-Dihydro-pyrrolo[2,3-b]pyridin-1-yl-acetyl)-piperazin-1-yl]-N-pyridin-4-yl-benzamide. MS MH+=443.2

2-[4-(2-2,3-Dihydro-pyrrolo[2,3-b]pyridin-1-yl-acetyl)-piperazin-1-yl]-N-pyridin-3-yl-benzamide. MS MH+=443.2

2-{4-[2-(2-Oxo-imidazolidin-1-yl)-acetyl]-piperazin-1-yl}-N-pyridin-4-yl-benzamide. MS MH+=409.2

2-[4-(2-Phenylamino-acetyl)-piperazin-1-yl]-N-pyridin-4-yl-benzamide. MS MH+=416.2

2-{4-[2-(3,5-Dimethyl-pyrazol-1-yl)-acetyl]-piperazin-1-yl}-N-pyrimidin-2-yl-benzamide. MS MH+=420.5

2-{4-[2-(3,5-Dimethyl-pyrazol-1-yl)-acetyl]-piperazin-1-yl}-N-pyridazin-4-yl-benzamide. MS MH+=420.5

2-{4-[2-(3,5-Dimethyl-pyrazol-1-yl)-acetyl]-piperazin-1-yl}-N-(5-methyl-pyridin-3-yl)-benzamide. MS MH+=433.5

2-{4-[2-(3,5-Dimethyl-pyrazol-1-yl)-acetyl]-piperazin-1-yl}-N-(6-phenyl-pyridin-3-yl)-benzamide. MS MH+=495.5

2-{4-[2-(3,5-Dimethyl-pyrazol-1-yl)-acetyl]-piperazin-1-yl}-N-(6-morpholin-4-yl-pyridin-3-yl)-benzamide. MS MH+=504.5

2-{4-[2-(3,5-Dimethyl-pyrazol-1-yl)-acetyl]-piperazin-1-yl}-N-(2-methoxy-pyridin-4-yl)-benzamide. MS MH+=449.5

2-{4-[2-(3,5-Dimethyl-pyrazol-1-yl)-acetyl]-piperazin-1-yl}-N-[2-(4-methyl-piperazin-1-yl)-pyridin-4-yl]-benzamide. MS MH+=517.6

2-{4-[2-(3,5-Dimethyl-pyrazol-1-yl)-acetyl]-piperazin-1-yl}-N-(1-isopropyl-1H-pyrazolo[3,4-b]pyridin-5-yl)-benzamide. MS MH+=501.5

N-(1,3-Dimethyl-1H-pyrazolo[3,4-b]pyridin-5-yl)-2-{4-[2-(3,5-dimethyl-pyrazol-1-yl)-acetyl]-piperazin-1-yl}-benzamide. MS MH+=487.5

2-{4-[2-(3-Methyl-2-oxo-2,3-dihydro-benzoimidazol-1-yl)-acetyl]-piperazin-1-yl}-N-pyridin-4-yl-benzamide. MS MH+=471.5

2-{4-[2-(3,5-Dimethyl-pyrazol-1-yl)-acetyl]-piperazin-1-yl}-N-(4-methyl-thiazol-2-yl)-benzamide. MS MH+=439.2

2-{4-[2-(3,5-Dimethyl-pyrazol-1-yl)-acetyl]-piperazin-1-yl}-N-(5-methyl-thiazol-2-yl)-benzamide. MS MH+=439.2

N-(4-tert-Butyl-thiazol-2-yl)-2-{4-[2-(3,5-dimethyl-pyrazol-1-yl)-acetyl]-piperazin-1-yl}-benzamide. MS MH+=481.2

2-{4-[2-(3,5-Dimethyl-pyrazol-1-yl)-acetyl]-piperazin-1-yl}-N-[4-(4-fluoro-phenyl)-thiazol-2-yl]-benzamide. MS MH+=519.2

N-(4-Cyclohexyl-thiazol-2-yl)-2-{4-[2-(3,5-dimethyl-pyrazol-1-yl)-acetyl]-piperazin-1-yl}-benzamide. MS MH+=507.2

N-(5-tert-Butyl-4-methyl-thiazol-2-yl)-2-{4-[2-(3,5-dimethyl-pyrazol-1-yl)-acetyl]-piperazin-1-yl}-benzamide. MS MH+=495.2

2-{4-[2-(3,5-Dimethyl-pyrazol-1-yl)-acetyl]-piperazin-1-yl}-N-(4-pyridin-3-yl-thiazol-2-yl)-benzamide. MS MH+=502.2

N-(5-Chloro-benzothiazol-2-yl)-2-{4-[2-(3,5-dimethyl-pyrazol-1-yl)-acetyl]-piperazin-1-yl}-benzamide. MS MH+=509.2

2-{4-[2-(3,5-Dimethyl-pyrazol-1-yl)-acetyl]-piperazin-1-yl}-N-(4,5,6,7-tetrahydro-benzothiazol-2-yl)-benzamide. MS MH+=479.2

N-(6,7-Dihydro-4H-pyrano[4,3-d]thiazol-2-yl)-2-{4-[2-(3,5-dimethyl-pyrazol-1-yl)-acetyl]-piperazin-1-yl}-benzamide. MS MH+=481.2

2-{4-[2-(4-Oxo-4H-quinazolin-3-yl)-acetyl]-piperazin-1-yl}-N-pyridin-4-yl-benzamide MS; MH+=469.7

2-{4-[2-(1-Oxo-1,3-dihydro-isoindol-2-yl)-acetyl]-piperazin-1-yl}-N-pyridin-4-yl-benzamide MS; MH+=456.8

2-{4-[2-(4-Methyl-1-oxo-1H-phthalazin-2-yl)-acetyl]-piperazin-1-yl}-N-pyridin-4-yl-benzamide MS; MH+=483.8

2-{4-[2-(1-Oxo-1H-phthalazin-2-yl)-acetyl]-piperazin-1-yl}-N-pyridin-4-yl-benzamide MS; MH+=469.7

N-Pyridin-4-yl-2-{4-[2-(1,1,3-trioxo-1,3-dihydro-116-benzo[d]isothiazol-2-yl)-acetyl]-piperazin-1-yl}-benzamide MS; MH+=506.8

3,4-Dimethoxy-N-{2-oxo-2-[4-(2-phenylcarbamoyl-phenyl)-piperazin-1-yl]-ethyl}-benzamide MS; MH+=503.8

2-{4-[2-(2,4-Dimethyl-thiazol-5-yl)-acetyl]-piperazin-1-yl}-N-pyridin-4-yl-benzamide MS; MH+=436.7

3,4-Dimethoxy-N—((S)-1-methyl-2-oxo-2-{4-[2-(pyridin-3-ylcarbamoyl)-phenyl]-piperazin-1-yl}-ethyl)-benzamide MS; MH+=518.8

3,4-Dimethoxy-N—((R)-1-methyl-2-oxo-2-{4-[2-(pyridin-3-ylcarbamoyl)-phenyl]-piperazin-1-yl}-ethyl)-benzamide MS; MH+=518.8

2-{4-[2-(3,5-Bis-trifluoromethyl-phenyl)-acetyl]-piperazin-1-yl}-N-pyridin-3-yl-benzamide MS; MH+=537.8

2-{4-[2-(4-Methyl-furazan-3-yl)-acetyl]-piperazin-1-yl}-N-pyridin-4-yl-benzamide MS; MH+=407.8

2-{4-[2-(3,5-Dimethyl-1H-pyrazol-4-yl)-acetyl]-piperazin-1-yl}-N-pyridin-4-yl-benzamide MS; MH+=419.8

2-{4-[2-(3,4-Dimethoxy-phenyl)-thiazole-4-carbonyl]-piperazin-1-yl}-N-pyridin-3-yl-benzamide MS; MH+=530.8

2-{4-[2-(3,5-Dimethyl-pyrazol-1-yl)-acetyl]-piperazin-1-yl}-N-(4-trifluoromethyl-thiazol-2-yl)-benzamide. MS MH+=493.4

N-(4-tert-Butyl-5-cyano-thiazol-2-yl)-2-{4-[2-(3,5-dimethyl-pyrazol-1-yl)-acetyl]-piperazin-1-yl}-benzamide. MS MH+=506.4

2-{4-[2-(3,5-Dimethyl-pyrazol-1-yl)-acetyl]-piperazin-1-yl}-N-(4-pyridin-2-yl-thiazol-2-yl)-benzamide. MS MH+=502.4

2-{4-[2-(3,5-Dimethyl-pyrazol-1-yl)-acetyl]-piperazin-1-yl}-N-(4-pyridin-4-yl-thiazol-2-yl)-benzamide. MS MH+=502.4

N-(4-Chloro-benzothiazol-2-yl)-2-{4-[2-(3,5-dimethyl-pyrazol-1-yl)-acetyl]-piperazin-1-yl}-benzamide. MS MH+=509.4

2-{4-[2-(3,5-Dimethyl-pyrazol-1-yl)-acetyl]-piperazin-1-yl}-N-(6-methanesulfonyl-benzothiazol-2-yl)-benzamide. MS MH+=553.4

2-{4-[2-(3,5-Dimethyl-pyrazol-1-yl)-acetyl]-piperazin-1-yl}-N-(6-methoxy-benzothiazol-2-yl)-benzamide. MS MH+=505.4

2-{4-[2-(3,5-Dimethyl-pyrazol-1-yl)-acetyl]-piperazin-1-yl}-N-(1-methyl-1H-benzoimidazol-2-yl)-benzamide. MS MH+=472.4

2-{4-[2-(3,5-Dimethyl-pyrazol-1-yl)-acetyl]-piperazin-1-yl}-N-pyridin-2-yl-benzamide. MS MH+=419.2

2-{4-[2-(3,5-Dimethyl-pyrazol-1-yl)-acetyl]-piperazin-1-yl}-N-pyrimidin-4-yl-benzamide. MS MH+=420.2

2-{4-[2-(3,5-Dimethyl-pyrazol-1-yl)-acetyl]-piperazin-1-yl}-N-(2-phenyl-pyrimidin-5-yl)-benzamide. MS MH+=495.2

N-(5-Chloro-pyridin-3-yl)-2-{4-[2-(3,5-dimethyl-pyrazol-1-yl)-acetyl]-piperazin-1-yl}-benzamide. MS MH+=451.2

2-{4-[2-(3,5-Dimethyl-pyrazol-1-yl)-acetyl]-piperazin-1-yl}-N-(2-trifluoromethyl-pyrimidin-5-yl)-benzamide. MS MH+=488.2

N-(1,3-Dimethyl-2,4-dioxo-1,2,3,4-tetrahydro-pyrido[2,3-d]pyrimidin-6-yl)-2-{4-[2-(3,5-dimethyl-pyrazol-1-yl)-acetyl]-piperazin-1-yl}-benzamide. MS MH+=531.2

2-{4-[2-(3,5-Dimethyl-pyrazol-1-yl)-acetyl]-piperazin-1-yl}-N-pyrazin-2-yl-benzamide. MS MH+=420.2

2-[4-(2-2,3-Dihydro-pyrrolo[2,3-b]pyridin-1-yl-acetyl)-piperazin-1-yl]-N-(4-methanesulfonyl-phenyl)-benzamide. MS MH+=518.2

N-(4-Methanesulfonyl-phenyl)-2-[4-(2-pyrrolo[2,3-b]pyridin-1-yl-acetyl)-piperazin-1-yl]-benzamide. MS MH+=520.2

N-(3-tert-Butyl-isoxazol-5-yl)-2-{4-[2-(3,5-dimethyl-pyrazol-1-yl)-acetyl]-piperazin-1-yl}-benzamide. MS MH+=465.2

2-{4-[2-(3,5-Dimethyl-pyrazol-1-yl)-acetyl]-piperazin-1-yl}-N-(3-trifluoromethyl-isoxazol-5-yl)-benzamide. MS MH+=477.2

N-[3-(2,2-Dimethyl-propyl)-isoxazol-5-yl]-2-{4-[2-(3,5-dimethyl-pyrazol-1-yl)-acetyl]-piperazin-1-yl}-benzamide. MS MH+=479.2

2-{4-[2-(3,5-Dimethyl-pyrazol-1-yl)-acetyl]-piperazin-1-yl}-N-(3-phenyl-isoxazol-5-yl)-benzamide. MS MH+=485.2

N-(3-Cyclohexyl-isoxazol-5-yl)-2-{4-[2-(3,5-dimethyl-pyrazol-1-yl)-acetyl]-piperazin-1-yl}-benzamide. MS MH+=491.2

N-(5-tert-Butyl-[1,3,4]thiadiazol-2-yl)-2-{4-[2-(3,5-dimethyl-pyrazol-1-yl)-acetyl]-piperazin-1-yl}-benzamide. MS MH+=482.2

N-(5-tert-Butyl-2H-pyrazol-3-yl)-2-{4-[2-(3,5-dimethyl-pyrazol-1-yl)-acetyl]-piperazin-1-yl}-benzamide. MS MH+=464.4

N-(3-tert-Butyl-isothiazol-5-yl)-2-{4-[2-(3,5-dimethyl-pyrazol-1-yl)-acetyl]-piperazin-1-yl}-benzamide. MS MH+=481.2

2-{4-[2-(2-Methyl-4-oxo-4H-quinazolin-3-yl)-acetyl]-piperazin-1-yl}-N-pyridin-4-yl-benzamide. MS; MH+=483.8

2-{4-[2-(1,3-Dioxo-3,4-dihydro-1H-isoquinolin-2-yl)-acetyl]-piperazin-1-yl}-N-pyridin-4-yl-benzamide. MS; MH+=484.8

2-{4-[2-(1-Methyl-2-oxo-2,3-dihydro-1H-indol-3-yl)-acetyl]-piperazin-1-yl}-N-pyridin-4-yl-benzamide. MS; MH+=470.8

N-Pyridin-4-yl-2-{4-[2-(1,3,5-trimethyl-1H-pyrazol-4-yl)-acetyl]-piperazin-1-yl}-benzamide. MS; MH+=433.8

2-{4-[2-(1-Methyl-1H-imidazol-4-yl)-acetyl]-piperazin-1-yl}-N-pyridin-4-yl-benzamide. MS; MH+=405.8

2-{4-[2-(1,3-Dioxo-1,3-dihydro-isoindol-2-yl)-acetyl]-piperazin-1-yl}-N-pyridin-4-yl-benzamide. MS; MH+=470.8

2-{4-[2-(2,5-Dimethyl-thiazol-4-yl)-acetyl]-piperazin-1-yl}-N-pyridin-4-yl-benzamide. MS; MH+=436.7

2-{4-[2-(5-Methyl-2-phenyl-oxazol-4-yl)-acetyl]-piperazin-1-yl}-N-pyridin-4-yl-benzamide. MS; MH+=482.8

2-{4-[2-(2-Methyl-4-phenyl-thiazol-5-yl)-acetyl]-piperazin-1-yl}-N-pyridin-4-yl-benzamide. MS; MH+=498.8

2-{4-[2-(3,5-Dimethyl-1-phenyl-1H-pyrazol-4-yl)-acetyl]-piperazin-1-yl}-N-pyridin-4-yl-benzamide. MS; MH+=495.8

2-[4-(2-Benzofuran-3-yl-acetyl)-piperazin-1-yl]-N-pyridin-4-yl-benzamide. MS; MH+=441.7

2-[4-(2-1H-Indazol-3-yl-acetyl)-piperazin-1-yl]-N-pyridin-4-yl-benzamide. MS; MH+=441.8

2-{4-[2-(1-Methyl-1H-indol-3-yl)-acetyl]-piperazin-1-yl}-N-pyridin-4-yl-benzamide. MS; MH+=454.8

2-[4-(2-Benzo[d]isoxazol-3-yl-acetyl)-piperazin-1-yl]-N-pyridin-4-yl-benzamide. MS; MH+=442.7

N-Pyridin-4-yl-2-[4-(2-quinolin-8-yl-acetyl)-piperazin-1-yl]-benzamide. MS; MH+=452.8

2-{4-[2-(6-Methyl-imidazo[2,1-b]thiazol-3-yl)-acetyl]-piperazin-1-yl}-N-pyridin-4-yl-benzamide. MS; MH+=461.7

2-[4-(2-Imidazo[1,2-a]pyridin-2-yl-acetyl)-piperazin-1-yl]-N-pyridin-4-yl-benzamide. MS; MH+=441.8

2-[4-(2-Imidazo[1,2-a]pyrimidin-2-yl-acetyl)-piperazin-1-yl]-N-pyridin-4-yl-benzamide. MS; MH+=442.7

2-[4-(2-Imidazo[2,1-b]thiazol-6-yl-acetyl)-piperazin-1-yl]-N-pyridin-4-yl-benzamide. MS; MH+=447.7

N-(2-Methoxy-pyridin-4-yl)-2-{4-[2-(1-oxo-1,3-dihydro-isoindol-2-yl)-acetyl]-piperazin-1-yl}-benzamide MS MH+=486.2

N-(2-Methoxy-pyridin-4-yl)-2-{4-[2-(2-oxo-piperidin-1-yl)-acetyl]-piperazin-1-yl}-benzamide MS MH+=452.2

2-{4-[2-(2-Oxo-piperidin-1-yl)-acetyl]-piperazin-1-yl}-N-(6-trifluoromethyl-pyridin-3-yl)-benzamide MS MH+=490.2

2-{4-[2-(2-Oxo-piperidin-1-yl)-acetyl]-piperazin-1-yl}-N-pyridin-4-yl-benzamide MS MH+=422.8

2-{4-[2-(3,5-Dimethyl-pyrazol-1-yl)-acetyl]-piperazin-1-yl}-N-(5-fluoro-6-methyl-pyridin-3-yl)-benzamide MS MH+=451.4

N-(2-Methoxy-pyridin-4-yl)-2-{(S)-3-methyl-4-[2-(2-oxo-piperidin-1-yl)-acetyl]-piperazin-1-yl}-benzamide MS MH+=466.4

2-{(S)-4-[2-(3,5-Dimethyl-pyrazol-1-yl)-acetyl]-3-methyl-piperazin-1-yl}-N-(2-methoxy-pyridin-4-yl)-benzamide MS MH+=463.4

2-{4-[2-(3,5-Dimethyl-pyrazol-1-yl)-acetyl]-piperazin-1-yl}-N-(5-methyl-4,5,6,7-tetrahydro-thiazolo[5,4-c]pyridin-2-yl)-benzamide MS MH+=458.4

N-(5-Methyl-4,5,6,7-tetrahydro-thiazolo[5,4-c]pyridin-2-yl)-2-{4-[2-(1-oxo-1,3-dihydro-isoindol-2-yl)-acetyl]-piperazin-1-yl}-benzamide MS MH+=531.2

2-{4-[2-(3,5-Dimethyl-pyrazol-1-yl)-acetyl]-piperazin-1-yl}-N-[2-(2,2,2-trifluoro-ethoxy)-pyridin-4-yl]-benzamide MS MH+=517.8

2-{4-[2-(2-Oxo-piperidin-1-yl)-acetyl]-piperazin-1-yl}-N-[2-(2,2,2-trifluoro-ethoxy)-pyridin-4-yl]-benzamide MS MH+=520.0

Example 2

Synthesis of 2-{4-[2-(3,5-Dimethyl-pyrazol-1-yl)-acetyl]-piperazin-1-yl}-N-pyridin-4-yl-benzamide

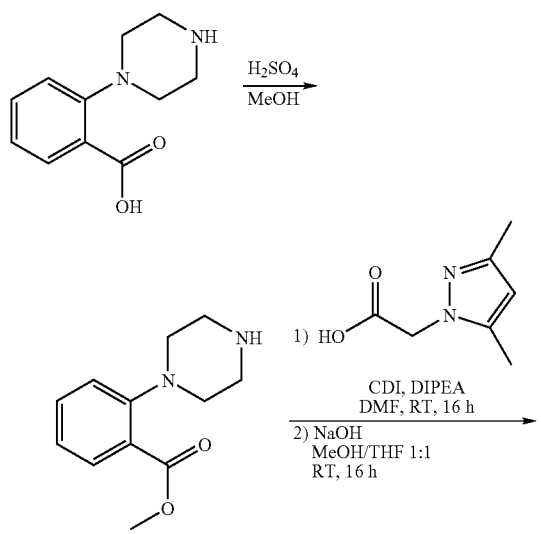

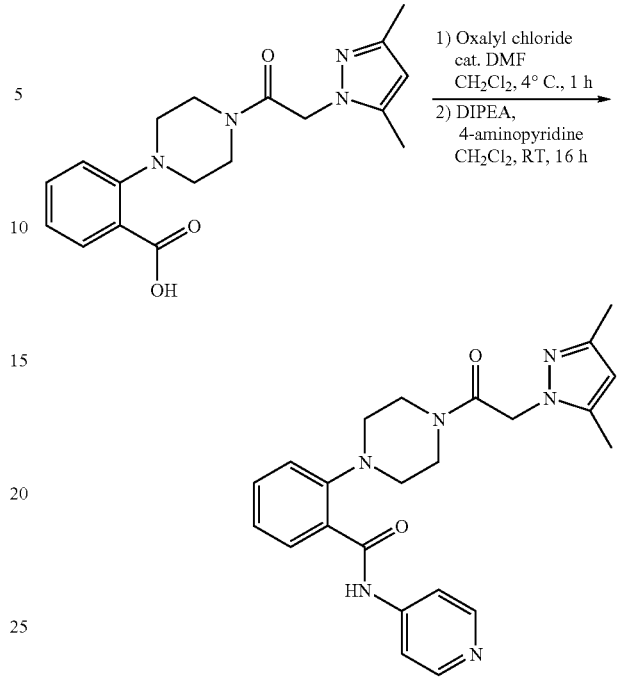

2-Piperazin-1-yl-benzoic acid (1.000 g, 4.89 mmol) is suspended in 10 mL of MeOH. To this is added 5 mL of conc. $H_2SO_4$. The mixture is stirred for 16 h resulting in a white precipitate. An additional 5 mL of $H_2SO_4$ is added with an additional 10 mL of MeOH. The reaction volume is increased by an additional 200 mL of MeOH and 60 mL of $H_2SO_4$ and the mixture is stirred an additional 2 h and then heated at reflux for 12 h. The reaction volume is then reduced to approximately 175 mL and applied to an ion exchange column, eluting with 5×200 mL of 10% $NH_3$/MeOH and then the product fractions are concentrated. The eluent is co-evaporated with toluene to remove residual water to give 0.667 g of 2-piperazin-1-yl-benzoic acid methyl ester in 63% yield.

To a vial containing the 2-piperazin-1-yl-benzoic acid methyl ester (0.667 g, 3.03 mmol) is added a pre-mixed solution containing (3,5-dimethyl-pyrazol-1-yl)-acetic acid (0.428 g, 2.78 mmol) and carbonyl dimidazole (0.567 g, 3.50 mmol). The mixture is stirred overnight and then diluted with 200 mL of EtOAc followed by 200 mL of saturated $NH_4Cl$. The organic phase is washed with 2×200 mL of $H_2O$ and 1×200 mL of brine, dried ($MgSO_4$), filtered and concentrated to give 0.849 g of 2-{4-[2-(3,5-dimethyl-pyrazol-1-yl)-acetyl]-piperazin-1-yl}-benzoic acid methyl ester in 86% yield.

2-{4-[2-(3,5-Dimethyl-pyrazol-1-yl)-acetyl]-piperazin-1-yl}-benzoic acid methyl ester (0.848 g, 2.38 mmol) is dissolved in 10 mL of 1:1 THF/MeOH and 2 mL of 15% aqueous NaOH is added. The mixture is stirred overnight and then concentrated to dryness and suspended in 50 mL of $H_2O$. The pH is adjusted to 4 by careful addition of conc. HCl. The aqueous phase is extracted with 3×100 mL of $CH_2Cl_2$. The combined organic phase is dried ($MgSO_4$), filtered and concentrated to give 0.730 g of 2-{4-[2-(3,5-dimethyl-pyrazol-1-yl)-acetyl]-piperazin-1-yl}-benzoic acid in 90% yield.

To 2-{4-[2-(3,5-dimethyl-pyrazol-1-yl)-acetyl]-piperazin-1-yl}-benzoic acid (0.051 g, 0.150 mmol) in 2 mL of $CH_2Cl_2$ at 4° C. is added 2 M oxalyl chloride solution (0.100 mL, 0.200 mmol) and 2 drops of dry DMF. The mixture is allowed to warm to room temperature over 1 h. To this is added 4-aminopyridine in one portion and diisopropylethyl amine (0.100 mL, 0.310 mmol). The mixture is stirred for 16 h. The mixture is concentrated and then purified via preparative HPLC (20-80% $CH_3CN/H_2O$). The product is further purified using a $SiO_2$ prep-plate, eluting with (10% MeOH/$CH_2Cl_2$) to give 0.032 g of the title compound in 63% yield. MS MH+=419.2

The following compounds are prepared analogously:

N-(2-Amino-phenyl)-2-{4-[2-(3,5-dimethyl-pyrazol-1-yl)-acetyl]-piperazin-1-yl}-benzamide. MS; MH+=433.2

2-{4-[2-(3,5-Dimethyl-pyrazol-1-yl)-acetyl]-piperazin-1-yl}-N-(2-hydroxy-phenyl)-benzamide. MS; MH+=434.2

2-{4-[2-(3,5-Dimethyl-pyrazol-1-yl)-acetyl]-piperazin-1-yl}-N-(6-methyl-pyridin-3-yl)-benzamide. MS; MH+=433.2

N-(6-Chloro-pyridin-3-yl)-2-{4-[2-(3,5-dimethyl-pyrazol-1-yl)-acetyl]-piperazin-1-yl}-benzamide. MS; MH+=453.2

N-(6-Acetylamino-pyridin-3-yl)-2-{4-[2-(3,5-dimethyl-pyrazol-1-yl)-acetyl]-piperazin-1-yl}-benzamide. MS; MH+=476.5

2-{4-[2-(3,5-Dimethyl-pyrazol-1-yl)-acetyl]-piperazin-1-yl}-N-(6-methoxy-pyridin-3-yl)-benzamide. MS; MH+=449.2

2-{4-[2-(3,5-Dimethyl-pyrazol-1-yl)-acetyl]-piperazin-1-yl}-N-(6-hydroxy-pyridin-3-yl)-benzamide. MS; MH+=435.2

2-{4-[2-(3,5-Dimethyl-pyrazol-1-yl)-acetyl]-piperazin-1-yl}-N-quinolin-3-yl-benzamide. MS; MH+=469.2

2-{4-[2-(3,5-Dimethyl-pyrazol-1-yl)-acetyl]-piperazin-1-yl}-N-(5-fluoro-pyridin-3-yl)-benzamide. MS; MH+=437.5

2-{4-[2-(3,5-Dimethyl-pyrazol-1-yl)-acetyl]-piperazin-1-yl}-N-(5-hydroxy-pyridin-3-yl)-benzamide. MS; MH+=435.5

2-{4-[2-(3,5-Dimethyl-pyrazol-1-yl)-acetyl]-piperazin-1-yl}-N-(6-trifluoromethyl-pyridin-3-yl)-benzamide. MS; MH+=487.6

N-(6-Bromo-pyridin-3-yl)-2-{4-[2-(3,5-dimethyl-pyrazol-1-yl)-acetyl]-piperazin-1-yl}-benzamide. MS; MH+=497.7

2-{4-[2-(3,5-Dimethyl-pyrazol-1-yl)-acetyl]-piperazin-1-yl}-N-(6-phenoxy-pyridin-3-yl)-benzamide. MS; MH+=511.6

N-(2-tert-Butyl-pyridin-4-yl)-2-{4-[2-(3,5-dimethyl-pyrazol-1-yl)-acetyl]-piperazin-1-yl}-benzamide. MS; MH+=475.6

N-(2-Chloro-pyridin-4-yl)-2-{4-[2-(3,5-dimethyl-pyrazol-1-yl)-acetyl]-piperazin-1-yl}-benzamide. MS; MH+=453.5

N-(2-Bromo-pyridin-4-yl)-2-{4-[2-(3,5-dimethyl-pyrazol-1-yl)-acetyl]-piperazin-1-yl}-benzamide. MS; MH+=497.4

2-{4-[2-(3,5-Dimethyl-pyrazol-1-yl)-acetyl]-piperazin-1-yl}-N-(2-methyl-pyridin-4-yl)-benzamide. MS; MH+=433.5

2-{4-[2-(3,5-Dimethyl-pyrazol-1-yl)-acetyl]-piperazin-1-yl}-N-(3-fluoro-pyridin-4-yl)-benzamide. MS; MH+=437.5

2-{4-[2-(3,5-Dimethyl-pyrazol-1-yl)-acetyl]-piperazin-1-yl}-N-quinolin-6-yl-benzamide. MS; MH+=469.6

2-{4-[2-(3,5-Dimethyl-pyrazol-1-yl)-acetyl]-piperazin-1-yl}-N-isoquinolin-6-yl-benzamide. MS; MH+=469.5

2-{4-[2-(3,5-Dimethyl-pyrazol-1-yl)-acetyl]-piperazin-1-yl}-N-(2-methyl-benzothiazol-6-yl)-benzamide. MS; MH+=489.5

2-{4-[2-(3,5-Dimethyl-pyrazol-1-yl)-acetyl]-piperazin-1-yl}-N-(2-methyl-benzooxazol-5-yl)-benzamide. MS; MH+=473.5

2-{4-[2-(3,5-Dimethyl-pyrazol-1-yl)-acetyl]-piperazin-1-yl}-N-(3-dimethylsulfamoyl-phenyl)-benzamide. MS; MH+=525.5

2-{4-[2-(3,5-Dimethyl-pyrazol-1-yl)-acetyl]-piperazin-1-yl}-N-(3-methanesulfonyl-phenyl)-benzamide. MS; MH+=496.5

2-{4-[2-(3,5-Dimethyl-pyrazol-1-yl)-acetyl]-piperazin-1-yl}-N-(4-methanesulfonyl-phenyl)-benzamide. MS; MH+=496.5

N-Pyridin-4-yl-2-[4-(2-pyrrolo[2,3-b]pyridin-1-yl-acetyl)-piperazin-1-yl]-benzamide. MS; MH+=441.2

N-(6-Cyano-pyridin-3-yl)-2-[4-(2-pyrrolo[2,3-b]pyridin-1-yl-acetyl)-piperazin-1-yl]-benzamide. MS; MH+=466.2

2-[4-(2-Pyrrolo[2,3-b]pyridin-1-yl-acetyl)-piperazin-1-yl]-N-(6-trifluoromethyl-pyridin-3-yl)-benzamide. MS; MH+=509.2

N-(6-Methyl-pyridin-3-yl)-2-[4-(2-pyrrolo[2,3-b]pyridin-1-yl-acetyl)-piperazin-1-yl]-benzamide. MS; MH+=455.2

N-(6-Methoxy-pyridin-3-yl)-2-[4-(2-pyrrolo[2,3-b]pyridin-1-yl-acetyl)-piperazin-1-yl]-benzamide. MS; MH+=471.2

2-[4-(2-Pyrrolo[2,3-b]pyridin-1-yl-acetyl)-piperazin-1-yl]-N-quinolin-3-yl-benzamide. MS; MH+=491.2

Example 3

Synthesis of 2-{4-[2-(2,4-Dimethyl-imidazol-1-yl)-acetyl]-piperazin-1-yl}-N-phenyl-benzamide

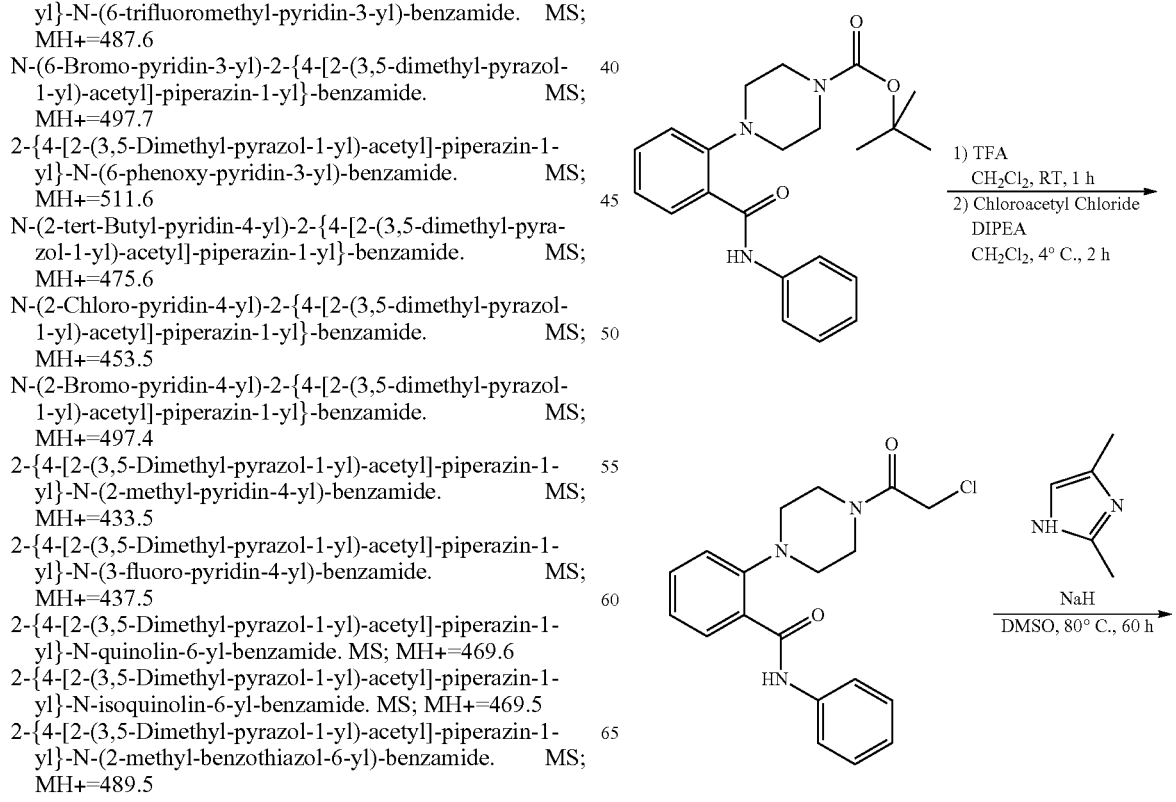

145
-continued

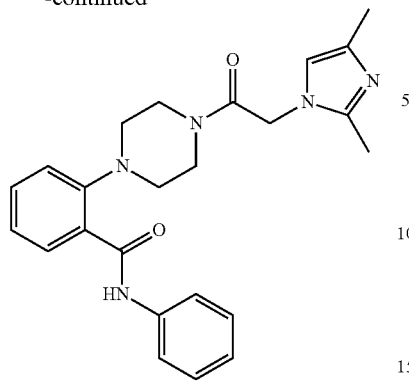

To a vial containing 4-(2-phenylcarbamoyl-phenyl)-piperazine-1-carboxylic acid tert-butyl ester (0.438 g, 1.150 mmol) is added 2 mL of CH$_2$Cl$_2$ and 2 mL of TFA. The mixture stirred for 1 h and then concentrated to dryness to give 0.454 g of 4-(2-phenylcarbamoyl-phenyl)-piperazine trifluroacetate in 100% yield.

4-(2-phenylcarbamoyl-phenyl)-piperazine trifluroacetate (0.454 g, 1.150 mmol) is dissolved in 10 mL of CH$_2$Cl$_2$ containing diisopropylethyl amine (0.554 mL, 3.000 mmol). The mixture is cooled to 4° C. and chloroacetyl chloride (0.105 mL, 0.130 mmol) is added in a dropwise fashion. The reaction is stirred for 2 h in ice bath and then quenched with 20 mL of saturated NH$_4$Cl. The reaction is diluted with 100 mL EtOAc and washed with 2×20 mL of H$_2$O and 1×20 mL of brine. The organic phase is dried with MgSO$_4$, filtered and concentrated. The crude product is purified via a SiO2 column and (0-75% EtOAc/hexanes) to give 310 mg of 2-[4-(2-chloro-acetyl)-piperazin-1-yl]-N-phenyl-benzamide in 75% yield.

To 2,5-dimethyl imidazole (0.060 g, 0.630 mmol) in 1 mL of DMSO in a reaction tube is added 60% NaH (0.030 g, 0.730 mmol). The mixture bubbles as deprotonation occurs. The mixture is stirred for 0.5 h and then 0.5 mL of a DMSO solution containing 2-[4-(2-chloro-acetyl)-piperazin-1-yl]-N-phenyl-benzamide (0.075 g, 0.210 mmol) is added. The flask is sealed and heated at 80° C. for 60 h. The product is purified via Prep HPLC (20-100% CH$_3$CN/H$_2$O) to give 74.7 mg of 2-{4-[2-(2,4-dimethyl-imidazol-1-yl)-acetyl]-piperazin-1-yl}-N-phenyl-benzamide in 85% yield. MS: MH+=418.9

The following compounds are prepared analogously:

N-Phenyl-2-[4-(2-pyrrolo[2,3-b]pyridin-1-yl-acetyl)-piperazin-1-yl]-benzamide. MS; MH+=440.8

N-Phenyl-2-{4-[2-(thiazol-2-ylamino)-acetyl]-piperazin-1-yl}-benzamide. MS; MH+=422.8

2-{4-[2-(4-Methyl-[1,4]diazepan-1-yl)-acetyl]-piperazin-1-yl}-N-phenyl-benzamide. MS; MH+=436.0

Example 4

2-[4-(2-Benzoylamino-acetyl)-piperazin-1-yl]-N-pyridin-3-yl-benzamide

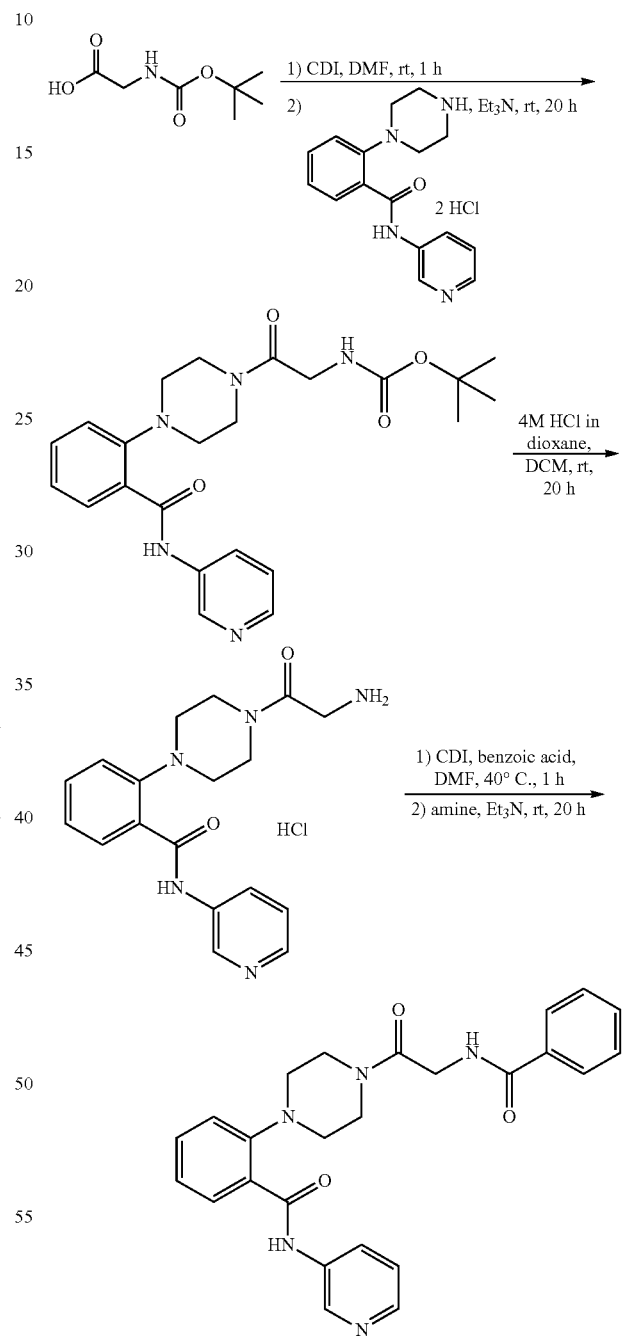

A solution of N-Boc-glycine (106 mg, 0.591 mmol) and carbonyl diimidazole (98 mg, 0.59 mmol) in DMF (10 mL) is stirred at room temperature for 60 min. To the solution is added 2-piperazin-1-yl-N-pyridin-3-yl-benzamide (200 mg, 0.563 mmol) and triethylamine (0.394 mL, 2.82 mmol) and the solution is stirred at room temperature for 24 h. The reaction is diluted ethyl acetate (100 mL) and washed with saturated NaHCO$_3$ (100 mL), 50% sat. NH$_4$Cl (100 mL), then water (100 mL). The aqueous layers are extracted again with more ethyl acetate (100 mL). The organics are dried (Na$_2$SO$_4$) and concentrated and dried to give 0.241 g of the desired amide intermediate in 93% yield as a gum.

To a solution of the above amide intermediate (241 mg, 0.521 mmol) in CH$_2$Cl$_2$ (15 mL) is added 4M HCl/dioxane (5.0 mL, 20 mmol) and the suspension is stirred vigorously at room temperature for 20 h with periodic venting. The suspension is diluted with Et$_2$O (100 mL) and hexane (100 mL) and stirred 1 h. The resulting hydroscopic white solid is filtered washed with Et$_2$O and hexane, then dried in vacuo under P$_2$O$_5$ to afford 0.201 g of the desired amine intermediate in 99% yield.

A solution of benzoic acid (14 mg, 0.11 mmol) and carbonyl diimidazole (18 mg, 0.11 mmol) in DMF (2 mL) is stirred at 40° C. for 1 h. To the solution is added the above amine intermediate (40 mg, 0.11 mmol) and triethylamine (0.075 mL, 0.54 mmol) and the solution is stirred at room temperature for 24 h. The reaction is diluted with water (1 mL), quenched with TFA (0.2 mL) and purified by reverse-phase preparative HPLC (10-100% CH$_3$CN/H$_2$O) to give 0.036 g of the title compound in 74% yield. MS MH+=444.8

The following compounds were prepared analogously:

1-Methyl-1H-pyrrole-2-carboxylic acid methyl-(2-oxo-2-{4-[2-(pyridin-4-ylcarbamoyl)-phenyl]-piperazin-1-yl}-ethyl)-amide MS; MH+=461.8

2-{4-[2-(Benzoyl-methyl-amino)-acetyl]-piperazin-1-yl}-N-pyridin-4-yl-benzamide MS; MH+=458.8

4-Methoxy-3-methyl-N-(2-oxo-2-{4-[2-(pyridin-3-ylcarbamoyl)-phenyl]-piperazin-1-yl}-ethyl)-benzamide MS; MH+=488.8

1-Methyl-1H-pyrrole-2-carboxylic acid (2-oxo-2-{4-[2-(pyridin-3-ylcarbamoyl)-phenyl]-piperazin-1-yl}-ethyl)-amide MS; MH+=447.7

2,3-Dimethoxy-N-(2-oxo-2-{4-[2-(pyridin-3-ylcarbamoyl)-phenyl]-piperazin-1-yl}-ethyl)-benzamide MS; MH+=504.8

Benzo[1,3]dioxole-5-carboxylic acid (2-oxo-2-{4-[2-(pyridin-3-ylcarbamoyl)-phenyl]-piperazin-1-yl}-ethyl)-amide MS; MH+=488.8

2,4-Dimethyl-thiazole-5-carboxylic acid (2-oxo-2-{4-[2-(pyridin-3-ylcarbamoyl)-phenyl]-piperazin-1-yl}-ethyl)-amide MS; MH+=479.8

4-Methoxy-N-methyl-N-(2-oxo-2-{4-[2-(pyridin-4-ylcarbamoyl)-phenyl]-piperazin-1-yl}-ethyl)-benzamide MS; MH+=488.8

2,3-Dimethoxy-N-methyl-N-(2-oxo-2-{4-[2-(pyridin-4-ylcarbamoyl)-phenyl]-piperazin-1-yl}-ethyl)-benzamide MS; MH+=518.8

3-Fluoro-4-methoxy-N-methyl-N-(2-oxo-2-{4-[2-(pyridin-4-ylcarbamoyl)-phenyl]-piperazin-1-yl}-ethyl)-benzamide MS; MH+=506.8

4-Methoxy-N-(2-oxo-2-{4-[2-(pyridin-3-ylcarbamoyl)-phenyl]-piperazin-1-yl}-ethyl)-benzamide MS; MH+=474.8

2-Ethyl-5-methyl-2H-pyrazole-3-carboxylic acid (2-oxo-2-{4-[2-(pyridin-3-ylcarbamoyl)-phenyl]-piperazin-1-yl}-ethyl)-amide MS; MH+=476.8

4-Difluormethoxy-N-(2-oxo-2-{4-[2-(pyridin-3-ylcarbamoyl)-phenyl]-piperazin-1-yl}-ethyl)-benzamide MS; MH+=510.8

3-Fluoro-4-methoxy-N-(2-oxo-2-{4-[2-(pyridin-3-ylcarbamoyl)-phenyl]-piperazin-1-yl}-ethyl)-benzamide MS; MH+=492.8

1,5-Dimethyl-1H-pyrazole-3-carboxylic acid (2-oxo-2-{4-[2-(pyridin-3-ylcarbamoyl)-phenyl]-piperazin-1-yl}-ethyl)-amide MS; MH+=462.8

2,5-Dimethyl-2H-pyrazole-3-carboxylic acid methyl-(2-oxo-2-{4-[2-(pyridin-4-ylcarbamoyl)-phenyl]-piperazin-1-yl}-ethyl)-amide MS; MH+=476.8

3,4-Dimethoxy-N-(2-oxo-2-{4-[2-(pyridin-3-ylcarbamoyl)-phenyl]-piperazin-1-yl}-ethyl)-benzamide MS; MH+=504.8

2,4-Dimethyl-thiazole-5-carboxylic acid methyl-(2-oxo-2-{4-[2-(pyridin-4-ylcarbamoyl)-phenyl]-piperazin-1-yl}-ethyl)-amide MS; MH+=493.7

3-Methoxy-N-(2-oxo-2-{4-[2-(pyridin-3-ylcarbamoyl)-phenyl]-piperazin-1-yl}-ethyl)-benzamide MS; MH+=474.8

2,5-Dimethyl-2H-pyrazole-3-carboxylic acid (2-oxo-2-{4-[2-(pyridin-3-ylcarbamoyl)-phenyl]-piperazin-1-yl}-ethyl)-amide MS; MH+=462.8

4-Fluoro-3-methoxy-N-(2-oxo-2-{4-[2-(pyridin-3-ylcarbamoyl)-phenyl]-piperazin-1-yl}-ethyl)-benzamide MS; MH+=492.8

3,4-Dimethoxy-N-methyl-N-(2-oxo-2-{4-[2-(pyridin-4-ylcarbamoyl)-phenyl]-piperazin-1-yl}-ethyl)-benzamide MS; MH+=518.8

3,4-Dimethoxy-N-(2-oxo-2-{4-[2-(pyridin-4-ylcarbamoyl)-phenyl]-piperazin-1-yl}-ethyl)-benzamide. MS; MH+=504.2

4-Methoxy-N-(2-oxo-2-{4-[2-(pyridin-4-ylcarbamoyl)-phenyl]-piperazin-1-yl}-ethyl)-benzamide. MS; MH+=474.2

1-Methyl-1H-pyrrole-2-carboxylic acid (2-oxo-2-{4-[2-(pyridin-4-ylcarbamoyl)-phenyl]-piperazin-1-yl}-ethyl)-amide. MS; MH+=447.2

2,3-Dimethoxy-N-(2-oxo-2-{4-[2-(pyridin-4-ylcarbamoyl)-phenyl]-piperazin-1-yl}-ethyl)-benzamide. MS; MH+=504.2

3-Fluoro-4-methoxy-N-(2-oxo-2-{4-[2-(pyridin-4-ylcarbamoyl)-phenyl]-piperazin-1-yl}-ethyl)-benzamide. MS; MH+=492.2

2,5-Dimethyl-2H-pyrazole-3-carboxylic acid (2-oxo-2-{4-[2-(pyridin-4-ylcarbamoyl)-phenyl]-piperazin-1-yl}-ethyl)-amide. MS; MH+=462.2

5-Methyl-oxazole-4-carboxylic acid (2-{4-[2-(2-methoxy-pyridin-4-ylcarbamoyl)-phenyl]-piperazin-1-yl}-2-oxo-ethyl)-methyl-amide MS MH+=493.2

Example 5

N-(2-{4-[2-(3,5-Dimethyl-pyrazol-1-yl)-acetyl]-piperazin-1-yl}-phenyl)-benzamide

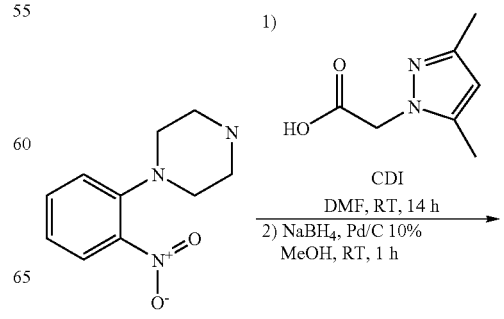

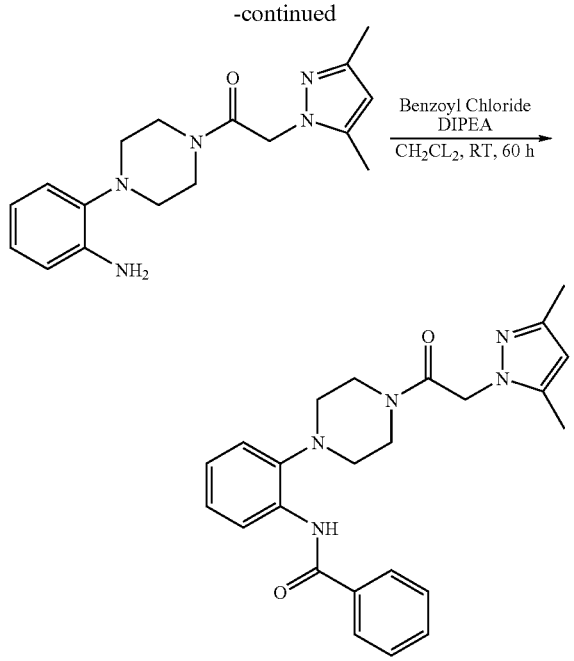

Pyridine-2-carboxylic acid (2-{4-[2-(3,5-dimethyl-pyrazol-1-yl)-acetyl]-piperazin-1-yl}-phenyl)-amide. MS; MH+=419.2

N-(2-{4-[2-(3,5-Dimethyl-pyrazol-1-yl)-acetyl]-piperazin-1-yl}-phenyl)-nicotinamide. MS; MH+=419.2

N-(2-{4-[2-(3,5-Dimethyl-pyrazol-1-yl)-acetyl]-piperazin-1-yl}-phenyl)-isonicotinamide. MS; MH+=419.2

5-Bromo-N-(2-{4-[2-(3,5-dimethyl-pyrazol-1-yl)-acetyl]-piperazin-1-yl}-phenyl)-nicotinamide. MS; MH+=497.2

6-Chloro-N-(2-{4-[2-(3,5-dimethyl-pyrazol-1-yl)-acetyl]-piperazin-1-yl}-phenyl)-nicotinamide. MS; MH+=453.2

N-(2-{4-[2-(3,5-Dimethyl-pyrazol-1-yl)-acetyl]-piperazin-1-yl}-phenyl)-6-phenoxy-nicotinamide. MS; MH+=511.2

2-Methyl-thiazole-4-carboxylic acid (2-{4-[2-(3,5-dimethyl-pyrazol-1-yl)-acetyl]-piperazin-1-yl}-phenyl)-amide. MS; MH+=439.2

Example 6

Synthesis of N-(5-Chloro-2-{4-[2-(4-chloro-3,5-dimethyl-2H-pyrrol-2-yl)-acetyl]-piperazin-1-yl}-pyridin-3-yl)-3-trifluoromethyl-benzamide To (3,5-dimethyl-pyrazol-1-yl)-acetic acid (0.140 g, 0.908 mmol) in DMF is added carbonyl diimidazole (0.140 g, 0.863 mmol) in one portion. The mixture is stirred for 1 h. To this is added 1-(2-nitro-phenyl)-piperazine (0.197 g, 0.950 mmol). The mixture is stirred for 14 h and then diluted with 100 mL EtOAc. The reaction is quenched with 20 mL of saturated NH$_4$Cl, washed with 2×20 mL of H$_2$O and 1×20 mL of brine. The organic phase is dried (MgSO$_4$), filtered and concentrated to give 2-(3,5-dimethyl-pyrazol-1-yl)-1-[4-(2-nitrophenyl)-piperazin-1-yl]-ethanone in 64% yield.

To a flask containing 2-(3,5-dimethyl-pyrazol-1-yl)-1-[4-(2-nitro-phenyl)-piperazin-1-yl]-ethanone (0.201 g, 0.584 mmol) and Pd/C (0.100 g) under Ar is added 10 mL of MeOH. To this mixture NaBH$_4$ (0.022 g, 0.584 mmol) is added and the mixture is stirred for 1 h. The mixture is filtered through diatomaceous earth and concentrated to dryness. The residue is diluted with 100 mL CH$_2$Cl$_2$ and quenched with 50 mL of saturated NH$_4$Cl. The organic phase is dried with MgSO$_4$, filtered and concentrated to give 1-[4-(2-amino-phenyl)-piperazin-1-yl]-2-(3,5-dimethyl-pyrazol-1-yl)-ethanone in 93% yield.

The 1-[4-(2-amino-phenyl)-piperazin-1-yl]-2-(3,5-dimethyl-pyrazol-1-yl)-ethanone (0.042 g, 0.136 mmol) is dissolved in 1.5 mL of CH$_2$Cl$_2$. To this is added diisopropylethyl amine (0.046 mL, 0.250 mmol) and benzoyl chloride (0.018 mL, 0.150). The mixture is stirred for 60 h. The reaction is quenched with 2 mL of saturated NH$_4$Cl and extracted in the reaction vial with 2×2 mL of CH$_2$Cl$_2$. The organic phase is concentrated. The residue is purified using a SiO$_2$ prep plate eluting with (75% EtOAc/hexanes) to give 58.1 mg of N-(2-{4-[2-(3,5-dimethyl-pyrazol-1-yl)-acetyl]-piperazin-1-yl}-phenyl)-benzamide in 100% Yield. MS: MH+=418.2.

The following compounds were prepared analogously:

3-Chloro-N-(2-{4-[2-(3,5-dimethyl-pyrazol-1-yl)-acetyl]-piperazin-1-yl}-phenyl)-benzamide. MS; MH+=452.2

N-(2-{4-[2-(3,5-Dimethyl-pyrazol-1-yl)-acetyl]-piperazin-1-yl}-phenyl)-3-trifluoromethyl-benzamide. MS; MH+=486.2

4-Chloro-N-(2-{4-[2-(3,5-dimethyl-pyrazol-1-yl)-acetyl]-piperazin-1-yl}-phenyl)-benzamide. MS; MH+=452.2

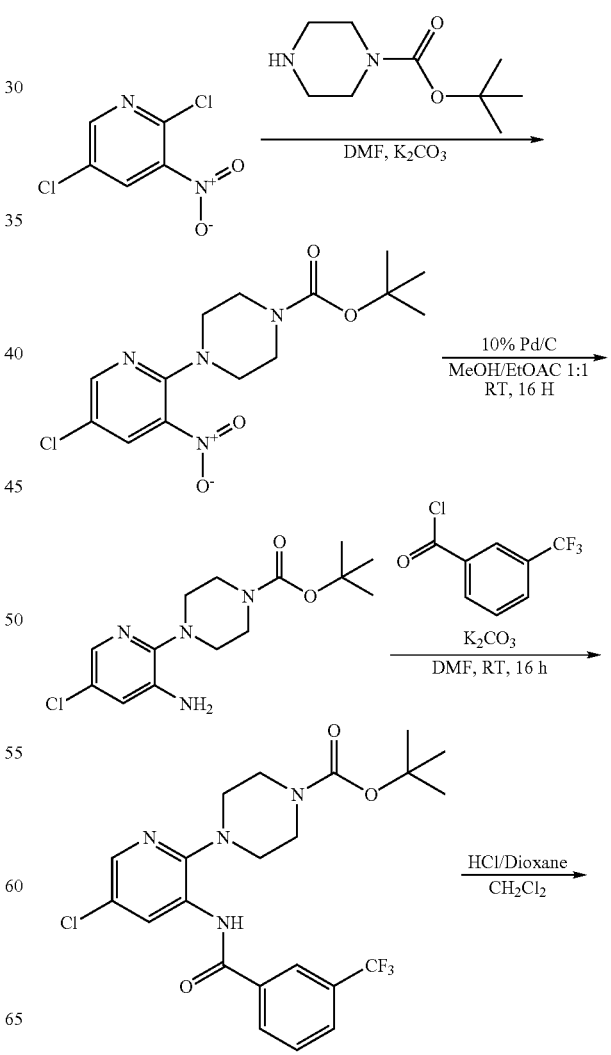

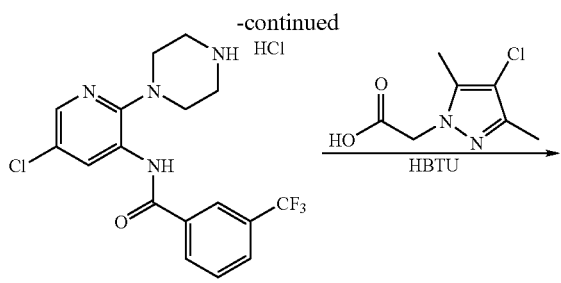

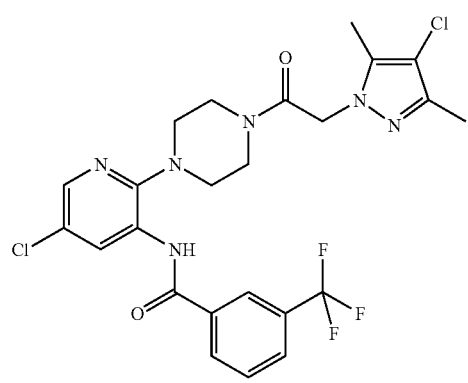

To a solution of 2,5-dichloro-3-nitro-pyridine (2.50 g, 13.0 mmol) in N,N-dimethylformamide (100 mL) is added 1-t-Boc-piperazine (2.80 g, 15.0 mmol) followed by potassium carbonate (9.00 g, 65.0 mmol). The mixture is stirred at room temperature for 1 h and then poured over ice water and stirred until all of the ice melts. During this time a solid precipitates from solution. The yellow solid is collected by filtration, washed with water, and dried on the filter pad to provide 4.40 g of 4-(5-chloro-3-nitro-pyridin-2-yl)-piperazine-1-carboxylic acid tert-butyl ester in 99% yield.

A round bottom flask is charged with 5% platinum sulfide on carbon (0.20 g, 0.039 mmol). The flask was evacuated and refilled with argon three times. To the flask is added 4-(5-chloro-3-nitro-pyridin-2-yl)-piperazine-1-carboxylic acid tert-butyl ester (2.80 g, 8.17 mmol) as a solution in a 1:1 mixture of ethyl acetate:methanol (100 mL). The mixture is placed under an atmosphere of hydrogen and stirred overnight at room temperature. The mixture is filtered through a pad of diatomaceous earth and concentrated under reduced pressure to provide 2.0 g of 4-(3-amino-5-chloro-pyridin-2-yl)-piperazine-1-carboxylic acid tert-butyl ester as a dark solid in 80% yield.

To a solution of 4-(3-amino-5-chloro-pyridin-2-yl)-piperazine-1-carboxylic acid tert-butyl ester (1.10 g, 3.50 mmol) in methylene chloride (100 mL) is added N,N-diisopropylethylamine (0.70 mL, 3.9 mmol) followed by of 3-trifluoromethylbenzoyl chloride (0.80 g, 3.8 mmol). The mixture is stirred at room temperature overnight. The mixture is washed with water followed by saturated aqueous sodium bicarbonate then dried over anhydrous $Na_2SO_4$ and concentrated under reduced pressure. The residue is purified by flash silica gel chromatography using an eluent of ethyl acetate/heptane to provide, after removal of the eluent under reduced pressure, 1.40 g of 4-[5-chloro-3-(3-trifluoromethyl-benzoylamino)-pyridin-2-yl]-piperazine-1-carboxylic acid tert-butyl ester as a clear oil in 93% yield.

To a solution of 4-[5-chloro-3-(3-trifluoromethyl-benzoylamino)-pyridin-2-yl]-piperazine-1-carboxylic acid tert-butyl ester (1.40 g, 2.89 mmol) in methylene chloride (100 mL) is added hydrogen chloride (3.00 mL, 12 mmol) as a 4.0 M solution in 1,4-dioxane. The mixture is stirred at room temperature for 2 days during which time a solid precipitates from solution. The off-white solid is collected by filtration, washed with methylene chloride and dried on the filter pad to afford 1.20 g of N-(5-chloro-2-piperazin-1-yl-pyridin-3-yl)-3-trifluoromethyl-benzamide in 100% yield.

To solution of (4-chloro-3,5-dimethyl-pyrazol-1-yl)-acetic acid (0.051 g, 0.160 mmol) in N,N-dimethylformamide (2 mL) is added pyridine (0.006 mL, 0.07 mmol) followed by 0.123 g (0.324 mmol) of tetramethyluroniumhydroxybenzotriazolehexaflourophosphate. The mixture stirred for 1 h. To this is added of N-(5-chloro-2-piperazin-1-yl-pyridin-3-yl)-3-trifluoromethyl-benzamide (0.031 g, 0.162 mmol). The mixture is allowed to stir overnight. The mixture is concentrated under reduced pressure and is purified by reverse phase HPLC to provide 0.010 g of N-(5-chloro-2-{4-[2-(4-chloro-3,5-dimethyl-2H-pyrrol-2-yl)-acetyl]-piperazin-1-yl}-pyridin-3-yl)-3-trifluoromethyl-benzamide in 21% yield. MS; MH+=558.8

The following compounds were prepared analogously:

N-(5-Chloro-2-{4-[2-(3,5-dimethyl-pyrazol-1-yl)-acetyl]-piperazin-1-yl}-pyridin-3-yl)-3-trifluoromethyl-benzamide MS; MH+=521.8

N-{5-Chloro-2-[4-(2-phenylamino-acetyl)-piperazin-1-yl]-pyridin-3-yl}-3-trifluoromethyl-benzamide MS; MH+=518.7

N-(5-Chloro-2-{4-[2-(4-chloro-phenoxy)-acetyl]-piperazin-1-yl}-pyridin-3-yl)-3-trifluoromethyl-benzamide MS; MH+=555.7

N-{5-Chloro-2-[4-(2-pyrrolo[2,3-b]pyridin-1-yl-acetyl)-piperazin-1-yl]-pyridin-3-yl}-3-trifluoromethyl-benzamide MS; MH+=543.8

N-(2-{4-[5-Chloro-3-(3-trifluoromethyl-benzoylamino)-pyridin-2-yl]-piperazin-1-yl}-2-oxo-ethyl)-3,4-dimethoxy-benzamide MS; MH+=606.7

3-Chloro-N-(2-{4-[2-(3,5-dimethyl-pyrazol-1-yl)-acetyl]-piperazin-1-yl}-5-methanesulfonyl-pyridin-3-yl)-benzamide MS; MH+=531.7

Example 7

Synthesis of 3-Chloro-N-(5-chloro-2-{4-[2-(3,5-dimethyl-pyrazol-1-yl)-acetyl]-piperazin-1-yl}-pyridin-3-yl)-benzamide

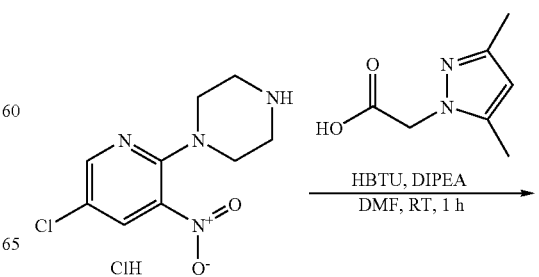

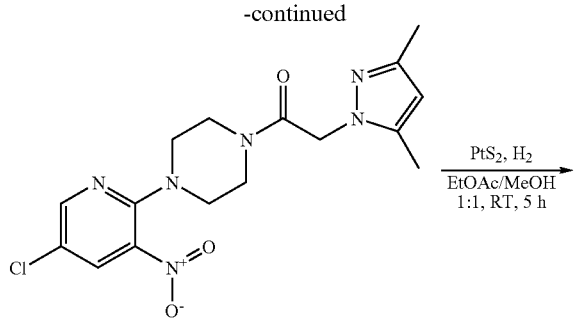

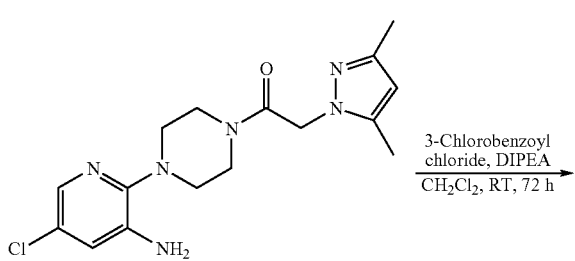

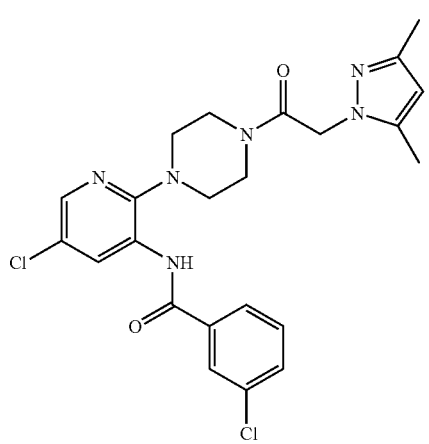

To a solution of (3,5-dimethyl-pyrazol-1-yl)-acetic acid (0.800 g, 5.19 mmol) in dimethylformamide (20 mL) is added 2.1 g (5.5 mmol) of tetramethyluroniumhydroxybenzotriazole hexafluorophosphate followed by of N,N-diisopropylethylamine (2.70 mL, 15 mmol). The mixture is stirred at room temperature for 1 h then 1-(5-chloro-3-nitro-pyridin-2-yl)-piperazine hydrochloride (1.60 g, 5.70 mmol) is added and the mixture is stirred at room temperature for 1 h. The mixture is diluted with water which causes a solid to precipitate from solution. The orange solid is collected by filtration, washed with water, and dried on the filter pad. The collected material is purified by flash silica gel chromatography to provide, after removal of the eluent under reduced pressure, 1.1 g of 1-[4-(5-chloro-3-nitro-pyridin-2-yl)-piperazin-1-yl]-2-(3,5-dimethyl-pyrazol-1-yl)-ethanone as a dark brown oil in 56% yield.

A round bottom flask is charged with 5% platinum sulfide on carbon (0.200 g, 0.039 mmol). The flask is evacuated and refilled with argon three times. To the flask is added 1-[4-(5-chloro-3-nitro-pyridin-2-yl)-piperazin-1-yl]-2-(3,5-dimethyl-pyrazol-1-yl)-ethanone (1.10 g, 2.90 mmol) as a solution in a 1:1 mixture of ethyl acetate:methanol (100 mL). The mixture is placed under an atmosphere of hydrogen and stirred for 5 h at room temperature. The mixture is filtered through a pad of diatomaceous earth and concentrated under reduced pressure to provide 0.67 g of 1-[4-(3-amino-5-chloro-pyridin-2-yl)-piperazin-1-yl]-2-(3,5-dimethyl-pyrazol-1-yl)-ethanone as a white solid in 66% yield.

To a solution of 1-[4-(3-amino-5-chloro-pyridin-2-yl)-piperazin-1-yl]-2-(3,5-dimethyl-pyrazol-1-yl)-ethanone (0.040 g, 0.11 mmol) in methylene chloride (2 mL) is added 3-chlorobenzoyl chloride (0.020 mL, 0.160 mmol) followed by of N,N-diisopropylethylamine (0.045 mL, 0.25 mmol). The mixture is stirred at room temperature for 3 days. The mixture is concentrated under a stream of nitrogen and the residue is purified by preparative reverse phase HPLC to provide, after removal of the eluent under reduced pressure, 0.030 g of 3-chloro-N-(5-chloro-2-{4-[2-(3,5-dimethyl-pyrazol-1-yl)-acetyl]-piperazin-1-yl}-pyridin-3-yl)-benzamide as a white solid in 53% yield. MS; MH+=487.7

N-(5-Chloro-2-{4-[2-(3,5-dimethyl-pyrazol-1-yl)-acetyl]-piperazin-1-yl}-pyridin-3-yl)-nicotinamide. MS; MH+=554.7

N-(5-Chloro-2-{4-[2-(3,5-dimethyl-pyrazol-1-yl)-acetyl]-piperazin-1-yl}-pyridin-3-yl)-isonicotinamide. MS; MH+=554.7

3-Chloro-N-(5-chloro-2-{4-[2-(2-oxo-piperidin-1-yl)-acetyl]-piperazin-1-yl}-pyridin-3-yl)-benzamide. MS; MH+=490.67

Example 8

Synthesis of N-(5-Chloro-2-{4-[2-(3,5-dimethyl-pyrazol-1-yl)-acetyl]-piperazin-1-yl}-pyridin-3-yl)-4-methanesulfonyl-benzamide

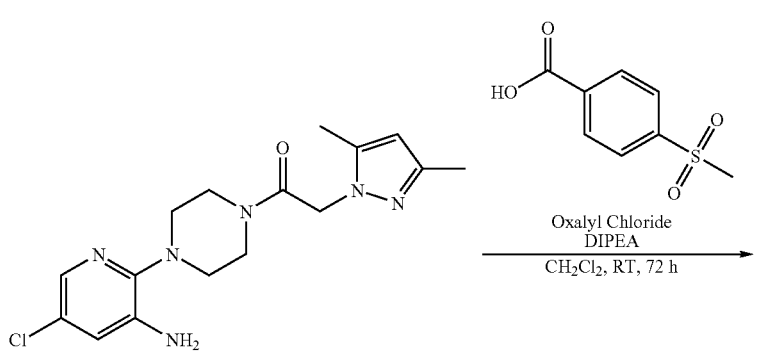

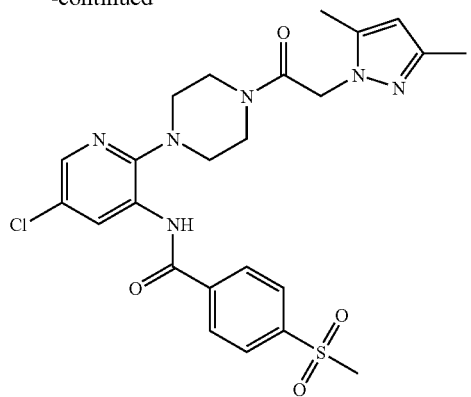

To a solution of 4-methanesulfonyl-benzoic acid (0.030 g, (0.150 mmol) in methylene chloride (2 mL) is added oxalyl chloride (0.017 mL, 0.200 mmol) followed by 1 drop of N,N-dimethylformamide. Vigourous bubbling is observed and the reaction mixture is stirred at room temperature for 2 h. The mixture is concentrated under a stream of nitrogen. The residue is dissolved in methylene chloride (2 mL) and 1-[4-(3-amino-5-chloro-pyridin-2-yl)-piperazin-1-yl]-2-(3,5-dimethyl-pyrazol-1-yl)-ethanone (0.040 g, 0.110 mmol) is added followed by (0.040 mL, 0.220 mmol) N,N-diisopropylethylamine (0.040 mL, 0.220 mmol). The mixture is stirred at room temperature for 3 days then concentrated under a stream of nitrogen. The residue is dissolved in dimethylsulfoxide and purified by reverse phase preparative HPLC to provide, after removal of the eluent, 0.022 g of N-(5-Chloro-2-{4-[2-(3,5-dimethyl-pyrazol-1-yl)-acetyl]-piperazin-1-yl}-pyridin-3-yl)-4-methanesulfonyl-benzamide as a white solid in 36% yield. MS; MH+=531.8

N-(5-Chloro-2-{4-[2-(3,5-dimethyl-pyrazol-1-yl)-acetyl]-piperazin-1-yl}-pyridin-3-yl)-3-methanesulfonyl-benzamide. MS; MH+=531.8

N-(5-Chloro-2-{4-[2-(3,5-dimethyl-pyrazol-1-yl)-acetyl]-piperazin-1-yl}-pyridin-3-yl)-3-cyano-benzamide. MS; MH+=478.8

Example 9

Synthesis of 3-Chloro-N-(5-chloro-2-{4-[2-(3,5-dimethyl-pyrazol-1-yl)-acetyl]-[1,4]diazepan-1-yl}-pyridin-3-yl)-benzamide

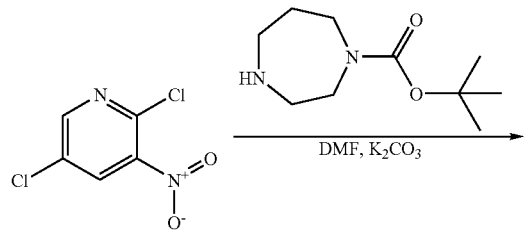

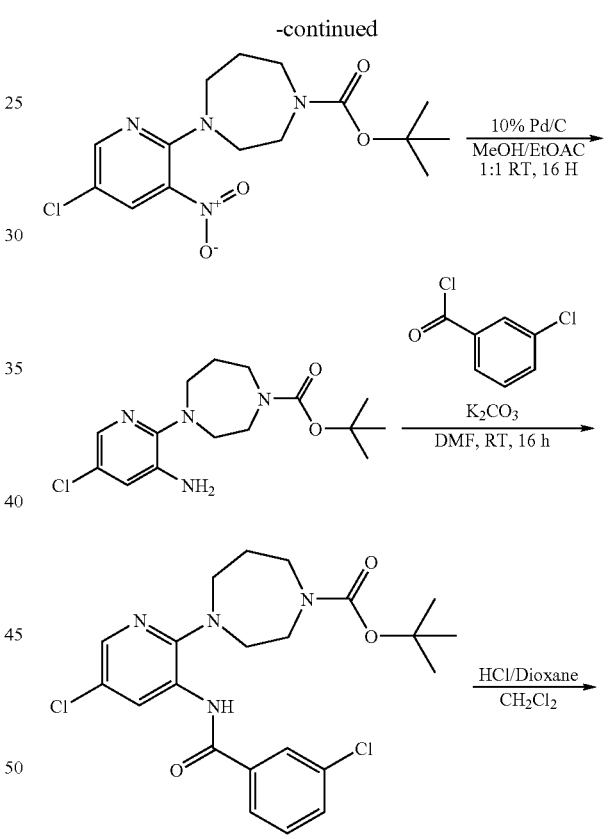

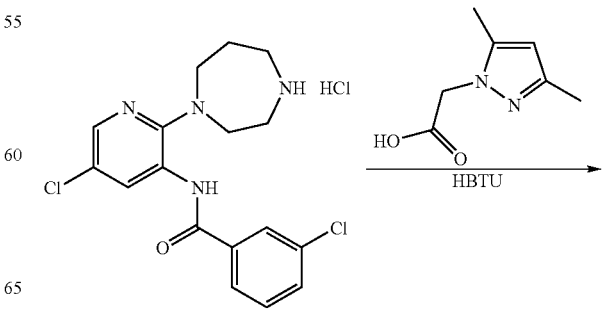

-continued

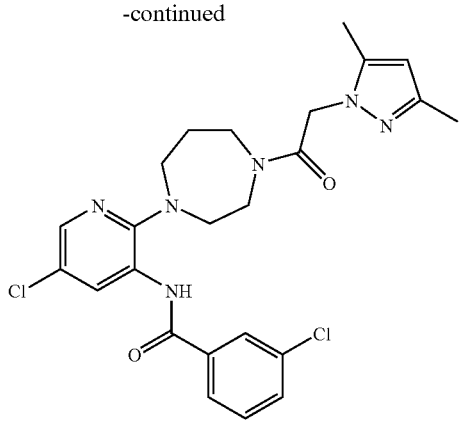

To a solution of 2,5-dichloro-3-nitro-pyridine (2.00 g, 11.0 mmol) in N,N-dimethylacetamide (100 mL) is added 1-t-Boc-piperazine (2.00 g, 11.0 mmol) followed by potassium carbonate (0.050 g). The mixture is stirred at 130° C. for 15 min and then poured over ice water and stirred until all of the ice melted. During this time a solid precipitates from solution. The yellow solid is collected by filtration, washed with water, and dried on the filter pad to provide 2.03 g of 4-(4-chloro-2-nitro-phenyl)-[1,4]diazepane-1-carboxylic acid tert-butyl ester in 57% yield.

A solution (2.00 g, 5.7 mmol) of 4-(4-chloro-2-nitro-phenyl)-[1,4]diazepane-1-carboxylic acid tert-butyl ester (2.00 g, 5.7 mmol) in a 1:1 mixture of ethyl acetate:methanol (200 mL) is stirred with 10% Pd/C (0.50 g, 1.43 mmol) under 1 atmosphere of hydrogen for 1 h. The mixture is filtered and concentrated under reduced pressure. The residue is purified by flash silica gel chromatography using an eluent of dichloromethane/methanol to provide, after removal of the eluent under reduced pressure, 1.10 g of 4-(2-amino-4-chloro-phenyl)-[1,4]diazepane-1-carboxylic acid tert-butyl ester in 58% yield.

To a solution of 4-(2-amino-4-chloro-phenyl)-[1,4]diazepane-1-carboxylic acid tert-butyl ester (1.10 g, 3.40 mmol) in acetonitrile (50 mL) is added 3-chlorobenzoyl chloride (0.80 g, 3.8 mmol). The mixture is stirred at room temperature overnight then concentrated under reduced pressure onto silica gel. The residue is purified by flash silica gel chromatography using an eluent of ethyl acetate/heptane to provide, after removal of the eluent under reduced pressure, 1.00 g of 4-[4-chloro-2-(3-chloro-benzoylamino)-phenyl]-[1,4]diazepane-1-carboxylic acid tert-butyl ester in 64% yield.

To a solution of 4-[4-chloro-2-(3-chloro-benzoylamino)-phenyl]-[1,4]diazepane-1-carboxylic acid tert-butyl ester (0.100 g, 0.215 mmol) in acetonitrile (5 mL) is added 2.0 mL of hydrogen chloride as a 4.0 M solution in 1,4-dioxane. The mixture is stirred at room temperature for 48 h during which time a solid precipitates from solution. The off-white solid is collected by filtration, washed with methylene chloride and dried on the filter pad to provide 0.070 g of 3-chloro-N-(5-chloro-2-[1,4]diazepan-1-yl-phenyl)-benzamide.

To solution of (3,5-dimethyl-pyrazol-1-yl)-acetic acid (0.010 g, 0.068 mmol) in N,N-dimethylformamide (2 mL) is added 0.006 mL (0.071 mmol) of pyridine followed by) tetramethyluroniumhydroxybenzotriazolehexaflourophosphate (0.123 g, 0.324 mmol). The mixture stirred for 1 hour. To this is added 3-chloro-N-(5-chloro-2-[1,4]diazepan-1-yl-phenyl)-benzamide (0.025 g, 0.068 mmol). The mixture is allowed to stir overnight. The mixture is concentrated under reduced pressure and is purified by reverse phase HPLC to provide 0.010 g of 3-chloro-N-(5-chloro-2-{4-[2-(3,5-dimethyl-pyrazol-1-yl)-acetyl]-[1,4]diazepan-1-yl}-pyridin-3-yl)-benzamide in 29% yield. MS MH+=501.8

The following compound is prepared analogously

3-Chloro-N-(5-chloro-2-{4-[2-(4-chloro-3,5-dimethyl-pyrazol-1-yl)-acetyl]-[1,4]diazepan-1-yl}-pyridin-3-yl)-benzamide MS; M+H=537.8

3-Chloro-N-{5-chloro-2-[4-(2-piperidin-1-yl-acetyl)-piperazin-1-yl]-pyridin-3-yl}-benzamide MH+=474.2

3-Chloro-N-{5-chloro-2-[4-(2-piperidin-1-yl-acetyl)-[1,4]diazepan-1-yl]-pyridin-3-yl}-benzamide MH+=490.2

Example 10

Synthesis of N-(5-Chloro-2-{1-[2-(3,5-dimethyl-pyrazol-1-yl)-acetyl]-piperidin-4-yl}-phenyl)-benzamide

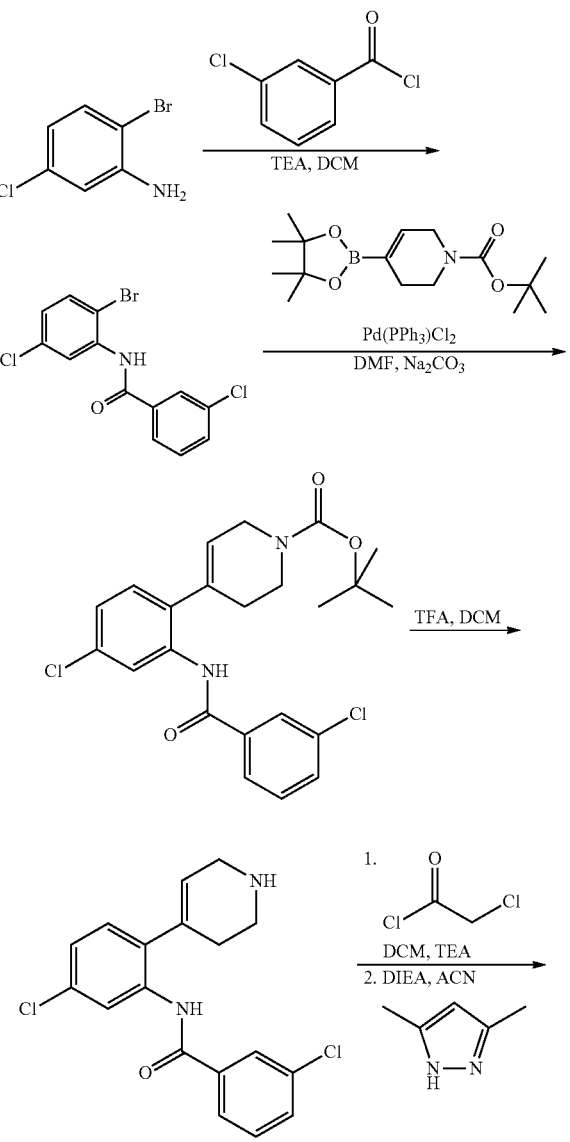

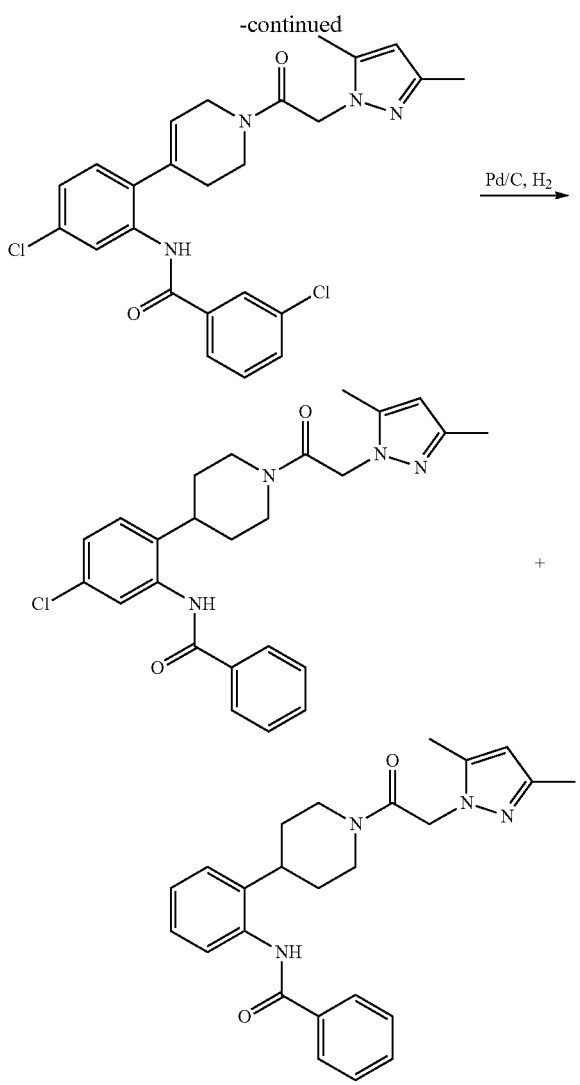

To a solution of 2-bromo-5-chloroaniline (0.380 g, 1.84 mmol) and triethylamine (0.768 mL, 5.52 mmol) in dichloromethane (15 mL) is added 3-chlorobenzoyl chloride (0.353 mL, 2.76 mmol) in a dropwise fashion. The resulting mixture is allowed to stir at room temperature for 2 h. Water (30 mL) is added and extracted with the mixture is extracted with dichloromethane 3×. The organic layer is combined, washed with brine 1×, dried (Na$_2$SO$_4$) and concentrated under vacuum to give 0.630 g of N-(2-bromo-5-chloro-phenyl)-3-chloro-benzamide in 99% yield.

In a 20 mL microwave tube is added N-(2-bromo-5-chlorophenyl)-3-chloro-benzamide (0.500 g, 1.45 mmol), 4-(4,4,5,5-tetramethyl-[1,3,2]dioxaborolan-2-yl)-3,6-dihydro-2H-pyridine-1-carboxylic acid tert-butyl ester (0.532 g, 1.74 mmol), bis(triphenylphosphine) palladium(II) chloride (0.102 g, 0.145 mmol), 2N Na$_2$CO$_3$ aqueous solution (3.62 mL, 7.25 mmol) and DMF (10 mL). The resulting mixture is placed in a microwave oven and heated to 100° C. for 30 min. The reaction turns black. The reaction mixture is poured into water (30 mL) and filtered. The cake is washed with 10 mL water and air dried. The cake is then dissolved in minimum dichloromethane and purified via flash chromatography using 0-30% EtOAc/hexane. The compound comes at 30% EtOAc. Removal of the solvent under vacuum gives 0.504 g of 4-[4-chloro-2-(3-chloro-benzoylamino)-phenyl]-3,6-dihydro-2H-pyridine-1-carboxylic acid tent-butyl ester in 78% yield.

To the solution of 4-[4-chloro-2-(3-chloro-benzoylamino)-phenyl]-3,6-dihydro-2H-pyridine-1-carboxylic acid tert-butyl ester (0.504 g, 1.13 mmol) in dichloromethane (10 mL) is added trifluoroacetic acid (1 mL) in a dropwise fashion. The resulting reaction is allowed to stir at room temperature for 2 h. 2N NaOH aqueous solution is added to adjust the pH>12. The mixture is then extracted with dichloromethane 3×. The organic layers are combined, washed with brine 1×, dried (Na$_2$SO$_4$) and concentrated under vacuum to give 0.391 g of 3-chloro-N-[5-chloro-2-(1,2,3,6-tetrahydro-pyridin-4-yl)-phenyl]-benzamide in 99% yield.

To a solution of 3-chloro-N-[5-chloro-2-(1,2,3,6-tetrahydro-pyridin-4-yl)-phenyl]-benzamide (0.140 g, 0.403 mmol) and triethylamine (0.168 mL, 1.21 mmol) in dichloromethane (3 mL) is added chloroacetyl chloride (0.039 mL, 0.484 mmol) in a drop-wise fashion. The reaction is allowed to stir at room temperature for 1 h. Water (30 mL) is added and extracted with dichloromethane 3×. The organic layer is combined, washed with brine 1×, dried (Na$_2$SO$_4$) and concentrated. The crude residue is dissolved in 2 mL acetonitrile and added to a 2-5 mL microwave tube with diisopropylethylamine (0.1 mL). The reaction is heated in a microwave oven at 170° C. for 1 h. The reaction mixture is filtered and purified via preparative HPLC. Removal of the solvent gives 0.165 g of 3-chloro-N-(5-chloro-2-{1-[2-(3,5-dimethyl-pyrazol-1-yl)-acetyl]-1,2,3,6-tetrahydro-pyridin-4-yl}-phenyl)-benzamide in 85% yield. MS MH+=483.20

To a solution of 3-chloro-N-(5-chloro-2-{1-[2-(3,5-dimethyl-pyrazol-1-yl)-acetyl]-1,2,3,6-tetrahydro-pyridin-4-yl}-phenyl)-benzamide (0.100 g, 0.207 mmol) in ethanol (5 mL) is added Pd on 5% activated carbon (10 mg) in a round bottom flask and the mixture is purged three times and back filled with H$_2$ using a H$_2$ filled balloon. The reaction is allowed to stir at room temperature for 20 h. The reaction is filtered through a pad of diatomaceous earth and washed with MeOH. The filtrate is concentrated and purified via preparative HPLC. Removal of the solvent gives 0.010 g of N-(5-chloro-2-{1-[2-(3,5-dimethyl-pyrazol-1-yl)-acetyl]-piperidin-4-yl}-phenyl)-benzamide in 10% yield. MS MH+=450.2 and 0.030 g of N-(2-{1-[2-(3,5-Dimethyl-pyrazol-1-yl)-acetyl]-piperidin-4-yl}-phenyl)-benzamide in 35% yield. MS MH+=417.3.

The following compounds are prepared analogously:
3-Chloro-N-(5-chloro-2-{1-[2-(3,5-dimethyl-pyrazol-1-yl)-acetyl]-1,2,3,6-tetrahydro-pyridin-4-yl}-phenyl)-benzamide MH+=483.20

Example 11

Synthesis of 5-chloro-1-(2-{4-[2-(4-methanesulfonyl-phenylcarbamoyl)-phenyl]-piperazin-1-yl}-2-oxo-ethyl)-1H-indole-2-carboxylic acid

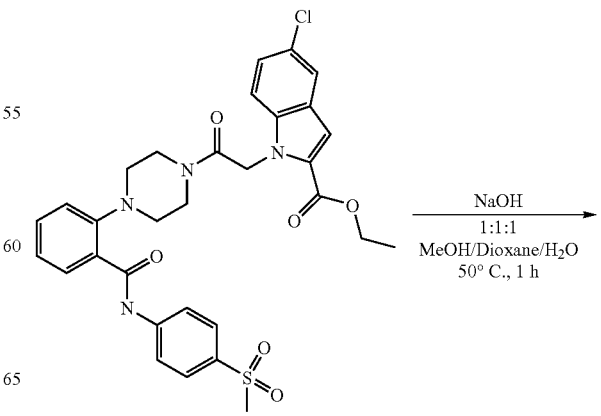

-continued

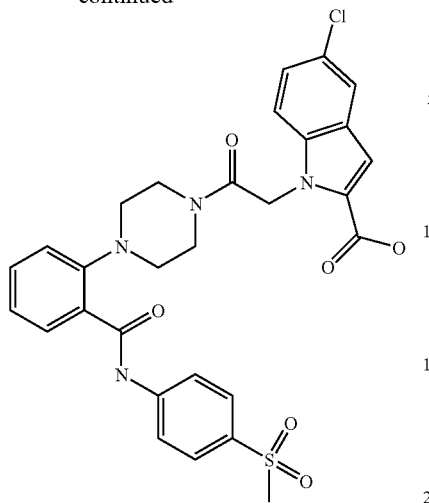

5-Chloro-1-(2-{4-[2-(4-methanesulfonyl-phenylcarbamoyl)-phenyl]-piperazin-1-yl}-2-oxo-ethyl)-1H-indole-2-carboxylic acid ethyl ester is prepared using the procedure outlined in Example 1 with the appropriate intermediates.

A suspension of 5-chloro-1-(2-{4-[2-(4-methanesulfonyl-phenylcarbamoyl)-phenyl]-piperazin-1-yl}-2-oxo-ethyl)-1H-indole-2-carboxylic acid ethyl ester (0.14 g, 0.22 mmol) of in a 1:1:1 mixture of water/MeOH/1,4-dioxane (9 mL) is heated at 50° C. for 1 hour during which time all of the solids went into solution. The mixture is cooled to room temperature and concentrated under reduced pressure to remove volatile organics. The pH of the mixture is adjusted to slightly acidic (approx pH 5) by the addition of a 2N solution of hydrochloric acid which caused a solid to precipitate from solution. The formed solid is collected by filtration, washed with water and dried on the filter pad to provide 0.025 g of 5-chloro-1-(2-{4-[2-(4-methanesulfonyl-phenylcarbamoyl)-phenyl]-piperazin-1-yl}-2-oxo-ethyl)-1H-indole-2-carboxylic acid as an off white powder.

Example 12

Synthesis of 5-fluoro-6-methyl-pyridin-3-ylamine

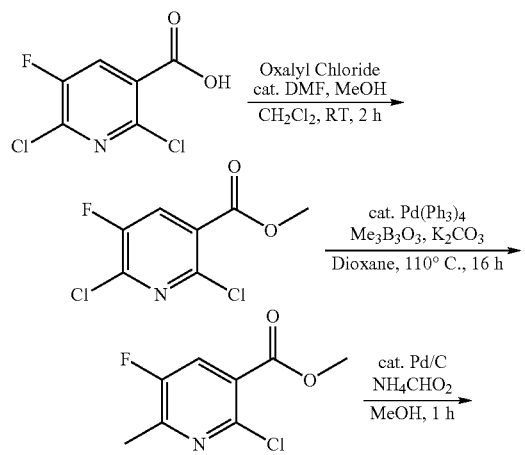

-continued

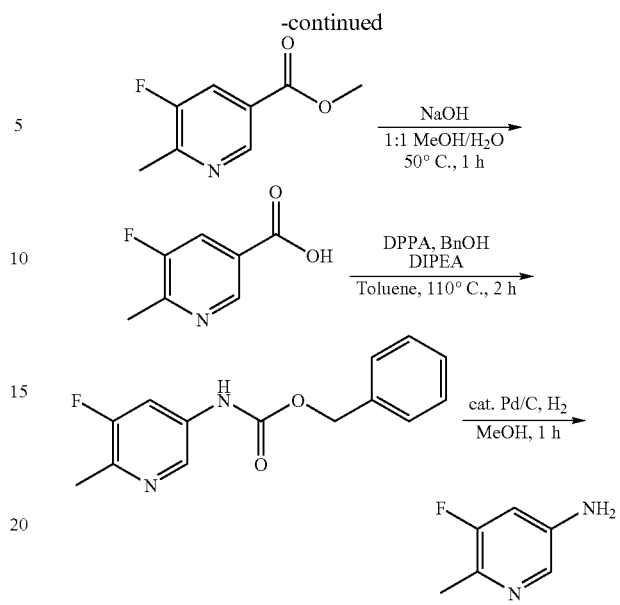

To a solution of 2,6-dichloro-5-fluoro-nicotinic acid (1.00 g, 4.46 mmol) in methylene chloride is added of oxalyl chloride (50 mL, 0.445 mL, 5.30 mmol) followed by 2 drops of N,N-dimethylformamide. Vigorous bubbling is observed and the mixture is stirred at room temperature for 1 h. The reaction mixture is concentrated under reduced pressure and the residue is taken back up into methylene chloride (50 mL). To the solution is added MeOH (20 mL) and the mixture is stirred at room temperature for 2 h. The reaction mixture is concentrated under reduced pressure to provide 2,6-dichloro-5-fluoro-nicotinic acid methyl ester as an oil.

A mixture of 2,6-dichloro-5-fluoro-nicotinic acid methyl ester (1.00 g 4.46 mmol), trimethylboroxin (0.620 mL, 4.40 mmol), tetrakis(triphenylphosphine)palladium (0.500 g, 0.433 mmol) and potassium carbonate (1.50 g, 12.0 mmol) is heated at 110° C. overnight. The mixture is cooled to room temperature, diluted with water, and extracted with EtOAc. The combined organic phase is washed with water followed by brine, then dried over anhydrous sodium sulfate and concentrated under reduced pressure. The residue is purified by flash silica gel chromatography using a gradient of 0-30% EtOAc/heptane to provide 0.410 g (45.1%) of 2-chloro-5-fluoro-6-methyl-nicotinic acid methyl ester as a solid.

A flask containing 10% Pd/C (0.20 g, 0.19 mmol) and 2-chloro-5-fluoro-6-methyl-nicotinic acid methyl ester (0.410 g, 2.01 mmol) is placed under an atmosphere of Ar. The atmosphere of the vessel is evacuated and refilled with Ar three times. To this is added MeOH (30 mL) followed by ammonium formate (1.0 g, 16 mmol). The mixture is stirred at room temperature for 1 h. The mixture is filtered through a pad of diatomaceous earth and concentrated under reduced pressure to provide a solid. The material is washed with EtOAc and filtered to remove insoluble material. The filtrate is concentrated under reduced pressure to provide 0.210 g (61.6%) of 5-fluoro-6-methyl-nicotinic acid methyl ester as a solid.

To a suspension of 5-fluoro-6-methyl-nicotinic acid methyl ester (0.21 g, 1.24 mmol) in a 1:1 mixture of MeOH: water (20 mL) is added sodium hydroxide as a 10% aqueous solution (1.0 mL, 2.5 mmol). The mixture is heated to 50° C. for 1 h then cooled to room temperature and concentrated under reduced pressure to remove volatile organics. The pH of the resulting solution is adjusted to slightly acidic (approximately pH 5) by the addition of a 2N solution of HCl. The mixture is extracted with EtOAc and the combined organic phase is dried over anhydrous sodium sulfate and concentrated to provide 0.170 g of 5-fluoro-6-methyl-nicotinic acid as a solid.

To a solution of 5-fluoro-6-methyl-nicotinic acid (0.17 g, 1.10 mmol) in toluene (10 mL) is added diphenylphosphoryl azide (0.30 mL, 1.3 mmol) followed by N,N-diisopropylethylamine (0.21 mL, 1.20 mmol). The mixture is stirred at room temperature for 1 h then benzyl alcohol (0.14 mL, 1.30 mmol) is added and the reaction mixture is heated to 110° C. for 2 h. The mixture is cooled to room temperature and concentrated under reduced pressure. The residue is purified by flash silica gel chromatography using a 0-30% gradient of EtOAc/heptanes to provide 0.196 g of (5-fluoro-6-methyl-pyridin-3-yl)-carbamic acid benzyl ester as a solid.

A flask is charged with (5-fluoro-6-methyl-pyridin-3-yl)-carbamic acid benzyl ester (0.20 g, 0.23 mmol) and 10% Pd/C (0.09 g, 0.08 mmol). The atmosphere is evacuated and refilled with Ar three times. To this mixture is added MeOH (10 mL). The reaction mixture is placed under an atmosphere of H₂ and stirred at room temperature for 1 h. The mixture is filtered through a syringe filter and concentrated under reduced pressure to provide 5-fluoro-6-methyl-pyridin-3-ylamine as a solid.

5-Fluoro-6-methyl-pyridin-3-ylamine is used to prepare 2-{4-[2-(3,5-dimethyl-pyrazol-1-yl)-acetyl]-piperazin-1-yl}-N-(5-fluoro-6-methyl-pyridin-3-yl)-benzamide MS MH+=451.4, using the procedure described in Example 1.

Example 13

Synthesis of (S)-4-(2-carboxy-phenyl)-2-methyl-piperazine-1-carboxylic acid tent-butyl ester

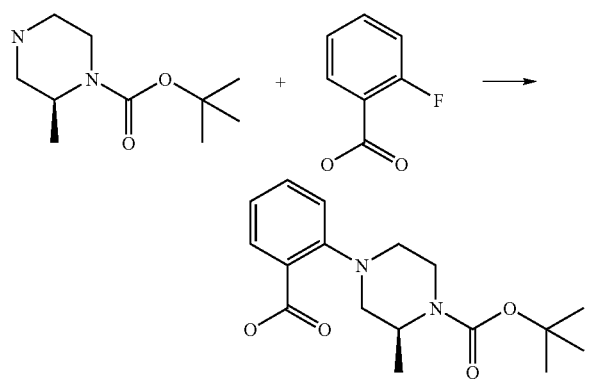

To a solution of (S)-2-methyl-piperazine-1-carboxylic acid tert-butyl ester (4.10 g, 19.8 mmol) in pyridine (41 mL) is added 2-fluoro-benzoic acid (20.2 g, 140 mmol) followed by DBU (43 ml). The mixture is stirred at 150° C. for 48 h. The mixture is diluted with 600 mL of 2N HCl followed by extraction with EtOAc (3×300 mL). Organics are collected and purified by flash chromoatography to provide 3.50 g, 53% yield of (S)-4-(2-carboxy-phenyl)-2-methyl-piperazine-1-carboxylic acid tert-butyl ester.

This intermediate is used in the preparation of the compounds listed below using the procedure described in Example 1:

N-(2-Methoxy-pyridin-4-yl)-2-{(S)-3-methyl-4-[2-(2-oxo-piperidin-1-yl)-acetyl]-piperazin-1-yl}-benzamide MS MH+=466.4

2-{(S)-4-[2-(3,5-Dimethyl-pyrazol-1-yl)-acetyl]-3-methyl-piperazin-1-yl}-N-(2-methoxy-pyridin-4-yl)-benzamide MS MH+=463.4

Example 14

Synthesis of 4-[2-(5-methyl-4,5,6,7-tetrahydro-thiazolo[5,4-e]pyridin-2-ylcarbamoyl)-phenyl]-piperazine-1-carboxylic acid tert-butyl ester

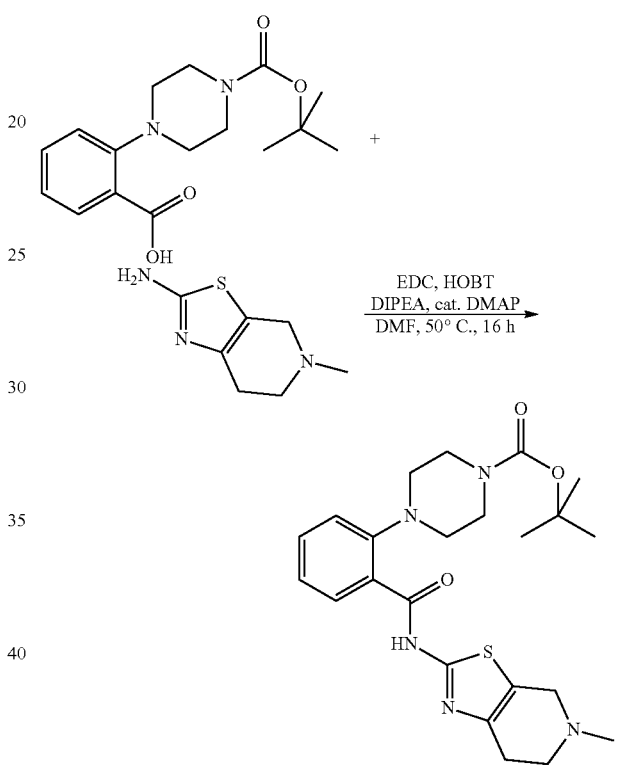

Dissolved 4-(2-carboxy-phenyl)-piperazine-1-carboxylic acid tert-butyl ester (0.30 g, 0.98 mmol), EDC (0.23 g, 1.20 mmol) and HOBT (0.18 g, 1.20 mmol) into 1 mL of DMF. The mixture stirred for 1 h. To this is added 5-methyl-4,5,6,7-tetrahydro-thiazolo[5,4-c]pyridin-2-ylamine (0.16 g, 0.98 mmol) and N,N-diisopropylethylamine (0.37 mL, 2.00 mmol). The mixture is placed under a stream of Ar and heated at 50° C. for 16 h. The mixture is then diluted with 50 mL CH₂Cl₂, quenched with 20 mL of saturated NH₄Cl; washed with 2×20 mL of H₂O, and washed with 1×20 mL of brine. The resultant organic phase was dried with MgSO₄, filtered and concentrated to provide 0.38 g, 85% yield of 4-[2-(5-methyl-4,5,6,7-tetrahydro-thiazolo[5,4-c]pyridin-2-ylcarbamoyl)-phenyl]-piperazine-1-carboxylic acid tert-butyl ester.

This intermediate is used in the preparation of the compounds listed below using the procedure described in Example 1:

2-{4-[2-(3,5-Dimethyl-pyrazol-1-yl)-acetyl]-piperazin-1-yl}-N-(5-methyl-4,5,6,7-tetrahydro-thiazolo[5,4-c]pyridin-2-yl)-benzamide MS MH+=458.4

N-(5-Methyl-4,5,6,7-tetrahydro-thiazolo[5,4-c]pyridin-2-yl)-2-{4-[2-(1-oxo-1,3-dihydro-isoindol-2-yl)-acetyl]-piperazin-1-yl}-benzamide MS MH+=531.2

Example 15

Synthesis of 2-(2,2,2-trifluoro-ethoxy)-pyridin-4-ylamine

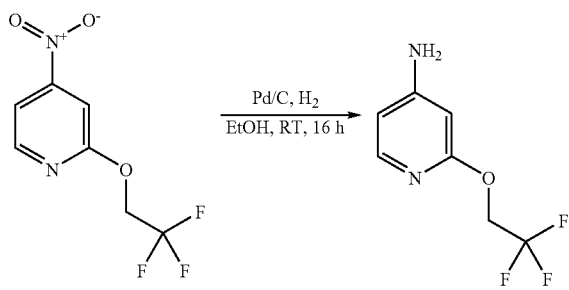 [SMILES: O=[N+]([O-])c1ccnc(OCC(F)(F)F)c1 ; Nc1ccnc(OCC(F)(F)F)c1]

4-Nitro-2-(2,2,2-trifluoro-ethoxy)-pyridine (1.11 g, 5 mmol) in 40 mL EtOH and 50 mg 10% Pd/C is placed under hydrogen atmosphere at room temp for 16 h. The solvent is removed under reduced pressure to give 0.9 g, 100% yield of 2-(2,2,2-trifluoro-ethoxy)-pyridin-4-ylamine.

This intermediate is used in the preparation of the compounds listed below using the procedure described in Example 1:
2-{4-[2-(3,5-Dimethyl-pyrazol-1-yl)-acetyl]-piperazin-1-yl}-N-[2-(2,2,2-trifluoro-ethoxy)-pyridin-4-yl]-benzamide MS MH+=517.8
2-{4-[2-(2-Oxo-piperidin-1-yl)-acetyl]-piperazin-1-yl}-N-[2-(2,2,2-trifluoro-ethoxy)-pyridin-4-yl]-benzamide MS MH+=520.0

Example 16

Synthesis of 2-trifluoromethyl-pyridin-4-ylamine

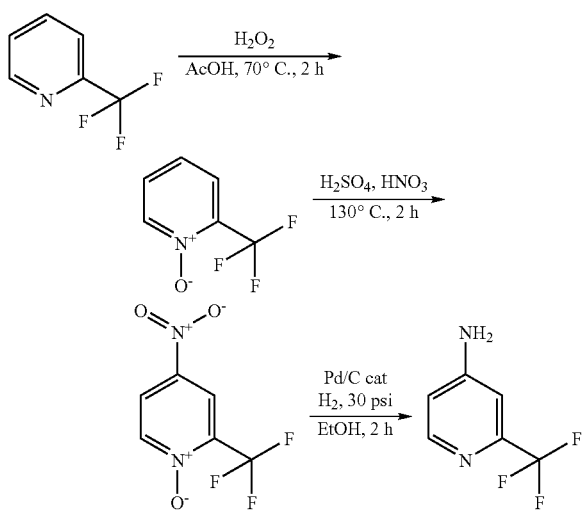

To a stirred solution of 2-trifluoromethyl pyridine (5 g, 34 mmol) in acetic acid (25 mL) is added 33% of aqueous $H_2O_2$ (20 mL) at room temperature. The reaction mixture is allowed to stir for 12 h at 70° C. After complete consumption of starting material the reaction mixture is concentrated under reduced pressure. The residue is dissolved in chloroform (250 mL) and pH is adjusted to 7 with $K_2CO_3$ (20 g approx). Resulting solid is filtered through glass sintered funnel and washed with chloroform. Filtrate is concentrated under reduced pressure to give 2-trifluoromethyl-pyridine 1-oxide as syrupy liquid (4.3 g).

To a stirred solution of 2-trifluoromethyl-pyridine 1-oxide (0.43 g, 2.43 mmol) in concentrated $H_2SO_4$ (2 mL) is added 70% $HNO_3$ (1.6 mL) dropwise at 0° C. Reaction mixture is allowed to stir for 2 h at 130° C. After completion of reaction it is quenched with ice (~200 g) and pH is adjusted 7 with solid $K_2CO_3$ (15-20 g) and extracted with EtOAc (3×20 mL). Organic part is washed with water, brine and dried over anhydrous $MgSO_4$. Solution is concentrated under reduced pressure. The residue is purified by column chromatography (silica-gel, 100-200 mesh, eluent; 20% EtOAc in hexane) to afford 4-nitro-2-trifluoromethyl-pyridine 1-oxide (0.1 g, 20%).

To a stirred solution of 4-nitro-2-trifluoromethyl-pyridine 1-oxide (0.4 g, 1.90 mmol) in EtOH (15 mL) is added 10% Pd—C (0.04 g) under nitrogen atmosphere. Hydrogenation is performed in a Parr shaker at 30 psi for 3 h at room temperature. After completion of reaction it is filtered through diatomaceous earth and washed with EtOH. Filtrate is concentrated to give 2-trifluoromethyl-pyridin-4-ylamine as a thick liquid (0.23 g, 74%).

This intermediate is used in the preparation of the compounds listed below using the procedure described in Example 1, with the exception that TBTU (O-(Benzotriazol-1-yl)-N,N,N',N'-tetramethyluronium tetrafluoroborate) in $CH_2Cl_2$ is used in the coupling step for this intermediate instead of oxalyl chloride with catalytic DMF in $CH_2Cl_2$:
2-{4-[2-(3,5-Dimethyl-pyrazol-1-yl)-acetyl]-piperazin-1-yl}-N-(2-trifluoromethyl-pyridin-4-yl)-benzamide MS MH+=487.9
2-{4-[2-(2-Oxo-piperidin-1-yl)-acetyl]-piperazin-1-yl}-N-(2-trifluoromethyl-pyridin-4-yl)-benzamide MS MH+=490.9

Example 17

Synthesis of 4-(2-carboxy-4-fluoro-phenyl)-piperazine-1-carboxylic acid tent-butyl ester

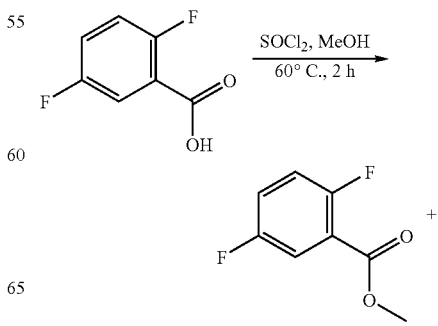

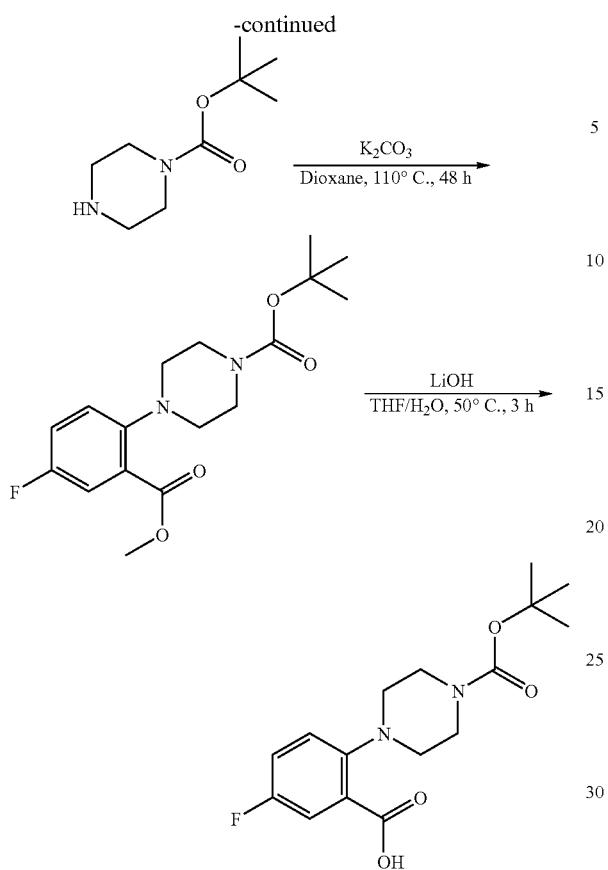

To a stirred solution of 2,5-difluorobenzoic acid (20 g, 126 mmol) in MeOH (250 mL) is added thionyl chloride (22.5 g, 190 mmol) dropwise at ice-cold conditions. After complete addition the reaction mixture is heated at 60° C. for 3 h. The reaction mixture is concentrated and the residue neutralized with aqueous $Na_2CO_3$ solution. It is extracted with $CH_2Cl_2$ (3×100 mL), dried over anhydrous $MgSO_4$ and concentrated under reduced pressure to afford the desired 2,5-difluorobenzoic acid methyl ester as a thick liquid (22 g).

2,5-Difluorobenzoic acid methyl ester (25 g, 145 mmol), piperazine-1-carboxylic acid tert-butyl ester (27 g, 145 mmol) and $K_2CO_3$ (50 g, 363 mmol) are added to 1,4-dioxane and the mixture is heated to 110° C. for 2 days. The reaction mixture is cooled, inorganic salts filtered through sintered funnel and filtrate is concentrated under reduced pressure. Crude compound is purified by column chromatography (silica-gel, 100-200 mesh, eluent; 5% EtOAc in hexane) to afford desired 4-(4-fluoro-2-methoxycarbonyl-phenyl)-piperazine-1-carboxylic acid tert-butyl ester as a syrupy liquid (8.1 g, 16.3%).

4-(4-Fluoro-2-methoxycarbonyl-phenyl)-piperazine-1-carboxylic acid tert-butyl ester (5.5 g, 16.2 mmol) is dissolved in THF (40 mL) and 1 M aqueous LiOH (33 mL) is added at room temperature. The solution is warmed to 50° C. for 3 h. THF is removed under reduced pressure and the aqueous part is washed with 50% EtOAc in hexane. The aqueous part is acidified with 1 M aqueous HCl followed by extraction with EtOAc (3×50 mL). Combined organic layer is dried over anhydrous $MgSO_4$ and concentrated under reduced pressure to afford 4-(2-carboxy-4-fluoro-phenyl)-piperazine-1-carboxylic acid tert-butyl ester as a solid (4.9 g, 98%).

This intermediate is used in the preparation of the compounds listed below using the procedure described in Example 1, with the exception that TBTU in $CH_2Cl_2$ is used in the coupling step for this intermediate instead of oxalyl chloride with catalytic DMF in $CH_2Cl_2$:

5-Fluoro-N-(5-methyl-4,5,6,7-tetrahydro-thiazolo[5,4-c]pyridin-2-yl)-2-{4-[2-(1-oxo-1,3-dihydro-isoindol-2-yl)-acetyl]-piperazin-1-yl}-benzamide MS MH+=549.9

2-{4-[2-(3,5-Dimethyl-pyrazol-1-yl)-acetyl]-piperazin-1-yl}-5-fluoro-N-(2-methoxy-pyridin-4-yl)-benzamide MS MH+=467.9

5-Fluoro-N-(2-methoxy-pyridin-4-yl)-2-{4-[2-(2-oxo-piperidin-1-yl)-acetyl]-piperazin-1-yl}-benzamide MS MH+=470.9

4-(2-Carboxy-4-chloro-phenyl)-piperazine-1-carboxylic acid tent-butyl ester is prepared as described above and is used to prepare the following compound as described above:

5-Chloro-2-{4-[2-(3,5-dimethyl-pyrazol-1-yl)-acetyl]-piperazin-1-yl}-N-(5-methyl-4,5,6,7-tetrahydro-thiazolo[5,4-c]pyridin-2-yl)-benzamide MS MH+=529.9

Example 18

Synthesis of pyrrolo[2,3-c]pyridin-1-yl-acetic acid

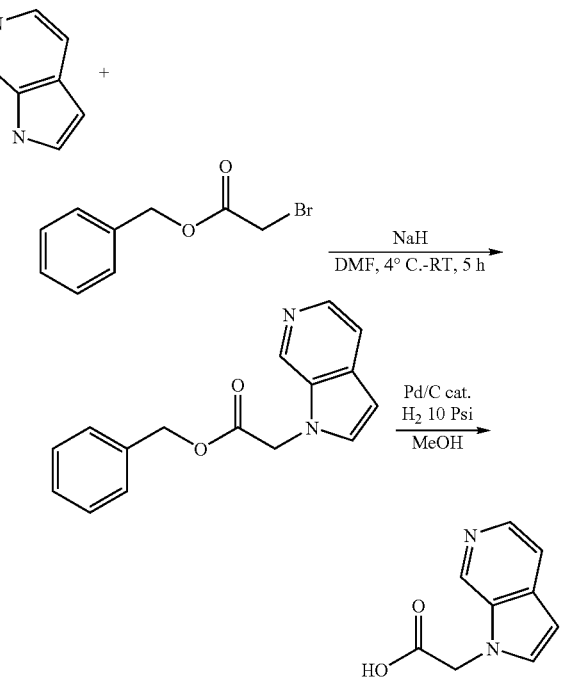

To a stirred solution of 1H-pyrrolo[2,3-c]pyridine (1 g, 8.46 mmol) in DMF (10 mL) under nitrogen atmosphere NaH (0.504 g, 12.6 mmol) is added in portions at ice-cold conditions. The reaction mixture is allowed to stir for 30 min at room temperature. It is then cooled in an ice-bath and bromoacetic acid benzyl ester (1.46 mL, 9.31 mmol) in DMF (10 mL) is added dropwise. The reaction mixture is stirred at room temperature for 5 h. Saturated aqueous $NH_4Cl$ solution is added to quench the reaction mixture at ice-cold conditions, then diluted with water (200 mL) and extracted with EtOAc (3×100 mL). Combined organic layer is washed with water followed by brine. It is then dried over anhydrous $MgSO_4$ and concentrated under reduced pressure. The residue is purified by column chromatography (silica-gel, 100-200 mesh, eluent; EtOAc to 2% MeOH in EtOAc) to afford pyrrolo[2,3-c]pyridin-1-yl-acetic acid benzyl ester (1.4 g) as a solid.

To a stirred solution of pyrrolo[2,3-c]pyridin-1-yl-acetic acid benzyl ester (1.0 g, 3.6 mmol) in MeOH (20 mL) in a Parr shaker vessel (250 mL), palladium-charcoal (100 mg) is added under nitrogen atmosphere. Nitrogen is flashed with hydrogen and the solution is hydrogenated at room temperature at 10 psi hydrogen pressure. Reaction is monitored by TLC. After complete consumption of starting material, the reaction mixture is taken out from the Parr shaker and diluted with water. The solution is filtered through a pad of diatomaceous earth and washed successively with hot water. Volatiles are removed under reduced pressure and crude solid obtained is washed with EtOAc (3×50 mL). It is concentrated and dried in vacuum to yield pyrrolo[2,3-c]pyridin-1-yl-acetic acid as a solid (0.565 g).

This intermediate is used in the preparation of the compound listed below using the procedure described in Example 1, with the exception that TBTU in $CH_2Cl_2$ is used in the coupling step for this intermediate instead of CDI in DMF: N-(5-Fluoro-pyridin-3-yl)-2-[4-(2-pyrrolo[2,3-c]pyridin-1-yl-acetyl)-piperazin-1-yl]-benzamide MS MH+=459.1

Assessment of Biological Properties

Compounds are assessed for the ability to block the interaction of CXCR3 and IP-10 in a functional cellular assay measuring calcium flux in CXCR3 transfected cells.

Cyno-CHO cells, stably expressing recombinant CXCR3 and G-alpha-16 are grown in F12 medium (Mediatech #45000-360) supplemented with 10% (V/V) FBS (Mediatech #35-01500), 1% Geneticin (Invitrogen #10131-027) and 0.2% Zeocin (Invitrogen #R250-05). The cells are spun down and re-suspended in growth media to a concentration of 4.8 E5 cells/mL. 25 microL of cell suspension is added to each well of a BD-384-well TC treated plate, providing 12,000 cells/well. The plate is incubated at 37° C./5% $CO_2$ overnight. On the day of the assay, the plates are removed, the media is flicked out and 25 microL of Ca-4 dye in assay buffer (HBSS, 10 mM HEPES ph 7.4), containing 2 mM probenacid is added to each well. The cell assay plates are then incubated at 37° C./5% $CO_2$ for one hour.

Test compounds are dissolved in DMSO and diluted to 1.045 mM in DMSO. Just prior to assay, 2.75 microL of appropriately diluted test compound are added to each well of a 384 well plate containing 45 microL of HBSS buffer. After mixing, 5 microL of diluted compound are added to each well of the cell assay plate for a final assay concentration of 10 microM. The plate is incubated at room temperature for 15 min. 10 microL of IP-10 stock solution in HBSS (4× EC80 concentration) are added to each well of the cell assay plate except those cells reserved as blank wells containing buffer only. Intracellular calcium flux is recorded on the HAMAMTSU FDSS6000, using excitation at 480 nm and emission at 540 nm. Data are analyzed using Activity Base software.

In general, the preferred potency range ($IC_{50}$) of compounds in the above assay is between 1 nM to 3 μM, and the most preferred potency range is 1 nM to 20 nM. The following table shows $IC_{50}$s for representative compounds of the invention in the above assay.

TABLE II

| Compound | $IC_{50}$ (nM) |
|---|---|
| 3-Chloro-N-{5-chloro-2-[4-(2-piperidin-1-yl-acetyl)-[1,4]diazepan-1-yl]-pyridin-3-yl}-benzamide | 3 |
| 4-Methoxy-N-(2-oxo-2-{4-[2-(pyridin-3-ylcarbamoyl)-phenyl]-piperazin-1-yl}-ethyl)-benzamide | 16 |
| 2,3-Dimethoxy-N-(2-oxo-2-{4-[2-(pyridin-3-ylcarbamoyl)-phenyl]-piperazin-1-yl}-ethyl)-benzamide | 12.5 |
| 2-{4-[2-(3,5-Dimethyl-pyrazol-1-yl)-acetyl]-piperazin-1-yl}-N-phenyl-benzamide | 13 |
| 2-{4-[2-(3,5-Dimethyl-pyrazol-1-yl)-acetyl]-piperazin-1-yl}-N-(3-trifluoromethyl-phenyl)-benzamide | 8 |
| 2-{4-[2-(3,5-Dimethyl-pyrazol-1-yl)-acetyl]-piperazin-1-yl}-N-(4-trifluoromethyl-phenyl)-benzamide | 4.2 |
| 2-{4-[2-(3,5-Dimethyl-pyrazol-1-yl)-acetyl]-piperazin-1-yl}-N-(3-methoxy-phenyl)-benzamide | 4.3 |
| 2-{4-[2-(3,5-Dimethyl-pyrazol-1-yl)-acetyl]-piperazin-1-yl}-N-(3-trifluoromethoxy-phenyl)-benzamide | 3.1 |
| N-(3-Cyano-phenyl)-2-{4-[2-(3,5-dimethyl-pyrazol-1-yl)-acetyl]-piperazin-1-yl}-benzamide | 4.5 |
| N-(3-Chloro-phenyl)-2-{4-[2-(3,5-dimethyl-pyrazol-1-yl)-acetyl]-piperazin-1-yl}-benzamide | 3.3 |
| 2-{4-[2-(3,5-Dimethyl-pyrazol-1-yl)-acetyl]-piperazin-1-yl}-N-pyridin-3-yl-benzamide | 6.6 |
| N-(6-Cyano-pyridin-3-yl)-2-{4-[2-(3,5-dimethyl-pyrazol-1-yl)-acetyl]-piperazin-1-yl}-benzamide | 4.2 |
| 2-{4-[2-(3,5-Dimethyl-pyrazol-1-yl)-acetyl]-piperazin-1-yl}-N-thiazol-2-yl-benzamide | 13 |
| N-Benzothiazol-2-yl-2-{4-[2-(3,5-dimethyl-pyrazol-1-yl)-acetyl]-piperazin-1-yl}-benzamide | 5.9 |
| 2-{4-[2-(3,5-Dimethyl-pyrazol-1-yl)-acetyl]-piperazin-1-yl}-N-(2-fluoro-phenyl)-benzamide | 5.5 |
| 3,4-Dimethoxy-N-{2-oxo-2-[4-(2-phenylcarbamoyl-phenyl)-piperazin-1-yl]-ethyl}-benzamide | 8.1 |
| 2-{4-[2-(2,4-Dimethyl-imidazol-1-yl)-acetyl]-piperazin-1-yl}-N-phenyl-benzamide | 5 |
| N-Phenyl-2-[4-(2-pyrrolo[2,3-b]pyridin-1-yl-acetyl)-piperazin-1-yl]-benzamide | 3.4 |
| 3-Chloro-N-(5-chloro-2-{1-[2-(3,5-dimethyl-pyrazol-1-yl)-acetyl]-1,2,3,6-tetrahydro-pyridin-4-yl}-phenyl)-benzamide | 7 |
| N-(5-Chloro-2-{1-[2-(3,5-dimethyl-pyrazol-1-yl)-acetyl]-piperidin-4-yl}-phenyl)-benzamide | 18.5 |

TABLE II-continued

| Compound | IC$_{50}$ (nM) |
|---|---|
| N-(2-{4-[2-(3,5-Dimethyl-pyrazol-1-yl)-acetyl]-piperazin-1-yl}-phenyl)-benzamide | 6.6 |
| 3-Chloro-N-(2-{4-[2-(3,5-dimethyl-pyrazol-1-yl)-acetyl]-piperazin-1-yl}-phenyl)-benzamide | 4.2 |
| N-(2-{4-[2-(3,5-Dimethyl-pyrazol-1-yl)-acetyl]-piperazin-1-yl}-phenyl)-3-trifluoromethyl-benzamide | 7.4 |
| 4-Chloro-N-(2-{4-[2-(3,5-dimethyl-pyrazol-1-yl)-acetyl]-piperazin-1-yl}-phenyl)-benzamide | 4.7 |
| 2-{4-[2-(3,5-Dimethyl-pyrazol-1-yl)-acetyl]-piperazin-1-yl}-N-pyridin-4-yl-benzamide | 4.7 |
| 2-{4-[2-(3,5-Dimethyl-pyrazol-1-yl)-acetyl]-piperazin-1-yl}-N-(6-methyl-pyridin-3-yl)-benzamide | 5.3 |
| N-(6-Chloro-pyridin-3-yl)-2-{4-[2-(3,5-dimethyl-pyrazol-1-yl)-acetyl]-piperazin-1-yl}-benzamide | 7.2 |
| N-(6-Acetylamino-pyridin-3-yl)-2-{4-[2-(3,5-dimethyl-pyrazol-1-yl)-acetyl]-piperazin-1-yl}-benzamide | 10.2 |
| 2-{4-[2-(3,5-Dimethyl-pyrazol-1-yl)-acetyl]-piperazin-1-yl}-N-(6-methoxy-pyridin-3-yl)-benzamide | 5.9 |
| 2-{4-[2-(3,5-Dimethyl-pyrazol-1-yl)-acetyl]-piperazin-1-yl}-N-quinolin-3-yl-benzamide | 4.8 |
| N-Pyridin-3-yl-2-[4-(2-pyrrolo[2,3-b]pyridin-1-yl-acetyl)-piperazin-1-yl]-benzamide | 4.6 |
| 3-Fluoro-4-methoxy-N-(2-oxo-2-{4-[2-(pyridin-3-ylcarbamoyl)-phenyl]-piperazin-1-yl}-ethyl)-benzamide | 19.5 |
| 2-{4-[2-(3,5-Dimethyl-pyrazol-1-yl)-acetyl]-piperazin-1-yl}-N-(5-fluoro-pyridin-3-yl)-benzamide | 10.8 |
| 2-{4-[2-(3,5-Dimethyl-pyrazol-1-yl)-acetyl]-piperazin-1-yl}-N-(5-hydroxy-pyridin-3-yl)-benzamide | 12.5 |
| 2-{4-[2-(3,5-Dimethyl-pyrazol-1-yl)-acetyl]-piperazin-1-yl}-N-(6-trifluoromethyl-pyridin-3-yl)-benzamide | 11 |
| N-(6-Bromo-pyridin-3-yl)-2-{4-[2-(3,5-dimethyl-pyrazol-1-yl)-acetyl]-piperazin-1-yl}-benzamide | 8.5 |
| 2-{4-[2-(3,5-Dimethyl-pyrazol-1-yl)-acetyl]-piperazin-1-yl}-N-(6-phenoxy-pyridin-3-yl)-benzamide | 10 |
| N-(2-tert-Butyl-pyridin-4-yl)-2-{4-[2-(3,5-dimethyl-pyrazol-1-yl)-acetyl]-piperazin-1-yl}-benzamide | 8.5 |
| N-(2-Chloro-pyridin-4-yl)-2-{4-[2-(3,5-dimethyl-pyrazol-1-yl)-acetyl]-piperazin-1-yl}-benzamide | 7.2 |
| N-(2-Bromo-pyridin-4-yl)-2-{4-[2-(3,5-dimethyl-pyrazol-1-yl)-acetyl]-piperazin-1-yl}-benzamide | 4.1 |
| 2-{4-[2-(3,5-Dimethyl-pyrazol-1-yl)-acetyl]-piperazin-1-yl}-N-(2-methyl-pyridin-4-yl)-benzamide | 12.5 |
| 2-{4-[2-(3,5-Dimethyl-pyrazol-1-yl)-acetyl]-piperazin-1-yl}-N-(3-fluoro-pyridin-4-yl)-benzamide | 19.5 |
| 2-{4-[2-(3,5-Dimethyl-pyrazol-1-yl)-acetyl]-piperazin-1-yl}-N-quinolin-6-yl-benzamide | 11.5 |
| 2-{4-[2-(3,5-Dimethyl-pyrazol-1-yl)-acetyl]-piperazin-1-yl}-N-isoquinolin-6-yl-benzamide | 13 |
| 2-{4-[2-(3,5-Dimethyl-pyrazol-1-yl)-acetyl]-piperazin-1-yl}-N-(2-methyl-benzothiazol-6-yl)-benzamide | 13 |
| 2-{4-[2-(3,5-Dimethyl-pyrazol-1-yl)-acetyl]-piperazin-1-yl}-N-(2-methyl-benzooxazol-5-yl)-benzamide | 17.5 |
| 2-{4-[2-(3,5-Dimethyl-pyrazol-1-yl)-acetyl]-piperazin-1-yl}-N-(3-dimethylsulfamoyl-phenyl)-benzamide | 17 |
| 2-{4-[2-(3,5-Dimethyl-pyrazol-1-yl)-acetyl]-piperazin-1-yl}-N-(3-methanesulfonyl-phenyl)-benzamide | 19 |
| 2-{4-[2-(3,5-Dimethyl-pyrazol-1-yl)-acetyl]-piperazin-1-yl}-N-(4-methanesulfonyl-phenyl)-benzamide | 8.8 |
| N-Pyridin-4-yl-2-[4-(2-pyrrolo[2,3-b]pyridin-1-yl-acetyl)-piperazin-1-yl]-benzamide | 4.9 |
| N-(6-Cyano-pyridin-3-yl)-2-[4-(2-pyrrolo[2,3-b]pyridin-1-yl-acetyl)-piperazin-1-yl]-benzamide | 6.3 |
| Benzo[1,3]dioxole-5-carboxylic acid (2-oxo-2-{4-[2-(pyridin-3-ylcarbamoyl)-phenyl]-piperazin-1-yl}-ethyl)-amide | 13.3 |
| 1,5-Dimethyl-1H-pyrazole-3-carboxylic acid (2-oxo-2-{4-[2-(pyridin-3-ylcarbamoyl)-phenyl]-piperazin-1-yl}-ethyl)-amide | 20 |
| 4-Methoxy-3-methyl-N-(2-oxo-2-{4-[2-(pyridin-3-ylcarbamoyl)-phenyl]-piperazin-1-yl}-ethyl)-benzamide | 11 |
| 4-Difluormethoxy-N-(2-oxo-2-{4-[2-(pyridin-3-ylcarbamoyl)-phenyl]-piperazin-1-yl}-ethyl)-benzamide | 18.3 |
| 2-[4-(2-Pyrrolo[2,3-b]pyridin-1-yl-acetyl)-piperazin-1-yl]-N-(6-trifluoromethyl-pyridin-3-yl)-benzamide | 6.9 |
| N-(6-Methyl-pyridin-3-yl)-2-[4-(2-pyrrolo[2,3-b]pyridin-1-yl-acetyl)-piperazin-1-yl]-benzamide | 6.8 |
| N-(6-Methoxy-pyridin-3-yl)-2-[4-(2-pyrrolo[2,3-b]pyridin-1-yl-acetyl)-piperazin-1-yl]-benzamide | 5.7 |
| 2-[4-(2-Pyrrolo[2,3-b]pyridin-1-yl-acetyl)-piperazin-1-yl]-N-quinolin-3-yl-benzamide | 8.4 |

TABLE II-continued

| Compound | IC$_{50}$ (nM) |
|---|---|
| 3,4-Dimethoxy-N-(2-oxo-2-{4-[2-(pyridin-4-ylcarbamoyl)-phenyl]-piperazin-1-yl}-ethyl)-benzamide | 4.6 |
| 4-Methoxy-N-(2-oxo-2-{4-[2-(pyridin-4-ylcarbamoyl)-phenyl]-piperazin-1-yl}-ethyl)-benzamide | 3.4 |
| 1-Methyl-1H-pyrrole-2-carboxylic acid (2-oxo-2-{4-[2-(pyridin-4-ylcarbamoyl)-phenyl]-piperazin-1-yl}-ethyl)-amide | 4.2 |
| 2,3-Dimethoxy-N-(2-oxo-2-{4-[2-(pyridin-4-ylcarbamoyl)-phenyl]-piperazin-1-yl}-ethyl)-benzamide | 3.7 |
| 3-Fluoro-4-methoxy-N-(2-oxo-2-{4-[2-(pyridin-4-ylcarbamoyl)-phenyl]-piperazin-1-yl}-ethyl)-benzamide | 4.2 |
| 2,5-Dimethyl-2H-pyrazole-3-carboxylic acid (2-oxo-2-{4-[2-(pyridin-4-ylcarbamoyl)-phenyl]-piperazin-1-yl}-ethyl)-amide | 5.4 |
| 2-[4-(2-2,3-Dihydro-pyrrolo[2,3-b]pyridin-1-yl-acetyl)-piperazin-1-yl]-N-pyridin-4-yl-benzamide | 9 |
| 2-[4-(2-2,3-Dihydro-pyrrolo[2,3-b]pyridin-1-yl-acetyl)-piperazin-1-yl]-N-pyridin-3-yl-benzamide | 10 |
| N-(5-Chloro-2-{4-[2-(3,5-dimethyl-pyrazol-1-yl)-acetyl]-piperazin-1-yl}-pyridin-3-yl)-3-trifluoromethyl-benzamide | 10.6 |
| N-(5-Chloro-2-{4-[2-(4-chloro-3,5-dimethyl-2H-pyrrol-2-yl)-acetyl]-piperazin-1-yl}-pyridin-3-yl)-3-trifluoromethyl-benzamide | 7.2 |
| 2-Ethyl-5-methyl-2H-pyrazole-3-carboxylic acid (2-oxo-2-{4-[2-(pyridin-3-ylcarbamoyl)-phenyl]-piperazin-1-yl}-ethyl)-amide | 18 |
| 1-Methyl-1H-pyrrole-2-carboxylic acid (2-oxo-2-{4-[2-(pyridin-3-ylcarbamoyl)-phenyl]-piperazin-1-yl}-ethyl)-amide | 12 |
| 2,4-Dimethyl-thiazole-5-carboxylic acid (2-oxo-2-{4-[2-(pyridin-3-ylcarbamoyl)-phenyl]-piperazin-1-yl}-ethyl)-amide | 13.9 |
| 2-[4-(2-Benzoylamino-acetyl)-piperazin-1-yl]-N-pyridin-3-yl-benzamide | 7.6 |
| 2-[4-(2-Phenylamino-acetyl)-piperazin-1-yl]-N-pyridin-4-yl-benzamide | 19 |
| 2-{4-[2-(1-Oxo-1,3-dihydro-isoindol-2-yl)-acetyl]-piperazin-1-yl}-N-pyridin-4-yl-benzamide | 5.1 |
| N-Pyridin-4-yl-2-{4-[2-(1,1,3-trioxo-1,3-dihydro-1l6-benzo[d]isothiazol-2-yl)-acetyl]-piperazin-1-yl}-benzamide | 6.6 |
| 2-{4-[2-(Benzoyl-methyl-amino)-acetyl]-piperazin-1-yl}-N-pyridin-4-yl-benzamide | 8.4 |
| N-{5-Chloro-2-[4-(2-pyrrolo[2,3-b]pyridin-1-yl-acetyl)-piperazin-1-yl]-pyridin-3-yl}-3-trifluoromethyl-benzamide | 8.9 |
| 3-Chloro-N-(5-chloro-2-{4-[2-(3,5-dimethyl-pyrazol-1-yl)-acetyl]-[1,4]diazepan-1-yl}-pyridin-3-yl)-benzamide | 15 |
| 3-Chloro-N-(5-chloro-2-{4-[2-(4-chloro-3,5-dimethyl-pyrazol-1-yl)-acetyl]-[1,4]diazepan-1-yl}-pyridin-3-yl)-benzamide | 15 |
| 2-{4-[2-(3,5-Dimethyl-pyrazol-1-yl)-acetyl]-piperazin-1-yl}-N-pyridazin-4-yl-benzamide | 17 |
| 2-{4-[2-(3,5-Dimethyl-pyrazol-1-yl)-acetyl]-piperazin-1-yl}-N-(5-methyl-pyridin-3-yl)-benzamide | 5.1 |
| 2-{4-[2-(3,5-Dimethyl-pyrazol-1-yl)-acetyl]-piperazin-1-yl}-N-(6-phenyl-pyridin-3-yl)-benzamide | 11.5 |
| 2-{4-[2-(3,5-Dimethyl-pyrazol-1-yl)-acetyl]-piperazin-1-yl}-N-(6-morpholin-4-yl-pyridin-3-yl)-benzamide | 12.5 |
| 2-{4-[2-(3,5-Dimethyl-pyrazol-1-yl)-acetyl]-piperazin-1-yl}-N-(2-methoxy-pyridin-4-yl)-benzamide | 8.5 |
| 2-{4-[2-(3,5-Dimethyl-pyrazol-1-yl)-acetyl]-piperazin-1-yl}-N-[2-(4-methyl-piperazin-1-yl)-pyridin-4-yl]-benzamide | 14 |
| 2-{4-[2-(3,5-Dimethyl-pyrazol-1-yl)-acetyl]-piperazin-1-yl}-N-(1-isopropyl-1H-pyrazolo[3,4-b]pyridin-5-yl)-benzamide | 11.5 |
| N-(1,3-Dimethyl-1H-pyrazolo[3,4-b]pyridin-5-yl)-2-{4-[2-(3,5-dimethyl-pyrazol-1-yl)-acetyl]-piperazin-1-yl}-benzamide | 8.7 |
| 2-{4-[2-(3-Methyl-2-oxo-2,3-dihydro-benzoimidazol-1-yl)-acetyl]-piperazin-1-yl}-N-pyridin-4-yl-benzamide | 4 |
| 2-{4-[2-(2,4-Dimethyl-thiazol-5-yl)-acetyl]-piperazin-1-yl}-N-pyridin-4-yl-benzamide | 13 |
| 2-{4-[2-(4-Methyl-1-oxo-1H-phthalazin-2-yl)-acetyl]-piperazin-1-yl}-N-pyridin-4-yl-benzamide | 5.4 |
| 2-{4-[2-(1-Oxo-1H-phthalazin-2-yl)-acetyl]-piperazin-1-yl}-N-pyridin-4-yl-benzamide | 6.1 |
| 2-{4-[2-(4-Oxo-4H-quinazolin-3-yl)-acetyl]-piperazin-1-yl}-N-pyridin-4-yl-benzamide | 3.4 |
| 4-Methoxy-N-methyl-N-(2-oxo-2-{4-[2-(pyridin-4-ylcarbamoyl)-phenyl]-piperazin-1-yl}-ethyl)-benzamide | 15 |
| 2,3-Dimethoxy-N-methyl-N-(2-oxo-2-{4-[2-(pyridin-4-ylcarbamoyl)-phenyl]-piperazin-1-yl}-ethyl)-benzamide | 15 |
| 3-Fluoro-4-methoxy-N-methyl-N-(2-oxo-2-{4-[2-(pyridin-4-ylcarbamoyl)-phenyl]-piperazin-1-yl}-ethyl)-benzamide | 15 |
| 1-Methyl-1H-pyrrole-2-carboxylic acid methyl-(2-oxo-2-{4-[2-(pyridin-4-ylcarbamoyl)-phenyl]-piperazin-1-yl}-ethyl)-amide | 6.5 |
| 2-{4-[2-(3,5-Dimethyl-pyrazol-1-yl)-acetyl]-piperazin-1-yl}-N-(4-methyl-thiazol-2-yl)-benzamide | 12 |

TABLE II-continued

| Compound | IC$_{50}$ (nM) |
|---|---|
| 2-{4-[2-(3,5-Dimethyl-pyrazol-1-yl)-acetyl]-piperazin-1-yl}-N-(5-methyl-thiazol-2-yl)-benzamide | 7.3 |
| N-(4-tert-Butyl-thiazol-2-yl)-2-{4-[2-(3,5-dimethyl-pyrazol-1-yl)-acetyl]-piperazin-1-yl}-benzamide | 15 |
| N-(5-tert-Butyl-4-methyl-thiazol-2-yl)-2-{4-[2-(3,5-dimethyl-pyrazol-1-yl)-acetyl]-piperazin-1-yl}-benzamide | 11 |
| 2-{4-[2-(3,5-Dimethyl-pyrazol-1-yl)-acetyl]-piperazin-1-yl}-N-(4-pyridin-3-yl-thiazol-2-yl)-benzamide | 20 |
| N-(5-Chloro-benzothiazol-2-yl)-2-{4-[2-(3,5-dimethyl-pyrazol-1-yl)-acetyl]-piperazin-1-yl}-benzamide | 17 |
| 2-{4-[2-(3,5-Dimethyl-pyrazol-1-yl)-acetyl]-piperazin-1-yl}-N-(4,5,6,7-tetrahydro-benzothiazol-2-yl)-benzamide | 12 |
| N-(6,7-Dihydro-4H-pyrano[4,3-d]thiazol-2-yl)-2-{4-[2-(3,5-dimethyl-pyrazol-1-yl)-acetyl]-piperazin-1-yl}-benzamide | 8.6 |
| 2-{4-[2-(3,5-Dimethyl-pyrazol-1-yl)-acetyl]-piperazin-1-yl}-N-(4-trifluoromethyl-thiazol-2-yl)-benzamide | 18 |
| N-(4-tert-Butyl-5-cyano-thiazol-2-yl)-2-{4-[2-(3,5-dimethyl-pyrazol-1-yl)-acetyl]-piperazin-1-yl}-benzamide | 18.5 |
| 2-{4-[2-(3,5-Dimethyl-pyrazol-1-yl)-acetyl]-piperazin-1-yl}-N-(4-pyridin-2-yl-thiazol-2-yl)-benzamide | 11.5 |
| 2-{4-[2-(3,5-Dimethyl-pyrazol-1-yl)-acetyl]-piperazin-1-yl}-N-(4-pyridin-4-yl-thiazol-2-yl)-benzamide | 13.5 |
| N-(4-Chloro-benzothiazol-2-yl)-2-{4-[2-(3,5-dimethyl-pyrazol-1-yl)-acetyl]-piperazin-1-yl}-benzamide | 13 |
| 2-{4-[2-(3,5-Dimethyl-pyrazol-1-yl)-acetyl]-piperazin-1-yl}-N-(6-methanesulfonyl-benzothiazol-2-yl)-benzamide | 6.6 |
| 2-{4-[2-(3,5-Dimethyl-pyrazol-1-yl)-acetyl]-piperazin-1-yl}-N-(6-methoxy-benzothiazol-2-yl)-benzamide | 9.8 |
| 2-{4-[2-(2-Methyl-4-oxo-4H-quinazolin-3-yl)-acetyl]-piperazin-1-yl}-N-pyridin-4-yl-benzamide | 8.6 |
| N-Pyridin-4-yl-2-{4-[2-(1,3,5-trimethyl-1H-pyrazol-4-yl)-acetyl]-piperazin-1-yl}-benzamide | 19.5 |
| 2-{4-[2-(1,3-Dioxo-1,3-dihydro-isoindol-2-yl)-acetyl]-piperazin-1-yl}-N-pyridin-4-yl-benzamide | 6.1 |
| 2-{4-[2-(2,5-Dimethyl-thiazol-4-yl)-acetyl]-piperazin-1-yl}-N-pyridin-4-yl-benzamide | 7 |
| 2-{4-[2-(3,5-Dimethyl-1-phenyl-1H-pyrazol-4-yl)-acetyl]-piperazin-1-yl}-N-pyridin-4-yl-benzamide | 16 |
| 2-[4-(2-Benzofuran-3-yl-acetyl)-piperazin-1-yl]-N-pyridin-4-yl-benzamide | 10.3 |
| 3-Chloro-N-(5-chloro-2-{4-[2-(3,5-dimethyl-pyrazol-1-yl)-acetyl]-piperazin-1-yl}-pyridin-3-yl)-benzamide | 11.5 |
| N-(2-{4-[5-Chloro-3-(3-trifluoromethyl-benzoylamino)-pyridin-2-yl]-piperazin-1-yl}-2-oxo-ethyl)-3,4-dimethoxy-benzamide | 8.8 |
| 2-{4-[2-(3,5-Dimethyl-pyrazol-1-yl)-acetyl]-piperazin-1-yl}-N-(2-phenyl-pyrimidin-5-yl)-benzamide | 10.5 |
| N-(5-Chloro-pyridin-3-yl)-2-{4-[2-(3,5-dimethyl-pyrazol-1-yl)-acetyl]-piperazin-1-yl}-benzamide | 7.6 |
| 2-{4-[2-(3,5-Dimethyl-pyrazol-1-yl)-acetyl]-piperazin-1-yl}-N-(2-trifluoromethyl-pyrimidin-5-yl)-benzamide | 5 |
| N-(1,3-Dimethyl-2,4-dioxo-1,2,3,4-tetrahydro-pyrido[2,3-d]pyrimidin-6-yl)-2-{4-[2-(3,5-dimethyl-pyrazol-1-yl)-acetyl]-piperazin-1-yl}-benzamide | 11.5 |
| 2-[4-(2-2,3-Dihydro-pyrrolo[2,3-b]pyridin-1-yl-acetyl)-piperazin-1-yl]-N-(4-methanesulfonyl-phenyl)-benzamide | 9.7 |
| N-(4-Methanesulfonyl-phenyl)-2-[4-(2-pyrrolo[2,3-b]pyridin-1-yl-acetyl)-piperazin-1-yl]-benzamide | 7.4 |
| N-(3-tert-Butyl-isoxazol-5-yl)-2-{4-[2-(3,5-dimethyl-pyrazol-1-yl)-acetyl]-piperazin-1-yl}-benzamide | 8.9 |
| 2-{4-[2-(3,5-Dimethyl-pyrazol-1-yl)-acetyl]-piperazin-1-yl}-N-(3-trifluoromethyl-isoxazol-5-yl)-benzamide | 5.1 |
| N-[3-(2,2-Dimethyl-propyl)-isoxazol-5-yl]-2-{4-[2-(3,5-dimethyl-pyrazol-1-yl)-acetyl]-piperazin-1-yl}-benzamide | 9.5 |
| 2-{4-[2-(3,5-Dimethyl-pyrazol-1-yl)-acetyl]-piperazin-1-yl}-N-(3-phenyl-isoxazol-5-yl)-benzamide | 8.8 |
| N-(3-Cyclohexyl-isoxazol-5-yl)-2-{4-[2-(3,5-dimethyl-pyrazol-1-yl)-acetyl]-piperazin-1-yl}-benzamide | 8.3 |
| N-(5-tert-Butyl-[1,3,4]thiadiazol-2-yl)-2-{4-[2-(3,5-dimethyl-pyrazol-1-yl)-acetyl]-piperazin-1-yl}-benzamide | 9.7 |
| N-(5-tert-Butyl-2H-pyrazol-3-yl)-2-{4-[2-(3,5-dimethyl-pyrazol-1-yl)-acetyl]-piperazin-1-yl}-benzamide | 4.8 |
| N-(3-tert-Butyl-isothiazol-5-yl)-2-{4-[2-(3,5-dimethyl-pyrazol-1-yl)-acetyl]-piperazin-1-yl}-benzamide | 10 |
| 3-Chloro-N-(5-chloro-2-{4-[2-(2-oxo-piperidin-1-yl)-acetyl]-piperazin-1-yl}-pyridin-3-yl)-benzamide | 7.7 |
| N-(5-Chloro-2-{4-[2-(3,5-dimethyl-pyrazol-1-yl)-acetyl]-piperazin-1-yl}-pyridin-3-yl)-4-methanesulfonyl-benzamide | 23 |

TABLE II-continued

| Compound | IC$_{50}$ (nM) |
|---|---|
| 2-[4-(2-1H-Indazol-3-yl-acetyl)-piperazin-1-yl]-N-pyridin-4-yl-benzamide | 7.2 |
| 2-[4-(2-Benzo[d]isoxazol-3-yl-acetyl)-piperazin-1-yl]-N-pyridin-4-yl-benzamide | 6.6 |
| N-Pyridin-4-yl-2-[4-(2-quinolin-8-yl-acetyl)-piperazin-1-yl]-benzamide | 14 |
| 2-[4-(2-Imidazo[1,2-a]pyridin-2-yl-acetyl)-piperazin-1-yl]-N-pyridin-4-yl-benzamide | 16 |
| N-(2-{4-[2-(3,5-Dimethyl-pyrazol-1-yl)-acetyl]-piperazin-1-yl}-phenyl)-nicotinamide | 15 |
| N-(2-{4-[2-(3,5-Dimethyl-pyrazol-1-yl)-acetyl]-piperazin-1-yl}-phenyl)-isonicotinamide | 7.6 |
| 5-Bromo-N-(2-{4-[2-(3,5-dimethyl-pyrazol-1-yl)-acetyl]-piperazin-1-yl}-phenyl)-nicotinamide | 5.7 |
| 6-Chloro-N-(2-{4-[2-(3,5-dimethyl-pyrazol-1-yl)-acetyl]-piperazin-1-yl}-phenyl)-nicotinamide | 15 |
| N-(2-{4-[2-(3,5-Dimethyl-pyrazol-1-yl)-acetyl]-piperazin-1-yl}-phenyl)-6-phenoxy-nicotinamide | 9.1 |
| N-(2-Methoxy-pyridin-4-yl)-2-{4-[2-(1-oxo-1,3-dihydro-isoindol-2-yl)-acetyl]-piperazin-1-yl}-benzamide | 3.4 |
| 5-Chloro-1-(2-{4-[2-(4-methanesulfonyl-phenylcarbamoyl)-phenyl]-piperazin-1-yl}-2-oxo-ethyl)-1-H-indole-2-carboxylic acid | 25 |
| 5-Methyl-oxazole-4-carboxylic acid (2-{4-[2-(2-methoxy-pyridin-4-ylcarbamoyl)-phenyl]-piperazin-1-yl}-2-oxo-ethyl)-methyl-amide | 5.5 |
| 2-{4-[2-(3,5-Dimethyl-pyrazol-1-yl)-acetyl]-piperazin-1-yl}-N-(5-fluoro-6-methyl-pyridin-3-yl)-benzamide | 14 |
| N-(2-Methoxy-pyridin-4-yl)-2-{(S)-3-methyl-4-[2-(2-oxo-piperidin-1-yl)-acetyl]-piperazin-1-yl}-benzamide | 13 |
| 2-{(S)-4-[2-(3,5-Dimethyl-pyrazol-1-yl)-acetyl]-3-methyl-piperazin-1-yl}-N-(2-methoxy-pyridin-4-yl)-benzamide | 21 |
| 2-{4-[2-(3,5-Dimethyl-pyrazol-1-yl)-acetyl]-piperazin-1-yl}-N-[2-(2,2,2-trifluoro-ethoxy)-pyridin-4-yl]-benzamide | 8.8 |
| 2-{4-[2-(2-Oxo-piperidin-1-yl)-acetyl]-piperazin-1-yl}-N-[2-(2,2,2-trifluoro-ethoxy)-pyridin-4-yl]-benzamide | 7.8 |
| 5-Fluoro-N-(5-methyl-4,5,6,7-tetrahydro-thiazolo[5,4-c]pyridin-2-yl)-2-{4-[2-(1-oxo-1,3-dihydro-isoindol-2-yl)-acetyl]-piperazin-1-yl}-benzamide | 8.1 |
| 5-Chloro-2-{4-[2-(3,5-dimethyl-pyrazol-1-yl)-acetyl]-piperazin-1-yl}-N-(5-methyl-4,5,6,7-tetrahydro-thiazolo[5,4-c]pyridin-2-yl)-benzamide | 15 |
| N-(5-Fluoro-pyridin-3-yl)-2-[4-(2-pyrrolo[2,3-c]pyridin-1-yl-acetyl)-piperazin-1-yl]-benzamide | 1.3 |
| 2-{4-[2-(3,5-Dimethyl-pyrazol-1-yl)-acetyl]-piperazin-1-yl}-N-(5-methyl-4,5,6,7-tetrahydro-thiazolo[5,4-c]pyridin-2-yl)-benzamide | 9.7 |
| N-(5-Methyl-4,5,6,7-tetrahydro-thiazolo[5,4-c]pyridin-2-yl)-2-{4-[2-(1-oxo-1,3-dihydro-isoindol-2-yl)-acetyl]-piperazin-1-yl}-benzamide | 2.9 |
| 2-{4-[2-(2-Oxo-piperidin-1-yl)-acetyl]-piperazin-1-yl}-N-(6-trifluoromethyl-pyridin-3-yl)-benzamide | 3 |
| N-(2-Methoxy-pyridin-4-yl)-2-{4-[2-(2-oxo-piperidin-1-yl)-acetyl]-piperazin-1-yl}-benzamide | 4.4 |
| 2-{4-[2-(3,5-Dimethyl-pyrazol-1-yl)-acetyl]-piperazin-1-yl}-N-(2-trifluoromethyl-pyridin-4-yl)-benzamide | 12 |
| 2-{4-[2-(2-Oxo-piperidin-1-yl)-acetyl]-piperazin-1-yl}-N-(2-trifluoromethyl-pyridin-4-yl)-benzamide | 11 |
| 2-{4-[2-(3,5-Dimethyl-pyrazol-1-yl)-acetyl]-piperazin-1-yl}-5-fluoro-N-(2-methoxy-pyridin-4-yl)-benzamide | 9.7 |
| 5-Fluoro-N-(2-methoxy-pyridin-4-yl)-2-{4-[2-(2-oxo-piperidin-1-yl)-acetyl]-piperazin-1-yl}-benzamide | 9 |
| 2-{4-[2-(2-Oxo-piperidin-1-yl)-acetyl]-piperazin-1-yl}-N-pyridin-4-yl-benzamide | 7.4 |

Methods of Use

The compounds of the invention are effective antagonists of the interaction of CXCR3 and its ligands and thus inhibit CXCR3 activation. Therefore, in one embodiment of the invention, there is provided methods of treating CXCR3-mediated disorders using compounds of the invention. In another embodiment, there is provided methods of treating inflammatory, autoimmune and cardiovascular diseases using compounds of the invention.

Without wishing to be bound by theory, by inhibiting the activity of CXCR3 the compounds of the invention block the migration of T-cells and other leukocytes that express CXCR3. Thus, the inhibition of CXCR3 activity is an attractive means for preventing and treating a variety of autoimmune and immunological diseases exacerbated by the influx of these leukocytes. These include multiple sclerosis, rheumatoid arthritis, psoriasis, inflammatory bowel disease, COPD and kidney disease. Furthermore, a genetic deletion study and a study in LDL receptor KO mice with a CXCR3 antagonist have both shown that inhibition of CXCR3 activity attenuates atherosclerotic lesion formation. Thus inhibition of CXCR3 activity is also an attractive means for treating and preventing atherosclerosis and secondary atherothrombotic events such as myocardial infarction and stroke.

For treatment of the above-described diseases and conditions, a therapeutically effective dose will generally be in the range of approximately 0.01 mg to about 100 mg/kg of body weight per dosage of a compound of the invention; preferably, from about 0.1 mg to about 20 mg/kg of body weight per dosage. For example, for administration to a 70 kg person, the dosage range would be approximately 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

What is claimed is:

1. A compound of formula (I):

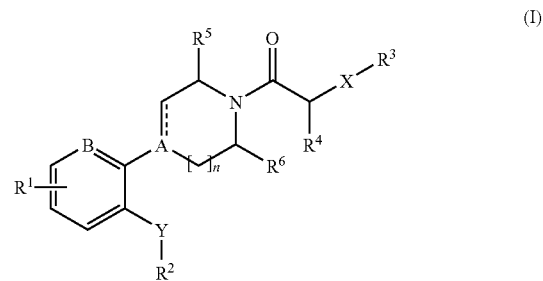

wherein:
A is N;
B is C or N;
X is —NHC(O)—;
Y is —C(O)NH—;
$R^1$ is H, —CN, halogen, —CF$_3$, —OCF$_3$, C$_{1-3}$alkyl, C$_{1-3}$alkoxy, —S(O)$_m$CH$_3$, amino, mono- or dimethylamino, —NHC(O)C$_{1-3}$alkyl, —NO$_2$—C(O)NH$_2$, —C(O)NHC$_{1-3}$alkyl or —C(O)C$_{1-3}$alkyl;
$R^2$ is aryl, heteroaryl or C$_{3-10}$cycloalkyl each optionally substituted with one to three $R^7$;
$R^3$ is heteroaryl, heterocyclyl, aryl or C$_{3-10}$cycloalkyl each optionally substituted with one to three $R^8$;
$R^4$ is H or C$_{1-6}$alkyl;
$R^5$ and $R^6$ are each independently selected from H, C$_{1-2}$alkyl and phenyl;
$R^7$ is —OH, oxo, hydroxyC$_{1-6}$alkyl, halogen, —(CH$_2$)$_m$—CN, nitro, C$_{1-6}$ alkyl, C$_{2-6}$ alkenyl, C$_{2-6}$ alkynyl, C$_{3-10}$ cycloalkyl, C$_{1-6}$ alkoxy, phenoxy, heteroaryloxy, C$_{1-6}$ alkoxycarbonyl, carboxyl, —C(O)C$_{1-6}$alkyl, —(CH$_2$)$_m$—NR$_9$R$_{10}$, —S(O)$_m$C$_{1-6}$alkyl, —NHS(O)$_2$C$_{1-6}$alkyl, NR$^9$C(O)C$_{1-6}$alkyl, —S(O)$_2$NR$_9$R$_{10}$, —C(O)NR$_9$R$_{10}$ heterocyclyl, heteroaryl, phenyl or benzyl, wherein each alkyl, alkenyl, alkynyl or alkoxy is optionally partially or fully halogenated and each heterocycle, heteroaryl, phenyl or benzyl of said $R^7$ is optionally substituted with one to three C$_{1-6}$ alkyl, C$_{1-6}$alkoxy(CH$_2$)$_m$, halogen, —CN, —CF$_3$, C$_{1-6}$ acyl, —NR⁹R¹⁰, —C(O)NR⁹R¹⁰, —OH, hydroxy $C_{1-6}$alkyl or —S(O)$_m$$C_{1-6}$alkyl;

$R^8$ is $C_{1-6}$ alkyl, $C_{2-6}$ alkenyl, $C_{2-6}$ alkynyl, carboxyl, $C_{3-10}$ cycloalkyl, $C_{1-6}$ alkoxy, halogen, oxo, or phenyl, wherein each alkyl, alkenyl, alkynyl, cycloalkyl or alkoxy is optionally partially or fully halogenated;

$R^9$ and $R^{10}$ are independently selected from hydrogen, $C_{1-6}$ alkyl, $C_{1-6}$ acyl, $C_{3-10}$ cycloalkyl, hydroxy$C_{1-6}$ alkyl, $C_{1-6}$ alkyl$C_{1-6}$ alkoxy, $C_{1-6}$ alkylsulfonyl and $C_{1-6}$ alkoxycarbonyl;

m is 0-2;

n is 1;

--------- is a single bond if A is N, or a single or double bond if A is C;

or a pharmaceutically acceptable salt thereof.

2. A compound selected from:

2-{4-[2-(3,5-Dimethyl-pyrazol-1-yl)-acetyl]-piperazin-1-yl}-N-[2-(4-methyl-piperazin-1-yl)-pyridin-4-yl]-benzamide;

2-{4-[2-(3,5-Dimethyl-pyrazol-1-yl)-acetyl]-piperazin-1-yl}-N-(2-methoxy-pyridin-4-yl)-benzamide;

N-(2-Methoxy-pyridin-4-yl)-2-{4-[2-(1-oxo-1,3-dihydro-isoindol-2-yl)-acetyl]-piperazin-1-yl}-benzamide;

5-Chloro-1-(2-{4-[2-(4-methanesulfonyl-phenylcarbamoyl)-phenyl]-piperazin-1-yl}-2-oxo-ethyl)-1-H-indole-2-carboxylic acid;

5-Methyl-oxazole-4-carboxylic acid (2-{4-[2-(2-methoxy-pyridin-4-ylcarbamoyl)-phenyl]-piperazin-1-yl}-2-oxo-ethyl)-methyl-amide;

2-{4-[2-(3,5-Dimethyl-pyrazol-1-yl)-acetyl]-piperazin-1-yl}-N-(5-fluoro-6-methyl-pyridin-3-yl)-benzamide;

N-(2-Methoxy-pyridin-4-yl)-2-{(S)-3-methyl-4-[2-(2-oxo-piperidin-1-yl)-acetyl]-piperazin-1-yl}-benzamide;

2-{(S)-4-[2-(3,5-Dimethyl-pyrazol-1-yl)-acetyl]-3-methyl-piperazin-1-yl}-N-(2-methoxy-pyridin-4-yl)-benzamide;

2-{4-[2-(3,5-Dimethyl-pyrazol-1-yl)-acetyl]-piperazin-1-yl}-N-[2-(2,2,2-trifluoro-ethoxy)-pyridin-4-yl]-benzamide;

2-{4-[2-(2-Oxo-piperidin-1-yl)-acetyl]-piperazin-1-yl}-N-[2-(2,2,2-trifluoro-ethoxy)-pyridin-4-yl]-benzamide;

5-Fluoro-N-(5-methyl-4,5,6,7-tetrahydro-thiazolo [5,4-c]pyridin-2-yl)-2-{4-[2-(1-oxo-1,3-dihydro-isoindol-2-yl)-acetyl]-piperazin-1-yl}-benzamide;

5-Chloro-2-{4-[2-(3,5-dimethyl-pyrazol-1-yl)-acetyl]-piperazin-1-yl}-N-(5-methyl-4,5,6,7-tetrahydro-thiazolo [5,4-c]pyridin-2-yl)-benzamide;

N-(5-Fluoro-pyridin-3-yl)-2-[4-(2-pyrrolo [2,3-c]pyridin-1-yl-acetyl)-piperazin-1-yl]-benzamide;

2-{4-[2-(3,5-Dimethyl-pyrazol-1-yl)-acetyl]-piperazin-1-yl}-N-(5-methyl-4,5,6,7-tetrahydro-thiazolo[5,4-c]pyridin-2-yl)-benzamide;

N-(5-Methyl-4,5,6,7-tetrahydro-thiazolo [5,4-c]pyridin-2-yl)-2-{4-[2-(1-oxo-1,3-dihydro-isoindol-2-yl)-acetyl]-piperazin-1-yl}-benzamide;

2-{4-[2-(2-Oxo-piperidin-1-yl)-acetyl]-piperazin-1-yl}-N-(6-trifluoromethyl-pyridin-3-yl)-benzamide;

N-(2-Methoxy-pyridin-4-yl)-2-{4-[2-(2-oxo-piperidin-1-yl)-acetyl]-piperazin-1-yl}-benzamide;

2-{4-[2-(3,5-Dimethyl-pyrazol-1-yl)-acetyl]-piperazin-1-yl}-N-(2-trifluoromethyl-pyridin-4-yl)-benzamide;

2-{4-[2-(2-Oxo-piperidin-1-yl)-acetyl]-piperazin-1-yl}-N-(2-trifluoromethyl-pyridin-4-y1)-benzamide;

2-{4-[2-(3,5-Dimethyl-pyrazol-1-yl)-acetyl]-piperazin-1-yl}-5-fluoro-N-(2-methoxy-pyridin-4-yl)-benzamide;

5-Fluoro-N-(2-methoxy-pyridin-4-yl)-2-{4-[2-(2-oxo-piperidin-1-yl)-acetyl]-piperazin-1-yl}-benzamide;

2-{4-[2-(2-Oxo-piperidin-1-yl)-acetyl]-piperazin-1-yl}-N-pyridin-4-yl-benzamide;

or a pharmaceutically acceptable salt thereof.

\* \* \* \* \*